United States Patent
Rapp et al.

(10) Patent No.: US 11,661,465 B2
(45) Date of Patent: May 30, 2023

(54) DIMER SELECTIVE METALLOCENE CATALYSTS, NON-AROMATIC HYDROCARBON SOLUBLE ACTIVATORS, AND PROCESSES TO PRODUCE POLY ALPHA-OLEFIN OLIGMERS THEREWITH

(71) Applicant: ExxonMobil Chemical Patents Inc., Baytown, TX (US)

(72) Inventors: Jennifer L. Rapp, Houston, TX (US); Patrick C. Chen, Houston, TX (US); Jo Ann M. Canich, Houston, TX (US); Mark H. Li, Sugar Land, TX (US); Jian Yang, Houston, TX (US); Catherine A. Faler, Houston, TX (US); Margaret T. Whalley, Houston, TX (US); Andrew E. Atalla, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 295 days.

(21) Appl. No.: 17/082,750

(22) Filed: Oct. 28, 2020

(65) Prior Publication Data
US 2021/0122859 A1 Apr. 29, 2021

Related U.S. Application Data

(60) Provisional application No. 62/926,969, filed on Oct. 28, 2019.

(51) Int. Cl.
| | |
|---|---|
| *C07C 2/30* | (2006.01) |
| *C07C 2/34* | (2006.01) |
| *B01J 31/22* | (2006.01) |
| *C08F 4/6592* | (2006.01) |
| *C10M 107/10* | (2006.01) |
| *C08F 210/16* | (2006.01) |

(52) U.S. Cl.
CPC .............. *C08F 210/16* (2013.01); *C07C 2/30* (2013.01); *C07C 2/34* (2013.01); *B01J 31/22* (2013.01); *C08F 2420/00* (2013.01); *C10M 107/10* (2013.01)

(58) Field of Classification Search
CPC ..... C07C 2/30; C07C 2/32; C07C 2/34; C08F 4/65925; C10M 107/10
See application file for complete search history.

(56) References Cited

U.S. PATENT DOCUMENTS

| | | | |
|---|---|---|---|
| 3,367,987 A | 2/1968 | Walsh | |
| 4,658,078 A | 4/1987 | Slaugh et al. | |
| 4,874,880 A | 10/1989 | Miya et al. | |
| 4,973,788 A | 11/1990 | Lin et al. | |
| 5,087,788 A | 2/1992 | Wu | |
| 5,605,219 A | 2/1997 | Aulbach et al. | |
| 5,625,105 A | 4/1997 | Lin et al. | |
| 5,741,868 A | 4/1998 | Winter et al. | |
| 5,919,983 A | 7/1999 | Rosen et al. | |
| 6,403,732 B2 | 6/2002 | Marks et al. | |
| 6,479,722 B1 | 11/2002 | De Wet et al. | |
| 6,548,723 B2 | 4/2003 | Bagheri et al. | |
| 6,818,585 B2 | 11/2004 | Crowther et al. | |
| 7,087,602 B2 | 8/2006 | Thomas et al. | |
| 7,101,940 B2 | 9/2006 | Schottek et al. | |
| 7,129,197 B2 | 10/2006 | Song et al. | |
| 7,199,072 B2 | 4/2007 | Crowther et al. | |
| 7,214,745 B2 | 5/2007 | Arai et al. | |
| 7,799,879 B2 | 9/2010 | Crowther et al. | |
| 8,318,998 B2 | 11/2012 | Crowther et al. | |
| 8,399,724 B2 | 3/2013 | Crowther et al. | |
| 8,426,659 B2 | 4/2013 | Holtcamp et al. | |
| 8,501,894 B2 | 8/2013 | Crowther et al. | |
| 8,580,902 B2 | 11/2013 | Crowther et al. | |

(Continued)

FOREIGN PATENT DOCUMENTS

| | | |
|---|---|---|
| CN | 105622807 | 6/2016 |
| JP | 2005-336092 | 12/2005 |

(Continued)

OTHER PUBLICATIONS

Rulhoff, S., et al. "Synthesis and Characterization of Defined Branched Poly(propylene)s with Different Microstructures by Copolymerization of Propylene and Linear Ethylene Oligomers ($C_n$=26-28) with Metallocenes/MAO Catalysts," Macromolecules, v.207, pp. 1450-1460, 2006.

Kaneyoshi, H., et al. "Synthesis of Block and Graft Copolymers with Linear Polyethylene Segments by Combination of Degenerative Transfer Coordination Polymerization and Atom Transfer Radical Polymerization," Macromolecules, v.38(13), pp. 5425-5543, 2005.

Teuben, J., et al. "Catalytic Olefin Oligomerization and Polymerization with Cationic Group IV Metal Complexes [$Cp*2MMe(THT)$] + [$BPh4$]-, $M=Ti$, Zr and Hf", J. Mol. Catal., v.62(3), pp. 277-287; 1990.

(Continued)

*Primary Examiner* — Caixia Lu
(74) *Attorney, Agent, or Firm* — ExxonMobil Technology and Engineering Company-Chemicals

(57) ABSTRACT

The present disclosure generally relates to process to produce a poly alpha-olefin (PAO), comprising: a) introducing a first alpha-olefin to a first catalyst system comprising non-aromatic hydrocarbon soluble activator and a metallocene compound into a continuous stirred tank reactor or a continuous tubular reactor under first reactor conditions, wherein the first alpha-olefin is preferably introduced to the reactor at a flow rate of about 100 g/hr or more, to form a first reactor effluent comprising PAO (such as at least 60 wt % of PAO dimer and 40 wt % or less of higher oligomers, where the higher oligomers are oligomers that have a degree of polymerization of 3 or more); and b) introducing the first reactor effluent and a second alpha-olefin to a second catalyst composition comprising an acid catalyst, such as $BF_3$, in a second reactor to form a second reactor effluent comprising PAO trimer.

36 Claims, 3 Drawing Sheets

(56) References Cited

U.S. PATENT DOCUMENTS

| | | | |
|---|---|---|---|
| 8,623,974 | B2 | 1/2014 | Jiang et al. |
| 8,642,497 | B2 | 2/2014 | Berris |
| 8,669,326 | B2 | 3/2014 | Hagadorn et al. |
| 8,669,330 | B2 | 3/2014 | Stewart |
| 8,748,361 | B2 | 6/2014 | Wu et al. |
| 8,754,170 | B2 | 6/2014 | Hagadorn et al. |
| 8,816,027 | B2 | 8/2014 | Crowther et al. |
| 8,835,563 | B2 | 9/2014 | Crowther et al. |
| 8,940,839 | B2 | 1/2015 | Hagadorn et al. |
| 9,365,788 | B2 | 6/2016 | Emett et al. |
| 9,688,792 | B2 | 6/2017 | Welle et al. |
| 2002/0062011 | A1 | 5/2002 | Campbell, Jr. et al. |
| 2004/0102590 | A1 | 5/2004 | McCullough et al. |
| 2005/0159299 | A1 | 7/2005 | Rodriguez et al. |
| 2009/0318644 | A1 | 12/2009 | Brant et al. |
| 2010/0038290 | A1 | 2/2010 | Wang et al. |
| 2013/0090273 | A1 | 4/2013 | Martin et al. |
| 2013/0303818 | A1 | 11/2013 | Inagaki et al. |
| 2014/0194277 | A1 | 7/2014 | Ishihama et al. |
| 2015/0203602 | A1 | 7/2015 | Sun et al. |
| 2017/0233516 | A1 | 8/2017 | Yang et al. |
| 2018/0094088 | A1 | 4/2018 | Crowther et al. |
| 2018/0146444 | A1 | 5/2018 | Chen et al. |
| 2019/0135961 | A1 | 5/2019 | Joung et al. |
| 2019/0248936 | A1 | 8/2019 | Yang et al. |
| 2019/0263942 | A1 | 8/2019 | Jeong et al. |
| 2019/0330392 | A1 | 10/2019 | Faler et al. |

FOREIGN PATENT DOCUMENTS

| | | |
|---|---|---|
| JP | 2011-037164 | 2/2011 |
| WO | 1995/027717 | 10/1995 |
| WO | WO 2001/021675 A1 | 3/2001 |
| WO | 2009/155471 | 12/2009 |
| WO | 2010/014344 | 2/2010 |
| WO | 2012/134720 | 10/2012 |
| WO | 2018/182982 | 10/2018 |
| WO | 2018/182984 | 10/2018 |
| WO | WO 2019/157169 A1 | 8/2019 |
| WO | WO 2020/060690 A1 | 3/2020 |

OTHER PUBLICATIONS

Yang, X., et al. "Cationic Metallocene Polymerization Catalysts. Synthesis and Properties of the First Base-Free Zirconocene Hydride" *Angew. Chem., Int'l Edn.*, Engl., v.31, No. 10, pp. 1375-1377, 1992.

Small, B. L., et al. "Polymerization of Propylene by a New Generation of Iron Catalysts: Mechanisms of Chain Initiation, Propagation, and Termination", *Macromol.*, v.32, pp. 2120-2130, 1999.

Weng, W., et al. "Synthesis of vinyl-terminated isotactic poly(propylene)", *Macromol Rapid Comm.*, v.21, pp. 1103-1107, 2000.

Markel, E. J., et al. "Metallocene-Based Branch-Block Thermoplastic Elastomers", *Macromolecules*, v.33, pp. 8541-8548, 2000.

Moscardi, G., et al. "Propene Polymerization with the Isospecific, Highly Regioselective $rac$-Me$_2$C(3-t-Bu-1-Ind)$_2$ZrCl$_2$/MAO Catalyst. 2. Combined DFT/MM Analysis of Chain Propagation and Chain Release Reactions", *Organometallics*, v. 20, pp. 1918, 2001.

Zhu, S., et al. "Copolymerization of Propylene with Poly(ethylene-co-propylene) Macromonomer and Branch Chain-Length Dependence of Rheological Properties" *Macromol.*, v.35, pp. 10062-10070, 2002.

Zhu, S., et al. "Synthesis and Characterization of Long-Chain-Branched Polyolefins with Metsllocene Catalysts: Copolymerization of Ethylene with Poly(ethylene-$co$-propylene) Macromonomer", *Macromol. Rap. Commun.*, v.24, pp. 311-315, 2003.

Coates, G. W., et al. "Synthesis of Allyl-Terminated Syndiotactic Polypropylene: Macromonomers for the Synthesis of Branched Polyolefins", *Macromolecules*, v.38, pp. 6259-6268, 2005.

Rose, J. M., et al. "Poly(ethylene-$co$-propylene macromonomer)s: Synthesis and Evidence for Starlike Conformations in Dilute Solution", *Macromolecules*, v.41, pp. 559-567, 2008.

Janiak, C., et al. "Metallocene Catalysts for Olefin Oligomerization", *Macromol. Symp.*, v.236, pp. 14-22, 2006.

Abu-Omar, M. M., "Highly Regioselective α-Olefin Dimerization Using Zirconium and Hafnium Amine Bis(phenolate) Complexes", *Organometallics*, v.36 (15), pp. 2934-2939, 2017.

Bazan, G. C., et al. "(Phenylboratabenzene)zirconium Complexes: Tuning the Reactivity of an Olefin Polymerization Catalyst", *Organometallics*, v.16, pp. 2492-2494, 1997.

Chemical Abstract Service (CAS) Registry No. 909721-53-5.
Chemical Abstract Service (CAS) Registry No. 943521-08-2.
U.S. Appl. No. 62/885,103, filed Aug. 9, 2019.
U.S. Appl. No. 62/629,200, filed Feb. 12, 2018.
U.S. Appl. No. 62/732,311, filed Sep. 17, 2018.
U.S. Appl. No. 62/662,972, filed Apr. 26, 2018.
U.S. Appl. No. 62/769,208, filed Nov. 19, 2018.

(Apparatus)

DIMER SELECTIVE METALLOCENE CATALYSTS, NON-AROMATIC HYDROCARBON SOLUBLE ACTIVATORS, AND PROCESSES TO PRODUCE POLY ALPHA-OLEFIN OLIGMERS THEREWITH

CROSS-REFERENCE TO RELATED APPLICATIONS

This application claims priority to and the benefit of U.S. Patent Application Ser. No. 62/926,969, filed Oct. 28, 2019, the disclosure of which is incorporated herein by reference in its entirety.

This application is related to U.S. Ser. No. 16/270,085, filed Feb. 7, 2019.

This application is related to U.S. Ser. No. 16/394,166, filed Apr. 25, 2019.

This application is related to U.S. Ser. No. 16/394,197, filed Apr. 25, 2019.

This application is related to U.S. Ser. No. 16/537,364, filed Aug. 9, 2019, U.S. Ser. No. 16/537,349, filed Aug. 9, 2019, U.S. Ser. No. 16/537,381, filed Aug. 9, 2019, and U.S. Ser. No. 62/885,103, filed Aug. 9, 2019.

This application is related to U.S. Ser. No. 15/706,088, filed Sep. 15, 2017 (which is published as US 2018/0094088).

This application is also related to U.S. Ser. No. 15/921,757, filed Mar. 15, 2018 (which is published as WO 2018/182982).

This application is also related to U.S. Ser. No. 16/270,085, filed Feb. 7, 2019 which claims priority to and the benefit of U.S. Ser. No. 62/629,200, filed Feb. 12, 2018, and U.S. Ser. No. 62/732,311, filed Sep. 17, 2018.

This application is also related to U.S. Ser. No. 16/394,197, filed Apr. 25, 2019, and U.S. Ser. No. 16/394,166, filed Apr. 25, 2019, both of which claim priority to and the benefit of U.S. Ser. No. 62/662,972, filed Apr. 26, 2018 and U.S. Ser. No. 62/769,208, filed Nov. 19, 2018.

FIELD

The present disclosure generally relates to processes to produce alpha-olefin oligomers and poly alpha-olefins using catalyst systems comprising a hydrocarbon soluble activator.

BACKGROUND

Equipment builders have accelerated design changes to improve energy efficiency in response to market demand. For example, passenger vehicles have drastically modified the design of their internal combustion engines, trending toward smaller engines that operate at higher (and more efficient) temperatures. There has also been a significant rise in the design of electrified vehicles, and in some designs, equipment builders have eliminated the internal combustion engine in favor of electric vehicles. Similar trends can be observed in industrial equipment design.

Alpha-olefins and poly alpha-olefins (PAOs), such as vinylidene-terminated PAOs, are used as intermediates in the manufacture of many commercial products such as lubricant base oil components, basestocks, and surfactants.

As a result of the equipment changes mentioned above, lubricant requirements have generally become more stringent. For example, there have been multiple engine oil viscosity grades added to development over the past decade (e.g. 0W-8, 0W-12, 0W-16). These engine oils require extremely low viscosity base oils without significantly increasing volatility of the lubricant. These lubricants are also required to deliver outstanding oxidative stability. Additionally electric vehicles have brought new and diverse challenges for driveline fluids and cooling systems, which require tailored lubricant design.

While mineral-oil base stocks are widely available, they generally lack tailored performance to meet specific lubricant needs. When analyzing available Group III base stocks, for example, nearly all suppliers offer three or four grades ranging from 3 cSt to 8 cSt. For very low viscosity engine oils (e.g. 0W-8), for example, these base stocks are often insufficient to meet both volatility and viscometric targets.

While polyalphaolefins (PAOs) have a wide availability of viscosity grades, the vast majority of commercial low viscosity PAOs (below 10 cSt KV100) are produced from $BF_3$ catalysts, which are difficult to tailor to specific product performance.

Catalyst systems to selectively produce solely or predominantly alpha-olefin dimers (e.g., >80%) at high yields and with high vinylidene unsaturation would allow for better tailoring of PAO molecules (through two-step processing or further functionalization). For example, conventional metallocene catalyst systems, such as supported dimethylsilyl bis(2-methyl-4-phenyl-indenyl) zirconium dimethyl, typically produce about 50% vinyl and about 50% vinylidene terminal unsaturations (of the termini that are unsaturated). Conventional metallocene catalyst systems to construct high vinylidene dimerized olefins require the use of an alumoxane, aluminum alkyl, or ionic activator, and in some cases the presence of hydrogen. Certain conventional processes to produce alpha-olefin dimers utilize bridged metallocenes, such as bis(cyclopentadienyl)zirconium dichloride, in the presence of methyl alumoxane (MAO), trialkylaluminum, or higher alkyl alumoxane and an activator such as trimethyl aluminum. Such processes can produce predominantly vinylidene dimer olefins at high yields, but lack in catalyst efficiency, kinetics, and/or high product yield.

An exemplary PAO molecule is a "hybrid trimer" which is a reaction product of a metallocene dimer, such as a PAO dimer, with linear alpha-olefin (LAO) using an acid catalyst system, e.g., $BF_3$-alcohol promoter catalyst system. For example, a hybrid C30 trimer is a reaction product of a C20 metallocene PAO dimer and C10 LAO. Conventional methods of forming hybrid trimers involve reaction of a PAO dimer feedstock that contains a significant amount of di-substituted vinylene. The di-substituted vinylene, however, is not highly reactive when added to a $BF_3$ catalyzed conventional reactor, and the reaction kinetics are very slow. In addition, the unreacted dimer in the stream going into the $BF_3$ catalyzed conventional reactor contaminates the stream produced from the $BF_3$ process and reduces the value of that reactor effluent.

Furthermore, conventional plants for the production of PAO molecules, such as hybrid trimers, can generate a PAO dimer from a first oligomerization reactor. The PAO dimer product from the first oligomerization reactor is of such poor quality (e.g., there are timers, tetramers, and higher oligomers) that it is enriched via a separation stage prior to being fed into a second oligomerization reactor. This process involves a separation stage, e.g., a distillation operation, prior to a second oligomerization reactor because feeding the trimer and higher (tetramer+) oligomers to the second oligomerization reactor produces an undesired heavier product from the second oligomerization reaction. The additional equipment, operators, and downtime involved for the separation stage, for example, can be a burden in terms of cost and efficiencies.

Therefore, there is a need for processes to selectively produce PAO dimers, with high vinylidene and very low vinylene content, at high catalyst efficiency, good kinetics, and high conversion. There is also a need for improved processes and apparatus for producing PAOs, such as low viscosity PAOs including hybrid trimers, from feedstocks containing the PAO dimers.

References of interest include: US 2010/0170829 A1; US 2010/0038290 A1; WO 2010/019545; WO 2011/014215; WO 2018/182982; WO 2018/182984; PCT Publication Nos. WO 2002/002577; WO 1995/027717; WO 2009/155471; WO 2009/155472; WO 2009/155510; WO 2009/155517; WO 2010/014344; WO 2012/134720; WO 2012/133717; WO 2017/188602; WO 2017/155149; WO 2018/0094088; WO 2018/182982; U.S. Pat. Nos. 3,367,987; 5,919,983; 9,796,645; 9,688,792; 9,365,788; 7,129,197; 6,548,724; 6,548,723; 6,479,722; 5,625,105; 5,087,788; 4,973,788; 4,658,078; 3,367,987; 7,214,745; 7,101,940; 8,816,027; 8,748,361; 8,318,998; 8,669,326; 8,940,839; 8,754,170; 8,426,659; 8,841,397; 8,501,894; 8,669,330; 8,835,563; 8,841,394; 8,399,724; 8,623,974; 8,981,029; 6,403,732; 6,818,585; 7,199,072; 7,799,879; 7,985,816; 8,580,902; 8,835,587; 7,087,602; 8,642,497; 6,121,185; US Patent Application Publication Nos. US 2002/0062011; US 2018/0094088; US 2017/0233516; US 2015/0344598; US 2013/0303818; US 2013/0023633; US 2009/0318644; US 2005/0159299; US 2015/0203602; and US 2004/0102590; Japanese Publication No. JP 2005-336092; JP 2011-037164A; Chinese Publication No. CN 105622807; EP Publication Nos. EP 0659756; EP 0610851; EP 0283739; Korean Publication No. KR 17250040000; Rulhoff, S. et al. (2006) "Synthesis and Characterization of Defined Branched Poly(propylene)s with Different Microstructures by Copolymerization of Propylene and Linear Ethylene Oligomers ($C_n$=26-28) with Metallocenes/MAO Catalysts," *Macromolecules*, v. 207, pp. 1450-1460; Kaneyoshi, Hiromu et al. (2005) "Synthesis of Block and Graft Copolymers with Linear Polyethylene Segments by Combination of Degenerative Transfer Coordination Polymerization and Atom Transfer Radical Polymerization," *Macromolecules*, v. 38(13), pp. 5425-5435; Teuben, J. et al. (1990) *J. Mol. Catal.*, v. 62(3), pp. 277-287; Yang, X. et al. (1992) *Angew. Chem., Int'l Edn.*, Engl., v. 31, pp. 1375-1377; Small and Brookhart (1999) *Macromol.*, v. 32, pp. 2120-2130; Weng et al. (2000) *Macromol Rapid Comm.*, v. 21, pp. 1103-1107; Markel, E. J. et al. (2000) *Macromolecules*, v. 33, pp. 8541-8548; Moscardi et al. (2001) *Organomet.*, v. 20, pp. 1918; Zhu et al. (2002) *Macromol.*, v. 35, pp. 10062-10070 and *Macromol. Rap. Commun.*, 2003, v. 24, pp. 311-315; Coates et al. (2005) *Macromol.*, v. 38, pp. 6259-6268; Rose et al. (2008) *Macromolecules*, v. 41, pp. 559-567; Janiak, C. et al. (2006) *Macromol. Symp.*, v. 236, pp. 14-22, U.S. Pat. Nos. 9,409,834; 6,548,724; 4,658,078; *Organometallics* (2017) v. 36, pp. 2934-2939; and *Organometallics* (1997), v. 16, pp. 2492-2494, U.S. Pat. No. 9,399,746; U.S. Ser. No. 16/394,166 filed Apr. 25, 2019, Chemical Abstract Service (CAS) number 909721-53-5, and Chemical Abstract Service (CAS) number 943521-08-2.

SUMMARY

The present disclosure relates to processes to produce alpha-olefin oligomers and poly alpha-olefins, and optional hydrogenated analogs thereof.

This invention further relates to a process to produce a poly alpha-olefin (PAO), comprising:

a) introducing a first alpha-olefin to a first catalyst system comprising non-aromatic hydrocarbon soluble activator and a metallocene compound into a first reactor under first reactor conditions to form a first reactor effluent comprising PAO dimer; and b) introducing the first reactor effluent and an optional second alpha-olefin to a second catalyst composition comprising an acid catalyst in a second reactor to form a second reactor effluent comprising PAO trimer.

In an embodiment, the present disclosure provides a process to produce a poly alpha-olefin (PAO), the process including:

introducing a $C_6$-$C_{32}$ alpha-olefin and a catalyst system comprising activator and a metallocene compound into a continuous stirred tank reactor or a continuous tubular reactor under reaction conditions, wherein the alpha-olefin is preferably introduced to the reactor at a flow rate of about 100 g/hr; and obtaining a product comprising PAO dimer, the PAO dimer preferably comprising 90 (alternately 93, alternately 95, alternately 97) mol % or more (such as alternately from 90 to 99 mol %) of vinylidene, based on total moles of vinylidene, di-substituted vinylene, and tri-substituted vinylene in the product, wherein the metallocene compound is represented by the formula (I):

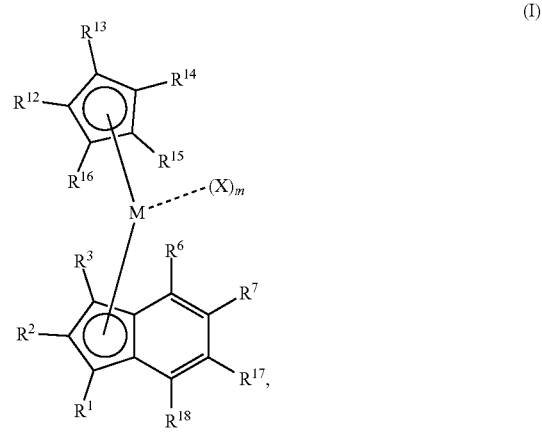

(I)

wherein:

each $R^1$, $R^2$, and $R^3$ is, independently, hydrogen or a substituted or unsubstituted linear, branched, or cyclic $C_1$-$C_{20}$ hydrocarbyl group, preferably wherein at least one of $R^1$, $R^2$, and $R^3$ is not hydrogen and at least one of $R^1$, $R^2$, and $R^3$ is hydrogen;

$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$ taken together with the carbon atoms in the indenyl ring to which they are directly connected, collectively form one or more substituted or unsubstituted rings annelated to the indenyl ring;

$R^{12}$, $R^{13}$, $R^{14}$, and $R^{15}$, are each independently a substituted or unsubstituted linear, branched, or cyclic $C_1$-$C_{20}$ hydrocarbyl group;

$R^{16}$ is a substituted or unsubstituted linear, branched, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a transition metal, preferably group 3, 4 or 5, having an integer coordination number of v, such as 3, 4, or 5; and m is an integer equal to v-2, such as 1, 2, or 3; and the activator is represented by the formula:

$$[R^{1'}R^{2'}R^{3'}EH]_{d^+}[Mt^{k+}Q_n]^{d-} \qquad (V)$$

wherein:

E is nitrogen or phosphorous;

d is 1, 2 or 3; k is 1, 2, or 3; n is 1, 2, 3, 4, 5, or 6; n−k=d (preferably d is 1, 2 or 3; k is 3; n is 4, 5, or 6);

$R^{1'}$, $R^{2'}$, and $R^{3'}$ are independently $C_1$ to $C_{50}$ hydrocarbyl group optionally substituted with one or more alkoxy groups, silyl groups, a halogen atoms, or halogen containing groups, wherein $R^{1'}$, $R^{2'}$, and $R^{3'}$ together comprise 15 or more carbon atoms;

Mt is an element selected from group 13 of the Periodic Table of the Elements, such as B or Al; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical; and optionally further combining the product with acid catalyst, such as $BF_3$, to obtain PAO trimer.

In at least one embodiment, the process to produce a poly alpha-olefin (PAO) includes introducing a first alpha-olefin to a first catalyst system comprising non-aromatic hydrocarbon soluble activator and a metallocene compound into a continuous stirred tank reactor or a continuous tubular reactor under first reactor conditions to form a first reactor effluent, preferrably wherein the reactor effluent is essentially free of aromatic solvents, and optionally free of non-alpha-olefin solvents. The first alpha-olefin is preferably introduced to the reactor at a flow rate of about 100 g/hr. The first reactor effluent typically comprises at least 60 wt % of PAO dimer and 40 wt % or less of higher oligomers, where the higher oligomers are oligomers that have a degree of polymerization of three or more. The process includes introducing the first reactor effluent and a second alpha-olefin to a second catalyst composition including an acid catalyst, such as $BF_3$ in a second reactor to form a second reactor effluent comprising PAO trimer. Optionally, the first reactor effluent is introduced to a separations unit to remove the higher oligomers prior to introduction into the second reactor. Optionally, the first reactor effluent is introduced to a separations unit to remove the higher oligomers and solvent prior to introduction into the second reactor. Optionally, the first reactor effluent is introduced to a separations unit to remove all or part of solvent (such as non-alpha-olefin-solvents, if present) or diluent that is not also being used as alpha-olefin monomer. Optionally, the first reactor effluent is introduced to a separations unit to remove all or part of solvent or diluent that is also being used as alpha-olefin monomer.

In at least one embodiment, a process includes functionalizing and/or hydrogenating a PAO product of the present disclosure.

In at least one embodiment, a blend includes a PAO product of the present disclosure.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements and features of one example may be beneficially incorporated in other examples without further recitation.

DETAILED DESCRIPTION

Figure 1:
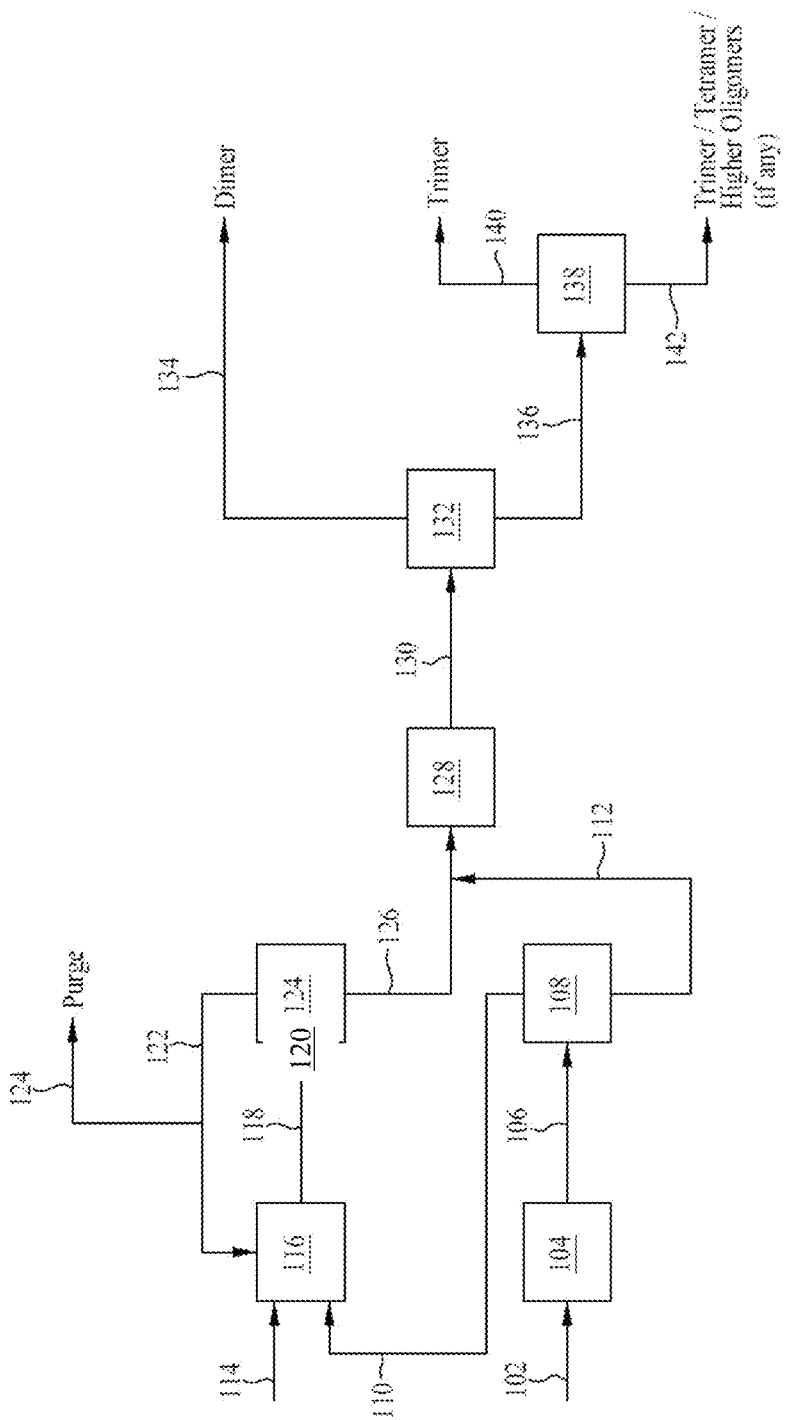
FIG. 1 shows an apparatus for forming poly alpha-olefins according to at least one embodiment.

The present disclosure provides processes for producing poly alpha-olefins using metallocene catalyst compounds, preferably asymmetric unbridged metallocene catalyst compounds and activators that are soluble in non-aromatic hydrocarbons. In some examples, these metallocenes contain tetrahydro-s-indacenyl-type ligands. The catalyst systems and processes incorporating such catalyst systems rival and/or surpass conventional catalyst systems in producing alpha-olefin oligomers and polymers.

Relative to conventional catalysts and catalyst systems, the catalysts and catalyst systems described herein can selectively produce alpha-olefin dimers at high product yield (high linear alpha-olefin conversion) and with very high vinylidene unsaturation with high catalyst efficiency and or high conversion. In at least one example, the inventors have found that the catalyst systems disclosed herein can produce alpha-olefin dimers with high selectivity (greater than 90%), with 93 mol % or more vinylidene, preferably 95 mol % or more preferably 97 mol % or more and, preferably, 0 mol % vinylene content.

The present disclosure also provides processes and apparatus for producing alpha-olefin oligomers from feedstocks containing predominantly PAO dimers. In an example, the inventors have found that a "hybrid trimer", which can be formed from a reaction of a PAO dimer with an alpha-olefin monomer, can be produced in high yields. The inventors have found that a higher purity PAO dimer feedstock, having low amounts of trimer, tetramer, and higher oligomers, can form higher amounts of the hybrid trimer relative to conventional processes. In addition, the inventors have found that reducing (or eliminating) the amount of di-substituted vinylene in the PAO dimer feedstock produces a PAO hybrid trimer at higher yields and higher purity relative to conventional processes.

The present disclosure also provides processes and apparatus for producing alpha-olefin oligomers. In an example, the process eliminates the need for a separation stage between a first oligomerization operation and a second oligomerization operation.

Processes and apparatus of the present disclosure can provide one or more the following:
a. Little or no aluminum species present in the PAO product, such as less than 1000 ppm (preferably to not have to remove Al species as it can be considered an impurity for final product)
  i. >60% dimer selectivity at a catalyst productivity of >10,000 g PAO/g cat without the use of alumoxane
  ii. >60% dimer selectivity at a catalyst productivity of >10,000 g PAO/g cat without the use of alumoxane or less than 10 equivalents of aluminum alkyl per metallocene
  iii. >60% dimer selectivity at a catalyst productivity of >10,000 g PAO/g cat with <500 ppm of an aluminum alkyl
  iv. >60% dimer selectivity at a catalyst productivity of >10,000 g PAO/g cat with <20 ppm of an aluminum alkyl
  v. >60% dimer selectivity at a catalyst productivity of >10,000 g PAO/g cat with <2% LAO isomerization
  vi. >60% dimer selectivity at a catalyst productivity of >5,000 g PAO/g cat with >80% vinylidene unsaturation
  vii. >60% dimer selectivity at a catalyst productivity of >5,000 g PAO/g cat without the use of alumoxane or less than 10 equivalents aluminum alkyl per metallocene
  viii. >60% dimer selectivity at a catalyst productivity of >5,000 g PAO/g cat with <1000 ppm of an aluminum alkyl
  ix. Little or no aromatic hydrocarbon species (such as toluene) present in the PAO product (preferable to not have to remove aromatic hydrocarbon as it can be considered an impurity for final product
b. Activity with selectivity (e.g., more efficient production of high dimer)
  i. >60% dimer selectivity with catalyst productivity >5,000 g PAO/g cat
  ii. >60% dimer selectivity with catalyst activity greater than 2000 g PAO/mol cat 1,000, alternately greater than 1000) kg PAO/mol cat, alternately greater than 2000 kg PAO/mol cat
  iii. >90% dimer selectivity with catalyst productivity >60,000 g PAO/g cat
c. Low residence times (which is another indicator of higher efficiency)
  i. <24 hrs; preferably <10 hrs; preferably <5 hrs
d. Vinylidene selectivity (useful for functionalization by alkylation, further oligomerization)
  i. >85%, preferably >90%; preferably >93%; preferably >95%1 preferably >97%
e. Catalyst family
  i. New type of catalyst system using a hydrocarbon soluble activator specifically suitable for highly efficient production of high vinylidene dimers.

Processes and apparatus of the present disclosure can provide one or more the following:
continuous processes or batch process,
PAO products having a low Mn (e.g., below 5,000 g/mol, preferably below 1,500 g/mol, preferably below 350 g/mol; preferably from 160 to 320 g/mol, such as 250 to 300 g/mol),
Processes at activity above 2,000 gPAO/mol catalyst with low Mn (e.g., below 5,000 g/mol, preferably below 1,500 g/mol, preferably below 350 g/mol; preferably from 160 to 320 g/mol, such as 250 to 300 g/mol),
Processes at monomer conversion above 80% with low Mn (e.g., below 5,000 g/mol, preferably below 1,500 g/mol, preferably below 350 g/mol; preferably from 160 to 320 g/mol, such as 250 to 300 g/mol),
Processes at monomer conversion above 80% with high vinylidene group content (e.g., >80%, >90%, >93%, >95%, >97%, >98%),
Processes that can operate at higher temperature of, for example, 110-148.5° C.,
Processes with reduced LAO isomerization,
Processes that can use $C_6$-$C_{20}$ LAOs,
Processes utilizing low level of aluminum alkyl such as less than 10 equivalents aluminum alkyl per metallocene,
Processes that can optionally be alumoxane (such as methylalumoxane, MAO)-free,
Processes that can be optionally aluminum-alkyl free.

Definitions

For the purposes of this present disclosure, and unless otherwise specified, the term "alkyl" or "alkyl group" interchangeably refers to a saturated hydrocarbyl group consisting of carbon and hydrogen atoms. An alkyl group can be substituted or unsubstituted and can be linear, branched, cyclic, or a combination thereof. Wherever "linear, branched, or cyclic" is used, combinations thereof are included. For example, methylcyclohexyl is a combination, and included in the definition of an alkyl group.

"Catalyst productivity" is the quantity of PAO produced per quantity of the metallocene compound used, reported in units of gramPAO/gram metallocene). For calculating catalyst productivity, only the weight of the transition metal component of the catalyst is used.

Unless otherwise indicated, "catalyst activity" is a measure of how active the catalyst is and is reported as the mass of product PAO (P) produced per mole of catalyst (cat) used (typically reported as kg P/mol catalyst in a continuous process or kg P/mmol/hr in a batch process). For calculating catalyst activity, the molar amount of the transition metal component of the catalyst is used.

"Residence time" is defined to be the average time the reactants and products are in the reactor in a continuous process under steady-state conditions. Residence time is measured as the amount of material in the reactor (i.e. grams), divided by the outflow (i.e. grams/hr).

For the purposes of this present disclosure, and unless otherwise specified, the term "cycloalkyl" or "cycloalkyl group" interchangeably refers to a saturated hydrocarbyl group wherein the carbon atoms form one or more ring structures.

For the purposes of this present disclosure, and unless otherwise specified, the term "alkenyl" or "alkenyl group" interchangeably refers to a linear unsaturated hydrocarbyl group comprising a C=C bond therein.

For the purposes of this present disclosure, and unless otherwise specified, the term "cycloalkenyl" or "cycloalkenyl group" interchangeably refers to cyclic hydrocarbyl group comprising a C=C bond in the ring.

For the purposes of this present disclosure, and unless otherwise specified, the term "aryl" or "aryl group" interchangeably refers to a hydrocarbyl group comprising an aromatic ring structure therein.

The terms "aryloxy" and "aryloxide" mean an aryl group bound to an oxygen atom, such as an aryl ether group/radical connected to an oxygen atom and can include those where the aryl group is a $C_6$ to $C_{20}$ hydrocarbyl. Examples of suitable aryloxy radicals can include phenoxy, biphenoxy, naththoxy, and the like.

The terms "alkoxy" and "alkoxide" mean an alkyl group bound to an oxygen atom, such as an alkyl ether group/radical connected to an oxygen atom and can include those where the alkyl group is a $C_1$ to $C_{20}$ hydrocarbyl. The alkyl group may be straight chain, branched, or cyclic. The alkyl group may be saturated or partially unsaturated. Examples of suitable alkoxy radicals can include methoxy, ethoxy, n-propoxy, iso-propoxy, n-butoxy, iso-butoxy, sec-butoxy, tert-butoxy, and the like.

The term "branched (such as branched linear)" is defined to mean a branched group that is not dendritic (i.e., branch on branch) or crosslinked, typically a branched (such as branched linear) group is a linear group that has one or more branches.

For the purposes of this present disclosure, unless otherwise indicated (such as for substituted hydrocarbyl, etc.), a substituted group refers to a group in which at least one atom is replaced by a different atom or a group. Thus, a substituted alkyl group is an alkyl group in which at least one hydrogen atom is replaced by a hydrocarbyl group, a halogen, any other non-hydrogen group, and/or at least one carbon atom and hydrogen atoms bonded thereto is replaced by a different group. As a non-limiting example, a substituted group is a radical in which at least one hydrogen atom has been substituted with a heteroatom or heteroatom containing group, such as with at least one functional group, such as halogen (Cl, Br, I, F), $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like or where at least one heteroatom has been inserted within the hydrocarbyl radical, such as halogen (Cl, Br, I, F), O, S, Se, Te, $NR^*$, $PR^*$, $AsR^*$, $SbR^*$, $BR^*$, $SiR^*_2$, $GeR^*_2$, $SnR^*_2$, $PbR^*_2$, and the like, where $R^*$ is, independently, hydrogen or a hydrocarbyl.

For the purposes of this present disclosure, and unless otherwise specified, the terms "hydrocarbyl radical," "hydrocarbyl group," or "hydrocarbyl" interchangeably refer to a group consisting of hydrogen and carbon atoms only. A hydrocarbyl group can be saturated or unsaturated, linear or branched, cyclic or acyclic, aromatic, or non-aromatic.

For the purposes of this present disclosure, and unless otherwise specified, substituted hydrocarbyl radicals are radicals in which at least one hydrogen atom has been substituted with a heteroatom or heteroatom containing group, such as with at least one functional group, such as halogen (Cl, Br, I, F), $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like or where at least one heteroatom has been inserted within the hydrocarbyl radical, such as halogen (Cl, Br, I, F), O, S, Se, Te, $NR^*$, $PR^*$, $AsR^*$, $SbR^*$, $BR^*$, $SiR^*_2$, $GeR^*_2$, $SnR^*_2$, $PbR^*_2$, and the like, where $R^*$ is, independently, hydrogen or a hydrocarbyl.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this present disclosure, when a radical is listed, it indicates that radical type and all other radicals formed when that radical type is subjected to the substitutions defined above. Alkyl, alkenyl, and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

Silyl groups (also referred to as silyl, silyl radicals, and silyl substituents) are defined as $SiR^*_3$ where $R^*$ is independently a hydrogen, hydrocarbyl or halocarbyl radical, and two or more $R^*$ may join together to form a substituted or unsubstituted saturated, partially unsaturated or aromatic cyclic or polycyclic ring structure. Silyl groups are bonded via a silicon atom.

For the purposes of this present disclosure, and unless otherwise specified, silylcarbyl radicals (also referred to as silylcarbyls, silylcarbyl groups or silylcarbyl substituents) are radicals in which one or more hydrocarbyl hydrogen atoms have been substituted with at least one $SiR^*_3$ containing group or where at least one $-Si(R^*)_2-$ has been inserted within the hydrocarbyl radical where $R^*$ is independently a hydrocarbyl or halocarbyl radical, and two or more $R^*$ may join together to form a substituted or unsubstituted saturated, partially unsaturated or aromatic cyclic or polycyclic ring structure. Silylcarbyl radicals can be bonded via a silicon atom or a carbon atom.

For the purposes of this present disclosure, and unless otherwise specified, substituted silylcarbyl radicals are silylcarbyl radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $GeR^*_3$, $SnR^*_3$, $PbR_3$ and the like or where at least one non-hydrocarbon atom or group has been inserted within the silylcarbyl radical, such as $-O-$, $-S-$, $-Se-$, $-Te-$, $-N(R^*)-$, $=N-$, $-P(R^*)-$, $=P-$, $-As(R^*)-$, $=As-$, $-Sb(R^*)-$, $=Sb-$, $-B(R^*)-$, $=B-$, $-Ge(R^*)_2-$, $-Sn(R^*)_2-$, $-Pb(R^*)_2-$ and the like, where $R^*$ is independently a hydrocarbyl or halocarbyl radical, and two or more $R^*$ may join together to form a substituted or unsubstituted saturated, partially unsaturated or aromatic cyclic or polycyclic ring structure.

For the purposes of this present disclosure, and unless otherwise specified, halocarbyl radicals are radicals in which one or more hydrocarbyl hydrogen atoms have been substituted with at least one halogen (e.g., F, Cl, Br, I) or halogen-containing group (e.g., $CF_3$).

For the purposes of this present disclosure, and unless otherwise specified, substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

For the purposes of this present disclosure, and unless otherwise specified, germanyl radicals (also referred to as germanyls, germanyl groups or germanyl substituents) are radicals in which one or more hydrocarbyl hydrogen atoms have been substituted with at least one $GeR^*_3$ containing group or where at least one —Ge(R*)$_2$— has been inserted within the hydrocarbyl radical where R* is independently a hydrocarbyl or halocarbyl radical, and two or more R* may join together to form a substituted or unsubstituted saturated, partially unsaturated or aromatic cyclic or polycyclic ring structure. Germanyl radicals can be bonded via a silicon atom or a carbon atom.

For the purposes of this present disclosure, and unless otherwise specified, substituted germanyl radicals are germanyl radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $SnR^*_3$, $PbR_3$ and the like or where at least one non-hydrocarbon atom or group has been inserted within the germanyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

As used herein, aromatic refers to cyclic compounds, ligands or substituents ("ring") that contain cyclic clouds of delocalized pi electrons above and below the plane of the "ring", and the pi clouds must contain a total of 4n+2 pi electrons wherein n is an integer. As used herein, the term "aromatic" also refers to pseudoaromatic heterocycles which are heterocyclic substituents that have similar properties and structures (nearly planar) to aromatic heterocyclic ligands, but are not by definition aromatic.

The term "substituted phenyl," or "substituted phenyl group" means a phenyl group having one or more hydrogen groups replaced by a hydrocarbyl, substituted hydrocarbyl, heteroatom or heteroatom containing group, such as halogen (such as Br, Cl, F or I) or at least one functional group such as —$NR^*_2$, —$OR^*$, —$SeR^*$, —$TeR^*$, —$PR^*_2$, —$AsR^*_2$, —$SbR^*_2$, —$SR^*$, —$BR^*_2$, —$SiR^*$, —$SiR^*_3$, —$GeR^*$, —$GeR^*_3$, —$SnR^*$, —$SnR^*_3$, —$PbR^*_3$, and the like, where each R* is independently a hydrocarbyl, halogen, or halocarbyl radical. Preferably the "substituted phenyl" group is represented by the formula:

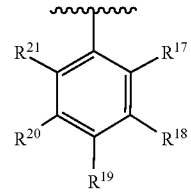

where each of $R^{17}$, $R^{18}$, $R^{19}$, $R^{20}$, and $R^{21}$ is independently selected from hydrogen, $C_1$-$C_{40}$ hydrocarbyl or $C_1$-$C_{40}$ substituted hydrocarbyl, a heteroatom, such as halogen, or a heteroatom-containing group (provided that at least one of $R^{17}$, $R^{18}$, $R^{19}$, $R^{20}$, and $R^{21}$ is not H), or a combination thereof.

A "fluorophenyl" or "fluorophenyl group" is a phenyl group substituted with one, two, three, four or five fluorine atoms.

The term "arylalkyl" means an aryl group where a hydrogen has been replaced with an alkyl or substituted alkyl group. For example, 3,5'-di-tert-butyl-phenyl indenyl is an indene substituted with an arylalkyl group. When an arylalkyl group is a substituent on another group, it is bound to that group via the aryl.

The term "alkylaryl" means an alkyl group where a hydrogen has been replaced with an aryl or substituted aryl group. For example, phenethyl indenyl is an indene substituted with an ethyl group bound to a benzene group. When an alkylaryl group is a substituent on another group, it is bound to that group via the alkyl.

Reference to an alkyl, alkenyl, alkoxide, or aryl group without specifying a particular isomer (e.g., butyl) expressly discloses all isomers (e.g., n-butyl, iso-butyl, sec-butyl, and tert-butyl), unless otherwise indicated.

The term "ring atom" means an atom that is part of a cyclic ring structure. Accordingly, a benzyl group has six ring atoms and tetrahydrofuran has 5 ring atoms.

For the purposes of this present disclosure, and unless otherwise specified, the term "$C_n$" group or compound refers to a group or a compound comprising carbon atoms at total number thereof of n. Thus, a "$C_m$-$C_n$" group or compound refers to a group or compound comprising carbon atoms at a total number thereof in the range from m to n. Thus, a $C_1$-$C_{50}$ alkyl group refers to an alkyl group comprising carbon atoms at a total number thereof in the range from 1 to 50.

For the purposes of this present disclosure, and unless otherwise specified, the term "olefin," alternatively termed "alkene," refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched, or cyclic. For purposes of this specification and the claims appended thereto, when a polymer or copolymer is referred to as comprising an olefin, including, but not limited to ethylene, propylene, and butene, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Thus, an "olefin" is intended to embrace all structural isomeric forms of olefins, unless it is specified to mean a single isomer or the context clearly indicates otherwise. An oligomer is a polymer having a low molecular weight, such as an Mn of 21,000 g/mol or less (such as 10,000 g/mol or less), and/or a low number of mer units, such as 100 mer units or less (such as 75 mer units or less). Preferred PAO's herein are oligomers having 10 mer units or less, such as 5 mer units or less, such as 3 mer units or 2 mer units and have an Mn of 21,000 g/mol or less (such as 10,000 g/mol or less, such as 7,500 g/mol or less, such as 5,000 g/mol or less, such as 3,000 g/mol or less, such as 2,000 g/mol or less, such as 1500 g/mol or less, such as 1000, or less, such as 750 or less, such as 500 or less, such as from 100 to 21,000 g/mol, or 150 to 5000 g/mol.).

For the purposes of this present disclosure, and unless otherwise specified, the term "alpha-olefin" refers to an olefin having a terminal carbon-to-carbon double bond in the structure thereof ((R'R'')—C=$CH_2$, where R' and R'' is independently hydrogen or any hydrocarbyl group; such as R' is hydrogen and R'' is an alkyl group). A "linear alpha-olefin" is an alpha-olefin defined in this paragraph wherein R' is hydrogen, and R'' is hydrogen or a linear alkyl group. Typically the alpha olefin is represented by the formula: $R^1$HC=$CH_2$, where R' is independently hydrogen or any hydrocarbyl group. Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

Cyclic olefins contain a carbon-to-carbon double bond within a ring structure. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, norbornadiene, dicyclopentadiene, 5-ethylidene-2-norbornene, vinylcyclohexene, and 5-vinyl-2-norbornene.

The term "vinyl" refers to an olefin having the following formula:

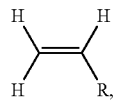

wherein R is a hydrocarbyl group, such as a saturated hydrocarbyl group, such as an alkyl group.

The term "vinylidene" refers to an olefin having the following formula:

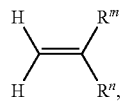

wherein $R'''$ and $R''$ are each independently a hydrocarbyl group, such as a saturated hydrocarbyl group, such as alkyl group. Vinylidenes are 1,1-di-substituted vinylene groups.

The term "vinylidene dimer" refers to PAO dimer having a vinylidene group having the following formula:

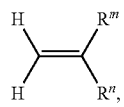

wherein $R'''$ and $R''$ are each independently a hydrocarbyl group, such as a saturated hydrocarbyl group, such as alkyl group.

The term "di-substituted vinylene" refers to:

(i) an olefin having the following formula:

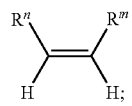

or (ii) an olefin having the following formula:

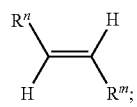

or (iii) a mixture of (i) and (ii) at any proportion thereof, wherein $R'''$ and $R''$, the same or different at each occurrence, are each independently a hydrocarbyl group, such as saturated hydrocarbyl group such as alkyl group. Di-substituted vinylenes represent only 1,2-di-substituted vinylene groups and do not include vinylidenes, or 1,1-di-substituted vinylenes. The term "vinylene," as used herein, is an alternative term for "di-substituted vinylene" only and not as a generic class of multiple vinylene species.

The term "tri-substituted vinylene" means an olefin having the following formula:

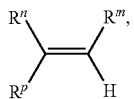

wherein $R^m$, $R^n$, and $R^p$ are each independently a hydrocarbyl group, such as a saturated hydrocarbyl group, such as alkyl group, or alternatively $R^m$ and $R^n$ can together form a non-aryl ring structure with $R^p$ being a pendant hydrocarbyl group.

As used herein, "poly alpha-olefin(s)" (PAO(s)) are polymers of one or more alpha-olefin monomers, particularly an oligomer of one or more alpha-olefins. PAOs are polymeric, typically oligomeric, molecules produced from the polymerization/oligomerization reactions of alpha-olefin monomer molecules in the presence of a catalyst system, optionally further partially or fully hydrogenated to remove residual carbon-carbon double bonds therein or optionally further functionalized by reaction with some or all of the residual carbon-carbon bonds therein. Thus, the PAO can be a dimer (resulting from two terminal olefin molecules), a trimer (resulting from three terminal olefin molecules), a tetramer (resulting from four terminal olefin molecules), or any other oligomer or polymer comprising two or more structure units derived from one or more terminal olefin monomer(s). The PAO molecule can be highly stereo-regular, such that the bulk material may exhibit an isotacticity, or a syndiotacticity when measured by $^{13}C$ NMR. The PAO molecule can be highly stereo-irregular, such that the bulk material can be substantially atactic when measured by $^{13}C$ NMR. Typically, tacticity is only relevant for higher viscosity (higher molecular weight) PAO molecules wherein at least triad distributions can be measured by $^{13}C$ NMR. The PAOs formed in the present disclosure typically have a kinematic viscosity (at 100° C.) of 3,000 cSt or less as determined by ASTM D445, or have an Mn of 20,000 g/mol or less as determined by GC (as described herein), or have a combination thereof.

The PAO molecule can be highly regio-regular, such that the bulk material may exhibit an isotacticity, or a syndiotacticity when measured by $^{13}C$ NMR. The PAO molecule can be highly regio-irregular, such that the bulk material can be substantially atactic when measured by $^{13}C$ NMR. A PAO material made by using a metallocene-based catalyst system is typically referred to as a metallocene-PAO (mPAO), and a PAO material made by using traditional non-metallocene-based catalysts (e.g., Lewis acids, supported chromium oxide, and the like) is typically called a conventional PAO (cPAO).

For the purposes of this present disclosure, and unless otherwise specified, the term "carbon backbone" refers to the longest straight carbon chain in the molecule of the compound or the group in question. "Branches" or "pendant groups" interchangeably refer to any non-hydrogen group connected to the carbon backbone other than those attached to the carbon atoms at the very ends of the carbon backbone. As used herein, the term "length" of a pendant group is defined as the total number of carbon atoms in the longest carbon chain in the pendant group, counting from the first carbon atom attached to the carbon backbone and ending with the final carbon atom therein, without taking into consideration any substituents or pendant groups on the chain. In some embodiments, the pendant group is free of substituents comprising more than 2 carbon atoms (or more than 1 carbon atom), or is free of any substituent. A pendant group may contain a cyclic group or a portion thereof in the longest carbon chain, in which case half of the carbon atoms in the cyclic group are counted toward the length of the pendant group. Thus, by way of examples, a linear $C_8$ pendant group has a length of 8; each of the pendant groups PG-1 (cyclohexylmethylene) and PG-2 (phenylmethylene) has a length of 4; and each of the pendant groups PG-3 (o-heptyl-phenylmethylene) and PG-4 (p-heptylphenylmethylene) has a length of 11. Where a PAO molecule contains multiple pendant groups, the arithmetic average of the lengths of all such pendant groups is calculated as the average length of all pendant groups in the PAO molecule.

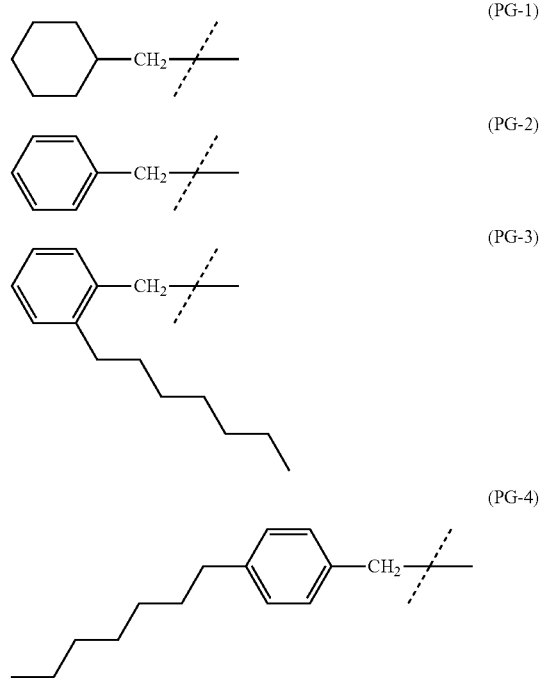

For nomenclature purposes, the following numbering schemes are used for cyclopentadienyl, indenyl, tetrahydro-s-indacenyl, tetrahydro-as-indacenyl, benz[f]indenyl, benz[e]indenyl ligands.

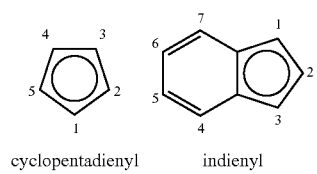

cyclopentadienyl    indenyl

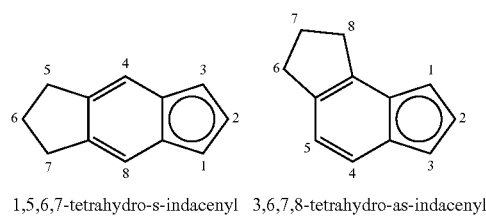

1,5,6,7-tetrahydro-s-indacenyl  3,6,7,8-tetrahydro-as-indacenyl

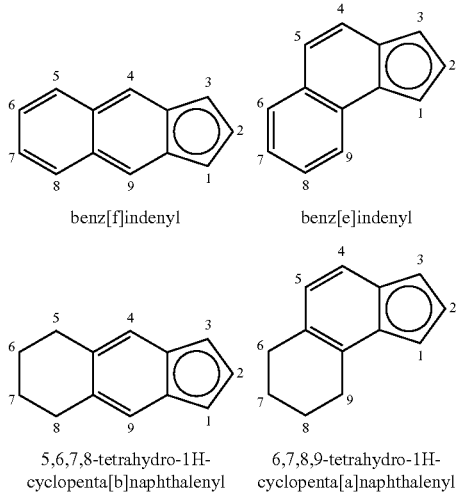

benz[f]indenyl  benz[e]indenyl 5,6,7,8-tetrahydro-1H-cyclopenta[b]naphthalenyl  6,7,8,9-tetrahydro-1H-cyclopenta[a]naphthalenyl In the present disclosure, any metallocene compound may have one or more optical isomers. All metallocene compounds identified herein by name or structure shall include all possible optical isomers thereof and mixtures of any such optical isomers. For example, metallocene compound Me$_2$Si(Me$_4$Cp)(3-PrInd)ZrMe$_2$ shall include the following two optical isomers and mixtures thereof, even if only one structure is given when it is described:

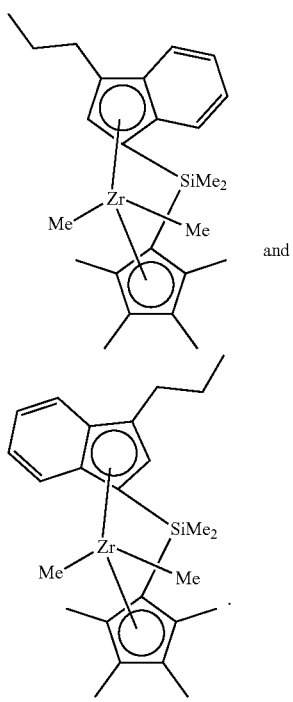

and

A "metallocene" catalyst compound is a transition metal catalyst compound having one, two or three, typically one or two, substituted or unsubstituted cyclopentadienyl ligands bound to the transition metal, typically a metallocene catalyst is an organometallic compound containing at least one η-bound cyclopentadienyl moiety (or substituted cyclopentadienyl moiety). Substituted or unsubstituted cyclopentadienyl ligands include substituted or unsubstituted indenyl, fluorenyl, tetrahydro-s-indacenyl, tetrahydro-as-indacenyl, benz[f]indenyl, benz[e]indenyl, tetrahydrocyclopenta[b]naphthalene, tetrahydrocyclopenta[a]naphthalene, and the like.

An unsymmetrical metallocene compound is a metallocene compound having two π-bound cyclopentadienyl moieties that differ by ring type such as by having one monocyclic arenyl ligand and one polycyclic arenyl ligand. For example, (cyclopentadienyl)(indenyl)zirconium dichloride would be considered unsymmetrical because is has one monocyclic arenyl ligand and one polycyclic arenyl ligand, while bis(indenyl)zirconium dichloride would be considered symmetrical since it has two polycyclic arenyl ligands.

As used herein, the term "monocyclic arenyl ligand" is used herein to mean a substituted or unsubstituted monoanionic C$_5$ to C$_{100}$ hydrocarbyl ligand that contains an aromatic five-membered single hydrocarbyl ring structure (also referred to as a cyclopentadienyl ring).

As used herein, the term "polycyclic arenyl ligand" is used herein to mean a substituted or unsubstituted monoanionic C$_8$ to C$_{103}$ hydrocarbyl ligand that contains an aromatic five-membered hydrocarbyl ring (also referred to as a cyclopentadienyl ring) that is fused to a partially unsaturated, or aromatic hydrocarbyl ring structures which may be fused to additional saturated, partially unsaturated, or aromatic hydrocarbyl rings.

Monocyclic arenyl ligands include substituted or unsubstituted cyclopentadienyls. Polycyclic arenyl ligands include substituted or unsubstituted, partially unsaturated or aromatic indenyls, fluorenyls, benz[f]indenyl, benz[e]indenyl, 5,6,7,8-tetrahydro-1H-cyclopenta[b]naphthalenyl, 6,7,8,9-tetrahydro-1H-cyclopenta[a]naphthalenyls, 1,5,6,7-tetrahydro-s-indacenyl, 3,6,7,8-tetrahydro-as-indacenyl and the like.

Non-limiting examples of polycyclic arene ligands, named also as monoanionic ligands, include indenyl, 4,5-dihydroindenyl, 4,7-dihydroindenyl, 4,5,6,7-tetrahydroindenyl, benz[f]indenyl, benz[e]indenyl, 5,6,7,8-tetrahydro-1H-cyclopenta[b]naphthalenyl, 6,7,8,9-tetrahydro-1H-cyclopenta[a]naphthalenyls, 1,5,6,7-tetrahydro-s-indacenyl, 3,6,7,8-tetrahydro-as-indacenyl, 5,6-trimethyleneindenyl, 4,5-trimethyleneindenyl, 5,6-pentamethyleneindenyl, 4,5-pentamethyleneindenyl, 5,6-hexamethyleneindenyl, 4,5-hexamethyleneindenyl, 5,6-heptamethyleneindenyl, 4,5-heptamethyleneindenyl, 5,6-octamethyleneindenyl, 4,5-octamethyleneindenyl, 5,6-nonamethyleneindenyl, 4,5-nonamethyleneindenyl, 5,6-decamethyleneindenyl, 4,5-decamethyleneindenyl, 5,6-undecamethyleneindenyl, 4,5-undecamethyleneindenyl, 5,6-dodecamethyleneindenyl, 4,5-dodecamethyleneindenyl, 5,6-tridecamethyleneindenyl, 4,5-tridecamethyleneindenyl, 5,6-tetradecamethyleneindenyl, 4,5-tetradecamethyleneindenyl, 5,6-pentadecamethyleneindenyl, 4,5-pentadecamethyleneindenyl, 5,6-hexadecamethyleneindenyl, 4,5-hexadecamethyleneindenyl, 5,6-heptadecamethyleneindenyl, 4,5-heptadecamethyleneindenyl, 5,6-octadecamethyleneindenyl, 4,5-octadecamethyleneindenyl, 5,6-nonadecamethyleneindenyl, 4,5-nonadecamethyleneindenyl, 5,6-eicosamethyleneindenyl, 4,5-eicosamethyleneindenyl, (6Z,8Z,10Z)-cycloocta[e]indenyl, (5Z,7Z,9Z)-cycloocta[f]indenyl, (5E,7Z,9E,11Z,13E)-cyclododeca[f]indenyl, (6E,8Z,10E,12Z,14E)-cyclododeca[e]indenyl.

Partially hydrogenated polycyclic arene ligands retain the numbering scheme of the parent polycyclic arene ligand, namely the numbering schemes defined for indenyl, benz[f]indenyl, benz[e]indenyl, 5,6,7,8-tetrahydro-1H-cyclopenta

[b]naphthalenyl, 6,7,8,9-tetrahydro-1H-cyclopenta[a]naphthalenyls, 1,5,6,7-tetrahydro-s-indacenyl, 3,6,7,8-tetrahydro-as-indacenyl.

For the purposes of this present disclosure, and unless otherwise specified, the term "substantially all" with respect to PAO molecules means at least 90 mol % (such as at least 95 mol %, at least 98 mol %, at least 99 mol %, or even 100 mol %).

Unless specified otherwise, the term "substantially free of" with respect to a particular component means the concentration of that component in the relevant composition is no greater than 10 mol % (such as no greater than 5 mol %, no greater than 3 mol %, no greater than 1 mol %, or about 0%, within the bounds of the relevant measurement method), based on the total quantity of the relevant composition. Preferably "substantially free of" means no greater than 10 mol % (such as no greater than 5 mol %, no greater than 3 mol %, no greater than 1 mol %, or about 0%, based on the total quantity of the relevant composition.

For the purposes of this present disclosure, and unless otherwise specified, a "reactor" refers to one or more vessels configured to perform oligomerization processes.

The terms "catalyst" and "catalyst compound" are defined to mean a compound capable of initiating catalysis and/or of facilitating a chemical reaction. In the description herein, the catalyst may be described as a catalyst precursor, a pre-catalyst compound, or a transition metal compound, and these terms are used interchangeably. When the catalyst compound is combined with an activator to initiate catalysis, the catalyst compound is often referred to as a pre-catalyst or catalyst precursor. A "catalyst system" is combination of at least one catalyst compound, at least one activator, and optional co-activator, where the system can polymerize monomers to form polymer (such as the oligomers escribed herein).

For the purposes of this present disclosure, and unless otherwise specified, a "metallocene" catalyst compound is a transition metal catalyst compound having one, two or three, typically one or two, substituted or unsubstituted cyclopentadienyl ligands bound to the transition metal, typically a metallocene catalyst is an organometallic compound containing at least one T-bound cyclopentadienyl moiety (or substituted cyclopentadienyl moiety). Substituted or unsubstituted cyclopentadienyl ligands include substituted or unsubstituted indenyl, fluroenyl, indacenyl, benzindenyl, and the like.

For the purposes of this present disclosure, and unless otherwise specified, the terms "catalyst" and "catalyst compound" are defined to mean a compound capable of initiating catalysis and/or of facilitating a chemical reaction with little or no poisoning/consumption. In the description herein, the catalyst may be described as a catalyst precursor, a pre-catalyst compound, or a transition metal compound, and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor.

A "catalyst system" is a combination of at least one catalyst compound, at least one activator, and optional co-activator, where the system can polymerize/oligomerize monomers to form polymer/oligomer.

For the purposes of this present disclosure, and unless otherwise specified, a scavenger is a compound typically added to facilitate oligomerization/polymerization by scavenging impurities. Some scavengers may also act as activators and may be referred to as co-activators. A co-activator, that is not a scavenger, may be used in conjunction with an activator in order to form an active catalyst. In some embodiments, a co-activator can be pre-mixed with the catalyst compound to form an alkylated catalyst compound.

A scavenger is a compound typically added to facilitate oligomerization/polymerization by scavenging impurities. Some scavengers may also act as activators and may be referred to as co-activators. A co-activator, that is not a scavenger, may be used in conjunction with an activator in order to form an active catalyst. In some embodiments, a co-activator can be pre-mixed with the catalyst compound to form an alkylated catalyst compound.

As used herein, a "lubricant" refers to a substance that can be introduced between two or more moving surfaces and lower the level of friction between two adjacent surfaces moving relative to each other. A lubricant "base stock" is a material, typically a fluid at the operating temperature of the lubricant, used to formulate a lubricant by admixing it with other components. Non-limiting examples of base stocks suitable in lubricants include API Group I, Group II, Group III, Group IV, Group V and Group VI base stocks. Fluids derived from Fischer-Tropsch process or Gas-to-Liquid ("GTL") processes are examples of synthetic base stocks useful for making modem lubricants. GTL base stocks and processes for making them can be found, e.g., in PCT Publication No. WO 2005/121280 and in U.S. Pat. Nos. 7,344,631; 6,846,778; 7,241,375; and 7,053,254.

For the purposes of this present disclosure, and unless otherwise specified, all kinematic viscosity values in the present disclosure are as determined according to ASTM D445. Kinematic viscosity at 100° C. is reported herein as KV100, and kinematic viscosity at 40° C. is reported herein as KV40. Unit of all KV100 and KV40 values herein is cSt, unless otherwise specified.

For the purposes of this present disclosure, and unless otherwise specified, all viscosity index (VI) values in the present disclosure are as determined according to ASTM D2270.

For the purposes of this present disclosure, and unless otherwise specified, all Noack volatility (NV) values in the present disclosure are as determined according to ASTM D5800 and units of all NV values are wt %.

For the purposes of this present disclosure, and unless otherwise specified, bromine number values in the present disclosure are determined according to ASTM D 1159.

For the purposes of this present disclosure, and unless otherwise specified, rotating pressure vessel oxidation test (RPVOT) values in the present disclosure are determined according to ASTM D2272.

For the purposes of this present disclosure, and unless otherwise specified, all numerical values within the detailed description and the claims herein are modified by "about" or "approximately" the indicated value, and consider experimental error and variations that would be expected by a person having ordinary skill in the art.

For the purposes of this present disclosure, and unless otherwise specified, all percentages of pendant groups, terminal carbon chains, and side chain groups are by mole, unless specified otherwise. Percent by mole is expressed as "mol %," and percent by weight is expressed as "wt %."

For the purposes of this present disclosure, and unless otherwise specified, all molecular weight data are in the unit of g·mol$^{-1}$.

Unless otherwise indicated, proton NMR ($^1$H-NMR) analysis is used to determine the number average molecular weight (Mn) of the polymer materials (including functionalized, hydrogenated, and unhydrogenated PAO materials) prepared herein. In addition, $^1$H-NMR analysis of the unsaturated PAO product can give a quantitative breakdown of the olefinic structure types (viz. vinyl, di-substituted vinylene, tri-substituted vinylene, and vinylidene in mol %). In the present invention, compositions of mixtures of olefins comprising terminal olefins (vinyls and vinylidenes) and internal olefins (di-substituted vinylenes and tri-substituted vinylenes) are determined by using $^1$H-NMR as described in the experimental section. All unsaturations are reported in Mol %.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) are g/mol (g·mol$^{-1}$).

The following abbreviations may be used through this specification: Cp is cyclopentadiene or cyclopentadienyl; Ind is indene or indenyl, Flu is fluorene or fluorenyl, Me is methyl, Et is ethyl, Pr is propyl, iPr is isopropyl, n-Pr is normal propyl, cPr is cyclopropyl, Bu is butyl, nBu is normal butyl, iBu is isobutyl, sBu is sec-butyl, tBu is tertiary butyl, MeCy is methylcyclohexane, and Cy is cyclohexyl, Ph is phenyl, p-tBu is para-tertiary butyl, p-Me is para-methyl, o-biphenyl is an ortho-biphenyl moiety represented by the structure

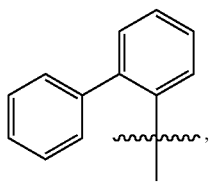 [SMILES: *c1ccccc1-c1ccccc1]

Cbz is Carbazole, Cy is cyclohexyl Oct is octyl, Ar* is 2,6-diisopropylphenyl, Bz or Bn are interchangeably benzyl (i.e., CH$_2$Ph), TMS is trimethylsilyl, TIBAL or TiBAl is triisobutylaluminum, TNOAL or TNOA or TnOAl is tri-n-octylaluminum, MAO is methylalumoxane, THF or thf is tetrahydrofuran, tol or Tol is toluene, dme is 1,2-dimethoxyethane, EtOAc is ethyl acetate, and RT is room temperature (and is 23° C. unless otherwise indicated).

The term "continuous" means a system that operates without interruption or cessation for a period of time, such as where reactants are continually fed into a reaction zone and products are continually or regularly withdrawn without stopping the reaction in the reaction zone. For example, a continuous process to produce a polymer would be one where the reactants are continually introduced into one or more reactors and polymer product is continually withdrawn.

A "solution polymerization" means a polymerization process in which the polymerization is conducted in a liquid polymerization medium, such as an inert solvent or monomer(s) or their blends. A solution polymerization is typically homogeneous. A homogeneous polymerization is one where the polymer product is dissolved in the polymerization medium. Such systems are typically not turbid as described in Oliveira, J. V. et al. (2000) "High-Pressure Phase Equilibria for Polypropylene-Hydrocarbon Systems," *Ind. Eng. Chem. Res.*, v. 39(12), pp. 4627-4633.

A bulk polymerization means a polymerization process in which the monomers and/or comonomers being polymerized are used as a solvent or diluent using little or no inert solvent or diluent. A small fraction of inert solvent might be used as a carrier for catalyst and scavenger. A bulk polymerization system contains less than about 25 wt % of inert solvent or diluent, such as less than about 10 wt %, such as less than about 1 wt %, such as 0 wt %.

DESCRIPTION

I. PAO Dimer Selective Process Using Metallocene Catalyst Compounds

The present disclosure includes catalyst compounds that can dimerize alpha-olefins, e.g., linear alpha-olefins, in the presence of metallocene catalysts to produce PAO dimers with high selectivity and high yields, with very low amounts of trimers, tetramers, and higher oligomers (if any), where the higher oligomers are oligomers that have degree of polymerization of 5 or more. As used herein, "degree of polymerization" refers to the number of monomeric units of an oligomer. For example, an oligomer having a degree of polymerization of 3 is an oligomer that is the reaction product of 3 monomers. A "dimer" has a degree of polymerization of 2, and a "trimer" has a degree of polymerization of 3.

In addition, the catalyst compounds can produce, based on the amount of PAO dimers produced, very low di-substituted and tri-substituted vinylene content (e.g., about 0 mol %), very low tri-substituted unsaturation (e.g., about 5 mol % or lower), and very high vinylidene content (e.g., about 95 mol % or higher). The metallocene catalysts, catalyst systems incorporating such, and processes using such, can produce this distribution of dimers with high catalyst efficiency, high product yield, good kinetics as compared to conventional catalysts for dimerizing alpha-olefins.

The dimer selective reaction using metallocene compound(s) is referred to interchangeably as "first oligomerization" or "first oligomerization process."

In some embodiments, the metallocene compound useful in the first oligomerization process for making PAOs can have a structure represented by formula (I):

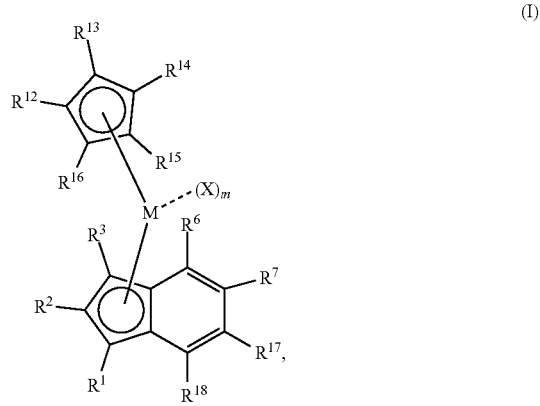

wherein:
each $R^1$, $R^2$, and $R^3$ is, independently, hydrogen or a substituted or unsubstituted linear, branched, or cyclic $C_1$-$C_{20}$ hydrocarbyl group, preferably wherein at least one of $R^1$, $R^2$, and $R^3$ is not hydrogen and at least one of $R^1$, $R^2$, and $R^3$ is hydrogen;

$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$, and $R^{15}$, are each independently a substituted or unsubstituted linear, branched, or cyclic $C_1$-$C_{20}$ hydrocarbyl group;

$R^{16}$ is a substituted or unsubstituted linear, branched, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a transition metal, preferably group 3, 4 or 5, having an integer coordination number of v, such as 3, 4, or 5; and m is an integer equal to v-2, such as 1, 2, or 3.

In at least one metallocene compound formula herein, the metallocene compound useful in the first oligomerization process for making PAOs can have a structure represented by formula (III):

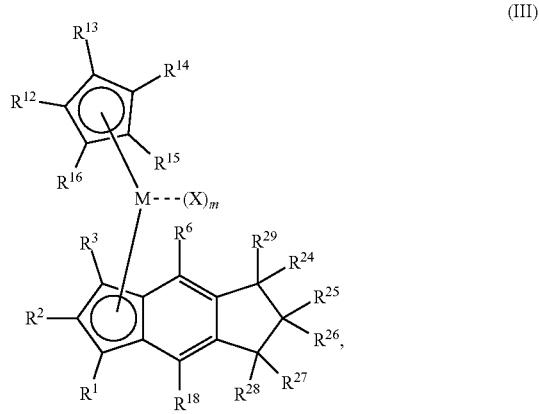

(III)

wherein one of $R^1$ and $R^3$ is a substituted or unsubstituted linear, branched, or cyclic $C_1$-$C_{20}$ hydrocarbyl group;

two of $R^1$, $R^2$, and $R^3$ are each hydrogen;

$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annelated to the cyclopentan-indenyl ring;

$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a group 3, 4, or 5 transition metal having an integer coordination number of v, such as 3, 4, or 5;

and m is an integer equal to v-2, such as 1, 2, or 3.

In at least one metallocene compound of formula I or III, $R^2$ is hydrogen, and $R^1$ and $R^3$ can be independently hydrogen or a substituted or unsubstituted linear, branched, or cyclic $C_1$-$C_6$ hydrocarbyl group (e.g., methyl, ethyl, and all isomers of propyl, butyl, pentyl, and hexyl, or a phenyl) provided that at least one $R^1$ or $R^3$ is not hydrogen.

In at least one metallocene compound of formula I or III, one of $R^1$ and $R^3$ can be a tertiary or quaternary beta branched ligand in which the alpha and beta atoms are a Group 14 atom, e.g., carbon, silicon, germanium, and two or more, such as three, substituted or unsubstituted linear, branched, or cyclic $C_1$-$C_{18}$, such as $C_1$-$C_8$, hydrocarbyl groups attached to the beta atom. Examples include neopentyl, beta trialkylsilyl-methyl, and beta-trialkylgermanyl-methyl moieties.

In at least one metallocene compound formula herein, examples of $C_1$-$C_{20}$ and/or $C_1$-$C_{30}$ substituted or unsubstituted linear, branched, or cyclic hydrocarbyl groups can include: methyl, ethyl, n-propyl, isopropyl, n-butyl, 1-methylpropyl, 1-ethylethyl, n-pentyl, neopentyl (2,2-methylpropyl), 1-methylpentyl, 1-ethylpropyl, 1-hexyl, 1-methylpentyl, 1-ethylbutyl, 1-propylpropyl, isomers thereof, and any ethylenically unsaturated group that can be derived from them by eliminating one available hydrogen group from each of two adjacent carbon atoms therein.

In at least one metallocene compound of formula I or III, M can comprise, can consist essentially of, or can be Ti, Zr, and/or Hf. In at least one embodiment, M can comprise, can consist essentially of, or can be Zr and/or Hf, such as Hf. In some embodiments, m can be an integer equal to 1, 2 or 3, such as 2.

In at least one metallocene compound of formula I or III, each X can be independently a halogen or a substituted or unsubstituted linear, branched, or cyclic $C_1$-$C_6$ hydrocarbyl group, e.g., a methyl, an ethyl, a propyl, a butyl, a phenyl, a benzyl, a chloride, a bromide, or an iodide, such as methyl.

In at least one metallocene compound of formula I or III, each X is a substituted or unsubstituted linear, branched, or cyclic $C_1$-$C_6$ hydrocarbyl group, e.g., a methyl, an ethyl, a propyl, a butyl, a phenyl, a benzyl, such as methyl.

In at least one metallocene compound of formula I or III, each X is not halogen.

In at least one metallocene compound of formula I or III, at least three of $R^{12}$, $R^{13}$, $R^{14}$, $R^{15}$, and $R^{16}$ are not hydrogen. In some embodiments, at least four of $R^{12}$, $R^{13}$, $R^{14}$, $R^{15}$, and $R^{16}$ are each independently a substituted or unsubstituted linear, branched, or cyclic $C_1$-$C_8$ hydrocarbyl group, such as methyl or ethyl.

In at least one metallocene compound of formula I, i) at least four of $R^{12}$, $R^{13}$, $R^{14}$, $R^{15}$, and $R^{16}$ are each independently a substituted or unsubstituted linear, branched, or cyclic $C_1$-$C_8$ hydrocarbyl group, such as methyl or ethyl; ii) $R^2$ is hydrogen, and $R^1$ and $R^3$ can be independently hydrogen or a substituted or unsubstituted linear, branched, or cyclic $C_1$-$C_6$ hydrocarbyl group (e.g., methyl, ethyl, and all isomers of propyl, butyl, pentyl, and hexyl, or a phenyl) provided that at least one $R^1$ or $R^3$ is not hydrogen; iii) two or more of $R^6$, $R^7$, $R^{17}$, and $R^{18}$ form a fused ring or ring system; iv) at least two of $R^6$, $R^7$, $R^{17}$, and $R^{18}$ are hydrogen; v) each X is independently a halogen or a substituted or unsubstituted linear, branched, or cyclic $C_1$-$C_6$ hydrocarbyl group; vi) M comprises Zr or Hf; or a combination thereof.

In at least one metallocene compound of formula III, i) at least four of $R^{12}$, $R^{13}$, $R^{14}$, $R^{15}$, and $R^{16}$ are each independently a substituted or unsubstituted linear, branched, or cyclic $C_1$-$C_8$ hydrocarbyl group, such as methyl or ethyl; ii) $R^2$ is hydrogen, and $R^1$ and $R^3$ can be independently hydrogen or a substituted or unsubstituted linear, branched, or cyclic $C_1$-$C_6$ hydrocarbyl group (e.g., methyl, ethyl, and all isomers of propyl, butyl, pentyl, and hexyl, or a phenyl) provided that at least one $R^1$ or $R^3$ is not hydrogen; iii) $R^6$ and $R^{18}$ are hydrogen; iv) at least two or $R^{29}$, $R^{24}$, $R^{25}$, $R^{26}$, $R^{27}$ and $R^{28}$ are a substituted or unsubstituted linear, branched, or cyclic $C_1$-$C_{10}$ hydrocarbyl group v) each X is independently a halogen or a substituted or unsubstituted linear, branched, or cyclic $C_1$-$C_6$ hydrocarbyl group; vi) M comprises Zr or Hf; or a combination thereof.

In some embodiments, a catalyst compound useful for the first oligomerization process can include catalyst I.A, catalyst I.B, catalyst I.C, or a combination thereof:

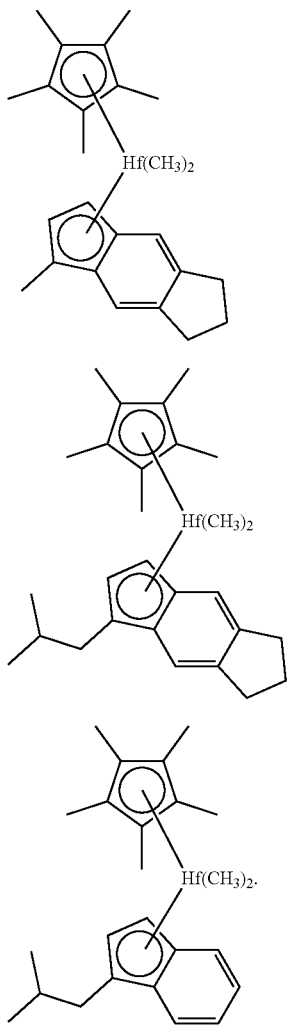

In some embodiments, a catalyst compound useful for the first oligomerization process can include those suitable oligomerization catalysts described herein.

In at least one embodiment, the catalyst compound can be part of a catalyst system, and such catalyst systems for the first oligomerization can include those suitable oligomerization catalysts described herein.

In at least one embodiment, a process to produce a poly alpha-olefin (PAO) includes introducing a $C_4$-$C_{32}$ alpha-olefin (e.g., a $C_6$-$C_{32}$ alpha-olefin) and a catalyst system comprising an activator and a metallocene compound into a reactor under reactor conditions and obtaining a product comprising PAO dimer, optional higher oligomers of alpha-olefin, or a combination thereof, the PAO dimer comprising 93 mol % or more of vinylidene based on total moles of vinylidene, di-substituted vinylene, and tri-substituted vinylene in the product, the metallocene compound is represented any metallocene formula described herein, such as formula (III).

In at least one embodiment, a first oligomerization process for making a poly alpha-olefin (e.g., a dimer of an alpha-olefin) can include introducing an alpha-olefin and a catalyst system into a reactor, e.g., a polymerization or oligomerization reactor, under reactor conditions to form a product comprising PAO dimer.

In at least one embodiment, the product produced from the first oligomerization process can include one or more PAO dimer, such as di-substituted vinylene, tri-substituted vinylene, vinylidene, or a combination thereof. In some embodiments, the product produced from the first oligomerization process can include PAO dimers (e.g., vinylidene, di-substituted vinylene, tri-substituted vinylene), trimer of alpha-olefins (PAO trimer), tetramer of alpha-olefins (PAO tetramer), higher oligomers of alpha-olefins (if any), vinyls, or a combination thereof.

In at least one embodiment, the first oligomerization process can have a selectivity towards vinylidenes at about 80 mol % or more, such as about 85 mol % or more, such as about 88 mol % or more, such as about 90 mol % or more, such as from about 91 mol % to about 100 mol %, such as from about 92 mol % to about 99 mol %, such as from about 93 mol % to about 98 mol %, such as about 94 mol % to about 99 mol %, about 95 mol % to about 99 mol %, about 96 mol % to about 99 mol %, or about 97 mol % to about 99 mol %, based on a total moles of a product produced.

In at least one embodiment, the first oligomerization process can have a selectivity towards products other than vinylidene (e.g., tri-substituted vinylene, di-substituted vinylene, vinyls, PAO trimer, PAO tetramer, higher oligomers, or a combination thereof) of about 20 mol % or less, such as about 15 mol % or less, such as about 12 mol % or less, such as about 10 mol % or less, such as from about 0 mol % to about 9 mol %, such as from about 1 mol % to about 8 mol %, such as from about 2 mol % to about 7 mol %, such as about 3 mol %, about 4 mol %, about 5 mol %, or about 6 mol %, based on the total moles of product produced.

In at least one embodiment, the first oligomerization process can have a selectivity towards a PAO trimer of about 20 wt % or less, such as about 15 wt % or less, such as about 12 wt % or less, such as about 10 wt % or less, such as from about 0 wt % to about 9 wt %, such as from about 1 wt % to about 8 wt %, such as from about 2 wt % to about 7 wt %, such as about 3 wt %, about 4 wt %, about 5 wt %, or about 6 wt %, based on the total moles of product produced.

In at least one embodiment, the first oligomerization process can have a selectivity towards a PAO tetramer and/or higher oligomers of alpha-olefins of about 20 wt % or less, such as about 15 wt % or less, such as about 12 wt % or less, such as about 10 wt % or less, such as from about 0 wt % to about 9 wt %, such as from about 1 wt % to about 8 wt %, such as from about 2 wt % to about 7 wt %, such as about 3 wt %, about 4 wt %, about 5 wt %, or about 6 wt %, based on the weight of product produced.

In at least one embodiment, the first oligomerization process can form an amount (in weight percent, wt %) of PAO dimer of about 40 wt % or more, such as from about 45 wt % to about 100 wt %, such as from about 50 wt % to about 99 wt %, such as from about 55 wt % to about 98 wt %, such as from about 60 wt % to about 95 wt %, such as from about 65 wt % to about 90 wt %, such as from about 70 wt % to about 85 wt %, such as from about 75 wt % to about 85 wt %, based on a total amount of product produced. In some embodiments, the first oligomerization process can form an amount of PAO dimer of about 80 wt % or more, such as about 81 wt % or more, about 82 wt % or more, about 83 wt % or more, about 84 wt % or more, about 85 wt % or more, about 86 wt % or more, about 87 wt % or more, about 88 wt % or more, about 89 wt % or more, about 90 wt % or more, about 91 wt % or more, about 92 wt % or more, about 93 wt % or more, about 94 wt % or more, about 95 wt % or more, about 96 wt % or more, about 97 wt % or more, about 98 wt % or more, about 99 wt % or more, or about 100 wt %, based on the total amount of product produced.

In at least one embodiment, the first oligomerization process can form an amount of PAO trimer, PAO tetramer, higher oligomers of alpha-olefin, or a combination thereof of about 60 wt % or less, such as from about 0 wt % to about 55 wt %, such as from about 1 wt % to about 50 wt %, such as from about 2 wt % to about 49 wt %, such as from about 5 wt % to about 40 wt %, such as from about 10 wt % to about 35 wt %, such as from about 15 wt % to about 30 wt %, such as from about 20 wt % to about 25 wt %, based on a total amount of product produced. In some embodiments, the first oligomerization process can form an amount of PAO trimer, PAO tetramer, higher oligomers of alpha-olefin, or a combination thereof of about 20 wt % or less, such as about 0 wt %, about 1 wt % or less, about 2 wt % or less, about 3 wt % or less, about 4 wt % or less, about 5 wt % or less, about 6 wt % or less, about 7 wt % or less, about 8 wt % or less, about 9 wt % or less, about 10 wt % or less, about 11 wt % or less, about 12 wt % or less, about 13 wt % or less, about 14 wt % or less, about 15 wt % or less, about 16 wt % or less, about 17 wt % or less, about 18 wt % or less, or about 19 wt % or less, based on the total amount of product produced.

In at least one embodiment, the first oligomerization process can form an amount of vinylidene, based on the total moles of PAO dimer produced, of about 50 mol % or more, such as from about 55 mol % to about 100 mol %, such as from about 60 mol % to about 99 mol %, such as from about 60 mol % to about 98 mol %, such as from about 65 mol % to about 97 mol %, such as from about 70 mol % to about 85 mol %, such as from about 75 mol % to about 80 mol %, such as from about 90 mol % to about 99 mol %, such as from about 93 mol % to about 97 mol % where PAO dimer includes vinylidenes, di-substituted vinylene, and tri-substituted vinylene. In some embodiments, the first oligomerization process can form an amount of vinylidene, based on the total moles of PAO dimer produced, of about 80 mol % or more, such as about 81 mol % or more, about 82 mol % or more, about 83 mol % or more, about 84 mol % or more, about 85 mol % or more, about 86 mol % or more, about 87 mol % or more, about 88 mol % or more, about 89 mol % or more, about 90 mol % or more, about 91 mol % or more, about 92 mol % or more, about 93 mol % or more, about 94 mol % or more, about 95 mol % or more, about 96 mol % or more, about 97 mol % or more, about 98 mol % or more, about 99 mol % or more, or about 100 mol %, where PAO dimer includes vinylidenes, di-substituted vinylene, and tri-substituted vinylene.

In at least one embodiment, the first oligomerization process can form an amount of di-substituted vinylene, tri-substituted vinylene, or a combination thereof, based on the total moles of PAO dimer produced, of about 50 mol % or less, such as about 0% to about 45%, such as from about 5% to about 40%, such as from about 10% to about 35%, such as from about 15% to about 30%, such as from about 20% to about 25%, where PAO dimer includes vinylidenes, di-substituted vinylene, and tri-substituted vinylene. In some embodiments, the first oligomerization process can form an amount of di-substituted vinylene, tri-substituted vinylene, or a combination thereof, based on the total moles of PAO dimer produced, of about 20 mol % or less, such as about 0 mol %, about 1 mol % or less, about 2 mol % or less, about 3 mol % or less, about 4 mol % or less, about 5 mol % or less, about 6 mol % or less, about 7 mol % or less, about 8 mol % or less, about 9 mol % or less, about 10 mol % or less, about 11 mol % or less, about 12 mol % or less, about 13 mol % or less, about 14 mol % or less, about 15 mol % or less, about 16 mol % or less, about 17 mol % or less, about 18 mol % or less, or about 19 mol % or less, based on the total moles of PAO dimer produced.

In at least one embodiment, the amount of PAO (e.g., dimer, trimer, tetramer, higher oligomers of an alpha olefin, or a combination thereof) produced per gram of catalyst (gPAO/gCat) in the first oligomerization process can be from about 1,000 gPAO/gCat to about to 150,000 gPAO/gCat, such as from about 5,000 gPAO/gCat to about 100,000 gPAO/gCat, such as from about 10,000 gPAO/gCat to about 100,000 gPAO/gCat, such as from about 30,000 gPAO/gCat to about 75,000 gPAO/gCat. In at least one embodiment, the amount of PAO (e.g., dimer, trimer, tetramer, higher oligomers of an alpha olefin, or a combination thereof) produced per gram of catalyst (gPAO/gCat) in the first oligomerization process can be from about 30,000 gPAO/gCat or more, such as from about 35,000 gPAO/gCat to about 80,000 gPAO/gCat, such as from about 40,000 gPAO/gCat to about 75,000 gPAO/gCat, such as from about 45,000 gPAO/gCat to about 70,000 gPAO/gCat, such as from about 50,000 gPAO/gCat to about 65,000 gPAO/gCat, such as from about 55,000 gPAO/gCat to about 60,000 gPAO/gCat.

In at least one embodiment, the amount of conversion in the first oligomerization of LAO to PAO dimer (e.g., vinylidenes, di-substituted vinylene, and tri-substituted vinylene, or a combination thereof), PAO trimer, higher oligomers of alpha-olefin, or a combination thereof can be greater than about 25%, such as greater than about 75%, such as greater than about 80%, such as greater than about 85%, such as greater than about 90%, such as greater than about 95%, such as greater than about 99%.

In at least one embodiment, the LAO can isomerize to branched and/or internal olefin during the first oligomerization. The amount of such isomerization can be less than about 5 wt %, such as less than about 3 wt %, such as less than about 2 wt %, such as less than about 1.9 wt %, such as less than about 1.5 wt %, such as less than about 1 wt %, such as less than about 0.9 wt %, such as less than about 0.5 wt %.

In some embodiments, the reactor conditions for the first oligomerization process can include a mol ratio of catalyst (e.g., metallocene compound) to activator, an amount of scavenger in the catalyst batch, an amount of scavenger in LAO, an amount of solvent, reactor temperature, reactor pressure, residence time, and catalyst amount.

In at least one embodiment, the reactor conditions for the first oligomerization process can include a mol ratio of catalyst to activator of from about 0.1:1 to 10:1, such as from about 0.5:1 to about 5:1, such as from about 0.75:1 to about 3:1, such as from about 1:1.2 to about 1:1, such as about 1:1.05, about 1:1.10, or about 1:1.15.

In at least one embodiment, the reactor conditions for the first oligomerization process can include an amount of scavenger in LAO of about 0 ppm or greater, such as about 4 ppm or greater, such as from about 1 ppm to about 1000 ppm, such as from about 5 ppm to about 500 ppm, such as from about 10 ppm to about 300, such as from about 50 ppm to about 200 ppm, such as from about 75 ppm to about 150 ppm. In at least one embodiment, the reactor conditions for the first oligomerization process can include an amount of scavenger in LAO of about 0 to about 1000 ppm, such as from 0 to about 500 ppm; such as from about 0.1 to about 500 ppm, such as from about 0.1 to about 100 ppm, such as from about 1 to about 20 ppm, such as less than 10 ppm.

In at least on embodiment, the amount of scavenger in the catalyst batch for the first oligomerization process can be about 0 wt % or more, such as from about 0.001 wt % to about 5 wt %, such as from about 0.01 wt % to about 2 wt %, such as from about 0.1 wt % to about 0.5 wt %.

In at least one embodiment, the reactor conditions for the first oligomerization process can include a reactor temperature of from about 0° C. to about 300° C., such as from about 10° C. to about 230° C., such as from about 25° C. to about 200° C., such as from about 100° C. to about 160° C., such as from about 110° C. to about 155° C., such as from about 130° C. to about 148° C., such as from about 135° C. to about 145° C. In some embodiments, the reactor conditions for the first oligomerization process can include a reactor temperature of about 110° C., of about 130° C., about 131° C., about 132° C., about 133° C., about 134° C., about 135° C., about 136° C., about 137° C., about 138° C., about 139° C., about 140° C., about 141° C., about 142° C., about 143° C., about 144° C., about 145° C., about 146° C., about 147° C., or about 148° C. In at least one embodiment, the reactor conditions for the first oligomerization process can include a reactor temperature of about 110° C. or more, about 120° C. or more, such as from about 110° C. to about 180° C., such as from about 120° C. to about 180° C., such as from about 130° C. to about 180° C.

In at least one embodiment, the reactor conditions for the first oligomerization process can include a reactor pressure of from about 1.5 psia to about 1500 psia, such as from about 7 psia to about 1200 psia, such as from about 15 psia to about 750 psia, such as from about 30 psia to about 100 psia.

In at least one embodiment, the reactor conditions for the first oligomerization process can include a residence time such as less than about 72 hours, such as from about 1 minute to about 20 hours, such as from about 5 minutes to about 10 hours, such as from about 30 minutes to about 9 hours, such as from about 1 hours to about 5 hours, such as from about 3 hours to about 4 hours. In at least one embodiment, the reactor conditions for the first oligomerization process can include a residence time of about 24 hours or less, such as about 10 hours or less, such as about 5 hours or less, such as about 3 hours or less.

In at least one embodiment, the reactor conditions for the first oligomerization process can include a catalyst loading/catalyst amount of from about 500 grams linear alpha-olefin (gLAO) per 1 g Cat (gCat) (gLAO/gCat) to about 150,000 gLAO/gCat, such as 1,000 gLAO/gCat or more, 5,000 gLAO/gCat or more, 10,000 gLAO/gCat or more, 20,000 gLAO/gCat or more, such as from about 5,000 gLAO/gCat to about 80,000 gLAO/gCat, such as from about 10,000 gLAO/gCat to about 80,000 gLAO/gCat, such as from about 20,000 gLAO/gCat to about 75,000 gLAO/gCat, such as from about 30,000 gLAO/gCat to about 65,000 gLAO/gCat, such as from about 40,000 gLAO/gCat to about 60,000 gLAO/gCat, such as from about 50,000 gLAO/gCat to about 55,000 gLAO/gCat. In at least one embodiment, the reactor conditions for the first oligomerization process can include a catalyst loading of from about 5,000 gLAO/gCat to 80,000 gLAO/gCat, such as from about 50,000 gLAO/gCat to about 75,000 gLAO/gCat.

In at least one embodiment, the reactor conditions for the first oligomerization process can include a flow rate of the catalyst system of greater than about 5 gCat/hr, such as from about 6 gCat/hr to about 70 kgCat/hr, such as about 6 gCat/hr to about 10 kgCat/hr, such as about 6 gCat/hr to about 1 kgCat/hr, such as about 6 gCat/hr to 50 gCat/hr, such as 6 gCat/hr to 25 gCat/hr, such as from about 7 gCat/hr to about 24 gCat/hr, such as from about 8 gCat/hr to about 23 gCat/hr, such as about 9 gCat/hr, about 10 gCat/hr, about 11 gCat/hr, about 12 gCat/hr, about 13 gCat/hr, about 14 gCat/hr, about 15 gCat/hr, about 16 gCat/hr, about 17 gCat/hr, about 18 gCat/hr, about 19 gCat/hr, about 20 gCat/hr, about 21 gCat/hr, or about 22 gCat/hr.

In at least one embodiment, the reactor conditions for the first oligomerization process can include a flow rate of the alpha-olefin of greater than about 100 g/hr, such as from about 200 g/hr to 45,000 kg/hr, such as from about 1,000 g/hr to 15,000 kg/hr, such as from about 1,500 g/hr to 1,000,000 g/hr, such as from 1,800 g/hr to 10,000 g/hr, such as about 1,900 g/hr, such as about 2,080 g/hr.

In at least one embodiment, the reactor conditions for the first oligomerization process can include a flow rate of the alpha-olefin of about 100 grams alpha-olefin per hour (ghr also written as g/hr) or more, such as from about 150 g/hr to about 7,500 g/hr, such as from about 300 g/hr to about 3,000 g/hr, such as from about 500 g/hr to about 2,000 g/hr, such as from about 750 g/hr to about 1,500 g/hr.

In at least one embodiment, the reactor conditions for the first oligomerization process can include a flow rate of the alpha-olefin of about 100 grams alpha-olefin per hour (ghr also written as g/hr) or more, such as 1,000 g/hr or more, such as 10,000 g/hr or more, such as 100,000 g/hr or more, such as 200,000 g/hr or more, such as 300,000 g/hr or more, such as 400,000 g/hr or more.

In at least one embodiment, the first oligomerization process can include a PAO dimer selectivity (in weight ratio) of about 60% or more with at least one of the following conditions: (i) at a catalyst productivity of about 10,000 gPAO/gCat or more (such as about 10,000 to about 100,000 gPAO/gCat) without the use of alumoxane; (ii) at a catalyst productivity of about 10,000 gPAO/gCat or more (such as about 10,000 to about 100,000 gPAO/gCat) without the use of alumoxane or less than 10 equivalents aluminum alkyl per metallocene; (iii) at a catalyst productivity of about 10,000 gPAO/gCat or more (such as about 10,000 to about 100,000 gPAO/gCat) with about 500 ppm or less of an aluminum alkyl; (iv) at a catalyst productivity of about 10,000 gPAO/gCat or more (such as about 10,000 to about 100,000 gPAO/gCat) with about 20 ppm or less of an aluminum alkyl; (v) at a catalyst productivity of about 10,000 gPAO/gCat or more (such as about 10,000 to about 100,000 gPAO/gCat) with a residence time of about 24 hours or less; (vi) at a catalyst productivity of about 10,000 gPAO/gCat or more (such as about 10,000 to about 100,000 gPAO/gCat) with a residence time of about 10 hours or less; or (vii) at a catalyst productivity of about 30,000 gPAO/gCat or more (such as about 30,000 to about 100,000 gPAO/gCat) with a residence time of about 10 hours or less. The PAO dimer selectivity is based on a weight ratio of PAO dimer/(PAO dimer+PAO trimer+PAO tetramer+heavier oligomers of LAO).

In at least one embodiment, the first oligomerization process can include a PAO dimer selectivity (in weight ratio) of about 85% or more with at least one of the following conditions: (i) at a catalyst productivity of about 30,000 gPAO/gCat or more (such as about 30,000 to about 100,000 gPAO/gCat) with a residence time of about 10 hours or less; (ii) at a catalyst productivity of about 30,000 gPAO/gCat or more (such as about 30,000 to about 100,000 gPAO/gCat) with a residence time of about 5 hours or less; or (iii) at a catalyst productivity of about 50,000 gPAO/gCat or more (such as about 50,000 to about 100,000 gPAO/gCat) with a residence time of about 5 hours or less. The PAO dimer selectivity is based on a weight ratio of PAO dimer/(PAO dimer+PAO trimer+PAO tetramer+heavier oligomers of LAO).

In at least one embodiment, the first oligomerization process can include a PAO dimer selectivity (in weight ratio) of about 90% or more with at least one of the following conditions: (i) at a catalyst productivity of about 50,000 gPAO/gCat or more (such as about 50,000 to about 100,000 gPAO/gCat) with a residence time of about 10 hours or less; (ii) at a catalyst productivity of about 50,000 gPAO/gCat or more (such as about 50,000 to about 100,000 gPAO/gCat) with a residence time of about 5 hours or less; (iii) at a catalyst productivity of about 60,000 gPAO/gCat or more (such as about 60,000 to about 100,000 gPAO/gCat) with a residence time of about 5 hours or less; (iv) at a catalyst productivity of about 60,000 gPAO/gCat or more (such as about 60,000 to about 100,000 gPAO/gCat) with a residence time of about 3 hours or less; or (v) at a catalyst productivity of about 65,000 gPAO/gCat or more (such as about 65,000 to about 100,000 gPAO/gCat) with a residence time of about 3 hours or less. The PAO dimer selectivity is based on a weight ratio of PAO dimer/(PAO dimer+PAO trimer+PAO tetramer+heavier oligomers of LAO).

In at least one embodiment, the reactor conditions for the first oligomerization process can include one or more of the following conditions: a mol ratio of catalyst:activator of about 1:1.05 in about 390 g alkane solvent such as methylcyclohexane with about 10 ppm to about 12 ppm TNOA (tri-n-octylaluminum); the activator is N,N-dioctadecyl-N-methylammonium tetrakis (pentafluorophenyl)borate; an alpha-olefin (LAO) flow rate of about 2080 g/hr; a catalyst loading of about 50,000 (alternately 55,000, 60,000, 65,000, 70,000, 75,000) gLAO/gCat or more where "Cat" refers to the metallocene component of the catalyst system; a catalyst system flow rate of about 0.24 mL/min (12.7 g/hr); an amount of TNOA as scavenger in LAO of about 0 to 100 ppm, 2 to 75 ppm, preferably less than 55 ppm, preferably less than 10 ppm; a temperature from about 130° C. to about 148° C.; and a residence time of about 3 hours.

In at least one embodiment, the reactor conditions for the first oligomerization process has a catalyst loading of about 50,000 (alternately 55,000, 60,000, 65,000, 70,000, 75,000) gLAO/gCat or more where "Cat" refers to the metallocene component of the catalyst system.

In at least one embodiment, the reactor conditions for the first oligomerization process has an amount of TNOA as scavenger in LAO of about 0 to 100 ppm, 2 to 75 ppm, preferably less than 55 ppm, preferably less than 10 ppm.

In at least one embodiment, the first oligomerization process is essentially free of all aromatic solvents including toluene.

In at least on embodiment, the first oligomerization process uses hydrocarbon solvents selected from $C_4$ to $C_{10}$ linear, branched or cyclic alkanes.

In at least on embodiment, the first oligomerization process the solvent is selected from one or more $C_6$ to $C_{32}$ alpha olefins (alternatively $C_8$ to $C_{16}$), and no additional solvents are used.

In at least on embodiment, the first oligomerization process the solvent is selected from one or more $C_6$ to $C_{32}$ alpha olefins (LAO) mixed with $C_4$ to $C_{10}$ linear, branched or cyclic alkanes (HC). Preferably the ratio of LAO to HC by weight is greater than 50%, alternatively greater than 60%, alternatively greater that 70%, alternatively greater than 80%, alternatively greater than 90%, alternatively greater than 92%, alternatively greater than 95%, alternatively greater than 96%, alternatively greater than 98%, alternatively greater than 99%.

Usefully, the reduction or elimination of $C_4$ to $C_{10}$ linear, branched or cyclic alkanes, along with high conversion of alpha olefin monomer allows for the PAO from the first oligomerization process to be directly used in the second oligomerization process described below. Alternatively, the feed stream containing the first oligomerization product can be passed though a filter or filter bed to remove catalyst system and aluminum alkyl residue. Suitable filters in include alumina, Celite™, cellulose, silica and the like.

In at least one embodiment, the alpha-olefin in the feed for the first oligomerization process can be one or more $C_2$-$C_{32}$ alpha-olefins, such as $C_4$-$C_{32}$ alpha-olefins, such as $C_6$-$C_{30}$ alpha-olefins, such as $C_6$-$C_{24}$ alpha-olefins, such as $C_6$-$C_{18}$ alpha-olefins, $C_8$-$C_{18}$ alpha-olefins, $C_6$ to $C_{16}$ alpha-olefins, $C_6$-$C_{12}$ alpha-olefins, or a combination thereof. Non-limiting examples of alpha-olefins include 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, and a combination thereof. Various suitable alpha-olefins (e.g., linear alpha-olefins) and their characteristics that can be used for the first oligomerization process are discussed below.

In at least one embodiment, hydrogen is optionally added to the reactor at a concentration of 0 to 100 psi; such as from 0 to 50 psi, such as from 5-10 psi.

In at least one embodiment, the heavy oligomers (degree of oligomerization of at least 3) are hydrogenated to create a finished PAO lubricant. In at least one embodiment, the kinematic viscosity at 100° C. of at least a portion of the hydrogenated first reactor effluent (e.g., the trimer) can be less than 5 cSt, such as less than 3.5 cSt.

In at least one embodiment, the Noack volatility of at least a portion of the hydrogenated first reactor effluent (e.g., the trimer) can be less than 15 wt %, such as less than 13 wt %.

In at least one embodiment, the rotating pressure vessel oxidation test (RPVOT) of at least a portion of the hydrogenated first reactor effluent (e.g., the trimer) can be greater than 40 minutes, such as greater than 60 minutes, such as greater than 75 minutes.

Embodiments for feed purification, the first oligomerization reaction, and the catalyst system for the first oligomerization reaction are found below. Other parameters for the selectivity and yield of products produced from the first oligomerization reaction are found below.

II. Process for Producing PAO Trimers from PAO Dimers (Second Oligomerization Process)

The present disclosure also includes processes using metallocene catalysts to improve yields for producing PAO trimer, such as a low viscosity PAO trimer. Conventional methods of forming PAO trimers involve a reaction of a PAO dimer feedstock made from an oligomerization process that contains a significant amount of di-substituted vinylene as well as PAO trimer, PAO tetramer, and higher oligomers of alpha-olefin. The di-substituted vinylene, however, is not highly reactive when added to a second oligomerization process (e.g., a $BF_3$ catalyzed process), and the reaction kinetics are very slow. In addition, the unreacted dimer in the stream going into the $BF_3$ catalyzed conventional reactor contaminates the stream produced out of the $BF_3$ process and reduces the value of that by-product.

The inventors have found that reducing (or eliminating) the amount of di-substituted vinylene in the PAO dimer feedstock from the first oligomerization process can provide production of a PAO trimer product at higher yields and higher purity than conventional processes. In addition, the higher purity intermediate PAO (e.g., the PAO dimer feedstock) produced from the first oligomerization process (having lower amounts of PAO trimer, lower amounts of PAO tetramer, and lower amounts of higher oligomers of alpha-olefin relative to conventional PAO dimer feedstocks) provides the production of high amounts of PAO trimer from the second oligomerization process.

The PAO produced from the first oligomerization process described above can include dimer (such as vinylidene dimers), trimer, optionally tetramer and higher oligomers of the respective alpha-olefin feedstocks, or a combination thereof. This PAO produced from the first oligomerization process described above is referred to interchangeably as "intermediate PAO" and "first reactor effluent." The oligomerization process described above can be performed in a first reactor, e.g., a metallocene reactor. The PAO produced from the second oligomerization process is referred to interchangeably as "hybrid trimer," and "second reactor effluent." The second oligomerization may be performed in a second reactor, and the second reactor may include one or more sub-reactors.

The hybrid process is referred to interchangeably as "second oligomerization process" or "second oligomerization."

The intermediate PAO (e.g., the PAO dimer feedstock) may be used as the sole olefin feedstock to the second oligomerization process or may be used together with an alpha-olefin feedstock, typically of the type used as the olefin starting material for the first oligomerization process. Other portions of the effluent from the first oligomerization process may also be used as a feedstock to the second oligomerization process, including unreacted LAO. Alpha-olefins with the same attributes as those used for the first oligomerization process may be used for the second oligomerization. 100% dimer in the intermediate PAO is preferred, however typical ratios for the PAO dimer portion of the intermediate PAO to the alpha-olefins fraction of the intermediate PAO can be from about 99:1 to 10:90, alternately 90:10 to about 10:90, such as from about 95:5 to about 50:50 by weight of the intermediate PAO. In at least one embodiment, the PAO dimer of the intermediate PAO can make up about 50 mol % of the olefinic feed material since the properties and distribution of the final product, dependent in part upon the starting material, can be favorably affected by feeding the intermediate PAO at an equimolar ratio with the alpha-olefins.

In at least one embodiment, the feed for second oligomerization process can have a distribution of PAO dimer, PAO trimer, PAO tetramer, higher oligomers of alpha-olefin, or a combination thereof, can have the same distribution of effluent produced in the metallocene dimer selective process described above. In at least one embodiment, the feed for the second oligomerization reactor is a product from the metallocene dimer selective process described above.

The PAO dimer of the intermediate PAO can possess at least one carbon-carbon unsaturated double bond. Portions of the PAO dimer can include vinylidene dimers, di-substituted vinylenes, tri-substituted vinylenes, and a combination thereof. The distribution of vinylidene dimers, di-substituted vinylenes, tri-substituted vinylenes, and a combination thereof in the PAO dimer can be the distribution as described above.

The structure of the intermediate PAO can be such that, when reacted in a second oligomerization, the intermediate PAO can react with the optional LAO to form a "hybrid trimer" at high yields. This allows for high conversion and yield rates of the PAO products. In at least one embodiment, the PAO product from the second oligomerization comprises primarily a hybrid trimer formed from the dimer and the respective LAO feedstock.

Any suitable oligomerization process and acid catalyst composition may be used for the second oligomerization process. A catalyst for the second oligomerization can be a non-transition metal catalyst. A catalyst can be a Lewis acid catalyst. US Patent Publication Nos. 2009/0156874 and 2009/0240012 describe a process that can be used for the second oligomerization, to which reference is made for details of feedstocks, compositions, catalysts and co-catalysts, and process conditions. The Lewis acid catalysts of US 2009/0156874 and US 2009/0240012 include the metal and metalloid halides conventionally used as Friedel-Crafts catalysts, and examples include $AlCl_3$, $BF_3$, $AlBr_3$, $TiCl_3$, and $TiCl_4$ either alone or with a protic promoter/activator. Boron trifluoride is commonly used but not particularly suitable unless it is used with a protic promoter. Useful co-catalysts are well known and described in detail in US 2009/0156874 and US 2009/0240012. Solid Lewis acid catalysts, such as synthetic or natural zeolites, acid clays, polymeric acidic resins, amorphous solid catalysts such as silica-alumina, and heteropoly acids such as the tungsten zirconates, tungsten molybdates, tungsten vanadates, phosphotungstates and molybdotungstovanadogermanates (e.g., $WOx/ZrO_2$, $WOx/MoO_3$) may also be used although these are not generally as favored economically. Additional process conditions and other details are described in detail in US 2009/0156874 and US 2009/0240012, and incorporated herein by reference.

In at least one embodiment, the second oligomerization can be performed in the presence of $BF_3$ and at least one activator such as an alcohol, or the second oligomerization can be performed in the presence of $BF_3$ and at least two different activators selected from alcohols and alkyl acetates. The alcohols can be $C_1$ to $C_{10}$ alcohols and the alkyl acetates are $C_1$ to $C_{10}$ alkyl acetates. For example, both co-activators are $C_1$ to $C_6$ based compounds. Two example combinations of co-activators can be i) ethanol and ethyl acetate and ii) n-butanol and n-butyl acetate. The ratio of alcohol to alkyl acetate can be from about 0.2 to about 15, such as about 0.5 to about 7.

Temperatures for the second oligomerization in the second reactor can be from about 0° C. to about 60° C., such as from about 10° C. to about 55° C., such as from about 20° C. to about 40° C., from about 10° C. to about 40° C., or from about 15° C. to about 25° C. In at least one embodiment, the temperatures for the second oligomerization in the second reactor can be less than about 32° C., such as from about 15° C. to about 30° C., such as from about 20° C. to about 25° C.

In at least one embodiment, the acid catalyst composition loading for the second oligomerization can be from about 0.5 mmol per 100 g LAO (mmolCat/100 gLAO) to about 30 mmolCat/100 gLAO, such as from about 5 mmolCat/100 gLAO to about 15 mmolCat/100 gLAO, such as from about 6 mmolCat/100 gLAO to about 14 mmolCat/100 gLAO, such as about 8 mmolCat/100 gLAO, about 10 mmolCat/ 100 gLAO, or about 12 mmolCat/100 gLAO.

In at least one embodiment, the LAO feedstock for the second oligomerization (as well as the first oligomerization) can be one or more $C_2$-$C_{32}$ alpha-olefins, such as a $C_4$-$C_{32}$ alpha-olefin, $C_6$-$C_{30}$ alpha-olefin, such as a $C_6$-$C_{24}$ alpha-olefin, such as a $C_6$-$C_{18}$ alpha-olefin, a $C_8$-$C_{18}$ alpha-olefin, a $C_6$ to $C_{16}$ alpha-olefin, or a $C_6$-$C_{12}$ alpha-olefin, or a combination thereof. Non-limiting examples of LAOs can be 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 1-icocene, $C_{22}$, $C_{24}$, $C_{26}$, $C_{28}$, $C_{30}$, and $C_{32}$ LAOs, and a combination thereof. Other suitable alpha-olefin monomers for the second oligomerization can be found in Section IV.

In at least one embodiment, a molar ratio of the PAO dimer of the intermediate PAO to LAO for the second oligomerization process can be about 1:1 or greater, such as from about 1.5 to about 10:1, such as from about 2:1 to about 5:1, such as from about 3:1 to about 4:1. In at least one embodiment, a molar ratio of the PAO dimer of the intermediate PAO to LAO for the second oligomerization process can be from about 0.1:1 to about 10:1, such as from about 0.5 to about 5:1, such as from about 0.5:1 to about 3:1, such as from about 0.8:1 to about 1.2:1, such as from about 0.9:1 to about 1.1:1.

In at least one embodiment, the reactor conditions for the second oligomerization can include a reactor pressure of from about 10 psia to about 35 psia, such as from about 15 psia to about 25 psia, such as from about 19 psia to about 21 psia.

In at least one embodiment, the second oligomerization can be carried out in two reactors in series, such as two continuous stirred tank reactors (CSTRs) in series. In some embodiments, the residence time in the first reactor of the second oligomerization can be from about 0.25 hour to about 5 hours, such as from about 0.5 hour to about 3 hours, and the residence time in the second reactor of the second oligomerization can be from about 0.25 hour to about 5 hours, such as from about 0.5 hour to about 3 hours.

In at least one embodiment, the second oligomerization can be carried out in one reactor such as a CSTR. In some embodiments, the residence time in the reactor for the second oligomerization can be from about 1 minute to 10 hours, such as from about 1 hour to about 7 hours, such as from about 1 hour to about 2 hours.

Table B shows non-limiting types of the PAO product (the hybrid trimer) that can be produced from the second oligomerization process of a PAO dimer with the LAO monomer.

TABLE B

|  | C6 | C8 | C9 | C10 | C12 | C14 | C16 |
| --- | --- | --- | --- | --- | --- | --- | --- |
| C6 dimer | C18 | C20 | C21 | C22 | C24 | C26 | C28 |
| C8 dimer | C22 | C24 | C25 | C26 | C28 | C30 | C32 |
| C9 dimer | C24 | C26 | C27 | C28 | C30 | C32 | C34 |
| C10 dimer | C26 | C28 | C29 | C30 | C32 | C34 | C36 |
| C12 dimer | C30 | C32 | C33 | C34 | C36 | C38 | C40 |
| C14 dimer | C34 | C36 | C37 | C38 | C40 | C42 | C44 |
| C16 dimer | C38 | C40 | C41 | C42 | C44 | C46 | C48 |

In at least one embodiment, where the LAO feedstock for the first oligomerization and the second oligomerization processes is the same, the incorporation of PAO dimer of the intermediate PAO into hybrid trimer, tetramer, higher oligomers, or a combination thereof can be about 75% or more, such as about 80% or more, such as about 85% or more, such as about 90% or more, such as about 95% or more, such as about 99% or more; the conversion of the LAO can be about 75% or more, such as about 80% or more, such as about 85% or more, such as about 90% or more, such as about 95% or more, such as about 99% or more; and/or the yield % of about 75% or more, such as about 80% or more, such as about 85% or more, such as about 90% or more, such as about 95% or more, such as about 99% or more.

In at least one embodiment, where the LAO feedstock for the first oligomerization and the second oligomerization processes is different, the incorporation of PAO dimer of the intermediate PAO into hybrid trimer, tetramer, higher oligomers, or a combination thereof can be about 75% or more, such as about 80% or more, such as about 85% or more, such as about 90% or more, such as about 95% or more, such as about 99% or more; the conversion of the LAO can be about 75% or more, such as about 80% or more, such as about 85% or more, such as about 90% or more, such as about 95% or more, such as about 99% or more; and/or the yield % of about 75% or more, such as about 80% or more, such as about 85% or more, such as about 90% or more, such as about 95% or more, such as about 99% or more.

In at least one embodiment, the yield % of PAO trimer in the second reactor effluent is about 60 wt % or more, such as about 70 wt % or more, such as about such as about 75 wt % or more, such as about 76 wt % or more, such as about 77 wt % or more, such as about 78 wt % or more, 79 wt % or more, such as about 80 wt % or more, such as about 81 wt % or more, such as about 82 wt % or more, such as about 83 wt % or more, such as about 84 wt % or more, such as about 85 wt % or more, such as about 86 wt % or more, such as about 87 wt % or more, such as about 88 wt % or more, such as about 89 wt % or more, such as about 90 wt % or more, such as about 91 wt % or more, such as about 92 wt % or more, such as about 93 wt % or more, such as about 94 wt % or more, such as about 95 wt % or more, such as about 96 wt % or more, such as about 97 wt % or more, such as about 98 wt % or more, such as about 99 wt % or more, such as about 100 wt %, based on a total moles of PAO dimer, PAO trimer, PAO tetramer, and higher oligomers of alpha-olefin in the second reactor effluent.

In at least one embodiment, the second oligomerization process can have a selectivity towards hybrid trimer of about 60 wt % or more, such as about 70 wt % or more, such as about 75 wt % or more, such as about 76 wt % or more, such as about 77 wt % or more, such as about 78 wt % or more, 79 wt % or more, such as about 80 wt % or more, such as about 81 wt % or more, such as about 82 wt % or more, such as about 83 wt % or more, such as about 84 wt % or more, such as about 85 wt % or more, such as about 86 wt % or more, such as about 87 wt % or more, such as about 88 wt % or more, such as about 89 wt % or more, such as about 90 wt % or more, such as about 91 wt % or more, such as about 92 wt % or more, such as about 93 wt % or more, such as about 94 wt % or more, such as about 95 wt % or more, such as about 96 wt % or more, such as about 97 wt % or more, such as about 98 wt % or more, such as about 99 wt % or more, such as about 100 wt %, based on a total moles of PAO dimer, PAO trimer, PAO tetramer, and higher oligomers of alpha-olefin in the second reactor effluent.

In at least one embodiment, the yield % of PAO dimer, PAO tetramer, higher oligomers of alpha-olefin, or a combination thereof, in the second reactor effluent can be about 40 wt % or less, such as about 30 wt % or less, such as about 25 wt % or less, such as about 24 wt % or less, such as about 23 wt % or less, such as about 22 wt % or less, such as about 21 wt % or less, such as about 20 wt % or less, such as about 19 wt % or less, such as about 18 wt % or less, such as about 17 wt % or less, such as about 16 wt % or less, such as about 15 wt % or less, such as about 14 wt % or less, such as about 13 wt % or less, such as about 12 wt % or less, such as about 11 wt % or less, such as about 10 wt % or less, such as about 9 wt % or less, such as about 8 wt % or less, such as about 7 wt % or less, such as about 6 wt % or less, such as about 5 wt % or less, such as about 4 wt % or less, such as about 3 wt % or less, such as about 2 wt % or less, such as about 1 wt % or less, such as about 0 wt %, based on a total weight of PAO dimer, PAO trimer, PAO tetramer, and higher oligomers of alpha-olefin in the second reactor effluent.

In at least one embodiment, the second oligomerization process can have a selectivity towards PAO dimer, PAO tetramer, higher oligomers of alpha-olefin, or a combination thereof, of about 40 mol % or less, such as about 30 mol % or less, such as about 25 mol % or less, such as about 24 mol % or less, such as about 23 mol % or less, such as about 22 mol % or less, such as about 21 mol % or less, such as about 20 mol % or less, such as about 19 mol % or less, such as about 18 mol % or less, such as about 17 mol % or less, such as about 16 mol % or less, such as about 15 mol % or less, such as about 14 mol % or less, such as about 13 mol % or less, such as about 12 mol % or less, such as about 11 mol % or less, such as about 10 mol % or less, such as about 9 mol % or less, such as about 8 mol % or less, such as about 7 mol % or less, such as about 6 mol % or less, such as about 5 mol % or less, such as about 4 mol % or less, such as about 3 mol % or less, such as about 2 mol % or less, such as about 1 mol % or less, such as about 0 mol %, based on a total moles of PAO dimer, PAO trimer, PAO tetramer, and higher oligomers of alpha-olefin in the second reactor effluent.

In at least one embodiment, the trimer has an A-A-B structure, where A and B are different alpha-olefins.

In at least one embodiment, the monomer can be optional as a feedstock in the second reactor (e.g., an oligomerization reactor). In some embodiments, the first reactor effluent comprises unreacted monomer, and the unreacted monomer can be fed to the second reactor. In some embodiments, monomer can be fed into the second reactor, and the monomer can be an LAO selected from the group including 1-hexene, 1-octene, 1-nonene, 1-decene, 1-dodecene, 1-tetradecene, 1-hexadecene. In some embodiments, the PAO produced in the second oligomerization can be derived from the PAO dimer portion of the intermediate PAO plus only one monomer to form one or more trimers. In some embodiments, the PAO produced in the second oligomerization can be derived from the PAO dimer of the intermediate PAO plus two or more monomers, or three or more monomers, or four or more monomers, or even five or more monomers. For example, the PAO dimer plus a $C_8$, $C_{10}$, $C_{12}$-LAO mixture, or a $C_6$, $C_7$, $C_8$, $C_9$, $C_{10}$, $C_{11}$, $C_{12}$, $C_{13}$, $C_{14}$-LAO mixture, or a $C_4$, $C_6$, $C_8$, $C_{10}$, $C_{12}$, $C_{14}$, $C_{16}$, $C_{18}$-LAO mixture can be used as a feed to form trimers.

In at least one embodiment, the second reactor effluent may contain trace amounts of transition metal compound if the catalyst in the first or subsequent oligomerization is a metallocene catalyst. A trace amount of transition metal compound may be any amount of transition metal compound or Group 4 metal present in the PAO. Presence of Group 4 metal may be detected at the ppm or ppb level by ASTM 5185. Optionally, the first reactor effluent can be passed through a filter or filter bed to remove trace amounts of transition metal compounds, activator and residual aluminum alkyls, if present.

In at least one embodiment, the second reactor effluent or a portion of the second reactor effluent is hydrogenated to a Bromine number less than 2.

In at least one embodiment, the kinematic viscosity at 100° C. of the second reactor effluent or a portion of the second reactor effluent (e.g., the hybrid trimer) can be less than about 10 cSt, such as less than about 6 cSt, such as less than about 4.5 cSt, such as less than about 3.2 cSt, such as from about 2.8 cSt to about 4.5 cSt. In some embodiments, the second reactor effluent or a portion of the second reactor effluent is hydrogenated to form a hydrogenated second reactor effluent having a kinematic viscosity at 100° C. less than about 10 cSt, such as less than about 6 cSt, such as less than about 4.5 cSt, such as less than about 3.2 cSt, such as from about 2.8 cSt to about 4.5 cSt.

In at least one embodiment, the kinematic viscosity at 40° C. of the second reactor effluent or a portion of the second reactor effluent can be less than about 25 cSt, such as less than about 15 cSt. In some embodiments, the second reactor effluent or a portion of the second reactor effluent is hydrogenated to form a hydrogenated second reactor effluent having a kinematic viscosity at 40° C. of the second reactor effluent or a portion of the second reactor effluent can be less than about 25 cSt, such as less than about 15 cSt.

In at least one embodiment, the pour point of the second reactor effluent or a portion of the second reactor effluent can be below about −30° C., such as below about −40° C., such as below about −50° C., such as below about −60° C., such as below about −70° C., such as below about −80° C. In some embodiments, the second reactor effluent or a portion of the second reactor effluent is hydrogenated to form a hydrogenated second reactor effluent having a pour point of the second reactor effluent or a portion of the second reactor effluent can be below about −30° C., such as below about −40° C., such as below about −50° C., such as below about −60° C., such as below about −70° C., such as below about −80° C.

In at least one embodiment, the Noack volatility of the second reactor effluent or a portion of the second reactor effluent can be less than about 19 wt %, such as less than about 14 wt %, such as less than about 12 wt %, such as less than about 10 wt %, such as less than about 9.0 wt %, such as less than about 8.5 wt %, such as less than about 8.0 wt %, such as less than about 7.5 wt %. In some embodiments, the second reactor effluent or a portion of the second reactor effluent is hydrogenated to form a hydrogenated second reactor effluent having a Noack volatility of the second reactor effluent or a portion of the second reactor effluent can be less than about 19 wt %, such as less than about 14 wt %, such as less than about 12 wt %, such as less than about 10 wt %, such as less than about 9.0 wt %, such as less than about 8.5 wt %, such as less than about 8.0 wt %, such as less than about 7.5 wt %.

In at least one embodiment, the viscosity index of the second reactor effluent or a portion of the second reactor effluent can be more than about 120, such as more than about 121, such as more than about 125, such as more than about 130, such as more than about 135, such as more than about 136. In some embodiments, the second reactor effluent or a portion of the second reactor effluent is hydrogenated to form a hydrogenated second reactor effluent having a viscosity index of the second reactor effluent or a portion of the second reactor effluent can be more than about 120, such as more than about 121, such as more than about 125, such as more than about 130, such as more than about 135, such as more than about 136.

In at least one embodiment, the cold crank simulator value (CCS) at −35° C. of the second reactor effluent or a portion of the second reactor effluent may be not more than about 1200 cP, such as not more than about 1000 cP, such as not more than about 900 cP. In some embodiments, the second reactor effluent or a portion of the second reactor effluent is hydrogenated to form a hydrogenated second reactor effluent having a cold crank simulator value (CCS) at −35° C. of the second reactor effluent or a portion of the second reactor effluent may be not more than about 1200 cP, such as not more than about 1000 cP, such as not more than about 900 cP.

In at least one embodiment, the second reactor effluent or a portion of the second reactor effluent can have a Brookfield viscosity at 40° C. of less than about 3000 cP, such as less than about 2000 cP, such as less than about 1500 cP. In some embodiments, the second reactor effluent or a portion of the second reactor effluent is hydrogenated to form a hydrogenated second reactor effluent having a Brookfield viscosity at 40° C. of less than about 3000 cP, such as less than about 2000 cP, such as less than about 1500 cP.

In at least one embodiment, the second reactor effluent or a portion of the second reactor effluent can have a rotating pressure vessel oxidation test (RPVOT) of about 70 minutes or more, such as about 80 minutes or more, such as about 90 minutes or more, such as about 100 minutes or more. In some embodiments, the second reactor effluent or a portion of the second reactor effluent is hydrogenated to form a hydrogenated second reactor effluent having a rotating pressure vessel oxidation test (RPVOT) of about 70 minutes or more, such as about 80 minutes or more, such as about 90 minutes or more, such as about 100 minutes or more.

In at least one embodiment, the second reactor effluent or a portion of the second reactor effluent can have a kinematic viscosity at 100° C. of not more than about 3.2 cSt and a Noack volatility of not more than about 19 wt %. In at least one embodiment, the second reactor effluent or a portion of the second reactor effluent can have a kinematic viscosity at 100° C. of not more than about 3.6 cSt and a Noack volatility of not more than about 13.0 wt %. In some embodiments, the second reactor effluent or a portion of the second reactor effluent is hydrogenated to form a hydrogenated second reactor effluent having a kinematic viscosity at 100° C. of not more than about 3.2 cSt and a Noack volatility of not more than about 19 wt %. In at least one embodiment, the second reactor effluent or a portion of the second reactor effluent is hydrogenated to form a hydrogenated second reactor effluent having have a kinematic viscosity at 100° C. of not more than about 3.6 cSt and a Noack volatility of not more than about 13.0 wt %.

Functionalized PAOs and Uses of Functionalized PAOs

PAO products (e.g., unhydrogenated LAO dimers and trimers) of the present disclosure can be functionalized with one or more reactants (and can be optionally hydrogenated) through various chemical reactions to produce a functionalized PAO product. For example, PAOs of the present disclosure that have been functionalized (and optionally hydrogenated) may be used in gear oils, industrial oils, hydraulic oils, compressor oils, or in a driveline or electric vehicle fluid.

PAOs prepared herein may be functionalized by reacting a heteroatom containing group with the PAO with or without a catalyst. Examples include catalytic hydrosilylation, ozonolysis, hydroformylation, or hydroamination, sulfonation, halogenation, hydrohalogenation, hydroboration, epoxidation, or Diels-Alder reactions with polar dienes, Friedel-Crafts reactions with polar aromatics, maleation with activators such as free radical generators (e.g. peroxides). The functionalized PAO's can be used in oil additives, as antifogging or wetting additives, surfactants for soaps, detergents, fabric softeners, antistatics, and many other applications. Preferred uses include additives for lubricants and or fuels, preferably where the heteroatom containing group includes one or more of amines, aldehydes, alcohols, acids, anhydrides, sulphonates, particularly succinic acid, maleic acid and maleic anhydride.

In some embodiments the PAO's produced herein are functionalized as described in U.S. Pat. No. 6,022,929; A. Toyota et al. (2002) Polymer Bulletin, v. 48, pp. 213-219; and *J. Am. Chem. Soc.* (1990) v. 112, pp. 7433-7434. In some embodiments the functionalized PAO's produced herein are further functionalized (derivatized), such as described in U.S. Pat. No. 6,022,929; A. Toyota et al. (2002) *Polymer Bulletin*, v. 48, pp. 213-219; and *J. Am. Chem. Soc.* (1990) v. 112, pp. 7433-7434; and WO 2009/155472.

In preferred embodiments, the PAO's of the present disclosure can be functionalized (e.g. chemically modified with one or more functional groups (also referred to as a heteroatom containing group) typically containing heteroatoms such as P, O, S, N, Br, Cl, F, I and or Br (preferably N, O, Cl and or Br, preferably N and or O). Preferred functional groups are selected from the group consisting of acids, esters, anhydrides, acid-esters, oxycarbonyls, carbonyls, formyls, formylcarbonyls, hydroxyls, and acetyl halides. Particularly preferred functional groups include those represented by the formula: —C(O)—X, where the O is double bonded to the C and the X is hydrogen, nitrogen, hydroxy, oxyhydrocarbyl (e.g. ester), oxygen, the salt moiety —OM wherein M is a metal, e.g. alkali, alkaline earth, transition metal, copper, zinc and the like, oxyhetero, e.g. —O—Z wherein Z represents a heteroatom such as phosphorus boron, sulfur, which heteroatom may be substituted with hydrocarbyl or oxyhydrocarbyl groups, or two acyl groups may be joined through (X).

Preferred heteroatom containing groups include acyl groups derived from monounsaturated mono- or dicarboxylic acids and their derivatives, e.g. esters and salts.

More specifically, PAO's functionalized with mono- or dicarboxylic acid material, i.e., acid, anhydride, salt or acid ester are preferred, including the reaction product of the PAO with a monounsaturated carboxylic reactant comprising at least one member selected from the group consisting of (i) monounsaturated $C_4$ to $C_{10}$ dicarboxylic acid (preferably wherein (a) the carboxyl groups are vicinyl, (i.e. located on adjacent carbon atoms) and (b) at least one, preferably both, of said adjacent carbon atoms are part of said monounsaturation); (ii) derivatives of (i) such as anhydrides or $C_1$ to $C_5$ alcohol derived mono- or diesters of (i); (iii) monounsaturated $C_3$ to $C_{10}$ monocarboxylic acid wherein the carbon-carbon double bond is conjugated to the carboxyl group, i.e., of the structure —C=C—C(O)— (where O is double bonded to C), and (iv) derivatives of (iii) such as $C_1$ to $C_5$ alcohol derived monoesters of (iii). Upon reaction with the PAO, the double bond of the monounsaturated carboxylic reactant becomes saturated. Thus, for example, maleic anhydride reacted with the PAO becomes succinic anhydride, and acrylic acid becomes a propionic acid.

Suitable unsaturated acid materials thereof which are useful functional compounds, include acrylic acid, crotonic acid, methacrylic acid, maleic acid, maleic anhydride, fumaric acid, itaconic acid, itaconic anhydride, citraconic acid, citraconic anhydride, mesaconic acid, glutaconic acid, chloromaleic acid, aconitic acid, crotonic acid, methylcrotonic acid, sorbic acid, 3-hexenoic acid, 10-decenoic acid, 2-pentene-1,3,5-tricarboxylic acid, cinnamic acid, and lower alkyl (e.g. $C_1$ to $C_4$ alkyl) acid esters of the foregoing, e.g. methyl maleate, ethyl fumarate, methyl fumarate, etc. Particularly preferred are the unsaturated dicarboxylic acids and their derivatives, especially maleic acid, fumaric acid and maleic anhydride.

Typically, from about 0.7 to about 4.0 (e.g., 0.8 to 2.6), preferably from about 1.0 to about 2.0, and most preferably from about 1.1 to about 1.7 moles of said monounsaturated carboxylic reactant are charged to the reactor per mole of PAO charged.

Functionalization can be achieved by any suitable method. Useful methods include the reaction of an olefinic bond of the PAO with an unsaturated, preferably a mono-unsaturated, carboxylic reactant. Alternatively, the oligomer can be halogenated using chlorine or bromine-containing compounds. The halogenated PAO can then be reacted with the monounsaturated carboxylic acid. The PAO and the monounsaturated carboxylic reactant can also be contacted at elevated temperatures to cause a thermal "ene" reaction to take place. Alternatively, the monounsaturated carboxylic acid can be reacted with the PAO by free radical induced grafting. The PAO of the present disclosure can be functionalized by contact with a hydroxy aromatic compound in the presence of a catalytically effective amount of at least one acidic alkylation catalyst. The alkylated hydroxy aromatic compound can then be further reacted to form a derivative by Mannich Base condensation with an aldehyde and an amine reagent to yield a Mannich Base condensate. In yet another means to functionalize the PAO, the PAO may be contacted with carbon monoxide in the presence of an acid catalyst under Koch reaction conditions to yield the PAO substituted with carboxylic acid groups. In addition to the above methods of functionalization, the PAO of the present disclosure can be functionalized by methods of air oxidation, ozonolysis, hydroformylation, epoxidation and chloroamination. (For more information please see U.S. Pat. No. 6,022,929 Column 21, line 16 to column 33, line 27.)

The polyalpha-olefins produced herein contain one or more unsaturated double bonds, rich in vinylidene content with some 1,2-di-substituted olefins. These unsaturated polymers are particularly suitable for further functionalization reactions. Examples of such functionalization reactants includes alkylation with aromatic compounds, such as benzene, toluene, xylene, naphthalene, anisole, phenol or alkylphenols. The PAO's can also react with maleic anhydride to give PAO-succinic anhydride, which can be further converted with amines or alcohols to corresponding succinimide or succinate esters. These imides and esters are superior dispersants.

The functionalized PAO can in turn be derivatized with a derivatizing compound. (For purposes of this disclosure and the claims thereto the term functionalized PAO encompasses derivatized PAO.) The derivatizing compound can react with the functional groups of the functionalized PAO by means such as nucleophilic substitution, Mannich Base condensation, and the like. The derivatizing compound can be polar and/or contain reactive derivative groups. Preferred derivatizing compounds are selected from hydroxy containing compounds, amines, metal salts, anhydride containing compounds and acetyl halide containing compounds. The derivatizing compounds can comprise at least one nucleophilic group and preferably at least two nucleophilic groups. A typical derivatized PAO is made by contacting a functionalized PAO, i.e., substituted with a carboxylic acid/anhydride or ester, with a nucleophilic reagent, e.g., amine, alcohol, including polyols, amino alcohols, reactive metal compounds and the like. (For more information please see U.S. Pat. No. 6,022,929 column 33, line 27 to column 74, line 63.) Alternately a derivatized PAO may be made by contacting a functionalized PAO, substituted with a carboxylic acid/anhydride or ester, with a nucleophilic reagent, e.g., amine, to make a quaternary ammonium compound or amine oxide.

The functionalized PAO's and/or derivatized PAO's have uses as lubricating additives which can act as dispersants, viscosity index improvers, or multifunctional viscosity index improvers. Additionally they may be used as disinfectants (functionalized amines) and or wetting agents.

The functionalized PAO prepared herein may be used in oil additivation, lubricants, fuels and many other applications. Preferred uses include additives for lubricants and or fuels.

In particular embodiments herein, the PAO's disclosed herein, or functionalized/derivatized analogs thereof, are useful as additives and/or base stocks, preferably in a lubricant.

The functionalized PAO's and/or derivatized PAO's produced herein have uses as lubricating additives which can act as dispersants, viscosity index improvers, or multifunctional viscosity index improvers. Additionally they may be used as disinfectants (functionalized amines) and or wetting agents.

Functionalized PAOs and/or derivatized PAOs having uses as dispersants typically have an Mn of less than 1,000 g/mol, preferably less than 500 g/mol, preferably less than 300 g/mol, and typically can range from 100 g/mol to 500 g/mol, preferably from 200 g/mol to 400 g/mol, preferably from 200 g/mol to 300 g/mol.

The functionalized PAOs and/or derivatized PAOs described herein having Mn's (g/mol) of greater than 100 g/mol, (preferably from 200 to 5000 g/mol, preferably from 300 to 3000 g/mol, preferably 200 to 400 g/mol, preferably 200 to 300 g/mol) are useful for viscosity index improvers for lubricating oil compositions, adhesive additives, anti-fogging and wetting agents, ink and paint adhesion promoters, coatings, tackifiers and sealants, and the like. In addition, such PAOs may be functionalized and derivatized to make multifunctional viscosity index improvers which also possess dispersant properties. (For more information please see U.S. Pat. No. 6,022,929.)

The functionalized PAOs and/or derivatized PAOs described herein may be combined with other additives (such as viscosity index improvers, corrosion inhibitor, oxidation inhibitor, dispersant, lube oil flow improver, detergents, demulsifiers, rust inhibitors, pour point depressant, anti-foaming agents, antiwear agents, seal swellant, friction modifiers, and the like (described for example in U.S. Pat. No. 6,022,929 at columns 60, line 42-column 78, line 54 and the references cited therein) to form compositions for many applications, including but not limited to lube oil additive packages, lube oils, and the like.

Compositions containing these additives are typically blended into a base oil in amounts which are effective to provide their normal attendant function. Representative effective amounts of such additives are illustrated as follows:

| Compositions | (Typical) wt %* | (Preferred) wt %* |
|---|---|---|
| Viscosity Index Improver | 1-12 | 1-4 |
| Corrosion Inhibitor | 0.01-3 | 0.01-1.5 |

-continued

| Compositions | (Typical) wt %* | (Preferred) wt %* |
|---|---|---|
| Oxidation Inhibitor | 0.01-5 | 0.01-1.5 |
| Dispersant | 0.1-10 | 0.1-5 |
| Lube Oil Flow Improver | 0.01-2 | 0.01-1.5 |
| Detergents and Rust inhibitors | 0.01-6 | 0.01-3 |
| Pour Point Depressant | 0.01-1.5 | 0.01-1.5 |
| Anti-Foaming Agents | 0.001-0.1 | 0.001-0.01 |
| Antiwear Agents | 0.001-5 | 0.001-1.5 |
| Seal Swellant | 0.1-8 | 0.1-4 |
| Friction Modifiers | 0.01-3 | 0.01-1.5 |
| Lubricating Base Oil | Balance | Balance |

*Wt %'s are based on active ingredient content of the additive, and/or upon the total weight of any additive-package, or formulation which will be the sum of the A. I. weight of each additive plus the weight of total oil or diluent.

When other additives are employed, it may be desirable, although not necessary, to prepare additive concentrates comprising concentrated solutions or dispersions of the subject additives of this disclosure (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The subject functionalized or derivatized PAOs of the present disclosure can be added to small amounts of base oil or other compatible solvents along with other desirable additives to form additive-packages containing active ingredients in collective amounts of typically from about 2.5 to about 90%, and preferably from about 15 to about 75%, and most preferably from about 25 to about 60% by weight additives in the appropriate proportions with the remainder being base oil.

The final formulations may employ typically about 10 wt % of the additive-package with the remainder being base oil.

In another embodiment, the PAO's described herein can be use in any process, blend or product disclosed in WO 2009/155472 or U.S. Pat. No. 6,022,929, which are incorporated by reference herein.

In a preferred embodiment, this disclosure relates to a fuel comprising any PAO produced herein.

In a preferred embodiment, this disclosure relates to a lubricant comprising any PAO produced herein.

Hydrogenation

Any of polyalphaolefins produced herein can be hydrogenated. In particular the polyalpha-olefin is preferably treated to reduce heteroatom containing compounds to less than 600 ppm, and then contacted with hydrogen and a hydrogenation catalyst to produce a polyalpha-olefin having a bromine number less than 1.8. In a preferred embodiment, the treated polyalpha-olefin comprises 100 ppm of heteroatom containing compounds or less, preferably 10 ppm of heteroatom containing compounds or less. (A heteroatom containing compound is a compound containing at least one atom other than carbon and hydrogen.) Preferably the hydrogenation catalyst is selected from the group consisting of supported Group 7, 8, 9, and 10 metals, preferably the hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports. A preferred hydrogenation catalyst is nickel supported on Kieselguhr, or platinum or palladium supported on alumina, or cobalt-molybdenum supported on alumina. Usually, a high nickel content catalyst, such as 60% Ni on Keiselguhr catalyst is used, or a supported catalyst with high amount of Co—Mo loading. Alternately, the hydrogenation catalyst is nickel supported on Keiselguhr, silica, alumina, clay or silica-alumina.

A polyalpha-olefin is contacted with hydrogen and a hydrogenation catalyst at a temperature from 25 to 350° C., preferably 100 to 300° C. In another preferred embodiment the polyalpha-olefin is contacted with hydrogen and a hydrogenation catalyst for a time period from 5 minutes to 100 hours, preferably from 5 minutes to 24 hours. In another preferred embodiment the polyalpha-olefin is contacted with hydrogen and a hydrogenation catalyst at a hydrogen pressure of from 25 psi to 2,500 psi, preferably from 100 to 2,000 psi. For further information on hydrogenation of PAO's please see U.S. Pat. No. 5,573,657 and Sequeira, A. et al. (1994) "Lubricant Base Oil Hydrogen Refining Processes" *Lubricant Base Oil and Wax Processing*, pp. 119-152.

This hydrogenation process can be accomplished in a slurry reactor in a batch operation or in a continuous stirred tank reactor (CSTR), where the catalyst in 0.001 wt % to 20 wt % of the PAO feed or preferably 0.01 to 10 wt %, hydrogen and the polyalpha-olefins are continuously added to the reactor to allow for certain residence time, usually 5 minutes to 10 hours to allow complete hydrogenation of the unsaturated olefins and to allow proper conversion of the mm diads. The amount of catalyst added is usually very small just to compensate for the catalyst deactivation. The catalyst and hydrogenated PAO are continuously withdrawn from the reactor. The product mixture was then filtered, centrifuged or settled to remove the solid hydrogenation catalyst. The catalyst can be regenerated and reused. The hydrogenated PAO can be used as is or further distilled or fractionated to the right component if necessary. In some cases, when the hydrogenation catalyst show no catalyst deactivation over long term operation, the stir tank hydrogenation process can be carried out in a manner where a fixed amount of catalyst is maintained in the reactor, usually 0.1 wt % to 10% of the total reactant, and only hydrogen and PAO feed are continuously added at certain feed rate and only hydrogenated PAO was withdrawn from the reactor.

The hydrogenation process can also be accomplished by a fixed bed process, in which the solid catalyst is packed inside a tubular reactor and heated to reactor temperature. Hydrogen and PAO feed can be fed through the reactor simultaneously from the top or bottom or counter-currently to maximize the contact between hydrogen, PAO and catalyst and to allow best heat management. The feed rate of the PAO and hydrogen are adjusted to give proper residence to allow complete hydrogenation of the unsaturated olefins in the feed and to allow desirable conversion of mm triads in the process. The hydrogenated PAO fluid can be used as is or further distilled or fractionated to give the right component, if necessary. Usually, the finished hydrocarbon PAO fluids have bromine number less than 2 and have reduced amount of mm triads than the unhydrogenated PAO.

III. Apparatus for Producing PAOs

The present disclosure also includes apparatus for producing a hybrid trimer from a PAO dimer. In conventional processes and apparatus to produce hybrid trimers, and after generation of the PAO dimer in a first oligomerization reactor, the PAO dimer starting material can be enriched by removing impurities, solvents, etc for feed into a second oligomerization reactor. This process typically involves an additional separation operation because feeding the trimer and higher (tetramer+) oligomers to the second oligomerization reactor often produces an undesired heavier product from the second oligomerization reaction.

Alternately, in an example, the process reduces or eliminates the need for a separation stage between a first oligomerization operation and a second oligomerization operation. The inventors have found that by using the metallocene dimer selective catalyst, the olefin distribution produced in the first oligomerization reactor (e.g., the metallocene reactor) contains significant amounts of dimer and very small amounts of trimer and higher oligomers (tetramer+). With that distribution, the inventors have also found that an apparatus for producing hybrid trimers can be designed without separation equipment disposed between the first oligomerization reactor and the second oligomerization reactor (e.g., separation equipment is merely optional) because there is no longer a requirement to separate out the higher molecules. Therefore, processes and configurations described herein can greatly simplify PAO processing while maintaining high yields of desired PAO products, such as low viscosity PAO trimers or "hybrid trimers".

An apparatus and processes, containing a separations step between the first and second reactors useful herein for the production of low viscosity PAO using metallocene technology is shown in FIG. 1. As shown in FIG. 1, the apparatus and processes requires a monomer/dimer separation operation after forming the PAO dimer in the first oligomerization reactor.

With reference to FIG. 1, the apparatus includes a feed line 102 (LAO feed 1) for directing alpha-olefin monomer into a first oligomerization reactor 104 to form a first oligomerization reactor effluent. The first oligomerization reactor effluent of line 106 is transferred to an optional separation stage 108 (e.g., a first distillation unit) to remove PAO trimers, tetramers, and higher oligomers (tetramer+), solvents, impurities, etc.) from the first oligomerization reactor effluent. Separation stage 108 can include a preheater, distillation column, vacuum system, overhead condenser, overhead accumulator, reflux pump, reboiler, and/or bottoms pump. The monomer/dimer is removed as a first tops fraction via a line 110 and is then transferred to a second oligomerization reactor 116 where it can combine with another alpha-olefin monomer of line 114 (LAO feed 2) and undergo a second oligomerization, by, e.g., a $BF_3$-mediated process, to form a second oligomerization reactor effluent. A first bottoms fraction of line 112 can also be separated. The second oligomerization reactor effluent flows to a second distillation unit 120 via line 118 where byproducts and/or contaminants can be separated from the second reactor effluent. The byproducts and/or contaminants may be removed as a second tops fraction via a line 122 and recycled back to second reactor 116 or purged from the process via line 124. The second bottoms fraction, including PAO dimer, trimer, tetramer, and higher oligomers, is then transferred to a hydrogenation unit 128 via line 126. The first bottoms fraction in line 112 (containing, e.g., PAO trimer, tetramer and heavier oligomers) can also combine with second bottoms fraction and flow into the hydrogenation unit 128. The hydrogenation effluent can be transferred, via line 130, to the third distillation unit 132 where PAO dimer is separated from the other components of the hydrogenation effluent such as trimers, tetramers, and higher oligomers. The dimers are removed as a third tops fraction from the third reactor effluent via a line 134. The bottoms fraction from the third distillation unit 132 is transferred to a fourth distillation unit 138 via a line 136, where PAO trimer is partially separated from other components of the third distillation effluent. The PAO trimer can be removed as a third tops fraction from the fourth distillation unit 138 via line 140, and a fourth distillation effluent that includes trimers, tetramers, and higher oligomers can be removed from the fourth distillation unit 138 via line 142.

In at least one embodiment, the separation stage is any suitable separation device such as one that separates a lighter component from a heavier component, such as a flash drum(s), multiple flash stages in series, atmospheric distillation column(s), vacuum distillation column(s), stripper(s), steam stripper(s), nitrogen stripper(s), membrane separation(s), chromatography column(s), and/or crystallization(s).

In at least one embodiment the effluent from first reactor is subjected to a separations means (such as a flash drum(s), multiple flash stages in series, atmospheric distillation column(s), vacuum distillation column(s), stripper(s), steam stripper(s), nitrogen stripper(s), membrane separation(s), chromatography column(s), and/or crystallization(s)) to remove higher PAO (oligomers having a degree of polymerization of three or higher) before entering the second reactor.

The metallocene technology used in the apparatus described above involves a separation stage (shown as 108, et sec.) between the first oligomerization and second oligomerization. However, as discussed below, the separation stage can be eliminated without substantially reducing the yield of desired PAO trimer, as compared to the above apparatus.

Figure 2:
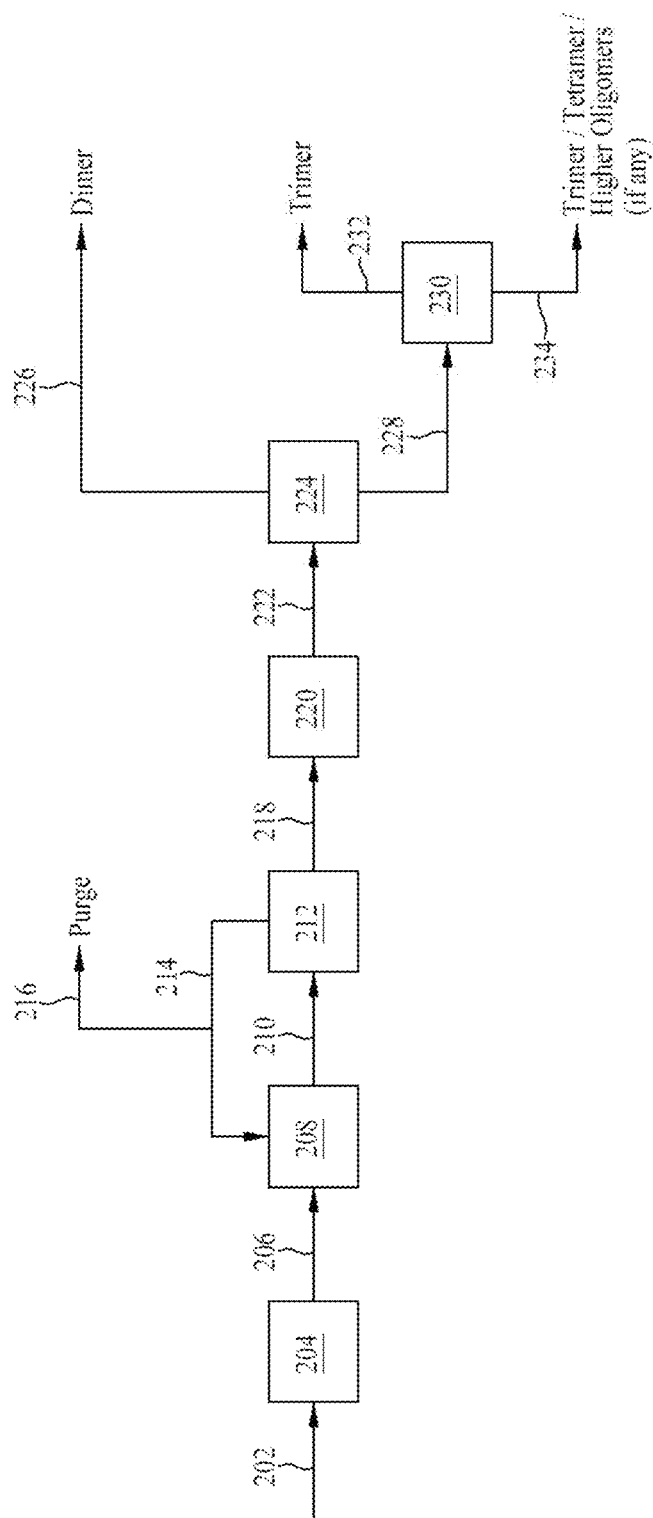
FIG. 2 is an example apparatus for forming poly alpha-olefins according to at least one embodiment, where a separations step is not included between the first and second reactors.

FIG. 2 is a diagram illustrating an apparatus for carrying out certain aspects of the present disclosure according to at least one embodiment. More generally, a configuration shown in FIG. 2 or similar to FIG. 2 can be used for forming poly alpha-olefins of the present disclosure. FIG. 2 is a non-limiting example of a configuration.

As shown in FIG. 2, an apparatus can include a feed line 202 (LAO feed 1) coupled with a first reactor 204 (e.g., an oligomerization reactor). During use, a feed of the feed line 202 can include an alpha-olefin. The first reactor 204 can be coupled (e.g., directly) with a second reactor 208 (e.g., an oligomerization reactor) via a line 206. A first reactor effluent (e.g., intermediate PAO) of the line 206 can be transferred to the second reactor 208 where the first reactor effluent can undergo a second oligomerization, by, e.g., a $BF_3$-mediated process, to form a second reactor effluent. The second reactor 208 can be coupled to a first distillation unit 212 via a line 210. The second reactor effluent (including the hybrid trimer) can be transferred to the first distillation unit 212 where byproducts and/or contaminants, such as monomer and catalyst components can be separated from the second reactor effluent. The byproducts and/or contaminants may be removed as a first tops fraction via a line 214 and recycled back to second reactor 208 or purged from the process via line 216. The first distillation unit 212 can be further coupled to a third reactor (e.g., a hydrogenation unit) 220. The first distillation effluent (including PAO trimer) of a line 218 can be transferred to the hydrogenation unit 220. The first distillation effluent may further include dimers, tetramers and higher oligomers (if any). The hydrogenation unit 220 can be coupled to a second distillation unit 224 via a line 222. The hydrogenation effluent can be transferred to the second distillation unit 224 where PAO dimer can be separated from the other components of the hydrogenation effluent such as trimers, tetramers, and higher oligomers (if any). The dimers may be removed as a second tops fraction from the hydrogenation effluent via a line 226. Optionally, the second distillation unit 224 can be further coupled to a third distillation unit 230 via a line 228. A second distillation effluent that includes trimers, tetramer, and higher oligomers (if any) can be transferred to the third distillation unit 230 where PAO trimer can be partially separated from other components of the second distillation effluent. The PAO trimer can be removed as a third tops fraction from the third distillation unit 230 via line 232, and a third distillation effluent (e.g., a low viscosity PAO effluent) that includes trimers, tetramers, and higher oligomers (if any) can be removed from the third distillation unit 230 via line 234.

In at least one embodiment, the line 206 can be free of a separation stage, e.g., any suitable separation device such as one that separates a lighter component from a heavier component, such as a flash drum(s), multiple flash stages in series, atmospheric distillation column(s), vacuum distillation column(s), stripper(s), steam stripper(s), nitrogen stripper(s), membrane separation(s), chromatography column(s), and/or crystallization(s).

In some embodiments, one or more additional apparatus components are disposed between the first reactor and the second reactor. For example, one or more heat exchangers or mixers is disposed between the first reactor and the second reactor.

In at least one embodiment, the third tops fraction or a portion of the third tops fraction can have a KV (100° C.) of 4 cSt or less, such as less than about 3.6 cSt.

In at least one embodiment, the third tops fraction or a portion of the third tops fraction has a KV (100° C.) between 3.4 and 4.0 and a Noack volatility (y) that does not exceed the value defined by the following equation, where x is the kinematic viscosity at 100° C.:

$$y=-21.0x^2+148.7x-248.9$$

In at least one embodiment, the third distillation effluent or a portion of the third distillation effluent can have a KV (100° C.) of from about 4 cSt to about 10 cSt, such as from about 5 cSt to about 7 cSt.

In at least one embodiment, the third distillation is performed such that at the bottoms stream consists of at least 5 wt % trimer, such as from 5 wt % trimer to 40 wt % trimer, such as from 10 wt % trimer to 30 wt % trimer, such as from 15 wt % trimer to 25 wt % trimer.

In at least one embodiment, the first oligomerization can utilize the metallocene dimer catalysts and the metallocene dimer selective processes discussed in Section I, and the first oligomerization can form the products discussed in Section I. In at least one embodiment, the second oligomerization can utilize the catalysts and processes for producing PAO trimers (hybrid trimers) discussed in Section II, and can form the products discussed in Section II.

IV. The First Oligomerization Reaction

In some embodiments according to the present disclosure, a process for making a poly alpha-olefin can include contacting a feed containing a $C_4$-$C_{32}$ (such as $C_6$-$C_{32}$) alpha-olefin and optional ethylene with a catalyst system comprising a metallocene compound in a polymerization reactor under polymerization conditions to effect a polymerization reaction to obtain a product, wherein the metallocene compound is represented by a metallocene compound described herein.

In some embodiments of the process, the polymerization reaction exhibits a selectivity toward a combination of greater than or equal to about 93 mol % vinylidenes, from 0.5 mol % to 3.5 mol % tri-substituted vinylenes, less than or equal to about 1.5 mol % di-substituted vinylenes, and less than or equal to about 1.5 mol % vinyls, based on total moles of vinyls, vinylidenes, di-substituted vinylenes, and tri-substituted vinylenes in the first reactor effluent.

In some embodiments of the process, the polymerization reaction exhibits a selectivity toward a combination of vinylidenes of equal to or greater than 94.0 mol %, such as equal to or greater than 5 mol %; tri-substituted vinylenes of less than 2.1 mol %; di-substituted vinylenes of 0.5 mol % or less; and vinyls of 1.0 mol % or less, based on total moles of vinyls, vinylidenes, di-substituted vinylenes, and tri-substituted vinylenes in the first reactor effluent. In some embodiments of the process, the polymerization reaction exhibits a selectivity towards a combination of vinylidenes and tri-substituted vinylenes of collectively greater than 98.0 mol %, such as greater than 98.5 mol %, and a combination of di-substituted vinylenes and vinyls of collectively less than 2.0 mol %, such as less than 1.5 mol %, based on total moles of vinyls, vinylidenes, di-substituted vinylenes, and tri-substituted vinylenes in the first reactor effluent.

In some embodiments of the process the polymerization reaction results in the first reactor effluent have a number average molecular weight (Mn) of 5,000 g/mol or less, such as 1500 g/mol or less, such as from 300 to 3000 g/mol, such as from 300 to 800 g/mol, as measured by $^1$H NMR.

In some embodiments of the process, the polymerization conditions comprise a reaction temperature from 40° C. to 150° C.; an average activity level of at least 1200 g/s·mol; the product exhibits an oligomer yield of at least 10%; or a combination thereof.

In some embodiments of the process, the feed (such as the feed to the first or second polymerization) comprises $C_6$-$C_{24}$ alpha-olefin; and any combination of $C_2$-$C_5$ alpha-olefins are collectively present in the alpha-olefin feed at no higher than 25 mol %, based on the total moles of the alpha-olefins supplied to the polymerization reactor, such as wherein the alpha-olefin feed is substantially free of ethylene, propylene, $C_4$ alpha-olefins, and $C_5$ alpha-olefins; or a combination thereof. In some embodiments, the alpha-olefin feed is substantially free (or absent, 0 mol %) of propylene, $C_4$ alpha-olefins, and $C_5$ alpha-olefins; or a combination thereof and optionally comprises less than 25 mol % ethylene, such as less than 15 mol %, such as less than 5 mol %.

In embodiments of the present disclosure, an unsaturated poly alpha-olefin product comprises greater than or equal to about 80 mol % vinylidenes, such as 90 mol % vinylidenes, such as 93 mol % vinylidenes, based on total moles of vinyls, vinylidenes, di-substituted vinylenes, and tri-substituted vinylenes contained therein. In some embodiments, the unsaturated poly alpha-olefin product comprises 93 mol % to 99.9 mol % of vinylidenes; 0.1 mol % to 3.5 mol % of tri-substituted vinylenes; 3.0 mol % or less of di-substituted vinylenes; 3.0 mol % or less of vinyl groups; based on total moles of vinylidenes, tri-substituted vinylenes, di-substituted vinylenes, and vinylidenes contained therein; and a number average molecular weight (Mn) of 1500 g/mol or less as measured by $^1$H NMR.

In some embodiments, the unsaturated poly alpha-olefin product comprises less than or equal to about 1.0 mol % di-substituted vinylenes, when present; less than or equal to about 1.0 mol % vinyl groups when present; and a number average molecular weight (Mn) of 1000 g/mol or less as measured by $^1$H NMR.

In embodiments of the present disclosure, a catalyst compound suitable to produce a first reactor effluent from $C_6$-$C_{32}$ alpha-olefin under polymerization conditions comprises a polymerization selectivity suitable to form a first reactor effluent comprising greater than or equal to about 80 mol % vinylidenes, such as 90 mol % vinylidenes, such as 93 mol % vinylidenes, based on total moles of vinyls, vinylidenes, di-substituted vinylenes, and tri-substituted vinylenes in the first reactor effluent.

In some embodiments, the catalyst compound comprises a polymerization selectivity suitable to form a first reactor effluent comprising 93 mol % to 99.9 mol % of vinylidenes; 0.1 mol % to 7 mol % of tri-substituted vinylenes; 2.0 mol % or less of di-substituted vinylenes; 2.0 mol % or less of vinyl groups; based on total moles of vinyls, vinylidenes, di-substituted vinylenes, and tri-substituted vinylenes in the first reactor effluent; and a number average molecular weight (Mn) of 1500 g/mol or less as measured by $^1$H NMR.

In some embodiments, the catalyst compound comprises a polymerization selectivity suitable to form a first reactor effluent comprising: greater than or equal to about 93 mol % vinylidenes; less than or equal to about 7 mol % tri-substituted vinylenes; less than or equal to about 1.0 mol % di-substituted vinylenes, when present; less than or equal to about 1.0 mol % vinyl groups when present; based on total moles of vinyls, vinylidenes, di-substituted vinylenes, and tri-substituted vinylenes in the first reactor effluent; and a number average molecular weight (Mn) of 1500 g/mol or less as measured by $^1$H NMR.

IV.A First Reactor Effluent

The first reactor effluent includes PAOs. PAOs are polymeric, typically oligomeric, molecules produced from the polymerization reactions of alpha-olefin monomer molecules in the presence of a catalyst system. An unsaturated poly alpha-olefin molecule in the material of the present disclosure contains a C=C bond therein. Each PAO molecule of the first reactor effluent has a carbon chain with the largest number of carbon atoms, which is designated the carbon backbone of the molecule. Any non-hydrogen group attached to the carbon backbone other than to the carbon atoms at the very ends thereof is defined as a pendant group. The number of carbon atoms in the longest carbon chain in each pendant group is defined as the length of the pendant group. The backbone typically comprises the carbon atoms derived from the C=C bonds in the monomer molecules participating in the polymerization reactions, and additional carbon atoms from monomer molecules and/or molecules in the catalyst system that form the two ends of the backbone. A typical PAO molecule of the first reactor effluent can be represented by the following formula (F-1):

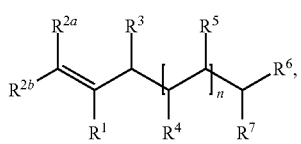

where $R^1$, $R^{2a}$, $R^{2b}$, $R^3$, each of $R^4$ and $R^5$, $R^6$, and $R^7$, the same or different at each occurrence, independently represents a hydrogen or a substituted or unsubstituted hydrocarbyl (such as an alkyl) group, and n is a non-negative integer corresponding to the degree of polymerization. Where $R^1$, $R^{2a}$ and $R^{2b}$ are all hydrogen, (F-1) represents a vinyl PAO; where $R^1$ is not hydrogen, and both $R^{2a}$ and $R^{2b}$ are hydrogen, (F-1) represents a vinylidene PAO; where $R^1$ is hydrogen, and only one of $R^{2a}$ and $R^{2b}$ is hydrogen, (F-1) represents a di-substituted vinylene PAO; and where $R^1$ is not hydrogen, and only one of $R^{2a}$ and $R^{2b}$ is hydrogen, then (F-1) represents a tri-substituted vinylene PAO.

Where n=0, (F-1) represents an PAO dimer produced from the reaction of two monomer molecules after a single addition reaction between two C=C bonds.

Where n=m, m being a positive integer, (F-1) represents a molecule produced from the reactions of m+2 monomer molecules after m+1 steps of linear addition reactions between two C=C bonds.

Thus, where n=1, (F-1) represents a trimer produced from the reactions of three monomer molecules after two steps of linear addition reactions between two C=C bonds.

Assuming a carbon chain starting from $R^1$ and ending with $R^7$ has the largest number of carbon atoms among all straight carbon chains existing in (F-1), that carbon chain starting from $R^1$ and ending with $R^7$ having the largest number of carbon atoms constitutes the carbon backbone of the first reactor effluent molecule (F-1). $R^2$, $R^3$, each of $R^4$ and $R^5$, and $R^6$, which can be substituted or unsubstituted hydrocarbyl (such as alkyl) groups, are pendant groups (if not hydrogen).

If only alpha-olefin monomers are used in the polymerization process, and no isomerization of the monomers and oligomers ever occurs in the reaction system during polymerization, about half, typically at least one more than half, of $R^1$, $R^{2a}$, $R^{2b}$, $R^3$, all $R^4$ and $R^5$, $R^6$, and $R^7$ would be hydrogen, and one of $R^1$, $R^{2a}$, $R^{2b}$, $R^6$, and $R^7$ would be a hydrocarbyl, such as methyl, and about half, typically less than half, of groups $R^1$, $R^{2a}$, $R^{2b}$, $R^3$, all $R^4$ and $R^5$, $R^6$, and $R^7$ would be hydrocarbyl groups introduced from the alpha-olefin monomer molecules. In a specific example of such case, assuming $R^{2a}$ and $R^{2b}$ are hydrogen, $R^3$, all $R^5$, and $R^6$ are hydrogen, and $R^1$, all $R^4$, and $R^7$ have 8 carbon atoms in the longest carbon chains contained therein, and n=8, then the carbon backbone of the (F-1) PAO molecule would comprise 35 carbon atoms, and the average pendant group length of the pendant groups (the initial =$CR^{2a}R^{2b}$ group, and all of $R^4$) would be 7.22 (i.e., (1+8*8)/9). Such an PAO molecule, which may be produced by polymerizing 1-decene using certain metallocene catalyst systems, such as described in greater detail below, can be represented by formula (F-2) below:

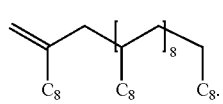

In such a molecule, the longest 5%, 10%, 20%, 40%, 50%, and 100% of the pendant groups have average pendant group length of Lpg(5%) of 8, Lpg(10%) of 8, Lpg(20%) of 8, Lpg(50%) of 8, and Lpg(100%) of 7.22, respectively.

Depending on the polymerization catalyst system used, however, different degrees of isomerization of the monomers and/or oligomers can occur in the reaction system during the polymerization process, resulting in different degrees of substitution on the carbon backbone. In a specific example of such case, assuming $R^{2a}$ and $R^{2b}$ are both hydrogen, $R^3$ and all $R^5$ are methyl, $R^6$ is hydrogen, $R^1$ has 8 carbon atoms in the longest carbon chain contained therein, all $R^4$ and $R^7$ have 7 carbon atoms in the longest carbon chain contained therein, and n=8, then the carbon backbone of the (F-1) PAO molecule would comprise 34 carbon atoms, and the average pendant group length of the pendant groups (the initial =$CR^{2a}R^{2b}$ group, all $R^4$, and $R^5$) would be 3.7 (i.e., (1+1+7*8+8*1)/18). Such a PAO molecule, which may be produced by polymerizing either 1-decene, with a given level and pattern of isomerization, or by polymerizing a combination of 1-decene and 2-decene, using certain non-metallocene catalyst systems, such as described in greater detail below, can be represented by the following formula (F-3):

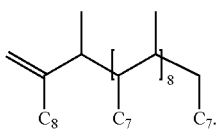

(F-3)

In this molecule, the longest 5%, 10%, 20%, 40%, 50%, and 100% of the pendant groups have average pendant group lengths of Lpg(5%) of 7, Lpg(10%) of 7, Lpg(20%) of 7, Lpg(50%) of 6.3, and Lpg(100%) of 3.7, respectively.

One skilled in the art, with knowledge of the molecular structure or the monomer(s) used in the polymerization step for making the first reactor effluent, the process conditions (catalyst used, reaction conditions, etc.), and the polymerization reaction mechanism, inter alia, can approximate the molecular structure of the PAO molecules, thus the pendant groups attached to the carbon backbone, and hence approximate values of Lpg(5%), Lpg(10%), Lpg(20%), Lpg(50%), and Lpg(100%), respectively.

One skilled in the art can determine the Lpg(5%), Lpg(10%), Lpg(20%), Lpg(50%), and Lpg(100%) values of a given first reactor effluent by using separation and characterization techniques available to polymer chemists. For example, gas chromatography/mass spectroscopy machines equipped with boiling point column separator can be used to separate and identify individual chemical species and fractions; and standard characterization methods such as NMR, IR, and UV spectroscopy can be used to further confirm the structures.

The first reactor effluent of the present disclosure may be a homopolymer made from a single alpha-olefin monomer or a copolymer made from a combination of two or more alpha-olefin monomers. In some embodiments, the alpha-olefin monomer(s) can include, consist essentially of, or be 1-hexene, 1-octene, 1-decene, 1-dodecene, or a combination thereof, such as 1-octene, 1-decene, and 1-dodecene.

The first reactor effluent of the present disclosure may be produced by using a catalyst system comprising a specific type of metallocene compound, such as described in detail below. The first reactor effluent can be substantially free of the alpha-olefin monomer(s), and may advantageously contain vinylidenes at a high concentration, such as in the range from c1 to c2 mol % in total, where c1 and c2 can be, independently, about 80, about 85, about 90, about 91, about 92, about 93, about 94, about 95, about 96, about 96.5, about 97, about 98, about 99, about 99.5, or about 99.9, based on the total moles of vinyls, vinylidenes, di-substituted vinylenes, and tri-substituted vinylenes, as long as c1<c2. In some embodiments, c1=90 and c2=99; c1=91 and c2=99; c1=92 and c2=98; c1=93 and c2=97; c1=96.5 and c2=99.9; or c1=98 and c2=99.5. Without intending to be bound by a particular theory, it is believed that the high concentrations of vinylidenes can be achieved partly by the unique structure of the metallocene compound used in the catalyst system.

Between the vinylidenes and tri-substituted vinylenes in the first reactor effluent of the present disclosure, tri-substituted vinylenes tend to have a considerably lower concentration than the vinylidenes. In some embodiments, the first reactor effluent of the present disclosure can contain a concentration of tri-substituted vinylenes in the range from c3 to c4 mol %, based on the total moles of the vinyls, vinylidenes, di-substituted vinylenes, and tri-substituted vinylenes, where c3 and c4 can be, independently, about 0, about 0.1, about 0.5, about 1.0, about 1.5, about 2.0, about 2.5, about 3.0, about 3.5, about 4.0, about 4.5, about 5.0, about 5.5 or about 6.0, as long as c3<c4. In some embodiments, c3=0.5 and c4=5.5; c3=1.0 and c4=5.0; c3=0.5 and c4=4.0; c3=0 and c4=4.0; c3=0.1 and c4=3.5; or c3=0.5 and c4=2.

In some embodiments, the first reactor effluent of the present disclosure can contain a high combined concentration of vinylidenes and tri-substituted vinylenes, the combined concentration being in the range from c5 to c6 mol %, based on the total moles of the vinyls, vinylidenes, di-substituted vinylenes, and tri-substituted vinylenes, where c5 and c6 can be, independently, about 85, about 90, about 91, about 92, about 93, about 94, about 95, about 96, about 97, about 98, about 99, or about 99.5, based on the total moles of vinyls, vinylidenes, di-substituted vinylenes, and tri-substituted vinylenes, as long as c5<c6. In some embodiments, c5=90 and c6=99.5; c5=92 and c6=99.5; c5=94 and c6=99; c5=95 and c6=99; or c5=98 and c6=99.5.

The first reactor effluent of the present disclosure can contain di-substituted vinylenes at a low concentration in the range from c7 to c8 mol %, based on the total moles of vinyls, vinylidenes, di-substituted vinylenes, and tri-substituted vinylenes, where c7 and c8 can be about 0, about 0.1, about 0.2, about 0.3, about 0.4, about 0.5, about 0.6, about 0.7, about 0.8, about 1.0, about 1.2, about 1.4, about 1.6, about 1.8, about 2.0, about 2.5, about 3.0, about 3.5, about 4.0, about 4.5, or about 5.0, as long as c7<c8. In some embodiments, c7=0 and c8=4.0; c7=0 and c8=3.0; c7=0 and c8=2.0; c7=0 and c8=1; c7=0 and c8=1.2; or c7=0.1 and c8=2.5. Without intending to be bound by a particular theory, it is believed that such low concentrations of di-substituted vinylenes in the first reactor effluent are achieved by the low selectivity toward these olefins in the polymerization reactions, which can be provided at least partially by the unique structure of the metallocene compound in the catalyst system used in the polymerization reaction.

Depending on the metallocene compound used in the catalyst system, the first reactor effluent of the present disclosure can contain vinyls at a low concentration, e.g., from c9 to c10 mol %, based on the total moles of vinyls, vinylidenes, di-substituted vinylenes, and tri-substituted vinylenes, where c9 and c10 can be about 0, about 0.1, about 0.2, about 0.3, about 0.4, about 0.5, about 0.6, about 0.7, about 0.8, about 1.0, about 1.2, about 1.4, about 1.6, about 1.8, about 2.0, about 2.5, about 3.0, about 3.5, about 4.0, about 4.5, or about 5.0, as long as c9<c10. In some embodiments, c9=0 and c10=4.0; c9=0 and c10=3.0; c9=0 and c10=2; c9=0 and c10=1.6; c9=0 and c10=1.0; or c9=0.1 and c10=1.2. Without intending to be bound by a particular theory, it is believed that such low concentration of vinyls in the first reactor effluent are achieved by the low selectivity toward vinyls in the polymerization reactions, which can be provided by choosing the molecular structure of the metallocene compound in the catalyst system used in the polymerization reaction.

In some embodiments, the first reactor effluent of the present disclosure can contain a low combined concentration of vinyls and di-substituted vinylenes, the combined concentration being in the range from c11 to c12 mol %, based on the total moles of the vinyls, vinylidenes, di-substituted vinylenes, and tri-substituted vinylenes, where c1 and c12 can be, independently, about 0, about 0.1, about 0.2, about 0.3, about 0.4, about 0.5, about 0.6, about 0.7, about 0.8, about 1.0, about 1.2, about 1.4, about 1.6, about 1.8, about 2.0, about 2.5, about 3.0, about 3.5, about 4.0, about 4.5, about 5.0, about 5.5, or 6.0, as long as c11<c12. In some embodiments, c11=0 and c12=5.0; c11=0 and c12=4.0; c11=0.5 and c12=2; c11=0.5 and c12=4.5; or c11=0.8 and c12=5.0.

Thus, the first reactor effluent of the present disclosure can typically comprise a plurality of PAO molecules, which may be the same or different. Each PAO molecule of the first reactor effluent can comprise a plurality of pendant groups, which may be the same or different, and the longest about 5%, about 10%, about 20%, about 40%, about 50%, and about 100% of the pendant groups of all of the olefin molecules of the first reactor effluent have an average pendent group length of Lpg(5%), Lpg(10%), Lpg(20%), Lpg(40%), Lpg(50%), and Lpg(100%), respectively. In some embodiments, at least one of the following conditions are met:

(i) a1≤Lpg(5%)≤a2, where a1 and a2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0 15.5, or 16.0, as long as a1<a2;

(ii) b1≤Lpg(10%)<b2, where b1 and b2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as b1<b2;

(iii) c1≤Lpg(20%)<c2, where c and c2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as c1<c2;

(iv) d1≤Lpg(40%)<d2; where d1 and d2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as d1<d2;

(v) e1≤Lpg (50%)<e2; where e1 and e2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, or 14.0, as long as e1<e2; and (vi) f1≤Lpg(100%)<f2, where f1 and f2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, or 13.0, as long as f1<f2.

In some embodiments, at least about 60% of the pendent groups on olefin molecules in the first reactor effluent are straight chain alkyls having at least 4 (e.g., at least 6, at least 8, or at least 10) carbon atoms. In some embodiments, at least 90% of the pendent groups on the olefin molecules in the first reactor effluent are straight chain alkyls having at least 4 (e.g., at least 6, at least 8, or at least 10) carbon atoms.

The first reactor effluent of the present disclosure may have various levels of regio-regularity. For example, each PAO molecule of the first reactor effluent may be substantially atactic, isotactic, or syndiotactic. A category of metallocene compounds can lack $C_1$, $C_2$, and $C_s$ symmetry. Without intending to be bound by a particular theory, it is believed that PAO materials made by using such asymmetrical metallocene-based catalyst system can tend to be atactic.

The first reactor effluent of the present disclosure can have viscosity varying in a broad range. For example, the first reactor effluent may have a KV100 in a range from about 1 to about 5000 cSt, such as about 1 to about 3000 cSt, about 2 to about 2000 cSt, about 2 to about 1000 cSt, about 2 to about 800 cSt, about 2 to about 600 cSt, about 2 to about 500 cSt, about 2 to about 400 cSt, about 2 to about 300 cSt, about 2 to about 200 cSt, or about 5 to about 100 cSt. The exact viscosity of the first reactor effluent can be controlled by, e.g., monomer used, polymerization temperature, polymerization reactor residence time, catalyst used, concentration of catalyst used, distillation and separation conditions, and mixing multiple first reactor effluent with different viscosity.

In addition, the first reactor effluent of the present disclosure advantageously have a low polydispersity index (PDI) in the range from about 1.0 to about 5.0 (e.g., from about 1.2 to about 4.0, from about 1.3 to about 3.0, from about 1.4 to about 2.5, from about 1.5 to about 2.0, or from about 1.6 to about 1.8). A narrow molecular weight distribution of the PAO molecules of the first reactor effluent can be achieved by using metallocene-compound-based catalyst systems in the polymerization step under controlled polymerization conditions (temperature fluctuation, residence time, and the like). Such narrow PDI can be desirable in that it defines a material with a high degree of homogeneity in molecular weight, molecular size, rheology behavior, viscosity index, and degrading behavior (such as shear stability and oxidation stability).

In general, the product in the first reactor effluent of the present disclosure can have an average molecular weight that can vary widely (and correspondingly, a KV100 that can vary widely). In some embodiments, the product of the first reactor effluent can have a number average molecular weight of Mn, where Mn1≤Mn≤Mn2, where Mn1 and Mn2 can be, independently, about 150, about 200, about 300, about 400, about 500, about 600, about 700, about 800, about 900, about 1000, about 1100, about 1200, about 1300, about 1400, about 1500, about 1700, about 2000, about 2500, about 3000, about 3500, about 4000, about 4500, about 5000, about 6000, about 7000, about 8,000, about 9000, or about 10000 g/mol, as long as Mn1<Mn2. In some embodiments, the product of the first reactor effluent can have a number average molecular weight of about 3000 g/mol or less, e.g., about 2500 g/mol or less, about 2000 g/mol or less, about 1700 g/mol or less, about 1500 g/mol or less, about 1400 g/mol or less, about 1300 g/mol or less, about 1200 g/mol or less, about 1100 g/mol or less, about 1000 g/mol or less, about 900 g/mol or less, about 800 g/mol or less, about 700 g/mol or less, about 650 g/mol or less, about 620 g/mol or less, about 600 g/mol or less, about 520 g/mol or less, about 500 g/mol or less, about 400 g/mol or less, about 380 g/mol or less, about 370 g/mol or less, about 360 g/mol or less, about 350 g/mol or less, about 340 g/mol or less, about 330 g/mol or less, or about 320 g/mol or less; typically, as the product can exclude olefin monomers but may include dimers and higher mers, the number average molecular weight can optionally be at least about 100 g/mol, e.g., at least about 150 g/mol or at least about 200 g/mol, depending upon the molecular weight of a monomeric feed olefin component.

In general, it can be desired that the first reactor effluent of the present disclosure has a bromine number in a range from Nb(PAO)1 to Nb(PAO)2, where Nb(PAO)1 and Nb(PAO)2 can be, independently, 1.0, 1.5, 2.0, 2.5, 3.0, 3.5, 4.0, 4.5, 5.0, 6.0, 7.0, 8.0, 9.0, or even 10.0, 15.0, 10.0, as long as Nb(PAO)1<Nb(PAO)2. In some embodiments, a great majority, such as at least about 80, about 85, about 90, about 95, about 98, or even about 99 mol % of the molecules in the first reactor effluent of the present disclosure may be unsaturated.

Because of the presence of the C=C bonds in the PAO molecules in the first reactor effluent, when exposed to 02 molecules (such as when exposed to air), the first reactor effluent can be oxidized if not protected by a more reactive material toward $O_2$. To that end, in the first reactor effluent, anti-oxidant materials may be added to prolong shelf life and facilitate handling, storage, and transportation thereof. Non-limiting examples of such anti-oxidants and the use quantity thereof are given in paragraphs [0101]-[0108], pages 9 and 10 of US Patent Publication No. 2010/0087349, the content of which is hereby incorporated by reference in its entirety.

IV.B the Catalyst System of the First Oligomerization

In embodiments, the catalyst system of the first oligomerization comprises a catalyst compound, such as a metallocene compound which is activated by one or more activators (preferably a non-coordinating anion activator). The catalyst system may further include a solvent, a support, one or more scavengers, accelerators, and/or the like.

Preferably, the catalyst system useful in the first oligomerization comprises an unsymmetric metallocene catalyst compound activated by one or more non-aromatic-hydrocarbon soluble activators, and may further include a solvent, a support, one or more scavengers, and/or the like.

The typical activator-to-catalyst ratio, e.g., all non-coordinating anion (NCA) activators-to-catalyst ratio is about a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

Solvents useful for combining the catalyst compound and activator and/or for introducing the catalyst system into the reactor, include, but are not limited to, aliphatic solvents, such as butanes, pentanes, hexanes, heptanes, octanes, nonanes, decanes, undecanes, dodecanes, tridecanes, tetradecanes, pentadecanes, hexadecanes, or a combination thereof; preferable solvents can include normal paraffins (such as NORPAR™ solvents available from ExxonMobil Chemical Company in Houston, Tex.), isoparaffin solvents (such as ISOPAR™ solvents available from ExxonMobil Chemical Company in Houston, Tex.), and combinations thereof. These solvents or diluents may typically be pretreated in same manners as the feed olefins.

Preferably the solvent is selected from $C_4$ to $C_{10}$ linear, branched or cyclic alkanes.

Preferably the solvent is essentially free of all aromatic solvents.

Preferably the solvent is essentially free of toluene.

Preferably the solvent is selected from one or more $C_6$ to $C_{32}$ alpha olefins, such as one or more C to $C_{16}$ alpha olefins.

Preferably the solvent is essentially free of all non-alpha-olefin solvents.

Particularly useful aliphatic hydrocarbon solvent can be isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In at least one embodiment, aromatics are present in the solvent at less than 1 wt %, such as less than 0.5 wt %, such as at 0 wt % based upon the weight of the solvents.

The activators of the present disclosure can be dissolved in one or more additional solvents provided such solvents are non-aromatic. Additional solvent includes halogenated or partially halogenated hydrocarbons solvents.

In at least one embodiment, the aliphatic solvent is isohexane and/or methylcyclohexane.

In at least one embodiment, the solvent is one or more $C_6$ to $C_{32}$ alpha olefins, such as one or more $C_8$ to $C_{16}$ alpha olefins, and no additional solvents are used.

In at least one embodiment, the solvent is 1-octene, 1-decene, 1-dodecene, or 1-tetradecene, or a combination of any two or more.

IV.B.1 The Metallocene Compound of the First Oligomerization

The initial part to a catalyst system of the first oligomerization described herein is a metallocene compound.

Metallocene compounds that are useful herein are preferably unsymmetrical, e.g., having two T-bound cyclopentadienyl moieties that differ by ring type, such as by having one monocyclic arenyl ligand and one polycyclic arenyl ligand. Unsymmetrical metallocene compounds useful herein included those represented by formula (I):

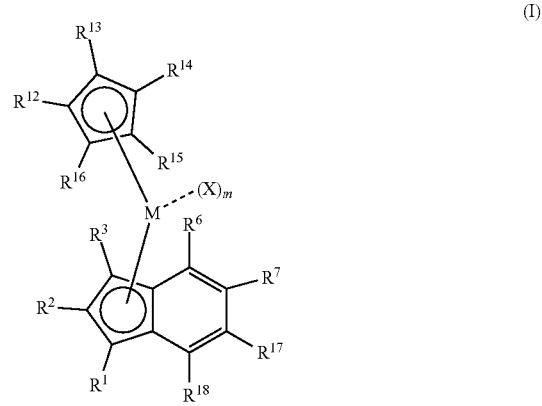

wherein:

each $R^1$, $R^2$, and $R^3$ is, independently, hydrogen or a substituted or unsubstituted linear, branched, or cyclic $C_1$-$C_{20}$ hydrocarbyl group, preferably wherein at least one of $R^1$, $R^2$, and $R^3$ not hydrogen and at least one of $R^1$, $R^2$, and $R^3$ is hydrogen;

$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$, and $R^{15}$, are each independently a substituted or unsubstituted linear, branched, or cyclic $C_1$-$C_{20}$ hydrocarbyl group;

$R^{16}$ is a substituted or unsubstituted linear, branched, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a transition metal, preferably group 3, 4 or 5, having an integer coordination number of v, such as 3, 4, or 5; and m is an integer equal to v-2, such as 1, 2, or 3.

Unsymmetrical metallocene compounds useful herein included those represented by formula (II):

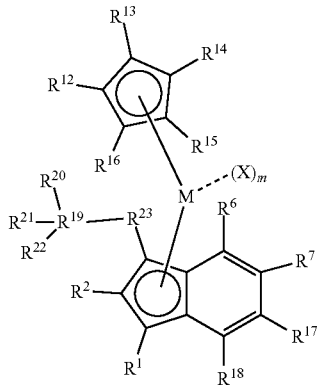

wherein:
$R^1$ and $R^2$ are hydrogen;
$R^{23}$ and $R^{19}$ comprise group 14 atoms, preferably C, Ge, or Si (preferably $R^{23}$ is C and $R^{19}$ is C or Si);
$R^{20}$, $R^{21}$, and $R^{22}$ are independently hydrogen or a substituted or unsubstituted linear, branched, or cyclic $C_1$-$C_{20}$ hydrocarbyl group and at least two of $R^{20}$, $R^{21}$, and $R^{22}$ are not hydrogen;
$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;
$R^{12}$, $R^{13}$, $R^{14}$, $R^{15}$, and $R^{16}$ are each independently a substituted or unsubstituted linear, branched, or cyclic $C_1$-$C_8$ hydrocarbyl group;
each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or two or more X moieties together form a fused ring or ring system;
M is a group 3, 4, or 5 transition metal having an integer coordination number of v, such as 3, 4 or 5;
and m is an integer equal to v-2, such as 1, 2 or 3.

Unsymmetrical metallocene compounds useful herein included those represented by formula (III):

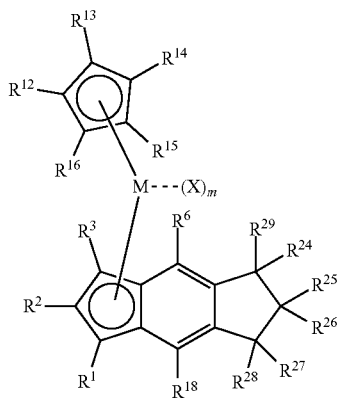

wherein one of $R^1$ and $R^3$ is a substituted or unsubstituted linear, branched, or cyclic $C_1$-$C_{20}$ hydrocarbyl group;
two of $R^1$, $R^2$, and $R^3$ are each hydrogen;
$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annelated to the cyclopentan-indenyl ring;
$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;
each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;
M is a group 3, 4, or 5 transition metal having an integer coordination number of v, such as 3, 4, or 5;
and m is an integer equal to v-2, such as 1, 2, or 3.

Unsymmetrical metallocene compounds useful herein included those represented by formula (IV):

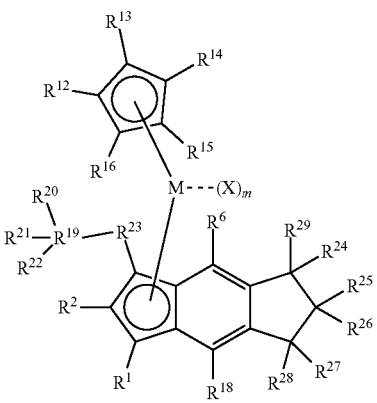

wherein:
$R^1$ and $R^2$ are hydrogen;
$R^{23}$ and $R^{19}$ comprise Group 14 atoms, preferably C, Ge, or Si (preferably $R^{23}$ is C and $R^{19}$ is C or Si);
$R^{20}$, $R^{21}$, and $R^{22}$ are independently hydrogen or a substituted or unsubstituted linear, branched, or cyclic $C_1$-$C_{20}$ hydrocarbyl group and at least two of $R^{20}$, $R^{21}$, and $R^{22}$ are not hydrogen;
$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annelated to the cyclopentan-indenyl ring;
$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;
each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a group 3, 4, or 5 transition metal having an integer coordination number of v, such as 3, 4, or 5;

and m is an integer equal to v-2, such as 1, 2, or 3.

Optionally, in any embodiment of formula (I) or (III) herein, $R^2$ is hydrogen and one of $R^1$ and $R^3$ is a substituted or unsubstituted linear, branched, or cyclic $C_1$-$C_6$ hydrocarbyl group, and the other one of $R^1$ and $R^3$ is a hydrogen.

Optionally, in any embodiment of formula (I) or (II) herein, $R^6$ and $R^7$, or $R^7$ and $R^{17}$, or $R^{17}$ and $R^{18}$, taken together with the respective carbon atoms in the indenyl ring to which they are directly connected, form a ring annelated to the indenyl ring.

Optionally, in any embodiment of formula (I) or (II) herein, $R^6$ and $R^7$, or $R^7$ and $R^{17}$, or $R^{17}$ and $R^{18}$, taken together with the respective carbon atoms in the indenyl ring to which they are directly connected, form a ring annelated to the indenyl ring comprising one or more saturated carbon atoms.

Optionally, in any embodiment of formula (I), (II), (III) or (IV) herein, M is a group 4 metal, preferably Zr or Hf, preferably Hf.

Optionally, in any embodiment of formula (I), (II), (III) or (IV) herein, M is a group 4 metal, preferably Zr or Hf, preferably Hf and m is 2.

Optionally, in any embodiment of formula (II) and (IV) herein, $R^{23}$ is carbon and at least two of $R^{20}$, $R^{21}$, and $R^{22}$ are not hydrogen.

Optionally, in any embodiment of formula (I), (II), (III) or (IV) herein, each X is independently chloro, bromo, iodo, hydride, methyl, ethyl, propyl, benzyl, neopentyl, dimethyl amide, methoxide, or two X are methylidene, ethylidene, 1,3-butadiene, 1,3-pentadiene, and the like, most preferably, X is methyl.

Non limiting examples of polycyclic arene ligands include:

1-methyl-1,5,6,7-tetrahydro-s-indacenyl,
1-ethyl-1,5,6,7-tetrahydro-s-indacenyl,
1-n-propyl-1,5,6,7-tetrahydro-s-indacenyl,
1-isopropyl-1,5,6,7-tetrahydro-s-indacenyl,
1-isopropyl-1,5,6,7-tetrahydro-s-indacenyl,
1-n-butyl-1,5,6,7-tetrahydro-s-indacenyl,
1-isobutyl-1,5,6,7-tetrahydro-s-indacenyl,
1-sec-butyl-1,5,6,7-tetrahydro-s-indacenyl,
1-n-pentyl-1,5,6,7-tetrahydro-s-indacenyl,
1-neopentyl-1,5,6,7-tetrahydro-s-indacenyl,
1-n-hexyl-1,5,6,7-tetrahydro-s-indacenyl,
1-n-heptyl-1,5,6,7-tetrahydro-s-indacenyl,
1-n-octyl-1,5,6,7-tetrahydro-s-indacenyl,
1-benzyl-1,5,6,7-tetrahydro-s-indacenyl,
1-phenethyl-1,5,6,7-tetrahydro-s-indacenyl,
1-(2-phenylpropyl)-1,5,6,7-tetrahydro-s-indacenyl,
1,6,6-trimethyl-1,5,6,7-tetrahydro-s-indacenyl,
1-ethyl-6,6-dimethyl-1,5,6,7-tetrahydro-s-indacenyl,
1-n-propyl-6,6-dimethyl-1,5,6,7-tetrahydro-s-indacenyl,
1-isopropyl-6,6-dimethyl-1,5,6,7-tetrahydro-s-indacenyl,
1-n-butyl-6,6-dimethyl-1,5,6,7-tetrahydro-s-indacenyl,
1-isobutyl-6,6-dimethyl-1,5,6,7-tetrahydro-s-indacenyl,
1-sec-butyl-6,6-dimethyl-1,5,6,7-tetrahydro-s-indacenyl,
1-n-pentyl-6,6-dimethyl-1,5,6,7-tetrahydro-s-indacenyl,
1-neopentyl-6,6-dimethyl-1,5,6,7-tetrahydro-s-indacenyl,
1-n-hexyl-6,6-dimethyl-1,5,6,7-tetrahydro-s-indacenyl,
1-n-heptyl-6,6-dimethyl-1,5,6,7-tetrahydro-s-indacenyl,
1-n-octyl-6,6-dimethyl-1,5,6,7-tetrahydro-s-indacenyl,
1-benzyl-6,6-dimethyl-1,5,6,7-tetrahydro-s-indacenyl,
1-phenethyl-6,6-dimethyl-1,5,6,7-tetrahydro-s-indacenyl,
1-(2-phenylpropyl)-6,6-dimethyl-1,5,6,7-tetrahydro-s-indacenyl,
1-methyl-6,6-diethyl-1,5,6,7-tetrahydro-s-indacenyl,
1,6,6-triethyl-1,5,6,7-tetrahydro-s-indacenyl,
1-n-propyl-6,6-diethyl-1,5,6,7-tetrahydro-s-indacenyl,
1-isopropyl-6,6-diethyl-1,5,6,7-tetrahydro-s-indacenyl,
1-n-butyl-6,6-diethyl-1,5,6,7-tetrahydro-s-indacenyl,
1-isobutyl-6,6-diethyl-1,5,6,7-tetrahydro-s-indacenyl,
1-n-pentyl-6,6-diethyl-1,5,6,7-tetrahydro-s-indacenyl,
1-neopentyl-6,6-diethyl-1,5,6,7-tetrahydro-s-indacenyl,
1-n-hexyl-6,6-diethyl-1,5,6,7-tetrahydro-s-indacenyl,
1-n-heptyl-6,6-diethyl-1,5,6,7-tetrahydro-s-indacenyl,
1-n-octyl-6,6-diethyl-1,5,6,7-tetrahydro-s-indacenyl,
1-benzyl-6,6-diethyl-1,5,6,7-tetrahydro-s-indacenyl,
1-phenethyl-6,6-diethyl-1,5,6,7-tetrahydro-s-indacenyl,
1-(2-phenylpropyl)-6,6-diethyl-1,5,6,7-tetrahydro-s-indacenyl,
1-methylindenyl,
1-ethylindenyl,
1-n-propylindenyl,
1-isopropylindenyl,
1-n-butylindenyl,
1-iso-butylindenyl,
1-sec-butylindenyl,
1-n-pentylindenyl,
1-neopentylindenyl,
1-n-hexylindenyl,
1-n-heptylindenyl,
1-n-octylindenyl, 1-benzylindenyl,
1-phenethylindenyl,
1-(2-phenylpropyl)indenyl,
1-methyl-3,6,7,8-tetrahydro-as-indacenyl,
1-ethyl-3,6,7,8-tetrahydro-as-indacenyl,
1-n-propyl-3,6,7,8-tetrahydro-as-indacenyl,
1-isopropyl-3,6,7,8-tetrahydro-as-indacenyl,
1-n-butyl-3,6,7,8-tetrahydro-as-indacenyl,
1-isobutyl-3,6,7,8-tetrahydro-as-indacenyl,
1-n-pentyl-3,6,7,8-tetrahydro-as-indacenyl,
1-neopentyl-3,6,7,8-tetrahydro-as-indacenyl,
1-n-hexyl-3,6,7,8-tetrahydro-as-indacenyl,
1-n-heptyl-3,6,7,8-tetrahydro-as-indacenyl,
1-n-octyl-3,6,7,8-tetrahydro-as-indacenyl,
1-benzyl-3,6,7,8-tetrahydro-as-indacenyl,
1-phenethyl-3,6,7,8-tetrahydro-as-indacenyl,
1-(2-phenylpropyl)-3,6,7,8-tetrahydro-as-indacenyl,
1-methyl-benz[f]indenyl,
1-ethyl-benz[f]indenyl,
1-n-propyl-benz[f]indenyl,
1-isopropyl-benz[f]indenyl,
1-n-butyl-benz[f]indenyl,
1-isobutyl-benz[f]indenyl,
1-sec-butyl-benz[f]indenyl,
1-tert-butyl-benz[f]indenyl
1-n-pentyl-benz[f]indenyl,
1-neopentyl-benz[f]indenyl,
1-n-hexyl-benz[f]indenyl,
1-n-heptyl-benz[f]indenyl,
1-n-octyl-benz[f]indenyl,
1-benzyl-benz[f]indenyl,
1-phenethyl-benz[f]indenyl,
1-(2-phenylpropyl)-benz[f]indenyl,
1-methyl-benz[e]indenyl,
1-ethyl-benz[e]indenyl,
1-n-propyl-benz[e]indenyl,
1-isopropyl-benz[e]indenyl, 1-n-butyl-benz[e]indenyl,
1-isobutyl-benz[e]indenyl,
1-n-pentyl-benz[le]indenyl,
1-neopentyl-benz[e]indenyl,
1-n-hexyl-benz[e]indenyl,
1-n-heptyl-benz[e]indenyl,
1-n-octyl-benz[e]indenyl,
1-benzyl-benz[e]indenyl,
1-phenethyl-benz[e]indenyl,
1-(2-phenylpropyl)-benze[e]indenyl,
1-methyl-5,6,7,8-tetrahydro-1H-cyclopenta[b]naphthalenyl,
1-ethyl-5,6,7,8-tetrahydro-1H-cyclopenta[b]naphthalenyl,
1-n-propyl-5,6,7,8-tetrahydro-1H-cyclopenta[b]naphthalenyl,
1-isopropyl-5,6,7,8-tetrahydro-1H-cyclopenta[b]naphthalenyl,
1-n-butyl-5,6,7,8-tetrahydro-1H-cyclopenta[b]naphthalenyl,
1-isobutyl-5,6,7,8-tetrahydro-1H-cyclopenta[b]naphthalenyl,
1-sec-butyl-5,6,7,8-tetrahydro-1H-cyclopenta[b]naphthalenyl,
1-tert-butyl-5,6,7,8-tetrahydro-1H-cyclopenta[b]naphthalenyl,
1-n-pentyl-5,6,7,8-tetrahydro-1H-cyclopenta[b]naphthalenyl,
1-neopentyl-5,6,7,8-tetrahydro-1H-cyclopenta[b]naphthalenyl,
1-n-hexyl-5,6,7,8-tetrahydro-1H-cyclopenta[b]naphthalenyl,
1-n-heptyl-5,6,7,8-tetrahydro-1H-cyclopenta[b]naphthalenyl,
1-n-octyl-5,6,7,8-tetrahydro-1H-cyclopenta[b]naphthalenyl,
1-benzyl-5,6,7,8-tetrahydro-1H-cyclopenta[b]naphthalenyl,
1-phenethyl-5,6,7,8-tetrahydro-1H-cyclopenta[b]naphthalenyl, and
1-(2-phenylpropyl)-5,6,7,8-tetrahydro-1H-cyclopenta[b]naphthalenyl.

Non limiting examples of monocyclic arene ligands include:
pentamethylcyclopentadienyl,
pentaethylcyclopentadienyl,
pentapropylcyclopentadienyl,
ethyltetramethylcyclopentadienyl,
propyltetramethylcyclopentadienyl,
butyltetramethylcyclopentadienyl,
diethyltrimethylcyclopentadienyl,
dipropyltrimethylcyclopentadienyl,
dibutyltrimethylcyclopentadienyl,
triethyldimethylcyclopentadienyl,
tripropyldimethylcyclopentadienyl,
tributyldimethylcyclopentadienyl,
tetraethylmethylcyclopentadienyl,
tetrapropylmethylcyclopentadienyl, and
tetrabutylmethylcyclopentadienyl.

Catalyst compounds that are particularly useful in this invention include those represented by formula (I-B), (III-B), (IV-B), (VI), (VIII), (IX), (X), (XI), (XII), (XV), (XVII), (XVIII), (XIX) or (XX):

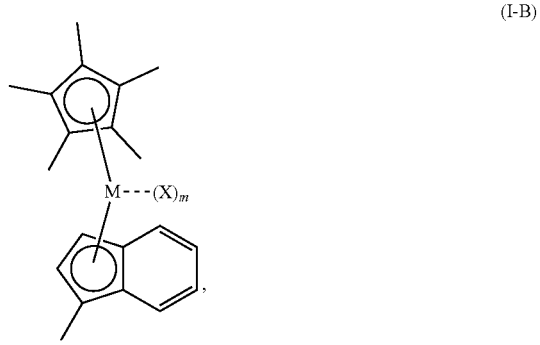

(I-B)

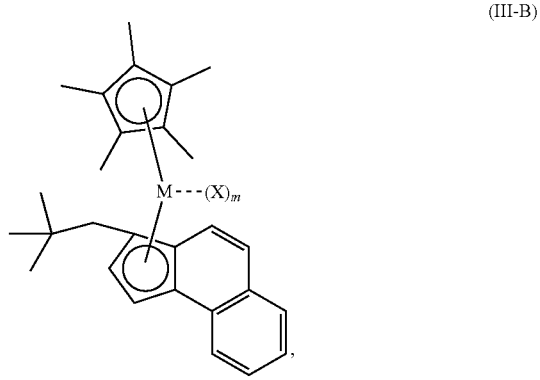

(III-B)

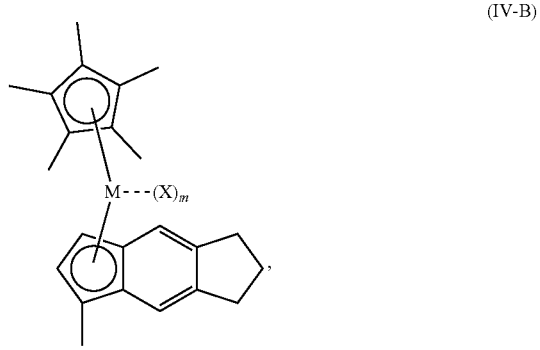

(IV-B)

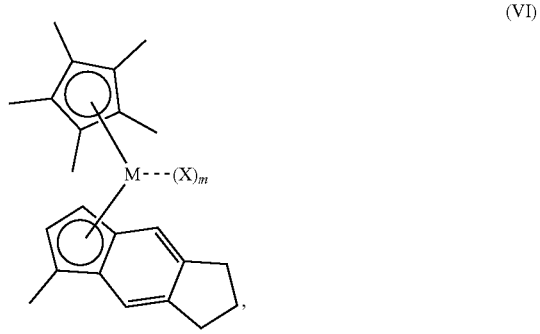

(VI)

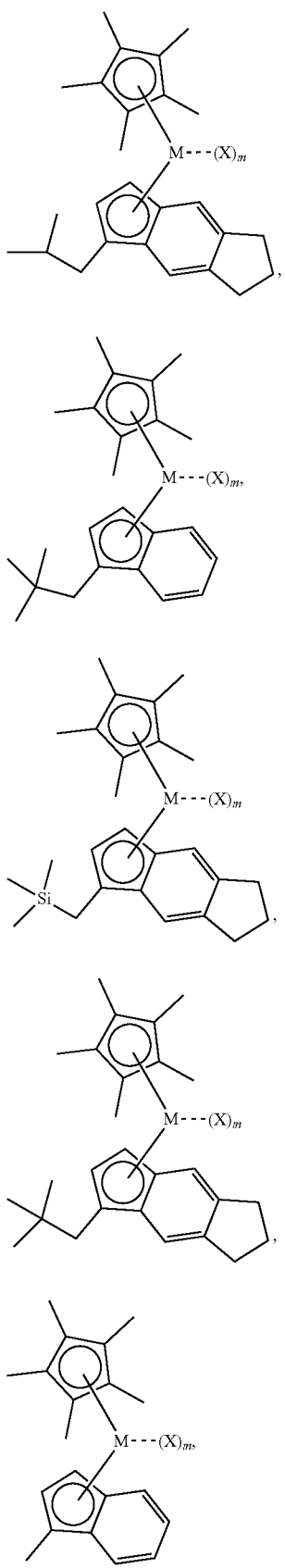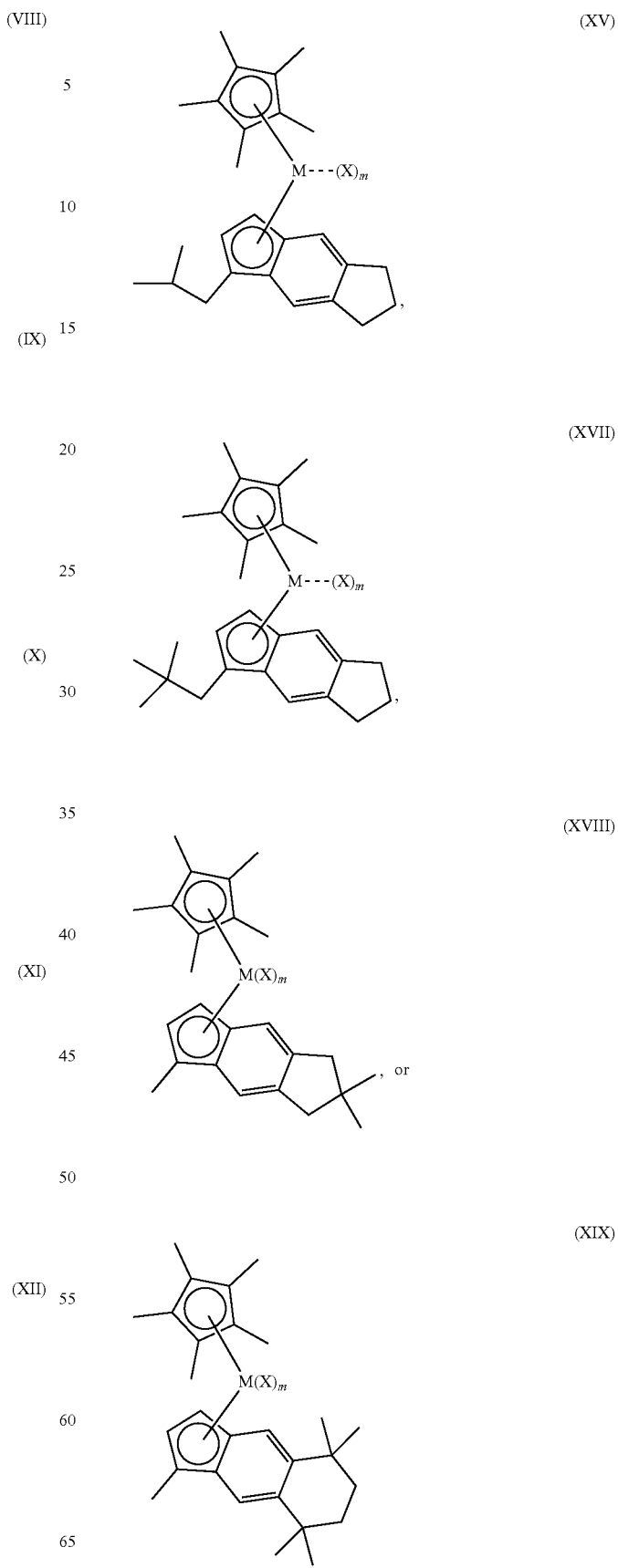

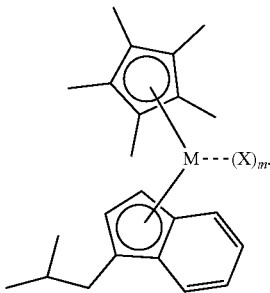

(XX)

wherein each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or two or more X moieties may together form a fused ring or ring system; M is Hf or Zr, preferably Hf; and m is 2. Optionally the metallocene is not represented by formula (I-B).

List A: Catalyst compounds that are useful in this invention include one or more of:

pentamethylcyclopentadienyl(1-methyl-1,5,6,7-tetrahydro-s-indacenyl)hafnium dimethyl,
pentamethylcyclopentadienyl(1-ethyl-1,5,6,7-tetrahydro-s-indacenyl)hafnium dimethyl,
pentamethylcyclopentadienyl(1-n-propyl-1,5,6,7-tetrahydro-s-indacenyl)hafnium dimethyl,
pentamethylcyclopentadienyl(1-isopropyl-1,5,6,7-tetrahydro-s-indacenyl)hafnium dimethyl,
pentamethylcyclopentadienyl(1-n-butyl-1,5,6,7-tetrahydro-s-indacenyl)hafnium dimethyl,
pentamethylcyclopentadienyl(1-isobutyl-1,5,6,7-tetrahydro-s-indacenyl)hafnium dimethyl,
pentamethylcyclopentadienyl(1-sec-butyl-1,5,6,7-tetrahydro-s-indacenyl)hafnium dimethyl,
pentamethylcyclopentadienyl(1-tert-butyl-1,5,6,7-tetrahydro-s-indacenyl)hafnium dimethyl,
pentamethylcyclopentadienyl(1-pentyl-1,5,6,7-tetrahydro-s-indacenyl)hafnium dimethyl,
pentamethylcyclopentadienyl(1-neopentyl-1,5,6,7-tetrahydro-s-indacenyl)hafnium dimethyl,
pentamethylcyclopentadienyl(1-n-hexyl-1,5,6,7-tetrahydro-s-indacenyl)hafnium dimethyl,
pentamethylcyclopentadienyl(1-n-heptyl-1,5,6,7-tetrahydro-s-indacenyl)hafnium dimethyl,
pentamethylcyclopentadienyl(1-n-octyl-1,5,6,7-tetrahydro-s-indacenyl)hafnium dimethyl,
pentamethylcyclopentadienyl(1-benzyl-1,5,6,7-tetrahydro-s-indacenyl)hafnium dimethyl,
pentamethylcyclopentadienyl(1-phenethyl-1,5,6,7-tetrahydro-s-indacenyl)hafnium dimethyl,
pentamethylcyclopentadienyl(1-(2-phenylpropyl)-1,5,6,7-tetrahydro-s-indacenyl)hafnium dimethyl,
pentamethylcyclopentadienyl(1,6,6-trimethyl-1,5,6,7-tetrahydro-s-indacenyl)hafnium dimethyl,
pentamethylcyclopentadienyl(1-ethyl-6,6-dimethyl-1,5,6,7-tetrahydro-s-indacenyl)hafnium dimethyl,
pentamethylcyclopentadienyl(1-n-propyl-6,6-dimethyl-1,5,6,7-tetrahydro-s-indacenyl)hafnium dimethyl,
pentamethylcyclopentadienyl(1-isopropyl-6,6-dimethyl-1,5,6,7-tetrahydro-s-indacenyl)hafnium dimethyl,
pentamethylcyclopentadienyl(1-n-butyl-6,6-dimethyl-1,5,6,7-tetrahydro-s-indacenyl)hafnium dimethyl,
pentamethylcyclopentadienyl(1-isobutyl-6,6-dimethyl-1,5,6,7-tetrahydro-s-indacenyl)hafnium dimethyl,
pentamethylcyclopentadienyl(1-sec-butyl-6,6-dimethyl-1,5,6,7-tetrahydro-s-indacenyl)hafnium dimethyl,
pentamethylcyclopentadienyl(1-tert-butyl-6,6-dimethyl-1,5,6,7-tetrahydro-s-indacenyl)hafnium dimethyl,
pentamethylcyclopentadienyl(1-pentyl-6,6-dimethyl-1,5,6,7-tetrahydro-s-indacenyl)hafnium dimethyl,
pentamethylcyclopentadienyl(1-neopentyl-6,6-dimethyl-1,5,6,7-tetrahydro-s-indacenyl)hafnium dimethyl,
pentamethylcyclopentadienyl(1-n-hexyl-6,6-dimethyl-1,5,6,7-tetrahydro-s-indacenyl)hafnium dimethyl,
pentamethylcyclopentadienyl(1-n-heptyl-6,6-dimethyl-1,5,6,7-tetrahydro-s-indacenyl)hafnium dimethyl,
pentamethylcyclopentadienyl(1-n-octyl-6,6-dimethyl-1,5,6,7-tetrahydro-s-indacenyl)hafnium dimethyl,
pentamethylcyclopentadienyl(1-benzyl-6,6-dimethyl-1,5,6,7-tetrahydro-s-indacenyl)hafnium dimethyl,
pentamethylcyclopentadienyl(1-phenethyl-6,6-dimethyl-1,5,6,7-tetrahydro-s-indacenyl)hafnium dimethyl,
pentamethylcyclopentadienyl(1-(2-phenylpropyl)-6,6-dimethyl-1,5,6,7-tetrahydro-s-indacenyl)hafnium dimethyl,
pentamethylcyclopentadienyl(1-methyl-6,6-diethyl-1,5,6,7-tetrahydro-s-indacenyl)hafnium dimethyl,
pentamethylcyclopentadienyl(1,6,6-triethyl-1,5,6,7-tetrahydro-s-indacenyl)hafnium dimethyl,
pentamethylcyclopentadienyl(1-n-propyl-6,6-diethyl-1,5,6,7-tetrahydro-s-indacenyl)hafnium dimethyl,
pentamethylcyclopentadienyl(1-isopropyl-6,6-diethyl-1,5,6,7-tetrahydro-s-indacenyl)hafnium dimethyl,
pentamethylcyclopentadienyl(1-n-butyl-6,6-diethyl-1,5,6,7-tetrahydro-s-indacenyl)hafnium dimethyl,
pentamethylcyclopentadienyl(1-isobutyl-6,6-diethyl-1,5,6,7-tetrahydro-s-indacenyl)hafnium dimethyl,
pentamethylcyclopentadienyl(1-sec-butyl-6,6-diethyl-1,5,6,7-tetrahydro-s-indacenyl)hafnium dimethyl,
pentamethylcyclopentadienyl(1-tert-butyl-6,6-diethyl-1,5,6,7-tetrahydro-s-indacenyl)hafnium dimethyl,
pentamethylcyclopentadienyl(1-pentyl-6,6-diethyl-1,5,6,7-tetrahydro-s-indacenyl)hafnium dimethyl,
pentamethylcyclopentadienyl(1-neopentyl-6,6-diethyl-1,5,6,7-tetrahydro-s-indacenyl)hafnium dimethyl,
pentamethylcyclopentadienyl(1-benzyl-6,6-diethyl-1,5,6,7-tetrahydro-s-indacenyl)hafnium dimethyl,
pentamethylcyclopentadienyl(1-phenethyl-6,6-diethyl-1,5,6,7-tetrahydro-s-indacenyl)hafnium dimethyl,
pentamethylcyclopentadienyl(1-(2-phenylpropyl)-6,6-diethyl-1,5,6,7-tetrahydro-s-indacenyl)hafnium dimethyl,
pentamethylcyclopentadienyl(1-methylindenyl)hafnium dimethyl,
pentamethylcyclopentadienyl(1-ethylindenyl)hafnium dimethyl,
pentamethylcyclopentadienyl(1-n-propylindenyl)hafnium dimethyl,
pentamethylcyclopentadienyl(1-isopropylindenyl)hafnium dimethyl,
pentamethylcyclopentadienyl(1-n-butylindenyl)hafnium dimethyl,
pentamethylcyclopentadienyl(1-isobutylindenyl)hafnium dimethyl,
pentamethylcyclopentadienyl(1-sec-butylindenyl)hafnium dimethyl,
pentamethylcyclopentadienyl(1-tert-butylindenyl)hafnium dimethyl,
pentamethylcyclopentadienyl(1-pentylindenyl)hafnium dimethyl, pentamethylcyclopentadienyl(1-neopentylindenyl)hafnium dimethyl,
pentamethylcyclopentadienyl(1-n-hexylindenyl)hafnium dimethyl,
pentamethylcyclopentadienyl(1-n-heptylindenyl)hafnium dimethyl,
pentamethylcyclopentadienyl(1-n-octylindenyl)hafnium dimethyl,
pentamethylcyclopentadienyl(1-benzylindenyl)hafnium dimethyl,
pentamethylcyclopentadienyl(1-phenethylindenyl)hafnium dimethyl,
pentamethylcyclopentadienyl(1-(2-phenylpropyl)indenyl)hafnium dimethyl,
pentamethylcyclopentadienyl(1-methyl-3,6,7,8-tetrahydro-as-indacenyl)hafnium dimethyl,
pentamethylcyclopentadienyl(1-ethyl-3,6,7,8-tetrahydro-as-indacenyl)hafnium dimethyl,
pentamethylcyclopentadienyl(1-n-propyl-3,6,7,8-tetrahydro-as-indacenyl)hafnium dimethyl,
pentamethylcyclopentadienyl(1-isopropyl-3,6,7,8-tetrahydro-as-indacenyl)hafnium dimethyl,
pentamethylcyclopentadienyl(1-n-butyl-3,6,7,8-tetrahydro-as-indacenyl)hafnium dimethyl,
pentamethylcyclopentadienyl(1-isobutyl-3,6,7,8-tetrahydro-as-indacenyl)hafnium dimethyl,
pentamethylcyclopentadienyl(1-sec-butyl-3,6,7,8-tetrahydro-as-indacenyl)hafnium dimethyl,
pentamethylcyclopentadienyl(1-tert-butyl-3,6,7,8-tetrahydro-as-indacenyl)hafnium dimethyl,
pentamethylcyclopentadienyl(1-pentyl-3,6,7,8-tetrahydro-as-indacenyl)hafnium dimethyl,
pentamethylcyclopentadienyl(1-neopentyl-3,6,7,8-tetrahydro-as-indacenyl)hafnium dimethyl,
pentamethylcyclopentadienyl(1-benzyl-3,6,7,8-tetrahydro-as-indacenyl)hafnium dimethyl,
pentamethylcyclopentadienyl(1-phenethyl-3,6,7,8-tetrahydro-as-indacenyl)hafnium dimethyl,
pentamethylcyclopentadienyl(1-(2-phenylpropyl)-3,6,7,8-tetrahydro-as-indacenyl)hafnium dimethyl,
pentamethylcyclopentadienyl(1-methyl-benz[f]indenyl)hafnium dimethyl,
pentamethylcyclopentadienyl(1-ethyl-benz[f]indenyl)hafnium dimethyl,
pentamethylcyclopentadienyl(1-n-propyl-benz[f]indenyl)hafnium dimethyl,
pentamethylcyclopentadienyl(1-isopropyl-benz[f]indenyl)hafnium dimethyl,
pentamethylcyclopentadienyl(1-n-butyl-benz[f]indenyl)hafnium dimethyl,
pentamethylcyclopentadienyl(1-isobutyl-benz[f]indenyl)hafnium dimethyl,
pentamethylcyclopentadienyl(1-sec-butyl-benz[f]indenyl)hafnium dimethyl,
pentamethylcyclopentadienyl(1-tert-butyl-benz[f]indenyl)hafnium dimethyl pentamethylcyclopentadienyl(1-pentyl-benz[f]indenyl)hafnium dimethyl,
pentamethylcyclopentadienyl(1-neopentyl-benz[f]indenyl)hafnium dimethyl,
pentamethylcyclopentadienyl(1-benzyl-benz[f]indenyl)hafnium dimethyl,
pentamethylcyclopentadienyl(1-phenethyl-benz[f]indenyl)hafnium dimethyl,
pentamethylcyclopentadienyl(1-(2-phenylpropyl)-benz[f]indenyl)hafnium dimethyl,
pentamethylcyclopentadienyl(1-methyl-benz[e]indenyl)hafnium dimethyl,
pentamethylcyclopentadienyl(1-ethyl-benz[e]indenyl)hafnium dimethyl,
pentamethylcyclopentadienyl(1-n-propyl-benz[e]indenyl)hafnium dimethyl,
pentamethylcyclopentadienyl(1-isopropyl-benz[e]indenyl)hafnium dimethyl,
pentamethylcyclopentadienyl(1-n-butyl-benz[e]indenyl)hafnium dimethyl,
pentamethylcyclopentadienyl(1-isobutyl-benz[e]indenyl)hafnium dimethyl,
pentamethylcyclopentadienyl(1-sec-butyl-benz[e]indenyl)hafnium dimethyl,
pentamethylcyclopentadienyl(1-tert-butyl-benz[e]indenyl)hafnium dimethyl,
pentamethylcyclopentadienyl(1-pentyl-benz[e]indenyl)hafnium dimethyl,
pentamethylcyclopentadienyl(1-neopentyl-benz[e]indenyl)hafnium dimethyl,
pentamethylcyclopentadienyl(1-benzyl-benz[e]indenyl)hafnium dimethyl,
pentamethylcyclopentadienyl(1-phenethyl-benz[e]indenyl)hafnium dimethyl,
pentamethylcyclopentadienyl(1-(2-phenylpropyl)-benzef]indenyl)hafnium dimethyl,
pentamethylcyclopentadienyl(1-methyl-5,6,7,8-tetrahydro-1H-cyclopenta[b]naphthalene)hafnium dimethyl,
pentamethylcyclopentadienyl(1-ethyl-5,6,7,8-tetrahydro-1H-cyclopenta[b]naphthalene)hafnium dimethyl,
pentamethylcyclopentadienyl(1-n-propyl-5,6,7,8-tetrahydro-1H-cyclopenta[b]naphthalene)hafnium dimethyl,
pentamethylcyclopentadienyl(1-isopropyl-5,6,7,8-tetrahydro-1H-cyclopenta[b]naphthalene)hafnium dimethyl,
pentamethylcyclopentadienyl(1-n-butyl-5,6,7,8-tetrahydro-1H-cyclopenta[b]naphthalene)hafnium dimethyl,
pentamethylcyclopentadienyl(1-isobutyl-5,6,7,8-tetrahydro-1H-cyclopenta[b]naphthalene)hafnium dimethyl,
pentamethylcyclopentadienyl(1-sec-butyl-5,6,7,8-tetrahydro-1H-cyclopenta[b]naphthalene)hafnium dimethyl,
pentamethylcyclopentadienyl(1-tert-butyl-5,6,7,8-tetrahydro-1H-cyclopenta[b]naphthalene)hafnium dimethyl,
pentamethylcyclopentadienyl(1-pentyl-5,6,7,8-tetrahydro-1H-cyclopenta[b]naphthalene)hafnium dimethyl,
pentamethylcyclopentadienyl(1-neopentyl-5,6,7,8-tetrahydro-1H-cyclopenta[b]naphthalene)hafnium dimethyl,
pentamethylcyclopentadienyl(1-benzyl-5,6,7,8-tetrahydro-1H-cyclopenta[b]naphthalene)hafnium dimethyl,
pentamethylcyclopentadienyl(1-phenethyl-5,6,7,8-tetrahydro-1H-cyclopenta[b]naphthalene)hafnium dimethyl,
pentamethylcyclopentadienyl(1-(2-phenylpropyl)-5,6,7,8-tetrahydro-1H-cyclopenta[b]naphthalene)hafnium dimethyl,
pentamethylcyclopentadienyl(1-methyl-6,7,8,9-tetrahydro-1H-cyclopenta[a]naphthalene)hafnium dimethyl,
pentamethylcyclopentadienyl(1-ethyl-6,7,8,9-tetrahydro-1H-cyclopenta[a]naphthalene)hafnium dimethyl,
pentamethylcyclopentadienyl(1-n-propyl-6,7,8,9-tetrahydro-1H-cyclopenta[a]naphthalene)hafnium dimethyl,
pentamethylcyclopentadienyl(1-isopropyl-6,7,8,9-tetrahydro-1H-cyclopenta[a]naphthalene)hafnium dimethyl,
pentamethylcyclopentadienyl(1-n-butyl-6,7,8,9-tetrahydro-1H-cyclopenta[a]naphthalene)hafnium dimethyl,
pentamethylcyclopentadienyl(1-isobutyl-6,7,8,9-tetrahydro-1H-cyclopenta[a]naphthalene)hafnium dimethyl,
pentamethylcyclopentadienyl(1-sec-butyl-6,7,8,9-tetrahydro-1H-cyclopenta[a]naphthalene)hafnium dimethyl,
pentamethylcyclopentadienyl(1-tert-butyl-6,7,8,9-tetrahydro-1H-cyclopenta[a]naphthalene)hafnium dimethyl, pentamethylcyclopentadienyl(1-pentyl-6,7,8,9-tetrahydro-1H-cyclopenta[a]naphthalene)hafnium dimethyl,
pentamethylcyclopentadienyl(1-neopentyl-6,7,8,9-tetrahydro-1H-cyclopenta[a]naphthalene)hafnium dimethyl,
pentamethylcyclopentadienyl(1-benzyl-6,7,8,9-tetrahydro-1H-cyclopenta[a]naphthalene)hafnium dimethyl,
pentamethylcyclopentadienyl(1-phenethyl-6,7,8,9-tetrahydro-1H-cyclopenta[a]naphthalene)hafnium dimethyl,
pentamethylcyclopentadienyl(1-(2-phenylpropyl)-6,7,8,9-tetrahydro-1H-cyclopenta[a]naphthalene)hafnium dimethyl,
pentamethylcyclopentadienyl(1,5,6-trimethylindenyl)hafnium dimethyl,
pentamethylcyclopentadienyl(1-ethyl-5,6-dimethylindenyl)hafnium dimethyl,
pentamethylcyclopentadienyl(1-n-propyl-5,6-dimethylindenyl)hafnium dimethyl,
pentamethylcyclopentadienyl(1-isopropyl-5,6-dimethylindenyl)hafnium dimethyl,
pentamethylcyclopentadienyl(1-n-buty-5,6-dimethyllindenyl)hafnium dimethyl,
pentamethylcyclopentadienyl(1-isobuty-5,6-dimethyllindenyl)hafnium dimethyl,
pentamethylcyclopentadienyl(1-sec-butyl-5,6-dimethylindenyl)hafnium dimethyl,
pentamethylcyclopentadienyl(1-tert-butyl-5,6-dimethylindenyl)hafnium dimethyl,
pentamethylcyclopentadienyl(1-pentyl-5,6-dimethylindenyl)hafnium dimethyl,
pentamethylcyclopentadienyl(1-neopentyl-5,6-dimethylindenyl)hafnium dimethyl,
pentamethylcyclopentadienyl(1-benzyl-5,6-dimethylindenyl)hafnium dimethyl,
pentamethylcyclopentadienyl(1-phenethyl-5,6-dimethylindenyl)hafnium dimethyl,
pentamethylcyclopentadienyl(1-(2-phenylpropyl)-5,6-dimethylindenyl)hafnium dimethyl,
pentamethylcyclopentadienyl(1-methyl-1,5,6,7-tetrahydro-s-indacenyl)zirconium dimethyl,
pentamethylcyclopentadienyl(1-isobutyl-1,5,6,7-tetrahydro-s-indacenyl)zirconium dimethyl,
pentamethylcyclopentadienyl(1,6,6-trimethyl-1,5,6,7-tetrahydro-s-indacenyl)zirconium dimethyl,
ethyltetramethylcyclopentadienyl(1-methyl-1,5,6,7-tetrahydro-s-indacenyl)hafnium dimethyl,
ethyltetramethylcyclopentadienyl(1-isobutyl-1,5,6,7-tetrahydro-s-indacenyl)hafnium dimethyl,
ethyltetramethylcyclopentadienyl(1,6,6-trimethyl-1,5,6,7-tetrahydro-s-indacenyl)hafnium dimethyl,
pentamethylcyclopentadienyl(1-methyl-1,5,6,7-tetrahydro-s-indacenyl)hafnium dibenzyl,
pentamethylcyclopentadienyl(1-isobutyl-1,5,6,7-tetrahydro-s-indacenyl)hafnium dibenzyl, and
pentamethylcyclopentadienyl(1,6,6-trimethyl-1,5,6,7-tetrahydro-s-indacenyl)hafnium dibenzyl.

Catalyst compounds that are particularly useful in this invention include one or more of:
pentamethylcyclopentadienyl(1-methyl-1,5,6,7-tetrahydro-s-indacenyl)hafnium dimethyl,
pentamethylcyclopentadienyl(1-ethyl-1,5,6,7-tetrahydro-s-indacenyl)hafnium dimethyl,
pentamethylcyclopentadienyl(1-n-propyl-1,5,6,7-tetrahydro-s-indacenyl)hafnium dimethyl,
pentamethylcyclopentadienyl(1-isopropyl-1,5,6,7-tetrahydro-s-indacenyl)hafnium dimethyl,
pentamethylcyclopentadienyl(1-n-butyl-1,5,6,7-tetrahydro-s-indacenyl)hafnium dimethyl,
pentamethylcyclopentadienyl(1-isobutyl-1,5,6,7-tetrahydro-s-indacenyl)hafnium dimethyl,
pentamethylcyclopentadienyl(1,6,6-trimethyl-1,5,6,7-tetrahydro-s-indacenyl)hafnium dimethyl,
pentamethylcyclopentadienyl(1-isobutyl-6,6-dimethyl-1,5,6,7-tetrahydro-s-indacenyl)hafnium dimethyl,
pentamethylcyclopentadienyl(1-methyl-6,6-diethyl-1,5,6,7-tetrahydro-s-indacenyl)hafnium dimethyl,
pentamethylcyclopentadienyl(1,6,6-triethyl-1,5,6,7-tetrahydro-s-indacenyl)hafnium dimethyl,
pentamethylcyclopentadienyl(1-isobutyl-6,6-diethyl-1,5,6,7-tetrahydro-s-indacenyl)hafnium dimethyl,
pentamethylcyclopentadienyl(1-methylindenyl)hafnium dimethyl,
pentamethylcyclopentadienyl(1-isobutylindenyl)hafnium dimethyl,
pentamethylcyclopentadienyl(1-methyl-3,6,7,8-tetrahydro-as-indacenyl)hafnium dimethyl,
pentamethylcyclopentadienyl(1-isobutyl-3,6,7,8-tetrahydro-as-indacenyl)hafnium dimethyl,
pentamethylcyclopentadienyl(1-methyl-5,6,7,8-tetrahydro-1H-cyclopenta[b]naphthalene)hafnium dimethyl,
pentamethylcyclopentadienyl(1-isobutyl-5,6,7,8-tetrahydro-1H-cyclopenta[b]naphthalene)hafnium dimethyl,
pentamethylcyclopentadienyl(1-methyl-6,7,8,9-tetrahydro-1H-cyclopenta[a]naphthalene)hafnium dimethyl,
pentamethylcyclopentadienyl(1-isobutyl-6,7,8,9-tetrahydro-1H-cyclopenta[a]naphthalene)hafnium dimethyl,
pentamethylcyclopentadienyl(1,5,6-trimethylindenyl)hafnium dimethyl, and
pentamethylcyclopentadienyl(1-isobuty-5,6-dimethyllindenyl)hafnium dimethyl.

Metallocene compounds generally can be synthesized by using typical chemical reagents (e.g., halides of hafnium, zirconium, titanium) and intermediates (such as ligands containing one or two substituted or unsubstituted Cp rings, substituted or unsubstituted annelated Cp ring such as indenyl rings or benzindenyl rings, and the like) that are commercially available, and following typical reaction schemes exemplified in various synthesis descriptions, see for example U.S. Ser. No. 16/394,197, filed Apr. 25, 2019, and U.S. Ser. No. 16/394,166, filed Apr. 25, 2019, which describe catalyst compounds useful herein and are incorporated by reference herein. See also U.S. Ser. No. 16/270,085, filed Feb. 7, 2019 which claims priority to and the benefit of U.S. Ser. No. 62/629,200, filed Feb. 12, 2018, and U.S. Ser. No. 62/732,311, filed Sep. 17, 2018, which describe catalyst compounds useful herein and are incorporated by reference herein.

Example metallocene compounds useful for the process of the present disclosure include the following compounds and their optical isomers, if applicable (not shown):

TABLE I

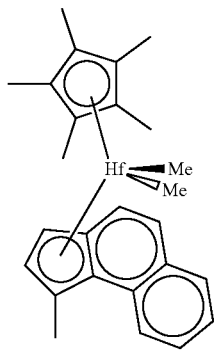

TABLE I-continued
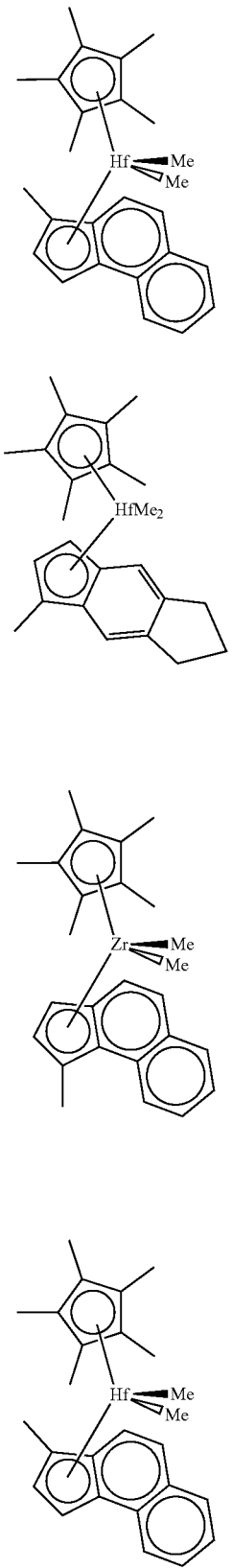
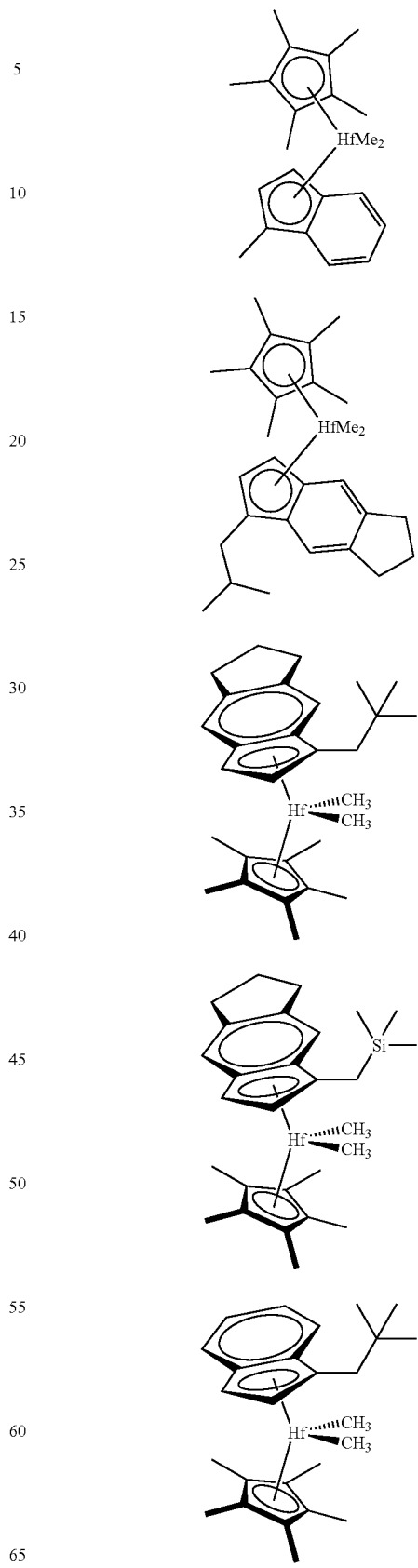

TABLE I-continued
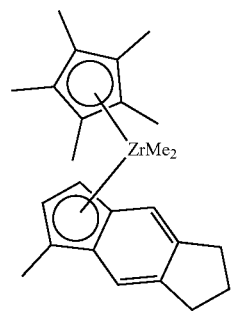
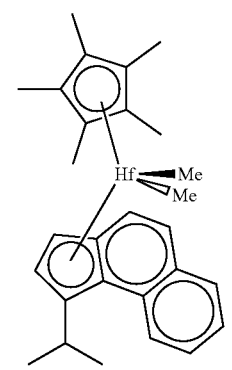
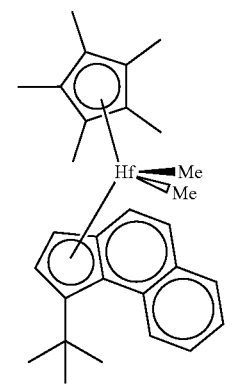
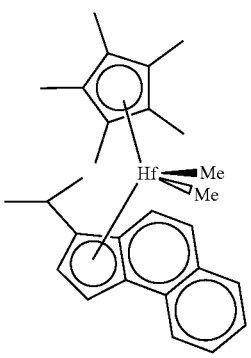
TABLE I-continued
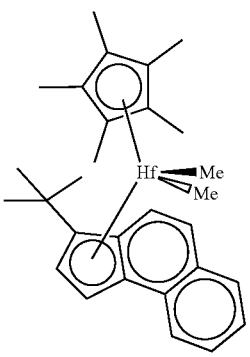
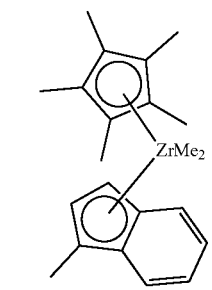
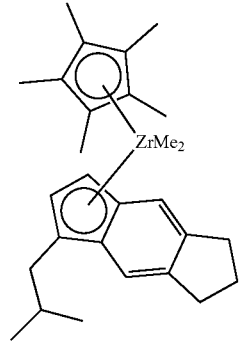
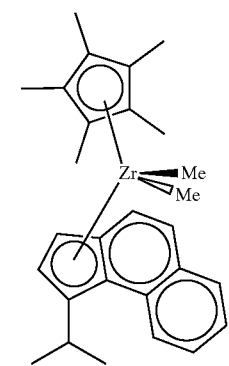

TABLE I-continued
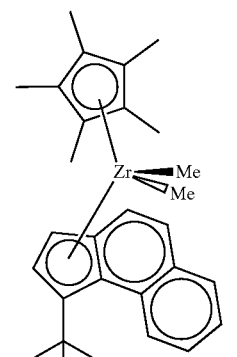
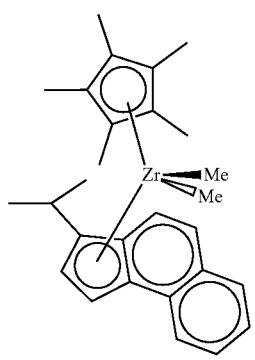
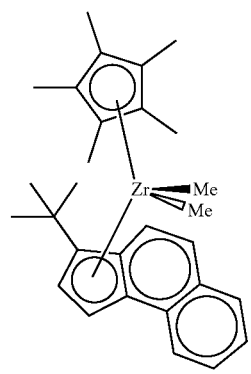
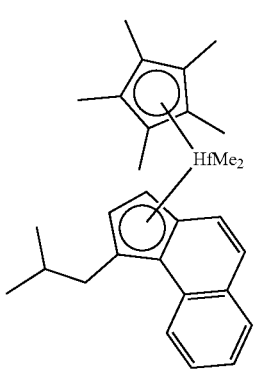
TABLE I-continued
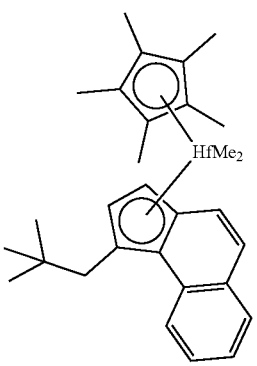
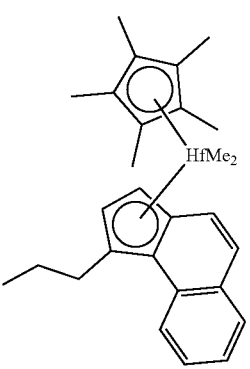
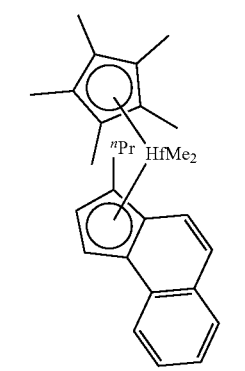
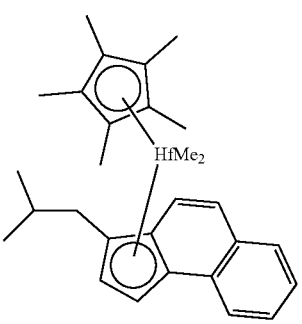

TABLE I-continued
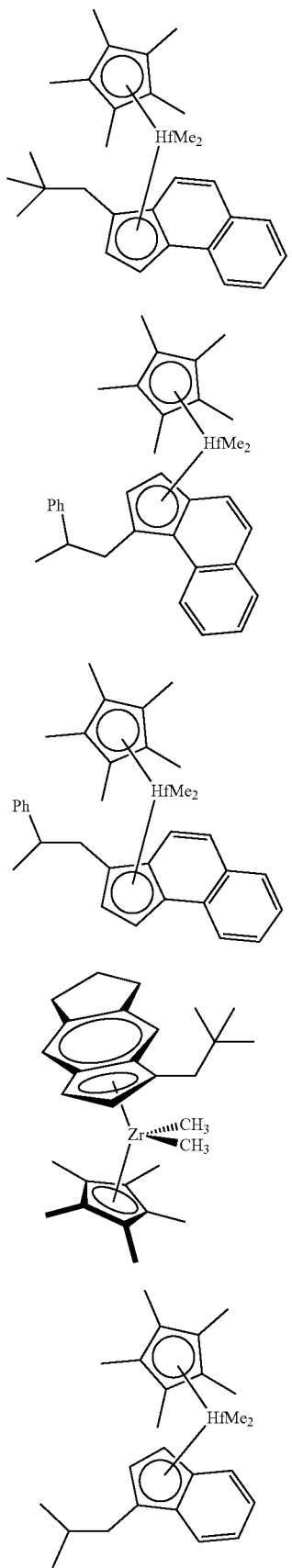

TABLE I-continued
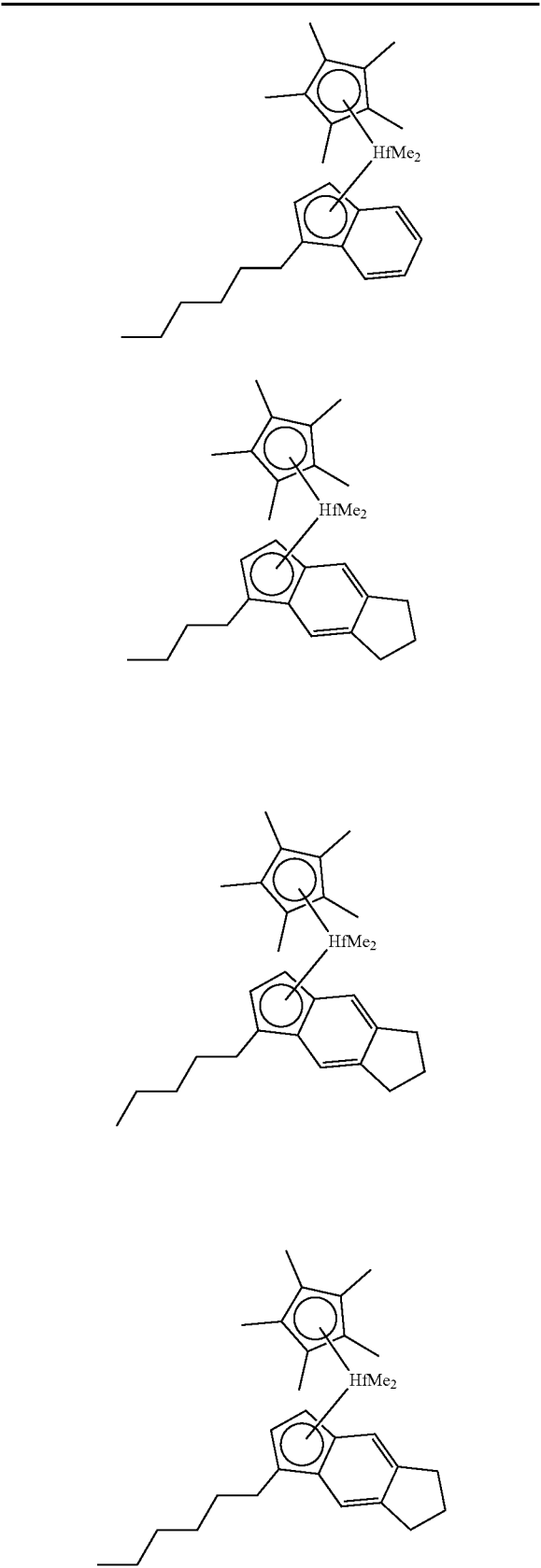
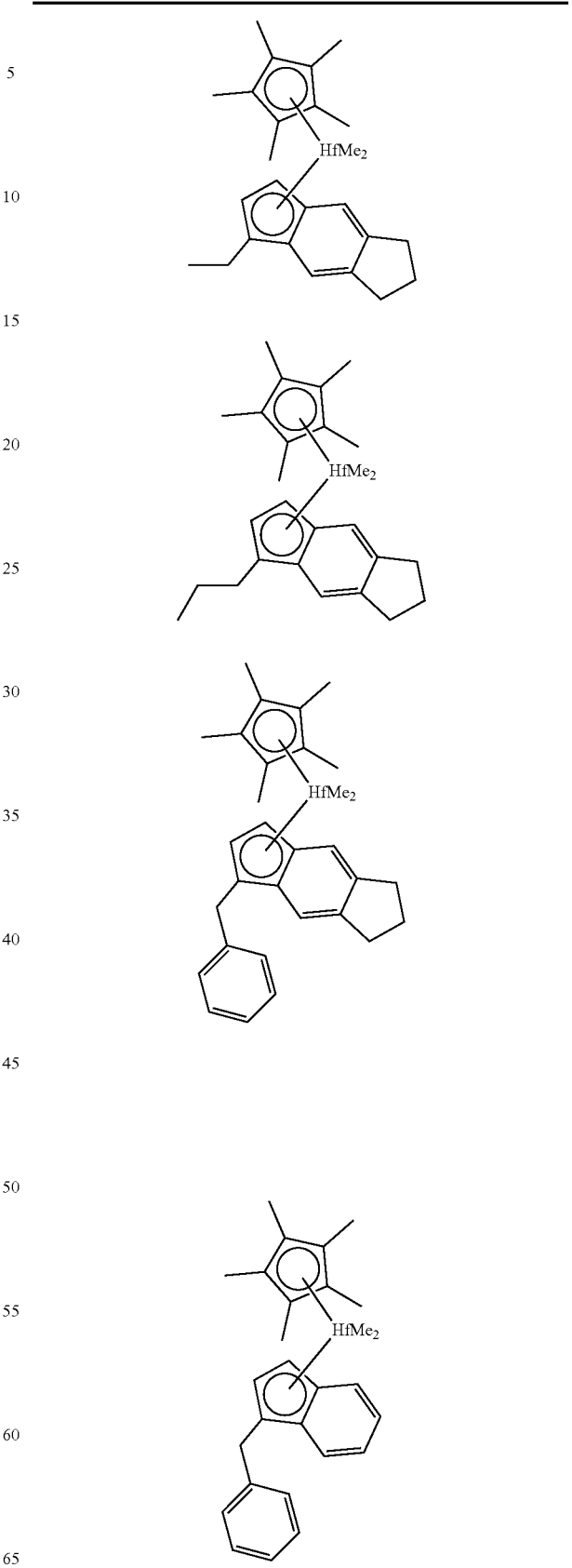

TABLE I-continued

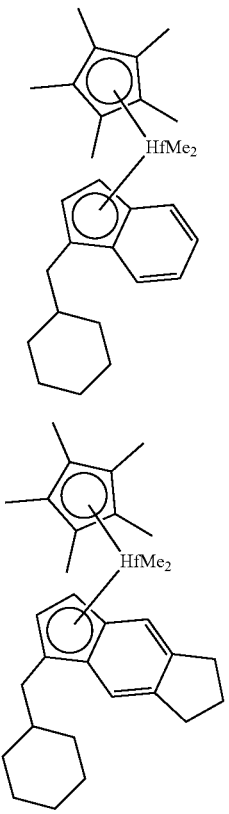

Metallocene compounds generally can be synthesized by using typical chemical reagents (e.g., halides of hafnium, zirconium, titanium) and intermediates (such as ligands containing one or two substituted or unsubstituted Cp rings, substituted or unsubstituted fused Cp ring such as indenyl rings or benzindenyl rings, and the like) that are commercially available, and following typical reaction schemes exemplified in various synthesis descriptions, e.g., as described in the example sections of U.S. Provisional Application Nos. 62/477,683 and 62/477,706, both filed Mar. 28, 2017, the contents of each of which are hereby incorporated by reference.

IV.B.2 Activators and Activation of the Metallocene Compound

The metallocene catalyst may be activated by any suitable activator such as a non-coordinating anion (NCA) activator that is soluble in hydrocarbon, such as non-aromatic hydrocarbon. An NCA is an anion which either does not coordinate to the catalyst metal cation or that coordinates only weakly to the metal cation. An NCA coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used or contained in the NCA. Suitable metals include aluminum, gold, and platinum. Suitable metalloids include boron, aluminum, phosphorus, and silicon.

Advantageously, the activators of the present disclosure are soluble in non-aromatic-hydrocarbon solvents, such as aliphatic solvents.

In one or more embodiments, a 20 wt % mixture of the activator compound in n-hexane, isohexane, cyclohexane, methylcyclohexane, or a combination thereof, forms a clear homogeneous solution at 25° C., preferably a 30 wt % mixture of the activator compound in n-hexane, isohexane, cyclohexane, methylcyclohexane, or a combination thereof, forms a clear homogeneous solution at 25° C.

In embodiments of the invention, the activators described herein have a solubility of more than 10 mM (or more than 20 mM, or more than 50 mM) at 25° C. (stirred 2 hours) in methylcyclohexane.

In embodiments of the invention, the activators described herein have a solubility of more than 1 mM (or more than 10 mM, or more than 20 mM) at 25° C. (stirred 2 hours) in isohexane.

In embodiments of the invention, the activators described herein have a solubility of more than 10 mM (or more than 20 mM, or more than 50 mM) at 25° C. (stirred 2 hours) in methylcyclohexane and a solubility of more than 1 mM (or more than 10 mM, or more than 20 mM) at 25° C. (stirred 2 hours) in isohexane.

The present disclosure relates to a catalyst system comprising a metallocene transition metal compound and an activator compound as described herein, to the use of such activator compounds for activating a transition metal compound in a catalyst system for polymerizing olefins, and to processes for polymerizing olefins, the process comprising contacting under polymerization conditions one or more olefins with a catalyst system comprising a metallocene transition metal compound and such activator compounds, where aromatic solvents, such as toluene, are absent (e.g. present at zero mol %, alternately present at less than 1 mol %, preferably the catalyst system, the polymerization reaction and/or the polymer produced are free of "detectable aromatic hydrocarbon solvent," such as toluene. For purposes of the present disclosure, "detectable aromatic hydrocarbon solvent" means 0.1 mg/m² or more as determined by gas phase chromatography. For purposes of the present disclosure, "detectable toluene" means 0.1 mg/m² or more as determined by gas phase chromatography.

The polyalpha-olefins produced herein preferably contain 0 ppm (alternately less than 1 ppm) of aromatic hydrocarbon. Preferably, the polyalpha-olefins produced herein contain 0 ppm (alternately less than 1 ppm) of toluene.

The catalyst systems used herein preferably contain 0 ppm (alternately less than 1 ppm) of aromatic hydrocarbon. Preferably, the catalyst systems used herein contain 0 ppm (alternately less than 1 ppm) of toluene.

Non-aromatic-hydrocarbon soluble activator compounds useful herein include those represented by the formula (V):

$$[R^{1'}R^{2'}R^{3'}EH]_{d^+}[Mt^{k+}Q_n]^{d-} \qquad (V)$$

wherein:
E is nitrogen or phosphorous;
d is 1, 2 or 3; k is 1, 2, or 3; n is 1, 2, 3, 4, 5, or 6; n−k=d (preferably d is 1, 2 or 3; k is 3;
n is 4, 5, or 6);
$R^{1'}$, $R^{2'}$, and $R^{3'}$ are independently $C_1$ to $C_{50}$ hydrocarbyl group optionally substituted with one or more alkoxy groups, silyl groups, a halogen atoms, or halogen containing groups,
wherein $R^{1'}$, $R^{2'}$, and $R^{3'}$ together comprise 15 or more carbon atoms;
Mt is an element selected from group 13 of the Periodic Table of the Elements, such as B or Al; and
each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Non-aromatic-hydrocarbon soluble activator compounds useful herein include those represented by the formula (VI):

$$[R^{1'}R^{2'}R^{3'}EH]^+[BR^{4'}R^{5'}R^{6'}R^{7'}]^{d-} \qquad (V)$$

wherein: E is nitrogen or phosphorous; $R^{1'}$ is a methyl group; $R^{2'}$ and $R^{3'}$ are independently is $C_4$-$C_{50}$ hydrocarbyl group optionally substituted with one or more alkoxy groups, silyl groups, a halogen atoms, or halogen containing groups wherein $R^{2'}$ and $R^{3'}$ together comprise 14 or more carbon atoms; B is boron; and $R^{4'}$, $R^{5'}$, $R^{6'}$, and $R^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Non-aromatic-hydrocarbon soluble activator compounds useful herein include those represented by the formula (VII) or formula (VIII):

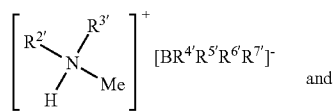  (VII)

and

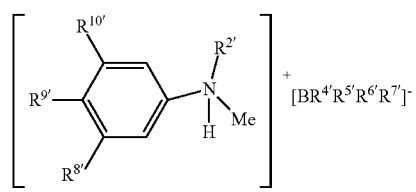  (VIII)

wherein:
N is nitrogen; $R^{2'}$ and $R^{3'}$ are independently is $C_6$-$C_{40}$ hydrocarbyl group optionally substituted with one or more alkoxy groups, silyl groups, a halogen atoms, or halogen containing groups wherein $R^{2'}$ and $R^{3'}$ (if present) together comprise 14 or more carbon atoms;
$R^{8'}$, $R^{9'}$, and $R^{10'}$ are independently a $C_4$-$C_{30}$ hydrocarbyl or substituted $C_4$-$C_{30}$ hydrocarbyl group;
B is boron;
and $R^{4'}$, $R^{5'}$, $R^{6'}$, and $R^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Optionally, in any of formulas (V), (VI), (VII), or (VIII) herein, $R^{4'}$, $R^{5'}$, $R^{6'}$, and $R^{7'}$ are pentafluorophenyl.

Optionally, in any of formulas (V), (VI), (VII), or (VIII) herein, $R^{4'}$, $R^{5'}$, $R^{6'}$, and $R^{7'}$ are pentafluoronaphthyl.

Optionally, in any embodiment of formula (VIII) herein, $R^{8'}$ and $R^{10'}$ are hydrogen atoms and $R^{9'}$ is a $C_4$-$C_{30}$ hydrocarbyl group which is optionally substituted with one or more alkoxy groups, silyl groups, a halogen atoms, or halogen containing groups.

Optionally, in any embodiment of formula (VIII) herein, $R^{9'}$ is a $C_8$-$C_{22}$ hydrocarbyl group which is optionally substituted with one or more alkoxy groups, silyl groups, a halogen atoms, or halogen containing groups.

Optionally, in any embodiment of formula (VII) or (VIII) herein, $R^{2'}$ and $R^{3'}$ are independently a $C_{12}$-$C_{22}$ hydrocarbyl group.

Optionally, $R^{1'}$, $R^{2'}$ and $R^{3'}$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 38 or more carbon atoms, such as 40 or more carbon atoms, such as 15 to 100 carbon atoms, such as 25 to 75 carbon atoms).

Optionally, $R^{2'}$ and $R^{3'}$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 38 or more carbon atoms, such as 40 or more carbon atoms, such as 15 to 100 carbon atoms, such as 25 to 75 carbon atoms).

Optionally, $R^{8'}$, $R^{9'}$, and $R^{10'}$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 38 or more carbon atoms, such as 40 or more carbon atoms, such as 15 to 100 carbon atoms, such as 25 to 75 carbon atoms).

Optionally, when Q is a fluorophenyl group, then $R^{2'}$ is not a $C_1$-$C_{40}$ linear alkyl group (alternately $R^{2'}$ is not an optionally substituted $C_1$-$C_{40}$ linear alkyl group).

Optionally, each of $R^{4'}$, $R^{5'}$, $R^{6'}$, and $R^{7'}$ is an aryl group (such as phenyl or naphthyl), wherein at least one of $R^{4'}$, $R^{5'}$, $R^{6'}$, and $R^{7'}$ is substituted with at least one fluorine atom, preferably each of $R^{4'}$, $R^{5'}$, $R^{6'}$, and $R^{7'}$ is a perfluoroaryl group (such as perfluorophenyl or perfluoronaphthyl).

Optionally, each Q is an aryl group (such as phenyl or naphthyl), wherein at least one Q is substituted with at least one fluorine atom, preferably each Q is a perfluoroaryl group (such as perfluorophenyl or perfluoronaphthyl).

Optionally, $R^{1'}$ is a methyl group; $R^{2'}$ is $C_6$-$C_{50}$ aryl group; and $R^3$ is independently $C_1$-$C_{40}$ linear alkyl or $C_5$-$C_{50}$-aryl group.

Optionally, each of $R^{2'}$ and $R^{3'}$ is independently unsubstituted or substituted with at least one of halide, $C_1$-$C_{35}$ alkyl, $C_8$-$C_{18}$ aryl, $C_6$-$C_{35}$ arylalkyl, $C_6$-$C_{35}$ alkylaryl, wherein $R^2$, and $R^3$ together comprise 20 or more carbon atoms.

Optionally, each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, provided that when Q is a fluorophenyl group, then $R^{2'}$ is not a $C_1$-$C_{40}$ linear alkyl group, preferably $R^{2'}$ is not an optionally substituted $C_1$-$C_{40}$ linear alkyl group (alternately when Q is a substituted phenyl group, then $R^{2'}$ is not a $C_1$-$C_{40}$ linear alkyl group, preferably $R^{2'}$ is not an optionally substituted $C_1$-$C_{40}$ linear alkyl group). Optionally, when Q is a fluorophenyl group (alternately when Q is a substituted phenyl group), then $R^{2'}$ is a meta- and/or para-substituted phenyl group, where the meta and para substituents are, independently, an optionally substituted $C_1$ to $C_{40}$ hydrocarbyl group (such as a $C_6$ to $C_4$ aryl group or linear alkyl group, a $C_{12}$ to $C_{30}$ aryl group or linear alkyl group, or a $C_{10}$ to $C_{20}$ aryl group or linear alkyl group), an optionally substituted alkoxy group, or an optionally substituted silyl group. Optionally, each Q is a fluorinated hydrocarbyl group having 1 to 30 carbon atoms, more preferably each Q is a fluorinated aryl (such as phenyl or naphthyl) group, and most preferably each Q is a perflourinated aryl (such as phenyl or naphthyl) group. Examples of suitable $[Mt^{k+}Q_n]^{d-}$ also include diboron compounds as disclosed in U.S. Pat. No. 5,447,895, which is fully incorporated herein by reference. Optionally, at least one Q is not substituted phenyl. Optionally all Q are not substituted phenyl. Optionally at least one Q is not perfluorophenyl. Optionally all Q are not perfluorophenyl.

In some embodiments of the invention, $R^{1'}$ is not methyl, $R^{2'}$ is not $C_{18}$ alkyl and $R^{3'}$ is not $C_{18}$ alkyl, alternately $R^{1'}$ is not methyl, $R^{2'}$ is not $C_{18}$ alkyl and $R^{3'}$ is not $C_{18}$ alkyl and at least one Q is not substituted phenyl, optionally all Q are not substituted phenyl.
Useful cation components in formulas (V) to (VIII) include those represented by the formula:
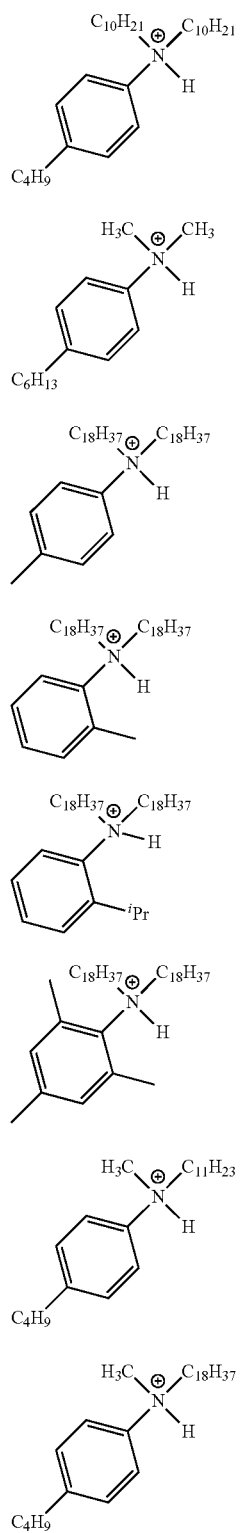
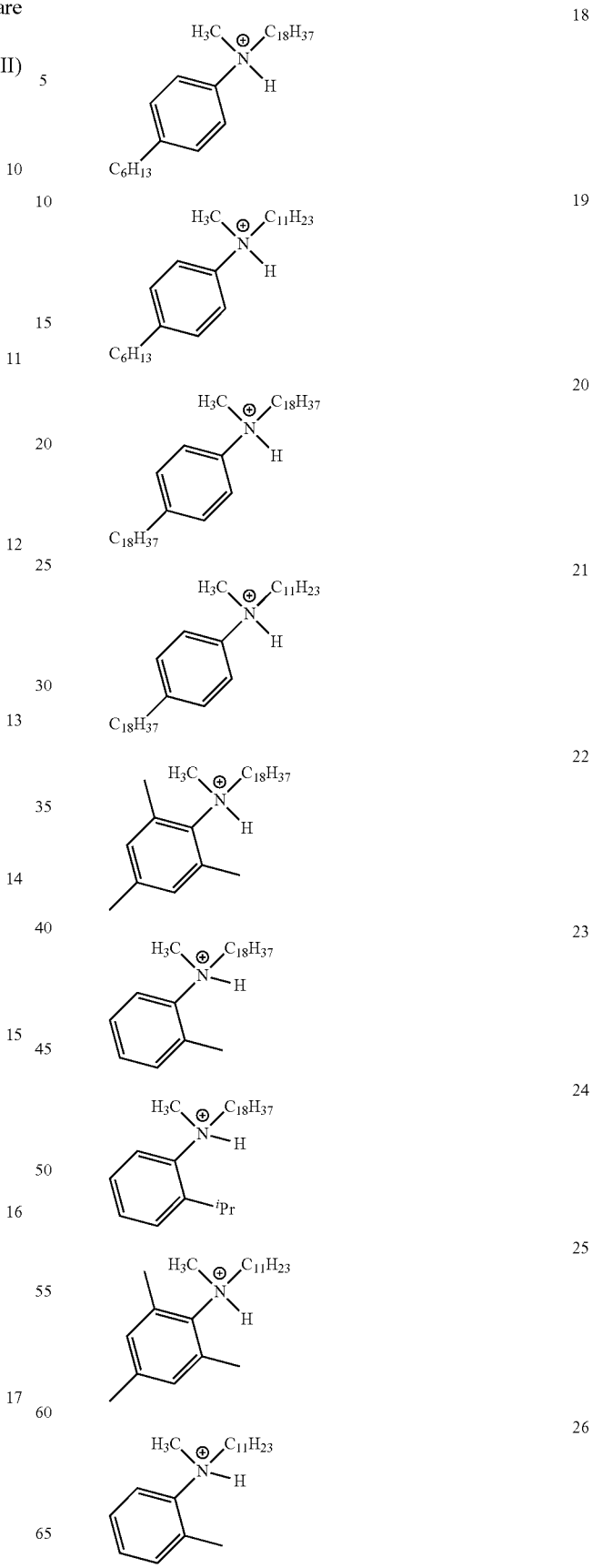

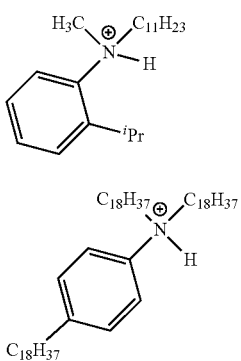

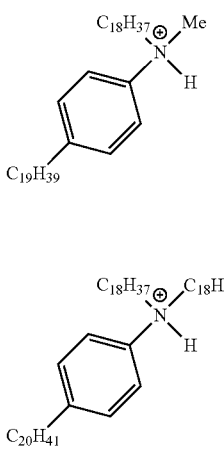

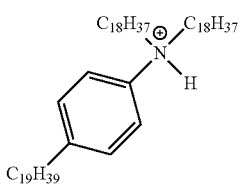

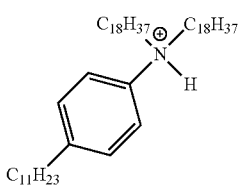

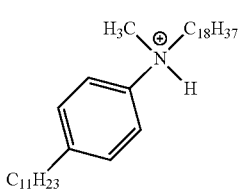

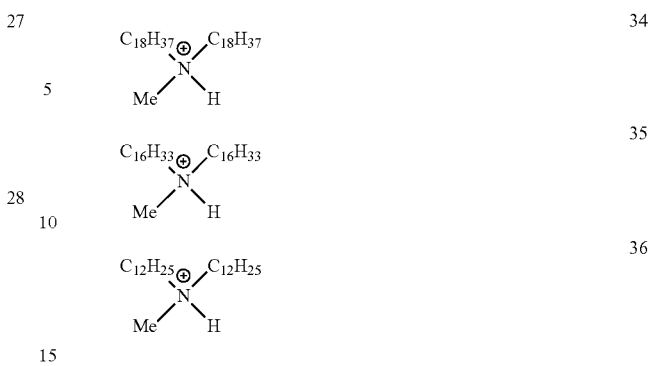

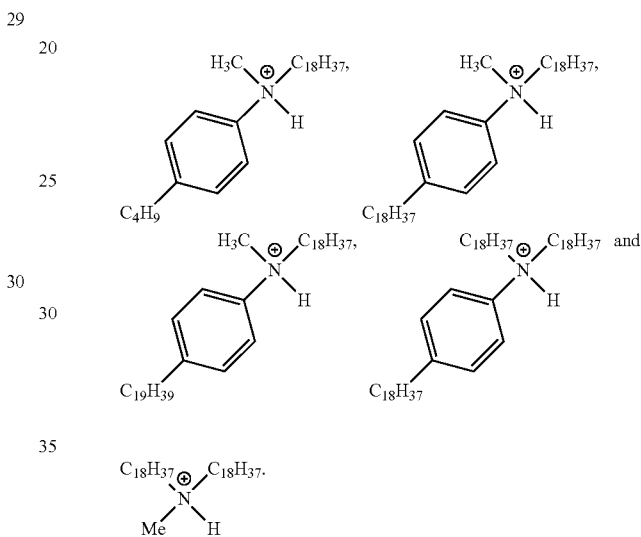

Useful cation components in formulas (V) to (VIII) include those represented by the formula:

The anion component of the activators described herein includes those represented by the formula $[Mt^{k+}Q_n]^-$ wherein k is 1, 2, or 3; n is 1, 2, 3, 4, 5, or 6 (preferably 1, 2, 3, or 4), (preferably k is 3; n is 4, 5, or 6, preferably when M is H, n is 4); Mt is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group, optionally having 1 to 20 carbon atoms, more preferably each Q is a fluorinated aryl group, and most preferably each Q is a perfluorinated aryl group. Preferably at least one Q is not substituted phenyl, such as perfluorophenyl, preferably all Q are not substituted phenyl, such as perfluorophenyl.

In one embodiment, the borate activator comprises tetrakis(heptafluoronaphth-2-yl)borate.

In one embodiment, the borate activator comprises tetrakis(pentafluorophenyl)borate.

Preferred anions for use in the non-coordinating anion activators described herein include those represented by Formula 7 below:

Formula 7

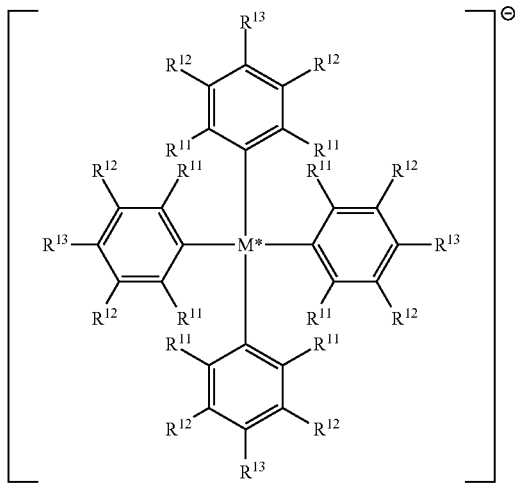

wherein:

M* is a group 13 atom, preferably B or Al, preferably B; each $R^{11}$ is, independently, a halide, preferably a fluoride;

each $R^{12}$ is, independently, a halide, a $C_6$ to $C_{20}$ substituted aromatic hydrocarbyl group or a siloxy group of the formula —O—Si—$R^a$, where $R^a$ is a $C_1$ to $C_{20}$ hydrocarbyl or hydrocarbylsilyl group, preferably $R^{12}$ is a fluoride or a perfluorinated phenyl group;

each $R^{13}$ is a halide, a $C_6$ to $C_{20}$ substituted aromatic hydrocarbyl group or a siloxy group of the formula —O—Si—$R^a$, where $R^a$ is a $C_1$ to $C_{20}$ hydrocarbyl or hydrocarbylsilyl group, preferably $R^{13}$ is a fluoride or a $C_6$ perfluorinated aromatic hydrocarbyl group;

wherein $R^{12}$ and $R^{13}$ can form one or more saturated or unsaturated, substituted or unsubstituted rings, preferably $R^{12}$ and $R^{13}$ form a perfluorinated phenyl ring. Preferably the anion has a molecular weight of greater than 700 g/mol, and, preferably, at least three of the substituents on the M* atom each have a molecular volume of greater than 180 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in Girolami, G. S. (1994) "A Simple "Back of the Envelope" Method for Estimating the Densities and Molecular Volumes of Liquids and Solids," *Journal of Chemical Education*, v. 71(11), pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using Table A below of relative volumes. For fused rings, the $V_s$ is decreased by 7.5% per fused ring. The Calculated Total MV of the anion is the sum of the MV per substituent, for example, the MV of perfluorophenyl is 183 Å$^3$, and the Calculated Total MV for tetrakis(perfluorophenyl)borate is four times 183 Å$^3$, or 732 Å$^3$.

TABLE A

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary anions useful herein and their respective scaled volumes and molecular volumes are shown in Table B below. The dashed bonds indicate bonding to boron.

TABLE B

| Ion | Structure of Boron Substituents | Molecular Formula of Each Substituent | $V_s$ | MV Per subst. (Å$^3$) | Calculated Total MV (Å$^3$) |
|---|---|---|---|---|---|
| tetrakis(perfluorophenyl)borate | | $C_6F_5$ | 22 | 183 | 732 |
| tris(perfluorophenyl)-(perfluoronaphthyl)borate | | $C_6F_5$ $C_{10}F_7$ | 22 34 | 183 261 | 810 |

TABLE B-continued

| Ion | Structure of Boron Substituents | Molecular Formula of Each Substituent | MV Per subst. $V_s$ (Å$^3$) | Calculated Total MV (Å$^3$) |
| --- | --- | --- | --- | --- |
| perfluorophenyl)tris-(perfluoronaphenyl)borate | | $C_6F_5$<br>$C_{10}F_7$ | 22<br>34 | 183<br>261 | 966 |
| tetrakis(perfluoronaphthyl)borate | | $C_{10}F_7$ | 34 | 261 | 1044 |
| tetrakis(perfluorobiphenyl)borate | | $C_{12}F_9$ | 42 | 349 | 1396 |
| [(C$_6$F$_3$(C$_6$F$_5$)$_2$)$_4$B] | | $C_{18}F_{13}$ | 62 | 515 | 2060 |

The activators may be added to a polymerization in the form of an ion pair using, for example, [M2HTH]+ [NCA]– in which the di(hydrogenated tallow)methylamine ("M2HTH") cation reacts with a basic leaving group on the transition metal complex to form a transition metal complex cation and [NCA]–. Alternatively, the transition metal complex may be reacted with a neutral NCA precursor, such as B(C$_6$F$_5$)$_3$, which abstracts an anionic group from the complex to form an activated species. Useful activators include di(hydrogenated tallow)methylammonium[tetrakis(pentafluorophenyl)borate] (i.e., [M2HTH]B(C$_6$F$_5$)$_4$) and di(octadecyl)tolylammonium[tetrakis(pentafluorophenyl)borate] (i.e., [DOdTH]B(C$_6$F$_5$)$_4$).

Activator compounds that are particularly useful in this invention include one or more of: N,N-di(hydrogenated tallow)methylammonium [tetrakis(perfluorophenyl)borate], N-methyl-4-nonadecyl-N-octadecylanilinium [tetrakis(perfluorophenyl)borate], N-methyl-4-hexadecyl-N-octadecylanilinium [tetrakis(perfluorophenyl)borate], N-methyl-4-tetradecyl-N-octadecylanilinium [tetrakis(perfluorophenyl)borate], N-methyl-4-dodecyl-N-octadecylanilinium [tetrakis(perfluorophenyl)borate], N-methyl-4-decyl-N-octadecylanilinium [tetrakis(perfluorophenyl)borate], N-methyl-4-octyl-N-octadecylanilinium [tetrakis(perfluorophenyl)borate], N-methyl-4-hexyl-N-octadecylanilinium [tetrakis(perfluorophenyl)borate], N-methyl-4-butyl-N-octadecylanilinium [tetrakis(perfluorophenyl)borate], N-methyl-4-octadecyl-N-decylanilinium [tetrakis(perfluorophenyl)borate], N-methyl-4-nonadecyl-N-dodecylanilinium [tetrakis(perfluorophenyl)borate], N-methyl-4-nonadecyl-N-tetradecylanilinium [tetrakis(perfluorophenyl)borate], N-methyl-4-nonadecyl-N-hexadecylanilinium [tetrakis(perfluorophenyl)borate], N-ethyl-4-nonadecyl-N-octadecylanilinium [tetrakis(perfluorophenyl)borate], N-methyl-N,N-dioctadecylammonium [tetrakis(perfluorophenyl)borate], N-methyl-N,N-dihexadecylammonium [tetrakis(perfluorophenyl)borate], N-methyl-N,N-ditetradecylammonium [tetrakis(perfluorophenyl)borate], N-methyl-N,N-didodecylammonium [tetrakis(perfluorophenyl)borate], N-methyl-N,N-didecylammonium [tetrakis(perfluorophenyl)borate], N-methyl-N,N-dioctylammonium [tetrakis(perfluorophenyl)borate], N-ethyl-N,N-dioctadecylammonium [tetrakis(perfluorophenyl)borate], N,N-di(octadecyl)tolylammonium [tetrakis(perfluorophenyl)borate], N,N-di(hexadecyl)tolylammonium [tetrakis(perfluorophenyl)borate], N,N-di(tetradecyl)tolylammonium [tetrakis(perfluorophenyl)borate], N,N-di(dodecyl)tolylammonium [tetrakis(perfluorophenyl)borate], N-octadecyl-N-hexadecyl-tolylammonium [tetrakis(perfluorophenyl)borate], N-octadecyl-N-hexadecyl-tolylammonium [tetrakis(perfluorophenyl)borate], N-octadecyl-N-tetradecyl-tolylammonium [tetrakis(perfluorophenyl)borate], N-octadecyl-N-dodecyl-tolylammonium [tetrakis(perfluorophenyl)borate], N-octadecyl-N-decyl-tolylammonium [tetrakis(perfluorophenyl)borate], N-hexadecyl-N-tetradecyl-tolylammonium [tetrakis(perfluorophenyl)borate], N-hexadecyl-N-dodecyl-tolylammonium [tetrakis(perfluorophenyl)borate], N-hexadecyl-N-decyl-tolylammonium [tetrakis(perfluorophenyl)borate], N-tetradecyl-N-dodecyl-tolylammonium [tetrakis(perfluorophenyl)borate], N-tetradecyl-N-decyl-tolylammonium [tetrakis(perfluorophenyl)borate], N-dodecyl-N-decyl-tolylammonium [tetrakis(perfluorophenyl)borate], N-methyl-N-octadecylanilinium [tetrakis(perfluorophenyl)borate], N-methyl-N-hexadecylanilinium [tetrakis(perfluorophenyl)borate], N-methyl-N-tetradecylanilinium [tetrakis(perfluorophenyl)borate], N-methyl-N-dodecylanilinium [tetrakis(perfluorophenyl)borate], N-methyl-N-decylanilinium [tetrakis(perfluorophenyl)borate], and N-methyl-N-octylanilinium [tetrakis(perfluorophenyl)borate].

Additional useful activators and the synthesis thereof, are described in U.S. Ser. No. 16/394,166 filed Apr. 25, 2019, U.S. Ser. No. 16/394,186, filed Apr. 25, 2019, and U.S. Ser. No. 16/394,197, filed Apr. 25, 2019, which are incorporated by reference herein.

Synthesis

In at least one embodiment, the general synthesis of the activators can be performed using a two-step process. In the first step, an amine or phosphine is dissolved in a solvent (e.g. hexane, cyclohexane, methylcyclohexane, ether, dichloromethane, toluene) and an excess (e.g., 1.2 molar equivalents) of hydrogen chloride is added to form a chloride salt. This salt is typically isolated by filtration from the reaction medium and dried under reduced pressure. The isolated chloride is then heated to reflux with about one molar equivalent of an alkali metal metallate or metalloid (such as a borate or aluminate) in a solvent (e.g. cyclohexane, dichloromethane, methylcyclohexane) to form the desired borate or aluminate along with byproduct alkali metal chloride, the latter of which can typically be removed by filtration.

In at least one embodiment, the general synthesis of the ammonium borate activators can be performed using a two-step process. In the first step, an amine is dissolved in a solvent (e.g. hexane, cyclohexane, methylcyclohexane, ether, dichloromethane, toluene) and an excess (e.g., 1.2 molar equivalents) of hydrogen chloride is added to form an ammonium chloride salt. This salt is typically isolated by filtration from the reaction medium and dried under reduced pressure. The isolated ammonium chloride is then heated to reflux with about one molar equivalent of an alkali metal borate in a solvent (e.g. cyclohexane, dichloromethane, methylcyclohexane) to form the ammonium borate along with byproduct alkali metal chloride, the latter of which can typically be removed by filtration.

A co-activator is a compound capable of alkylating the transition metal complex, such that when used in combination with an activator, an active catalyst is formed. Co-activators can include alumoxanes such as methylalumoxane, modified alumoxanes such as modified methylalumoxane, and aluminum alkyls such trimethylaluminum, tri-isobutylaluminum, triethylaluminum, and tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the pre-catalyst is not a dihydrocarbyl or dihydride complex. Sometimes co-activators are also used as scavengers to deactivate impurities in feed or reactors.

Additional activators that may be used with the above non-aromatic hydrocarbon soluble activators include alumoxanes or alumoxanes in combination with an NCA. Alumoxanes are generally oligomeric compounds containing $-Al(R^1)-O$ sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkyl-alumoxanes are suitable as catalyst co-activators, such as when the abstractable ligand is an alkyl, halide, alkoxide or amide. Mixtures of different alumoxanes and modified alumoxanes may also be used.

The reaction time or reactor residence time using the catalyst systems described herein can be dependent on the type of catalyst used, the amount of catalyst used, and the desired conversion level. Different transition metal compounds (also referred to as metallocene) have different activities. A high amount of catalyst loading tends to give high conversion at short reaction time. However, a high amount of catalyst usage can make the production process uneconomical and difficult to manage the reaction heat or to control the reaction temperature. Therefore, it is useful to choose a catalyst with maximum catalyst productivity to minimize the amount of metallocene and the amount of activators needed. For a catalyst system of metallocene plus a Lewis Acid or an ionic promoter with NCA component, the transition metal compound used may be from about 0.01 microgram to about 500 micrograms of metallocene component/gram of alpha-olefin feed, such as from about 0.1 microgram to about 100 microgram of metallocene component per gram of alpha-olefin feed. Furthermore, the molar ratio of the NCA activator to metallocene can be from about 0.1 to about 10, such as about 0.5 to about 5, such as about 0.5 to about 3. For the co-activators of alkylaluminums, the molar ratio of the co-activator to metallocene can be from about 1 to about 1000, such as about 2 to about 500, such as about 4 to about 400.

In selecting oligomerization conditions, to obtain the desired first reactor effluent, the system uses the transition metal compound (also referred to as the catalyst), activator, and co-activator. US 2007/0043248 and US 2010/029242 provide additional details of metallocene catalysts, activators, co-activators, and appropriate ratios of such compounds in the feedstock that may be useful, and these additional details are hereby incorporated by reference.

IV. B.3 Scavengers for the First Oligomerization

A scavenger can be an additional component of a catalyst system described herein. A scavenger is a compound typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene. To the extent scavengers facilitate the metallocene compound in performing the intended catalytic function, scavengers, if used, are sometimes considered as a part of the catalyst system.

U.S. Pat. No. 9,409,834 (e.g., at line 37, column 33 to line 61, column 34) provides detailed description of scavengers useful in the process of the present disclosure for making PAO. The relevant portions in this patent on scavengers, their identities, quantity, and manner of use are incorporated herein in their entirety.

The co-activator may also be used as a scavenger to deactivate impurities in feed or reactors. A scavenger is a compound that is sufficiently Lewis acidic to coordinate with polar contaminates and impurities adventitiously occurring in the polymerization feedstocks or reaction medium. Such impurities can be inadvertently introduced with any of the reaction components, and adversely affect catalyst activity and stability. Scavenging compounds may be organometallic compounds such as triethyl aluminum, triethyl borane, tri-isobutyl aluminum, methylalumoxane, isobutyl aluminumoxane, tri-n-hexyl aluminum, tri-n-octyl aluminum, and those having bulky substituents covalently bound to the metal or metalloid center being exemplary to minimize adverse interaction with the active catalyst. Other useful scavenger compounds may include those mentioned in U.S. Pat. No. 5,241,025; EP-A 0426638; and WO 1997/022635, which are hereby incorporated by reference for such details.

Particularly useful scavengers include tri-n-octylaluminum, triethylaluminum, triisobutylaluminum, tri-n-hexyl-aluminum, and the like.

IV.C. Process for Making PAO

The process for making a PAO in the first oligomerization includes a step of contacting a feed comprising a $C_6$-$C_{32}$ alpha-olefin (preferably $C_6$-$C_{30}$, particularly $C_6$-$C_{24}$, $C_6$-$C_{18}$, $C_8$-$C_{18}$, or $C_6$-$C_{12}$) with a catalyst system comprising a metallocene compound described above in a polymerization reactor under polymerization conditions to effect a polymerization reaction to obtain a polymerization reaction mixture comprising vinylidenes, tri-substituted vinylenes, optional di-substituted vinylenes, and optional vinyls; and obtaining an unsaturated PAO product from the polymerization reaction mixture, wherein the unsaturated PAO product comprises vinylidenes, tri-substituted vinylenes, optional di-substituted vinylenes, and optional vinyls.

IV. C.1 Monomer(s)

The alpha-olefin feed for making the PAO materials of the present disclosure may comprise one or more of $C_6$-$C_{32}$ alpha-olefins (such as $C_6$-$C_{24}$, such as $C_6$-$C_{18}$, $C_8$-$C_{18}$, or $C_6$-$C_{12}$). The alpha-olefin feed may comprise ethylene, propylene, $C_4$ alpha-olefins, and $C_5$ alpha-olefins. In certain embodiments, each of ethylene, propylene, $C_4$ alpha-olefins (1-butene and 2-methyl-1-propene), and $C_5$ alpha-olefins (1-pentene and various isomers of methyl-1-butene) is supplied to the polymerization reactor, each independently at no higher than c1 mol %, based on the total moles of the alpha-olefins supplied to the polymerization reactor, where c1 can be 25, 20, 10, 5, 4, 3, 2, 1, 0.5, 0.1, or 0.01, for each monomer; additionally or alternatively, any combination of $C_2$-$C_5$ alpha-olefins (including two or more, three or more, or all four of ethylene, propylene, $C_4$ alpha-olefins, and $C_5$ alpha-olefins) are supplied to the polymerization reactor collectively at no higher than c1 mol %, based on the total moles of the alpha-olefins supplied to the polymerization reactor. In some embodiments, the alpha-olefin feed is substantially free of ethylene, propylene, $C_4$ alpha-olefins, and $C_5$ alpha-olefins (or completely free of intentionally added $C_2$-$C_5$ alpha-olefins, allowing for impurities present in other feed components). In some embodiments, substantially all alpha-olefins in the feed are $C_6$-$C_{30}$ (e.g., $C_6$-$C_{24}$, such as $C_6$-$C_{18}$, $C_8$-$C_{18}$, or $C_6$-$C_{12}$) alpha-olefins. "Substantially all" means at least 90 mol % (e.g., at least about 92 mol %, at least about 94 mol %, at least about 95 mol %, at least about 96 mol %, at least about 98 mol %, at least about 99%, at least about 99.5 mol %, or completely all, allowing for some impurities present in feed components), based on the total moles of the alpha-olefins present in the feed. In some embodiments, any combination of $C_2$-$C_5$ alpha-olefins are collectively present in the alpha-olefin feed at no higher than c1 mol %, (where c1 can be about 25, about 20, about 10, about 5, about 4, about 3, about 2, about 1, about 0.5, about 0.1, or about 0.01), based on the total moles of the alpha-olefins supplied to the polymerization reactor.

In some embodiments, at least a portion (e.g., at least about 80 mol %, at least about 85 mol %, at least about 90 mol %, at least about 95 mol %, at least about 96 mol %, at least about 98 mol %, at least about 99 mol %, at least about 99.5 mol %, or completely all, allowing for some impurities present in feed components) of the alpha-olefins present in the feed are linear alpha-olefins (LAOs), i.e., those without a branch attached to the carbon backbone thereof. Non-limiting examples of LAOs are 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 1-icocene, $C_{22}$, $C_{24}$, $C_{26}$, $C_{28}$, $C_{30}$ and $C_{32}$ LAOs, and a combination thereof. Without being bound by theory, PAO products made from such LAOs by using the process of the present disclosure can tend to have fewer branches and pendant groups, leading to generally more uniform PAO molecular structures.

Where a single alpha-olefin is fed to the polymerization reactor, the thus obtained PAO is a homopolymer. Homopolymers can have substantially uniform molecular structure, and accordingly desirable physical and rheological properties such as viscosity index. A homopolymer can tend to have pendant groups attached to the carbon backbone with highly uniform length.

In certain situations, a mixture of two, three, or even more alpha-olefins in the feed may be desired to produce a copolymer PAO product. To that end, alpha-olefins with the following combinations can be advantageous: $C_6/C_8$, $C_6/C_{10}$, $C_6/C_{12}$, $C_6/C_{14}$, $C_6/C_{16}$, $C_8/C_{10}$, $C_8/C_{12}$, $C_8/C_{14}$, $C_8/C_{16}$, $C_{10}/C_{12}$, $C_{10}/C_{14}$, $C_{10}/C_{16}$, $C_{10}/C_{18}$, $C_{12}/C_{14}$, $C_{12}/C_{16}$, $C_{12}/C_{18}$, $C_{12}/C_{20}$, $C_6/C_8/C_{10}$, $C_6/C_8/C_{12}$, $C_6/C_8/C_{14}$, $C_6/C_{10}/C_{12}$, $C_6/C_{10}/C_{14}$, $C_8/C_{10}/C_{12}$, $C_8/C_{11}/C_{14}$, $C_8/C_{12}/C_{14}$, $C_{10}/C_{12}/C_{16}$, $C_{10}/C_{12}/C_{18}$, $C_{10}/C_{14}/C_{16}$, $C_{10}/C_{14}/C_{18}$, and the like. In some embodiments, at least one of the alpha-olefins in the mixture feed can be an LAO. In some embodiments, substantially all of the alpha-olefins in the mixture feed can be LAOs.

In some embodiments, alpha-olefin monomers are mono-olefins containing one C=C bond per monomer molecule, though those olefins containing two or more C=C bonds per monomer molecule can be used as well.

In some embodiments, monomers useful herein include substituted or unsubstituted $C_6$ to $C_{32}$ alpha-olefins, or $C_6$ to $C_{20}$ alpha-olefins, or $C_6$ to $C_{14}$ alpha-olefins, or hexene, heptene, octene, nonene, decene, undecene, dodecene, tetradecene and isomers thereof. In some embodiments, the poly alpha-olefin prepared herein comprises about 50 mol % or more (such as about 60 mol % or more, such as about 70 mol % or more, such as about 80 mol % or more, such as about 90 mol % or more, such as about 99 mol % or more) of one or more $C_6$ to $C_{32}$ (such as $C_6$ to $C_{20}$, such as $C_8$ to $C_{18}$) alpha-olefin monomers.

Useful $C_6$ to $C_{32}$ alpha-olefin monomers include hexene, heptane, octene, nonene, decene, undecene, dodecene, tetradecene, substituted derivatives thereof, and isomers thereof.

In some embodiments, the monomers comprise $C_6$ to $C_{20}$ alpha-olefins, or $C_6$ to $C_{14}$ alpha-olefins, and/or $C_8$ to $C_{12}$ alpha-olefins.

In some embodiments, olefin monomers include one (alternately two, alternately three) or more of hexene, heptene, octene, nonene, decene, dodecene, and tetradecene.

In an embodiment the PAO is a homopolymer of any $C_8$ to $C_{12}$ alpha-olefin, i.e., the PAO is a homopolymer of 1-hexene, 1-heptene, 1-octene, 1-nonene, 1-decene, 1-undecene, 1-dodecene or 1-tetradecene. In some embodiments, the PAO is a homopolymer of decene. In at least one embodiment the PAO is a copolymer comprising decene and one or more of any of the monomers listed above.

In an embodiment, the PAO comprises two or more monomers, or three or more monomers, or four or more monomers, or five or more monomers. For example, a $C_8$, $C_{10}$, $C_{12}$-linear alpha-olefin mixture, or a $C_6$, $C_7$, $C_8$, $C_9$, $C_{10}$, $C_{11}$, $C_{12}$, $C_{13}$, $C_{14}$-linear alpha-olefin mixture, or a $C_6$, $C_8$, $C_{10}$, $C_{12}$, $C_{14}$, $C_{16}$, $C_{18}$-linear alpha-olefin mixture can be used as a feed.

In at least one embodiment, the PAO comprises less than about 50 mol % of $C_2$, $C_3$, and $C_4$ monomers, or less than about 40 mol %, or less than about 30 mol %, or less than about 20 mol %, or less than about 10 mol %, or less than about 5 mol %, or less than about 3 mol %, or about 0 mol %. Specifically, in at least one embodiment, the PAO comprises less than about 50 mol % of ethylene, propylene and butene, or less than about 40 mol %, or less than about 30 mol %, or less than about 20 mol %, or less than about 10 mol %, or less than about 5 mol %, or less than about 3 mol %, or about 0 mol %. In at least one embodiment, the PAO comprises less than about 40 mol %, or less than about 20 mol %, or less than about 10 mol %, or less than about 5 mol %, or less than about 3 mol %, or about 0 mol % of ethylene.

In at least one embodiment, the PAO comprises less than 25 mol % of $C_2$, $C_3$, and $C_4$ monomers, or less than about 20 mol %, or less than about 15 mol %, or less than about 10 mol %, or less than about 5 mol %, or less than about 1 mol %, or about 0 mol %. Specifically, in at least one embodiment, the PAO comprises less than about 25 mol % of ethylene, propylene and butene, or less than about 20 mol %, or less than about 15 mol %, or less than about 10 mol %, or less than about 5 mol %, or less than about 1 mol %, or about 0 mol %. In at least one embodiment, the PAO comprises less than about 25 mol %, or less than about 20 mol %, or less than about 10 mol %, or less than about 5 mol %, or less than about 1 mol %, or about 0 mol % of ethylene.

In at least one embodiment, the PAO comprises less than about 40 mol % of propylene. In at least one embodiment, the PAO comprises less than about 40 mol % of butene. In at least one embodiment, the PAO comprises less than about 10 mol % of ethylene. In at least one embodiment, the PAO comprises less than about 10 mol % of propylene. In at least one embodiment, the PAO comprises less than about 10 mol % of butene.

In at least one embodiment, the PAO comprises less than about 25 mol % of propylene. In at least one embodiment, the PAO comprises less than about 25 mol % of butene. In at least one embodiment, the PAO comprises less than about 5 mol % of ethylene. In at least one embodiment, the PAO comprises less than about 5 mol % of propylene. In at least one embodiment, the PAO comprises less than about 5 mol % of butene. In at least one embodiment, the PAO comprises less than about 1 mol % of ethylene. In at least one embodiment, the PAO comprises less than about 1 mol % of propylene. In at least one embodiment, the PAO comprises less than about 1 mol % of butene.

The alpha-olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other alpha-olefin synthesis routes. An exemplary feed for this disclosure can be at least 80 wt % alpha-olefin (such as linear alpha-olefin), such as at least 90 wt % alpha-olefin (such as linear alpha-olefin), or approximately 100% alpha-olefin (such as linear alpha-olefin). However, alpha-olefin mixtures can also be used as feeds in this disclosure, especially if the other components are internal-olefins, branched olefins, paraffins, cyclic paraffins, aromatics (such as toluene and or xylenes). These components may have diluent effects and are believed to not have a substantial detrimental effect on the polymerization of alpha-olefins. In other words, the process described herein can selectively convert alpha-olefins in a mixture and leave the other components largely, if not completely, unreacted. This can be useful when ethylene is not present in the mixture. This technology can be used to separate out alpha-olefins from a mixture by selectively reacting them with polymerization or oligomerization catalyst systems, effectively if not completely eliminating the need to separate alpha-olefins from the remainder of the components in a mixed feed stream. This can be economically advantageous, for example, in a process utilizing Fisher-Tropsch synthesis olefin product streams containing alpha-olefins, internal-olefins and branched olefins. Such a mixture can be fed to oligomerization technology as described herein and to selectively react away the alpha-olefin. No separate step to isolate the alpha-olefin may be needed. Another example of the utility of this process involves alpha-olefins produced by the metathesis of internal olefins with ethylene, which may contain some internal olefins. This mixed olefin base stock feed can be reacted as-is in the polymerization/oligomerization process of the present disclosure, which selectively converts the alpha-olefins into lube products. Thus, one can use the alpha-olefin for the base stock synthesis without having to separate the alpha-olefin from internal olefin. This can bring a significant improvement in process economics. The feed olefins can be the mixture of olefins produced from other linear alpha-olefin process containing $C_4$ to $C_{20}$ alpha-olefins as described in Chapter 3 "Routes to Alpha-Olefins" of the book *Alpha Olefins Applications Handbook*, Edited by G. R. Lappin and J. D. Sauer, published by Marcel Dekker, Inc. N.Y. 1989.

IV. C.2 Feed Purification

Olefin feed and or solvents may be treated to remove catalyst poisons, such as peroxides, oxygen, or nitrogen-containing organic compounds or acetylenic compounds before being supplied to the polymerization reactor. For example, the treatment of the linear alpha-olefin with an activated 13 Å molecular sieve and a de-oxygenate catalyst (i.e., a reduced copper catalyst) can increase catalyst activity (expressed in terms of quantity of PAO produced per micromole of the metallocene compound used) more than 10-fold. Alternatively, the feed olefins and or solvents may be treated with an activated molecular sieve, such as 3 Å, 4 Å, 8 Å, or 13 Å molecular sieve, and/or in combination with an activated alumina or an activated de-oxygenate catalyst. Such treatment can increase catalyst activity y 2- to 10-fold or more.

IV. C.3 Polymerization Reaction

Many polymerization/oligomerization processes and reactor types used for metallocene-catalyzed polymerization or oligomerization such as solution, slurry, and bulk polymerization or oligomerization processed can be used in this present disclosure. If a solid or supported catalyst is used, a slurry or continuous fixed bed or plug flow process may be suitable. In some embodiments, the monomers are contacted with the metallocene compound and the activator in the solution phase, bulk phase, or slurry phase, for example in a continuous stirred tank reactor or a continuous tubular reactor. In some embodiments, the temperature in any reactor used herein can be from about −10° C. to about 250° C., e.g., from about 30° C. to about 220° C., such as from about 50° C. to about 180° C., from about 60° C. to about 170° C., or from about 70° C. to about 150° C. In some embodiments, the pressure in any reactor used herein can be from about 0.1 to about 100 atmospheres, e.g., from about 0.5 to about 75 atmospheres or from about 1 to about 50 atmospheres. Alternatively, the pressure in any reactor used herein can be from about 1 to about 50,000 atmospheres, e.g., from about 1 to about 25,000 atmospheres. Additionally or alternatively, the monomer(s), metallocene and activator can be contacted for a residence time of about 1 second to about 100 hours, e.g., about 30 seconds to about 50 hours, about 2 minutes to about 6 hours, or about 1 minute to about 4 hours. Additionally or alternatively, solvent or diluent may be present in the reactor and may include butanes, pentanes, hexanes, heptanes including methylcyclohexane, octanes, nonanes, decanes, undecanes, dodecanes, tridecanes, tetradecanes, pentadecanes, hexadecanes; solvents can isoparaffin solvents (such as ISOPAR® solvents available from ExxonMobil Chemical Company in Houston, Tex.), or a combination thereof. These solvents or diluents may typically be pre-treated in same manners as the feed olefins.

Suitable solvents also include liquid olefins which may act as monomers or comonomers including $C_3$ to $C_{32}$ alpha-olefins such as propylene, 1-butene, 1-hexene, 1-pentene, 3-methyl-1-pentene, 4-methyl-1-pentene, 1-octene, 1-decene, 1-dodecene, 1-tetradecene, 1-hexadecene, 1-octadecene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In a preferred embodiment the solvents used are $C_6$ to $C_{18}$ alpha-olefins, alternatively $C_8$ to $C_{16}$ alpha-olefins, alternatively $C_8$ to $C_{14}$ alpha-olefins, or mixtures thereof. Mixtures of any of the above listed solvents may be used.

In another embodiment, the solvent is not aromatic, preferably aromatics are present in the solvent at less than 3 wt %, preferably less than 3 wt %, preferably less than 1 wt %, preferably less than 0.5 wt %, preferably less than 0.1 wt % based upon the weight of the solvents. Preferably, the solvent or mixture of solvents is aromatic free.

Preferably the solvent is selected from $C_4$ to $C_{10}$ linear, branched or cyclic alkanes.

Preferably the solvent is essentially free of all aromatic solvents.

Preferably the solvent is selected from one or more $C_6$ to $C_{32}$ alpha olefins, such as one or more $C_8$ to $C_{16}$ alpha olefins.

Preferably the solvent is essentially free of all non-alpha-olefin solvents.

In some embodiments of the invention, where all solvent is the alpha-olefin feed (monomer feed), the pre-catalyst is dissolved in the monomer feed in a first feed tank and the activator is dissolved in the monomer feed in a second feed tank. The pre-catalyst solution is then fed into the reactor separately from the activator solution, and catalyst activation occurs in the reactor. If used, the scavenger can be fed in independently, or with the activator feed, the pre-catalyst feed, or the monomer feed if a separate monomer feed is being used.

In other embodiments of the invention where all solvent is the alpha-olefin feed (monomer feed), the pre-catalyst is dissolved in the monomer feed in a first feed tank and the activator is dissolved in the monomer feed in a second feed tank, and the pre-catalyst solution is premixed with the activator solution in a zone prior to entering the reactor, typically immediately before entering the reactor. Alternately the two solutions are contacted for 1 hour or less, 30 minutes or less, 10 minutes or less, 5 minutes or less, 1 minute or less before entering the reactor.

When $C_4$ to $C_{10}$ linear, branched or cyclic alkanes are used in the process as solvent/diluent, the pre-catalyst and activator can be pre-mixed in a feed tank, and fed into the reactor together.

Regardless of the type of reactor or process, it can be desired that the average activity level of the catalyst system be maintained at or above a sufficiently high level, so as to attain a minimum reasonable yield of oligomeric product, relative to monomeric reactant(s). For example, in some embodiments, the catalytic reaction can have an average activity level of at least about 800 g/s·mol, e.g., at least about 900 g/s·mol, at least about 1000 g/s·mol, at least about 1100 g/s·mol, at least about 1200 g/s·mol, at least about 1300 g/s·mol, at least about 1400 g/s·mol, at least about 1500 g/s·mol, at least about 1700 g/s·mol, at least about 1900 g/s·mol, at least about 2100 g/s·mol, at least about 2500 g/s·mol, or at least about 2800 g/s·mol; although average activity levels are not often characterized as being "too high," it is theoretically possible for the average activity level to be so high that control of the reaction product may be difficult to achieve in practice, such that the average catalytic reaction activity level can optionally be less than about 1000 kg/s·mol, e.g., less than about 500 kg/s·mol, in some embodiments. Additionally or alternatively, in some embodiments, the catalytic reaction can provide a minimum reasonable yield (grams of oligomer per grams of monomer feed) of at least about 18%, e.g., at least about 19%, at least about 20%, at least about 22%, at least about 24%, at least about 27%, at least about 30%, at least about 33%, at least about 36%, at least about 38%, or at least 40%, based on a reaction time of about 1 hour (about 3600 s); although reasonable catalytic yield is not often characterized as being "too high," with a maximum of approximately 100% in a 1-hour reaction time, it is theoretically possible for relatively high yields, such as high yields in relatively short reaction times, to detrimentally affect the ability to control the reaction product, e.g., such that a maximum reasonable yield may optionally be approximately 100% in a reaction time of about 1 minute or less, e.g., approximately about 100% in a reaction time of about 10 minutes or less, approximately 100% in a reaction time of about 30 minutes or less, approximately 100% in a reaction time of about 1 hour or less, approximately about 95% in a reaction time of about 1 hour or less, or approximately 90% in a reaction time of about 1 hour or less.

In some embodiments, it can be desirable to attain both relatively low product molecular weight and relatively high product vinylidene content. However, in many metallocene reactions where a vinylidene bond is a significant unsaturation product (at least 30 mol %, relative to the total number of moles of vinyls, vinylidenes, di-substituted vinylenes, and tri-substituted vinylenes), increasing reaction temperature can cause a decrease (or at least no increase) in both molecular weight and vinylidene content. Because reaction temperature can be one of the most ubiquitous ways to control product characterization parameters for a given catalyst system, it can often be a challenge to attain a product having both relatively low molecular weight and relatively high vinylidene content in many conventional systems. Thus, in some embodiments of the present disclosure, the combination of the reaction/polymerization/oligomerization conditions with certain metallocene catalyst systems can advantageously result in both decreasing molecular weight and increasing vinylidene content with increasing reaction temperature, thereby allowing heightened control of desired parameters without having to sacrifice one too much to attain the other. In some embodiments, e.g., by carefully selecting the elements of the metallocene catalyst system, the average activity level of the catalyst system be can be further advantageously maintained at or above a sufficiently high level, so as to attain a minimum reasonable yield of oligomeric product, relative to monomeric reactant(s).

Typically, one or more metallocene compounds, one or more activators, and one or more monomers are contacted to produce polymer or oligomer. These catalysts may be supported and, as such, may be useful in the known slurry, solution, or bulk operating modes conducted in single, series, or parallel reactors. If the catalyst, activator, or co-activator is a soluble compound, the reaction can be carried out in a solution mode. Even if one of the components is not completely soluble in the reaction medium or in the feed solution, either at the beginning of the reaction or during or at later stages of the reaction, a solution or slurry type operation may still be applicable. In any instance, the catalyst system components, dissolved or suspended insolvents, such as an aliphatic solvent, or in the feed alpha-olefin stream, can be fed into the reactor under inert atmosphere (usually nitrogen or argon blanketed atmosphere) to allow the polymerization or oligomerization to take place.

The polymerization or oligomerization can be run in a batch mode, where all the components are added into a reactor and allowed to react to a pre-designed degree of conversion, either to partial conversion or full conversion. Subsequently, the catalyst can be deactivated by any possible means, such as exposure to air or water, or by addition of alcohols or solvents containing deactivating agents.

The polymerization or oligomerization can additionally or alternatively be carried out in a semi-continuous operation, where feeds and catalyst system components can be continuously and/or simultaneously added to the reactor so as to maintain a constant ratio of catalyst system components to feed olefin(s). When all feeds and catalyst system components are added, the reaction may be allowed to proceed to a pre-determined stage. The reaction can then be discontinued by catalyst deactivation in the same manner as described for batch operation.

The polymerization or oligomerization can additionally or alternatively be carried out in a continuous operation, where feeds and catalyst system components can be continuously and/or simultaneously added to the reactor so to maintain a constant ratio of catalyst system and feed olefins. The reaction product can be continuously withdrawn from the reactor, as in a typical continuous stirred tank reactor (CSTR) operation. The residence times of the reactants can be controlled by a pre-determined degree of conversion. The withdrawn product can then typically be quenched in the separate reactor in a similar manner as other operation. In some embodiments, any of the processes to prepare PAOs described herein are continuous processes, which can include a) continuously introducing a feed stream comprising at least 10 mol % of the one or more $C_6$ to $C_{24}$ alpha-olefins into a reactor, b) continuously introducing the metallocene compound and the activator into the reactor, and c) continuously withdrawing the PAO from the reactor. Additionally or alternatively, the continuous process can include the step of maintaining a partial pressure of hydrogen in the reactor of about 215 psi (about 1.5 MPa) or less, based upon the total pressure of the reactor, e.g., about 175 psi (about 1.2 MPa) or less, about 115 psi (about 790 kPa) or less, about 100 psi (about 690 kPa) or less, about 65 psi (about 450 kPa) or less, about 50 psi (about 350 kPa) or less, about 40 psi (about 280 kPa) or less, about 25 psi (about 170 kPa) or less, or about 10 psi (about 69 kPa) or less. Additionally or alternatively the hydrogen, if present in the reactor, in the feed, or in both, at a concentration of about 1000 ppm or less by weight, e.g., about 750 wppm or less, about 500 wppm or less, about 250 wppm or less, about 100 wppm or less, about 50 wppm or less, about 25 wppm or less, about 10 wppm or less, or about 5 wppm or less.

Example reactors can range in size from 2 mL and up. Usually, the reactors are larger than one liter in volume for commercial production. The production facility may have one single reactor, or several reactors, arranged in series or in parallel or in both to improve productivity, product properties, and general process efficiency. The reactors and associated equipment are usually pre-treated to ensure proper reaction rates and catalyst performance. The reaction is usually conducted under inert atmosphere, where the catalyst system and feed components may be out of contact with any catalyst deactivator or poison, e.g., polar oxygen, nitrogen, sulfur, and/or acetylenic compounds.

One or more reactors in series or in parallel may be used in the present disclosure. The metallocene compound, activator and when required, co-activator, may be delivered as a solution or slurry in a solvent or in the alpha-olefin feed stream, either separately to the reactor, activated in-line just prior to the reactor, or pre-activated and pumped as an activated solution or slurry to the reactor. Polymerizations/oligomerization can be carried out in either single reactor operation, in which monomer, or several monomers, catalyst/activator/co-activator, optional scavenger, and optional modifiers may be added continuously to a single reactor or in series reactor operation, in which the above components can be added to each of two or more reactors connected in series. The catalyst system components can be added to the first reactor in the series. The catalyst system component may alternatively be added to both reactors, with one component being added to first reaction and another component to other reactors. In some embodiments, the metallocene compound can be activated in the reactor in the presence of olefin. Alternatively, the metallocene compound (such as a dichloride form of the metallocene compound) may be pre-treated with an alkylaluminum reagent, especially triisobutylaluminum, tri-n-hexylaluminum, and/or tri-n-octylaluminum, followed by charging into the reactor containing other catalyst system component and the feed olefins, or followed by pre-activation with the other catalyst system component to give the fully activated catalyst, which can then be fed into the reactor containing feed olefins. In another alternative, the pre-catalyst metallocene can be mixed with the activator and/or the co-activator, and this activated catalyst can then be charged into reactor, together with feed olefin stream containing some scavenger or co-activator. In another alternative, the whole or part of the co-activator can be pre-mixed with the feed olefins and charged into the reactor at the same time as the other catalyst solution containing metallocene and activators and/or co-activator.

The catalyst compositions can be used individually or can be mixed with other known polymerization catalysts to prepare polymer or oligomer blends. Monomer and catalyst selection can allow polymer or oligomer blend preparation under conditions analogous to those using individual catalysts. Polymers having increased PDI are available from polymers made with mixed catalyst systems and can thus be achieved. Mixed catalyst can comprise two or more metallocene compounds and or two or more activators.

The PAOs described herein can additionally or alternatively be produced in homogeneous solution processes. Generally, this involves polymerization or oligomerization in a continuous reactor in which the polymer formed and the starting monomer and catalyst materials supplied may be agitated to reduce or avoid concentration or temperature gradients. Temperature control in the reactor can generally be obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers, or solvent) or a combination thereof. Adiabatic reactors with pre-chilled feeds may additionally or alternatively be used. The reactor temperature may vary with the catalyst used and the product desired. Higher temperatures can tend to give lower molecular weights, and lower temperatures can tend to give higher molecular weights; however, this is not a fixed rule. In general, the reactor temperature can vary between about 0° C. and about 300° C., e.g., from about 10° C. to about 230° C. or from about 25° C. to about 200° C. Usually, it is important to control the reaction temperature as pre-determined. In order to produce fluids with narrow polydispersity, such as to promote the highest possible shear stability, it can be useful to control the reaction temperature to obtain minimum of temperature fluctuation in the reactor or over the course of the reaction time. If multiple reactors are used in series or in parallel, it may be useful to keep the temperature constant in a pre-determined value, e.g., to minimize any broadening of molecular weight distribution. In order to produce a product with broader molecular weight distribution, one can adjust the reaction temperature swing or fluctuation, or, as in series operation, the second reactor temperature may be higher than the first reactor temperature. In parallel reactor operation, the temperatures of the two reactors may be independent. More than one type of metallocene catalyst can be used.

The pressure in any reactor used herein can vary from about 0.1 atmosphere to about 100 atmospheres (about 1.5 psia to about 1500 psia), e.g., from about 0.5 atm to about 80 atm (from about 7 psia to about 1200 psia) or from about 1.0 atm to about 50 atm (from about 15 psia to about 750 psia). The reaction can be carried out under an atmosphere of nitrogen or with some hydrogen. Sometimes a small amount of hydrogen may be added to the reactor to improve catalyst performance. When present, the amount of hydrogen can be kept at such a level to improve catalyst productivity and or activity, but not induce too much (such as any significant) hydrogenation of olefins, especially the feed alpha-olefins (the reaction of alpha-olefins into saturated paraffins can be very detrimental to the efficiency of the process). The amount of hydrogen partial pressure can be kept low, e.g., less than about 50 psi (about 350 kPa), less than about 25 psi (about 170 kPa), less than about 10 psi (about 69 kPa), or less than about 5 psi (about 35 kPa); additionally or alternatively, the concentration of hydrogen in the reactant phase, in the reactor and/or feed, can be less than about 10,000 ppm (by wt.), e.g., less than about 1000 ppm, less than about 500 ppm, less than about 100 ppm, less than about 50 ppm, less than about 25 ppm, or less than about 10 ppm.

The reaction time or reactor residence time can depend on the catalyst used, the amount of catalyst used, and the desired alpha-olefin conversion level. Different metallocene compounds typically have different activities. Usually, a higher degree of alkyl substitution on the Cp ring, or bridging can improve catalyst productivity and or activity. High amounts of catalyst loading can tend to give higher alpha-olefin conversion at shorter reaction times. However, high amount of catalyst usage can make the production process uneconomical and difficult to manage the reaction heat or to control the reaction temperature. Therefore, it can be useful to choose a catalyst with maximum catalyst productivity and or activity to minimize the amount of metallocene and activator needed. When the catalyst system is a metallocene plus non-aromatic hydrocarbon soluble activator plus methylalumoxane, the range of methylalumoxane used can be in the range of about 0.1 milligram/gram (mg/g) to about 500 mg/g of alpha-olefin feed, e.g., from about 0.05 mg/g to about 10 mg/g. Furthermore, the molar ratios of the aluminum to metallocene (Al/M molar ratio) can range from about 2 to about 4000, e.g., from about 10 to about 2000, from about 50 to about 1000, or from about 100 to about 500. When the catalyst system is a metallocene plus a Lewis Acid or an ionic promoter with NCA component (such as the non-aromatic hydrocarbon soluble activators described herein), the metallocene use can be in the range of about 0.01 microgram/gram (mcg/g) to about 500 mcg/g of metallocene component relative to alpha-olefin feed, e.g., from about 0.1 mcg/g to about 100 mcg/g, and/or the molar ratio of the NCA activator to metallocene can be in the range from about 0.1 to about 10, e.g., from about 0.5 to about 5 or from about 0.5 to about 3. If a co-activator of alkylaluminum compound is used, the molar ratio of the Al to metallocene can be in the range from about 1 to about 1000, e.g., from about 2 to about 500 or from about 4 to about 400.

In some embodiments, the process can have the highest possible alpha-olefin conversion (close to 100%) of feed alpha-olefin in shortest possible reaction time. However, in CSTR operation, sometimes it can be beneficial to run the reaction at an optimum alpha-olefin conversion, which can be less than about 100% alpha-olefin conversion, but can be close to about 100%. There are also occasions, when partial alpha-olefin conversion can be more desirable, e.g., when a narrow product PDI is desirable, because partial conversion can avoid a PDI broadening effect. If the reaction is conducted to less than 100% conversion of the alpha-olefin, the unreacted starting material after separation from other product and solvents/diluents can be simply removed, or may be recycled to increase the total process efficiency. Conversion, also called alpha-olefin conversion, is determined by dividing the amount (grams) of isolated PAO recovered from the polymerization mixture (after the polymerization has been stopped) by the amount (grams) of alpha-olefin introduced into the reactor. (When reported in %, conversion=(grams isolated PAO/grams alpha-olefin used)×100). In some embodiments, the conversion for the polymerization reactions described herein is about 20% or more, alternatively about 40% or more, alternatively about 60% or more, alternatively about 70% or more, alternatively about 80% or more, alternatively about 90% or more, alternatively about 95% or more. Isolated PAO is the PAO product obtained after solvent, unreacted monomer and other volatiles (such as dimer) have been removed (such as by vacuum flash).

Example residence times for any process described herein can be from about 1 minute to about 20 hours, e.g., from about 5 minutes to about 10 hour.

Each of these processes may also be employed in single reactor, parallel or series reactor configurations. The process can be carried out in a continuous stirred tank reactor or plug flow reactor, or more than one reactor operated in series or parallel. These reactors may or may not have internal cooling and the monomer feed may or may not be refrigerated. See the general disclosure of U.S. Pat. No. 5,705,577 for general process conditions.

When a solid supported catalyst is used, a slurry polymerization/oligomerization process generally operates in the similar temperature, pressure, and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge, or settlement. The fluid is then distilled to remove solvent, any unreacted components and light product. A portion or all of the solvent and unreacted component or light components can be recycled for reuse.

If the catalyst used is un-supported or is a solution catalyst, when the reaction is complete or when the product is withdrawn from the reactor (such as in a CSTR), the product may still contain soluble, suspended, or mixed catalyst system components. These components can be deactivated and/or removed. Any of the usual catalyst deactivation methods or aqueous wash methods can be used to remove the catalyst system component. Typically, the reaction can be deactivated by addition of stoichiometric amount or excess of air, moisture, alcohol, isopropanol, etc. The mixture can then be washed with dilute sodium hydroxide or with water to remove catalyst system components. The residual organic layer may then be subjected to distillation to remove solvent, which can optionally be recycled for reuse. The distillation can further remove any light reaction product, e.g., from $C_{18}$ and less.

Polymerization or oligomerization in absence of hydrogen may be advantageous to provide polymers or oligomers with high degree of unsaturated double bonds.

In some embodiments, in the process of the present disclosure, due to the structure features of the metallocene compound, the polymerization reaction mixture exiting the polymerization reactor can typically comprise oligomers including vinylidenes, tri-substituted vinylenes, optionally di-substituted vinylenes, and optionally vinyls, optionally residual olefin monomer feed, optionally solvents, and components derived from the catalyst system.

The polymerization reaction mixture can then be quenched, e.g., by the addition of a quenching agent such as water, $CO_2$, methanol, ethanol, mixtures thereof, and the like. Subsequently, the polymerization reaction mixture can be separated to remove the residual monomer, which can be recycled to the polymerization reactor. Monomer removal can be carried out by means such as flashing under vacuum, distillation, or extraction. The resultant mixture can comprise a first reactor effluent including vinylidenes, tri-substituted vinylenes, optionally di-substituted vinylenes, and optionally vinyls.

Without being bound by theory, it is believed that, a non-coordinating anion with a large molecular size (e.g., di-n-octadecylanilinium tetrakisperfluoronaphthylborate) can tend to result in higher selectivity toward vinyls and a lower selectivity toward vinylidenes, as compared to non-coordinating anions with a small molecular size (e.g., di-n-octadecylanilinium tetrakisperfluorophenylborate) when used as the activator for the same metallocene compound of the present disclosure.

Optionally, hydrogen is absent or present at 1 mol % or less, preferably 0.5 mol % or less in the polymerization reaction. Optionally no hydrogen is added into the polymerization process.

In an embodiment of the invention, little or no scavenger is used in the polymerization to produce the polymer, i.e., scavenger (such as trialkyl aluminum, e.g. tri-n-octylaluminum) is present at zero mol %, alternately the scavenger is present at a molar ratio of scavenger metal to transition metal of less than 100:1, preferably less than 50:1, preferably less than 15:1, preferably less than 10:1. Alternately less than 100 ppm of scavenger is present in the polymerization. Preferably less than 100 ppm of alkylaluminum, such as trialkyl aluminum, is present in the polymerization reaction. Trialkyl aluminum is typically represented by the formula $R_3Al$, where each R is independently, a $C_1$ to $C_{40}$, preferably $C_1$ to $C_{20}$ alkyl group, such as methyl, ethyl, propyl, butyl, pentyl, hexyl, heptyl, octyl, nonyl, decyl, undecyl, docecyl, isomers thereof, and mixtures thereof.

In an embodiment, little or no alumoxane (i.e., less than 0.001 wt %) is used in the polymerization processes described herein. In an embodiment, alumoxane is present at 0.00 mol %, or the alumoxane is present at a molar ratio of aluminum to catalyst compound transition metal less than 500:1, or less than 300:1, or less than 100:1, or less than 1:1.

Alternately $C_4$ olefins (such as isobutylene, butadiene, n-butene) are substantially absent from the PAO and or the polymerization process (first and or second polymerizations). Alternately $C_2$ to $C_4$ olefins are substantially absent from the PAO and or the polymerization process (first and or second polymerizations). Alternately isobutylene is substantially absent from the PAO and or the polymerization process (first and or second polymerizations). By substantially absent is meant that the monomer(s) is/are present in the PAO at 1 wt % or less, preferably at 0.5 wt % or less, preferably at 0 wt %. Likewise substantially absent in relation to the polymerization process means that the monomer(s) is/are present in the monomer feed at 1 wt % or less, preferably at 0.5 wt % or less, preferably at 0 wt %.

Optionally the catalyst productivity is 50,000 grams of PAO product per gram of first catalyst (gPAO/gCat) or more, preferably 55,000 gPAO/gCat or more, preferably 60,000 gPAO/gCat or more, preferably 100,000 gPAO/gCat or more.

Optionally PAO dimer selectivity is 85% or more, preferably 90% or more, preferably 95% or more, based upon the PAO produced.

Optionally the first polymerization temperature is 100° C. or more, preferably 100° C. or more, preferably 120° C. or more.

Optionally the first polymerization reactor residence time is 1 hour or more, preferably 2 hours or more, preferably 3 hours or more, optionally up to 5 hours.

Optionally hydrogen is absent or present at 1 mol % or less in the polymerization reaction (first and/or second), preferably 0.5 mol % or less in the first and or second polymerization reaction; little or no scavenger is used in the first and or second polymerization to produce the polymer; the catalyst productivity is 50,000 grams of PAO product per gram of catalyst (gPAO/gCat) or more, preferably 55,000 gPAO/gCat or more, preferably 60,000 gPAO/gCat or more, preferably 100,000 gPAO/gCat or more; the PAO dimer selectivity in the first polymerization is 85% or more, preferably 90% or more, preferably 95% or more, based upon the PAO produced; and the reactor temperature of the first polymerization is 100° C. or more, preferably 100° C. or more, preferably 120° C. or more.

Optionally, the PAO produced has an Mn of 3,000 g/mol or less, such as 1,000 g/mol or less, such as 500 g/mol or less, such as 350 g/mol or less and the catalyst has high conversion (e.g., at least 60%, at least 70%, at least 80%, at least 90%, based upon the weight of the monomer entering the first reactor and the PAO produced).

Optionally the catalyst loading is 0.1 gram catalyst per gram of monomer or less (gCat/gMon), preferably 0.01 gCat/gMon or less, preferably 0.005 gCat/gMon or less, preferably 0.001 gCat/gMon or less, preferably 0.0001 gCat/gMon or less.

Optionally, the PAO produced has an Mn of 3,000 g/mol or less, such as 1,000 g/mol or less, such as 500 g/mol or less, such as 350 g/mol or less and the catalyst has high conversion (e.g., at least 60%, at least 70%, at least 80%, at least 90%, based upon the weight of the monomer entering the first reactor and the PAO produced), and the catalyst loading is 0.1 gram catalyst per gram of monomer or less (gCat/gMon) in the first reactor, preferably 0.01 gCat/gMon or less, preferably 0.005 gCat/gMon or less, preferably 0.001 gCat/gMon or less, preferably 0.0001 gCat/gMon or less.

Optionally, vinylidene content (mol %) of the PAO produced is 95% or more, alternately 95% or more (based upon the total moles of vinylidene, disubstituted vinylene, and trisubstituted vinylene in the PAO product), the Mn is 3,000 g/mol or less (preferably 1500 g/mol or less, preferably 750 g/mol or less, preferably 350 g/mol or less, preferably 320 g/mol or less, preferably 300 g/mol or less), the conversion is at least 60%, at least 70%, at least 80%, at least 90%, based upon the weight of the monomer entering the reactor and the PAO produced, the PAO dimer selectivity (wt %) is at least 60%, at least 70%, at least 80%, at least 90%, based upon the weight of the PAO produced in the first reactor, and the process-productivity of the continuous process is at least 60,000 g/hour (preferably 70,000 g/hour or more, preferably 100,000 g/hr or more) with a catalyst loading of 0.1 gram catalyst per gram of monomer or less (gCat/gMon) in the first reactor, preferably 0.01 gCat/gMon or less, preferably 0.005 gCat/gMon or less, preferably 0.001 gCat/gMon or less, preferably 0.0001 gCat/gMon or less.

V. Additional Embodiments

The present disclosure provides, among others, the following embodiments, each of which may be considered as optionally including any alternate embodiments: Clause 1. A process to produce a poly alpha-olefin (PAO), the process comprising: introducing a $C_6$-$C_{32}$ alpha-olefin and a catalyst system comprising non-aromatic hydrocarbon soluble activator and a metallocene compound into a continuous stirred tank reactor or a continuous tubular reactor under reaction conditions, wherein the alpha-olefin is preferably introduced to the reactor at a flow rate of about 100 g/hr; and obtaining a product comprising PAO dimer and optional higher oligomers of alpha-olefin, or a combination thereof, the PAO dimer comprising 93 mol % or more (such as 96 mol % or more) of vinylidene, based on total moles of vinylidene, di-substituted vinylene, and tri-substituted vinylene in the product, and, preferably, the metallocene compound is represented by the formula (I):

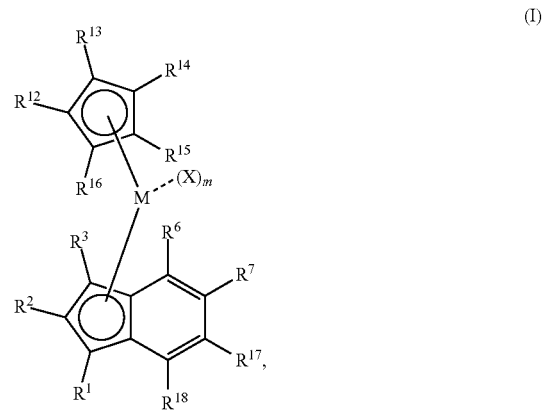

wherein:

each $R^1$, $R^2$, and $R^3$ is, independently, hydrogen or a substituted or unsubstituted linear, branched, or cyclic $C_1$-$C_{20}$ hydrocarbyl group, preferably wherein at least one of $R^1$, $R^2$, and $R^3$ is not hydrogen and at least one of $R^1$, $R^2$, and $R^3$ is hydrogen;

$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$, and $R^{15}$, are each independently a substituted or unsubstituted linear, branched, or cyclic $C_1$-$C_{20}$ hydrocarbyl group;

$R^{16}$ is a substituted or unsubstituted linear, branched, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a group 3, 4 or 5 transition metal having an integer coordination number of v (such as 3, 4, 5 or 6), preferably M is Hf or Zr;

m is an integer equal to v-2 (preferably 2, 3 or 4); and the activator is represented by the formula (V):

$$[R^{1'}R^{2'}R^{3'}EH]_{d+}[Mt^{k+}Q_n]^{d-} \qquad (V)$$

wherein: E is nitrogen or phosphorous; d is 1, 2 or 3; k is 1, 2, or 3; n is 1, 2, 3, 4, 5, or 6; n–k=d (preferably d is 1, 2 or 3; k is 3; n is 4, 5, or 6); $R^{1'}$, $R^{2'}$, and $R^{3'}$ are independently $C_1$ to $C_{50}$ hydrocarbyl group optionally substituted with one or more alkoxy groups, silyl groups, a halogen atoms, or halogen containing groups, wherein $R^{1'}$, $R^{2'}$, and $R^{3'}$ together comprise 15 or more carbon atoms; Mt is an element selected from group 13 of the Periodic Table of the Elements, such as B or Al; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Clause 2. The process of Clause 1, wherein the metallocene compound is represented by the formula: (III):

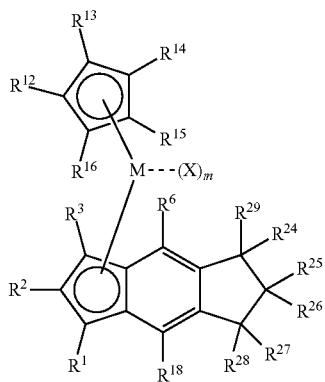

wherein one of $R^1$ and $R^3$ is a substituted or unsubstituted linear, branched, or cyclic $C_1$-$C_{20}$ hydrocarbyl group;
two of $R^1$, $R^2$, and $R^3$ are each hydrogen;
$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annelated to the cyclopentan-indenyl ring;
$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;
each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;
M is a group 3, 4, or 5 transition metal having an integer coordination number of v (such as 3, 4 5, or 6), preferably M is Hf or Zr; and
m is an integer equal to v-2 (such as 2, 3 or 4).

Clause 3. The process of Clauses 1 or 2, wherein the reaction conditions comprise a reactor temperature of about 120° C. or greater and a reactor pressure of from 15 psia to 750 psia.

Clause 4. The process of any one of Clauses 1-3, wherein the reaction conditions comprise a catalyst loading of from 25,000 g alpha-olefin (gAO) per 1 g catalyst (gCat) to 90,000 gAO/gCat.

Clause 5. The process of any one of Clauses 1-4, wherein the reaction conditions comprise a flow rate of the catalyst system of from 6 gCat/hr to about 25 gCat/hr.

Clause 6. The process of any one of Clauses 1-5, wherein the product further comprises, based on total moles (100 mol %) of vinylidene, di-substituted vinylene, and tri-substituted vinylene in the product:
up to 4 mol % tri-substituted vinylene,
up to 4 mol % di-substituted vinylene, or
up to 4 mol % tri-substituted vinylene and di-substituted vinylene.

Clause 7. The process of any one of Clauses 1-5, wherein the product comprises, based on total moles (100 mol %) of vinylidene, di-substituted vinylene, and tri-substituted vinylene in the product:
95 mol % or more vinylidene, and
up to 2 mol % (alternately up to 1 mol %, alternately up to 0.5 mol %) tri-substituted vinylene,
up to 2 mol % (alternately up to 1 mol %, alternately up to 0.5 mol %) di-substituted vinylene, or
up to 2 mol % (alternately up to 1 mol %, alternately up to 0.5 mol %) tri-substituted vinylene and di-substituted vinylene.

Clause 8. The process of any one of Clauses 1-7, wherein each of $R^1$, $R^2$, and $R^3$ is independently hydrogen or a substituted or unsubstituted linear, branched linear, or cyclic $C_1$-$C_6$ hydrocarbyl group.

Clause 9. The process of Clause 8, wherein one of $R^1$, $R^2$, and $R^3$ is a substituted or unsubstituted linear, branched linear, or cyclic $C_1$-$C_6$ hydrocarbyl group, and two of $R^1$, $R^2$, and $R^3$ are hydrogen.

Clause 10. The process of any one of Clauses 1-7, wherein the metallocene compound is represented by the formula:

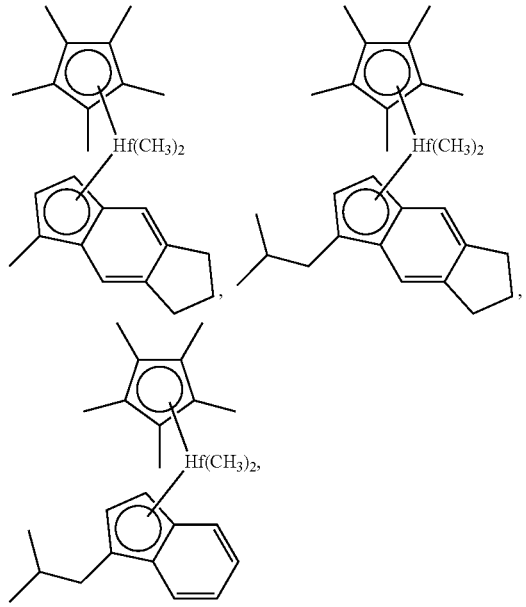

or a combination thereof.

Clause 11. The process of any one of Clauses 1-11, wherein the metallocene compound is one or more of those enumerated in Table I or List A above.

Clause 12. The process of any one of Clauses 1-11, wherein the activator is represented by the formula: $[R^1R^2R^3EH]^+$ $[BR^{4'}R^{4'}R^{5'}R^{6'}R^{7'}]^-$, wherein: E is nitrogen or phosphorous; R is a methyl group; $R^{2'}$ and $R^{3'}$ are independently is $C_4$-$C_{50}$ hydrocarbyl group optionally substituted with one or more alkoxy groups, silyl groups, a halogen atoms, or halogen containing groups wherein $R^{2'}$ and $R^{3'}$ together comprise 14 or more carbon atoms; B is boron; and $R^{4'}$, $R^{5'}$, $R^{6'}$, and $R^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Clause 13. The process of any one of Clauses 1-10, wherein the activator is represented by the formula: (VII) or formula (VIII):

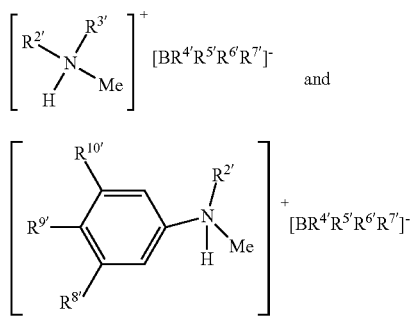

wherein:
N is nitrogen;
$R^{2'}$ and $R^{3'}$ are independently is $C_6$-$C_{40}$ hydrocarbyl group optionally substituted with one or more alkoxy groups, silyl groups, a halogen atoms, or halogen containing groups wherein $R^{2'}$ and $R^{3'}$ (if present) together comprise 14 or more carbon atoms;
$R^{8'}$, $R^{9'}$, and $R^{10'}$ are independently a $C_4$-$C_{30}$ hydrocarbyl or substituted $C_4$-$C_{30}$ hydrocarbyl group;
B is boron;
and $R^{4'}$, $R^{6'}$, and $R^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Clause 14. The process of any one of Clauses 1-13, wherein the activator comprises one or more of:
N,N-di(hydrogenated tallow)methylammonium [tetrakis(perfluorophenyl)borate],
N-methyl-4-nonadecyl-N-octadecylanilinium [tetrakis(perfluorophenyl)borate],
N-methyl-4-hexadecyl-N-octadecylanilinium [tetrakis(perfluorophenyl)borate],
N-methyl-4-tetradecyl-N-octadecylanilinium [tetrakis(perfluorophenyl)borate],
N-methyl-4-dodecyl-N-octadecylanilinium [tetrakis(perfluorophenyl)borate],
N-methyl-4-decyl-N-octadecylanilinium [tetrakis(perfluorophenyl)borate],
N-methyl-4-octyl-N-octadecylanilinium [tetrakis(perfluorophenyl)borate],
N-methyl-4-hexyl-N-octadecylanilinium [tetrakis(perfluorophenyl)borate],
N-methyl-4-butyl-N-octadecylanilinium [tetrakis(perfluorophenyl)borate],
N-methyl-4-octadecyl-N-decylanilinium [tetrakis(perfluorophenyl)borate],
N-methyl-4-nonadecyl-N-dodecylanilinium [tetrakis(perfluorophenyl)borate],
N-methyl-4-nonadecyl-N-tetradecylanilinium [tetrakis(perfluorophenyl)borate],
N-methyl-4-nonadecyl-N-hexadecylanilinium [tetrakis(perfluorophenyl)borate],
N-ethyl-4-nonadecyl-N-octadecylanilinium [tetrakis(perfluorophenyl)borate],
N-methyl-N,N-dioctadecylammonium [tetrakis(perfluorophenyl)borate],
N-methyl-N,N-dihexadecylammonium [tetrakis(perfluorophenyl)borate],
N-methyl-N,N-ditetradecylammonium [tetrakis(perfluorophenyl)borate],
N-methyl-N,N-didodecylammonium [tetrakis(perfluorophenyl)borate],
N-methyl-N,N-didecylammonium [tetrakis(perfluorophenyl)borate],
N-methyl-N,N-dioctylammonium [tetrakis(perfluorophenyl)borate],
N-ethyl-N,N-dioctadecylammonium [tetrakis(perfluorophenyl)borate],
N,N-di(octadecyl)tolylammonium [tetrakis(perfluorophenyl)borate],
N,N-di(hexadecyl)tolylammonium [tetrakis(perfluorophenyl)borate],
N,N-di(tetradecyl)tolylammonium [tetrakis(perfluorophenyl)borate],
N,N-di(dodecyl)tolylammonium [tetrakis(perfluorophenyl)borate],
N-octadecyl-N-hexadecyl-tolylammonium [tetrakis(perfluorophenyl)borate],
N-octadecyl-N-hexadecyl-tolylammonium [tetrakis(perfluorophenyl)borate],
N-octadecyl-N-tetradecyl-tolylammonium [tetrakis(perfluorophenyl)borate],
N-octadecyl-N-dodecyl-tolylammonium [tetrakis(perfluorophenyl)borate],
N-octadecyl-N-decyl-tolylammonium [tetrakis(perfluorophenyl)borate],
N-hexadecyl-N-tetradecyl-tolylammonium [tetrakis(perfluorophenyl)borate],
N-hexadecyl-N-dodecyl-tolylammonium [tetrakis(perfluorophenyl)borate],
N-hexadecyl-N-decyl-tolylammonium [tetrakis(perfluorophenyl)borate],
N-tetradecyl-N-dodecyl-tolylammonium [tetrakis(perfluorophenyl)borate],
N-tetradecyl-N-decyl-tolylammonium [tetrakis(perfluorophenyl)borate],
N-dodecyl-N-decyl-tolylammonium [tetrakis(perfluorophenyl)borate],
N-methyl-N-octadecylanilinium [tetrakis(perfluorophenyl)borate],
N-methyl-N-hexadecylanilinium [tetrakis(perfluorophenyl)borate],
N-methyl-N-tetradecylanilinium [tetrakis(perfluorophenyl)borate],
N-methyl-N-dodecylanilinium [tetrakis(perfluorophenyl)borate],
N-methyl-N-decylanilinium [tetrakis(perfluorophenyl)borate], and
N-methyl-N-octylanilinium [tetrakis(perfluorophenyl)borate].

Clause 15. The process of any one of Clauses 1-14, wherein the $C_6$-$C_{32}$ alpha-olefin is selected from the group consisting of 1-hexene, 1-heptene, 1-octene, 1-nonene, 1-decene, 1-undecene, 1-dodecene, 1-tridecene, 1-tetradecene, 1-pentadecene, 1-hexadecene, and combinations thereof.

Clause 16. The process of any one of Clauses 1-14, wherein the $C_6$-$C_{32}$ alpha-olefin is selected from the group consisting of 1-hexene, 1-octene, 1-nonene, 1-decene, 1-dodecene, 1-tetradecene, 1-hexadecene, and combinations thereof.

Clause 17. The process of any of Clauses 1 to 16 wherein the reaction conditions include: a reactor temperature of from 130° C. to 180° C., a reactor pressure of from 15 psia to 750 psia, and a catalyst loading of from 25,000 g alpha-olefin (gAO) per 1 g catalyst (gCat) to 90,000 gAO/gCat.

Clause 18. The process of Clause 17, wherein the reactor conditions comprise a reactor temperature of from 130° C. to 148° C., a reactor pressure of from 30 psia to 100 psia, and a catalyst loading of from 50,000 g alpha-olefin (gAO) per 1 g catalyst (gCat) to 80,000 gAO/gCat.

Clause 19. The process of any of Clauses 1 to 18, further comprising functionalizing the PAO dimer with a reactant to form a functionalized PAO product.

Clause 20. The process of Clause 19, wherein the reactant is a naphthalene and the functionalized PAO product is a naphthalene PAO dimer adduct.

Clause 21. The process of Clause 19, wherein the reactant is an anisole and the functionalized PAO product is an anisole PAO dimer adduct.

Clause 22. The process of any of Clauses 1 to 21, further comprising hydrogenating the product, PAO dimer, or functionalized PAO product to form a hydrogenated PAO product.

Clause 23. A lubricant comprising the product, PAO dimer, functionalized PAO product, or hydrogenated product produced in any of Clauses 1 to 22.

Clause 24. A fuel comprising the product, PAO dimer, functionalized PAO product, or hydrogenated product produced in any of Clauses 1 to 22.

Clause 25. A driveline or electric vehicle fluid comprising the product, PAO dimer, functionalized PAO product, or hydrogenated product produced in any of Clauses 1 to 22.

Clause 26. An engine oil comprising the product, PAO dimer, functionalized PAO product, or hydrogenated product in any of Clauses 1 to 22.

Clause 27. A gear oil comprising the product, PAO dimer, functionalized PAO product, or hydrogenated product produced in any of Clauses 1 to 22.

Clause 28. A compressor oil comprising the product, PAO dimer, functionalized PAO product, or hydrogenated product produced in any of Clauses 1 to 22.

Clause 29. A process to produce a lubricant comprising a poly alpha-olefin (PAO), the process comprising:
1) introducing a $C_6$-$C_{32}$ alpha-olefin and a catalyst system comprising activator and a metallocene compound into a reactor under reaction conditions and obtaining a product comprising PAO dimer and optional higher oligomers of alpha-olefin, or a combination thereof, the PAO dimer comprising 96 mol % or more of vinylidene, based on total moles of vinylidene, di-substituted vinylene, and tri-substituted vinylene in the product, and the metallocene compound is represented by the formula (I) and the activator is represented by the formula (V) as described in Clause 1, and 2) forming a lubricant comprising the product or the PAO dimer.

Clause 30. A process for making functionalized PAO comprising:
1) a first process for making a PAO, said first process having a catalyst activity of at least 4500 g/mmol/hr, wherein the first process comprises: contacting, at a temperature of from 35° C. to 150° C., one or more $C_6$ to $C_{32}$ alpha-olefins and a catalyst system comprising an activator and at least one metallocene compound represented by the formula (I) and the activator is represented by the formula (V) as described in Clause 1; and 2) a second process comprising contacting the PAO produced in the first process with a functionalizing species to form a functionalized PAO.

Clause 31. The process of Clause 30, wherein said functionalizing species is selected from the group consisting of aromatic compounds, benzene, toluene, xylenes, naphthalene, alkylnaphthalene, maleic anhydride, organic amine, organic acid and alcohol.

Clause 32. The process of Clause 31, further comprising hydrogenating at least a portion of said functionalized PAO to form a hydrogenated PAO, then formulating a lubricating composition comprising the hydrogenated PAO.

Clause 33. The process of Clause 31, further comprising functionalizing at least a portion of said functionalized PAO, then formulating a lubricating composition comprising the functionalized PAO.

Clause 34. The process of Clause 31, further comprising partially hydrogenating said functionalized PAO, then further functionalizing at least a portion of said PAO to form a PAO product, then formulating a lubricating composition comprising the PAO product.

Clause 35. The process of Clause 31, further comprising functionalizing at least a portion of said functionalized PAO to form a second functionalized PAO; hydrogenating said second functionalized PAO to form a PAO product; then formulating a lubricating composition comprising the PAO product.

This invention further relates to:

Clause 1A. A process to produce a poly alpha-olefin (PAO), comprising:
a) introducing a first alpha-olefin (such as a $C_6$-$C_{32}$ alpha-olefin) to a first catalyst system comprising non-aromatic hydrocarbon soluble activator and a metallocene compound into a continuous stirred tank reactor or a continuous tubular reactor under first reactor conditions, wherein the first alpha-olefin is preferably introduced to the reactor at a flow rate of about 100 g/hr, to form a first reactor effluent comprising PAO dimer (such as 60 wt % of PAO dimer or more and 40 wt % or less of higher oligomers, where the higher oligomers are oligomers that have a degree of polymerization of three or more); and
b) introducing the first reactor effluent and optional second alpha-olefin to a second catalyst composition comprising an acid catalyst in a second reactor to form a second reactor effluent comprising PAO trimer.

Clause 2A. The process of Clause 1A, wherein the first reactor effluent is transferred to a separations unit (such as a flash drum(s), multiple flash stages in series, atmospheric distillation column(s), vacuum distillation column(s), stripper(s), steam stripper(s), nitrogen stripper(s), membrane separation(s), chromatography column(s), crystallization(s), distillation or filtration unit), prior to introduction into the second reactor.

Clause 3A. The process of Clause 1A or Clause 2A, further comprising: introducing the second reactor effluent to a first distillation unit to form a first distillation effluent; and introducing the first distillation effluent to a hydrogenation unit and hydrogenating the first distillation effluent to form a hydrogenated effluent.

Clause 4A. The process of Clause 2A or Clause 3A, further comprising: introducing the hydrogenated effluent to a second distillation unit to form a second distillation effluent; and introducing the second distillation effluent to a third distillation unit to form a PAO effluent having a viscosity of from 3 cSt to about 10 cSt.

Clause 5A. The process of any one of Clauses 1A-4A, wherein the acid catalyst is a Lewis acid.

Clause 6A. The process of any one of Clauses 1A-5A, wherein the acid catalyst is present in the second reactor at an acid catalyst loading of from about 5 mmolCat/100 gLAO to about 15 mmolCat/100 gLAO.

Clause 7A. The process of any one of Clauses 1A-6A, wherein the second reactor comprises a temperature of from about 10° C. to about 40° C.

Clause 8A. The process of any one of Clauses 1A-7A, wherein the acid catalyst is $BF_3$.

Clause 9A. The process of any one of Clauses 1A-8A, wherein the first reactor effluent includes 50 wt % or less of higher oligomers, based on a total weight percent of the first reactor effluent.

Clause 10A. The process of any one of Clauses 1A-9A, wherein the first reactor effluent includes 10 wt % or less of higher oligomers of alpha-olefin, based on a total weight percent of the first reactor effluent.

Clause 11A. The process of any one of Clauses 1A-10A, wherein the first alpha-olefin and the second alpha-olefin are different.

Clause 12A. The process of any one of Clauses 1A-11A, wherein the second reactor effluent comprises 50 wt % or more of the PAO trimer based on a total weight percent of the second reactor effluent.

Clause 13A. The process of any one of Clauses 1A-12A, wherein the second reactor effluent comprises 65 wt % or more of the PAO trimer based on a total weight percent of the second reactor effluent.

Clause 14A. The process of any one of Clauses 1A-13A, wherein the second reactor effluent comprises 75 wt % or more of the PAO trimer, based on a total weight percent of the second reactor effluent.

Clause 15A. The process of any one of Clauses 1A-14A, wherein the second reactor conditions include a second reactor temperature of less than 60° C.

Clause 16A. The process of any one of Clauses 1A-15A, wherein the second catalyst composition further comprises an alcohol and an alkyl acetate.

Clause 17A. The process of any one of Clauses 1A-16A, wherein, the PAO dimer of the first product effluent comprises 93 mol % or more of vinylidene, and 4 mol % or less of disubstituted vinylene and trisubstituted vinylene, based on total moles (100 mol %) of vinylidene, disubstituted vinylene, and trisubstituted vinylene in the PAO dimer of the first product effluent.

Clause 18A. The process of any one of Clauses 1A-17A, wherein, the PAO dimer of the first product effluent comprises 95 mol % or more of vinylidene, and 2 mol % or less of disubstituted vinylene and trisubstituted vinylene, based on total moles (100 mol %) of vinylidene, disubstituted vinylene, and trisubstituted vinylene in the PAO dimer of the first product effluent.

Clause 19A. The process of any one of Clauses 1A-18A, wherein the metallocene compound is represented by the formula (I) as described in Clause 1, List A and or Table I.

Clause 20A. The process of any one of Clauses 1A-18A, wherein the metallocene compound is represented by the formula (III) as described herein.

Clause 21A. The process of any one of Clauses 1A-20A, wherein the activator is represented by the formula (V): $[R^{1'}R^{2'}R^{3'}EH]_{d^+}[Mt^{k+}Q_n]^{d-}$ (V) wherein: E is nitrogen or phosphorous; d is 1, 2 or 3; k is 1, 2, or 3; n is 1, 2, 3, 4, 5, or 6; n−k=d (preferably d is 1, 2 or 3; k is 3; n is 4, 5, or 6); $R^{1'}$, $R^{2'}$, and $R^{3'}$ are independently $C_1$ to $C_{50}$ hydrocarbyl group optionally substituted with one or more alkoxy groups, silyl groups, a halogen atoms, or halogen containing groups, wherein $R^{1'}$, $R^{2'}$, and $R^{3'}$ together comprise 15 or more carbon atoms; Mt is an element selected from group 13 of the Periodic Table of the Elements, such as B or Al; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Clause 22A. The process of any one of Clauses 1A-20A, the activator comprises one or more of the activators of Clause 12, 13 or 14 above.

Clause 23A. The process of any one of Clauses 1A-22A, wherein the metallocene compound is selected from the group consisting of:

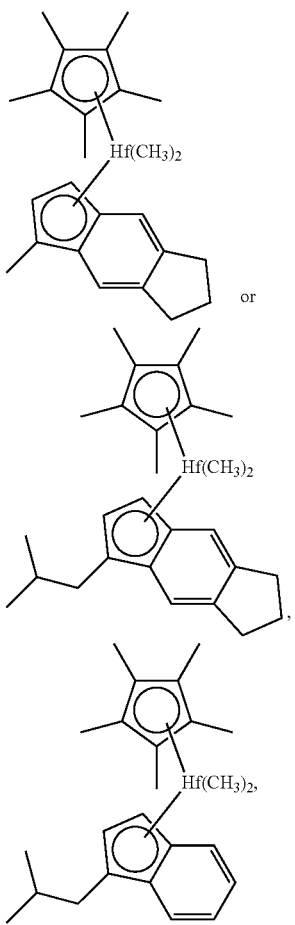

or a combination thereof.

Clause 24A. The process of any one of Clauses 1A-23A, wherein the PAO dimer has a number average molecular weight (Mn) of 1,000 or less, in accordance with $^1$H nuclear magnetic resonance spectroscopy.

Clause 25A. The process of any of Clauses 1A to 24A, further comprising functionalizing the PAO trimer with a reactant to form a functionalized PAO product, and optionally further hydrogenating the functionalized PAO product to for a hydrogenated PAO product.

Clause 26A. A lubricant comprising the PAO trimer, PAO effluent, functionalized PAO product, or hydrogenated PAO product produced in any of Clauses 1A to 25A.

Clause 27A. A fuel comprising the PAO trimer, PAO effluent, functionalized PAO product, or hydrogenated PAO product produced in any of Clauses 1A to 25A.

Clause 28A. A driveline or electric vehicle fluid comprising the PAO trimer, PAO effluent, functionalized PAO product, or hydrogenated PAO product produced in any of Clauses 1A to 25A.

Clause 29A. An engine oil comprising the PAO trimer, PAO effluent, functionalized PAO product, or hydrogenated PAO product produced in any of Clauses 1A to 25A.

Clause 30A. A gear oil comprising the PAO trimer, PAO effluent, functionalized PAO product, or hydrogenated PAO product produced in any of Clauses 1A to 25A.

Clause 31A. A compressor oil comprising the PAO trimer, PAO effluent, functionalized PAO product, or hydrogenated PAO product produced in any of Clauses 1A to 25A.

Clause 32A. An apparatus comprising: a first reactor that is a continuous stirred tank reactor or a continuous tubular reactor, the first reactor connected to second reactor that is a continuous stirred tank reactor or a continuous tubular, wherein the first reactor is configured to perform metallocene oligomerization with a non-aromatic hydrocarbon soluble activator and the second reactor is configured to perform acid-catalyzed oligomerization.

Clause 33A. The apparatus of Clause 32A, further comprising: a first end of a first separation unit is coupled to a second end of the second reactor; and a first end of a hydrogenation unit is coupled to a second end of the first distillation unit.

Clause 34A. The apparatus of any one of Clauses 32A-33A, further comprising a second distillation unit coupled at a first end to a second end of the hydrogenation unit.

Clause 35A. The apparatus of any one of Clauses 32A-34A, further comprising a third distillation unit coupled at a first end to a second end of the second distillation unit.

Clause 36A. The apparatus of any one of Clauses 32A-35A, a separations unit is disposed between the first and second reactors.

Clause 37A. The process of any of clauses 1A to 25A wherein the process has a conversion of at least 60%, based upon the weight of the monomer entering the reactor and the PAO produced and a selectivity for dimer of at least 85 wt %, based upon the PAO produced.

Clause 38A. The process of any of clauses 1A to 25A wherein the metallocene compound is as described in Clauses 1, 2, 8-11 above.

Clause 39A. The process of Clause 37A or 38A wherein the first polymerization reactor is a continuous stirred tank reactor or a continuous tubular reactor, the alpha-olefin is introduced to the reactor at a flow rate of at least 100 g/hr, the polymerization residence time is from 2 to 5 hours, and the polymerization temperature is 120° C. or more.

Clause 40A. The process of Clause 37A to 39A where the vinylidene content of the PAO produced is 95% or more based on total moles of vinylidene, disubstituted vinylene, and trisubstituted vinylene in the PAO product, the Mn of the PAO product is 1500 g/mol or less, the conversion is at least 60%, at least 70%, at least 80%, at least 90%, based upon the weight of the monomer entering the reactor and the PAO produced, the PAO dimer selectivity is at least 60%, based upon the weight of the PAO produced, and the process-productivity of the continuous process is at least 60,000 g/hour with a catalyst loading of 0.1 gram catalyst per gram of monomer or less.

This invention further relates to:

1. A process to produce a poly alpha-olefin (PAO), comprising:

a) introducing a first alpha-olefin to a first catalyst system comprising non-aromatic hydrocarbon soluble activator and a metallocene compound (preferably into a continuous stirred tank reactor or a continuous tubular reactor) under first reactor conditions, wherein the first alpha-olefin is preferably introduced to the reactor at a flow rate of about 100 g/hr or more, to form a first reactor effluent comprising PAO (preferably at least 60 wt % of PAO dimer and 40 wt % or less of higher oligomers, where the higher oligomers are oligomers that have a degree of polymerization of 3 or more); and b) introducing the first reactor effluent and a second alpha-olefin to a second catalyst composition comprising an acid catalyst, such as $BF_3$, in a second reactor under second reactor conditions to form a second reactor effluent comprising PAO trimer, and wherein the activator is preferably represented by the formula: (V): $[R^{1'}R^{2'}R^{3'}EH]_{d^+}[Mt^{k+}Q_n]^{d-}$ (V), where E is nitrogen or phosphorous; d is 1, 2 or 3; k is 1, 2, or 3; n is 1, 2, 3, 4, 5, or 6; n−k=d; $R^{1'}$, $R^{2'}$, and $R^{3'}$ are independently $C_1$ to Co hydrocarbyl group optionally substituted with one or more alkoxy groups, silyl groups, a halogen atoms, or halogen containing groups, wherein $R^{1'}$, $R^{2'}$, and $R^{3'}$ together comprise 15 or more carbon atoms; Mt is an element selected from group 13 of the Periodic Table of the Elements, such as B or Al; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

2. The process of paragraph 1, wherein the first alpha-olefin is a $C_6$-$C_{32}$ alpha-olefin and the PAO dimer comprises 70 mol % or more of vinylidene, based on total moles of vinylidene, di-substituted vinylene, and tri-substituted vinylene in the product.

3. The process of paragraph 1, wherein the metallocene compound is represented by the formula (I):

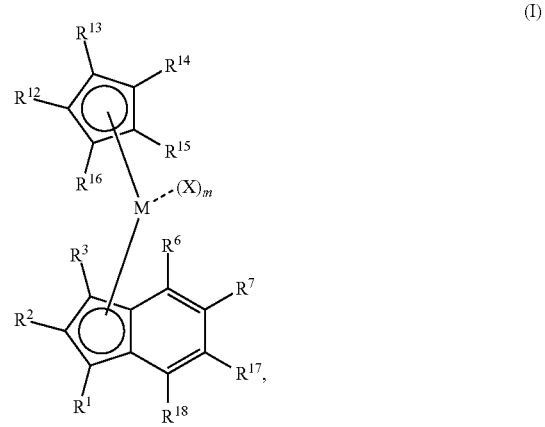

(I)

wherein:

each $R^1$, $R^2$, and $R^3$ is, independently, hydrogen or a substituted or unsubstituted linear, branched, or cyclic $C_1$-$C_{20}$ hydrocarbyl group, preferably wherein at least one of $R^1$, $R^2$, and $R^3$ is not hydrogen and at least one of $R^1$, $R^2$, and $R^3$ is hydrogen;

$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$ taken together with the carbon atoms in the indenyl ring to which they are directly connected, collectively form one or more substituted or unsubstituted rings annelated to the indenyl ring;

$R^{12}$, $R^{13}$, $R^{14}$, and $R^{15}$, are each independently a substituted or unsubstituted linear, branched, or cyclic $C_1$-$C_{20}$ hydrocarbyl group;

$R^{16}$ is a substituted or unsubstituted linear, branched, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a group 3, 4 or 5 transition metal having an integer coordination number of v (such as 3, 4, 5 or 6), preferably M is Hf or Zr, preferably Hf;

m is an integer equal to v-2 (such as 1, 2, 3 or 4).

4. The process of paragraph 1, wherein the metallocene compound is represented by the formula (III):

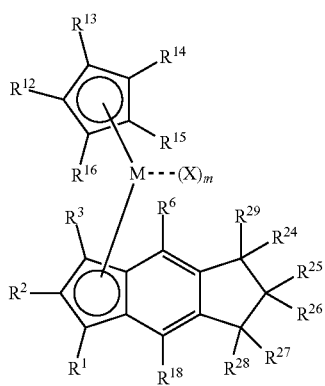

(III)

wherein one of $R^1$ and $R^3$ is a substituted or unsubstituted linear, branched, or cyclic $C_1$-$C_{20}$ hydrocarbyl group;
two of $R^1$, $R^2$, and $R^3$ are each hydrogen;
$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annelated to the cyclopentan-indenyl ring;
$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;
each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;
M is a group 3, 4, or 5 transition metal having an integer coordination number of v (such as 3, 4 5 or 6), preferably M is Hf or Zr, preferably Hf;
and m is an integer equal to v-2 (such as 1, 2, 3 or 4).

5. The process of paragraph 1, 2, 3 or 4 wherein the first reactor effluent is transferred to a separations unit (such as a flash drum(s), multiple flash stages in series, atmospheric distillation column(s), vacuum distillation column(s), stripper(s), steam stripper(s), nitrogen stripper(s), membrane separation(s), chromatography column(s), crystallization(s), distillation or filtration unit), prior to introduction into the second reactor.

6. The process of any of paragraphs 1-5, further comprising: introducing the second reactor effluent to a first distillation unit to form a first distillation effluent; and introducing the first distillation effluent to a hydrogenation unit and hydrogenating the first distillation effluent to form a hydrogenated effluent.

7. The process of paragraph 5, further comprising: introducing the hydrogenated effluent to a second distillation unit to form a second distillation effluent; and introducing the second distillation effluent to a third distillation unit to form PAO effluents having a viscosity of from 3 cSt to about 10 cSt.

8. The process of any of paragraphs 1-7, wherein the reaction conditions in the first reactor comprise a reactor temperature of about 110° C. or greater and a reactor pressure of from 15 psia to 750 psia.

9. The process of any of paragraphs 1-8, wherein the reaction conditions in the first reactor comprise a catalyst loading of at least 5,000 g alpha-olefin (gAO) per gram of catalyst (gCat) and a flow rate of the catalyst system of at least 6 gCat/hr.

10. The process of any of paragraphs 1-9, wherein the reaction conditions in the first reactor comprise a reactor residence time of less than 5 hours.

11. The process of any of paragraphs 1-10, wherein the acid catalyst is a Lewis acid, preferably $BF_3$.

12. The process of any of paragraphs 1-11, wherein the acid catalyst is present in the second reactor at an acid catalyst loading of from about 5 mmolCat/100 gLAO to about 15 mmolCat/100 gLAO.

13. The process of any of paragraphs 1-12, wherein the second reactor comprises a temperature of from about 10° C. to about 40° C.

14. The process of any of paragraphs 1-13, wherein the first reactor effluent includes 50 wt % or less of higher oligomers, based on a total weight percent of the first reactor effluent.

15. The process of any of paragraphs 1-14, wherein the first alpha-olefin and the second alpha-olefin are different.

16. The process of any of paragraphs 1-15, wherein the second reactor effluent comprises 50 wt % or more of the PAO trimer based on a total weight percent of the second reactor effluent.

17. The process of any of paragraphs 1-16, wherein the second reactor effluent comprises 75 wt % or more of the PAO trimer, based on a total weight percent of the second reactor effluent.

18. The process of any of paragraphs 1-17, wherein the second reactor conditions include a second reactor temperature of less than 60° C.

19. The process of any of paragraphs 1-18, wherein the second catalyst composition further comprises an alcohol and an alkyl acetate.

20. The process of any of paragraphs 1-19, wherein, the PAO dimer of the first product effluent comprises 93 mol % or more (alternately 94 mol % or more) of vinylidene, and 4 mol % (preferably 2 mol % or less) or less of disubstituted vinylene and trisubstituted vinylene, based on total moles of vinylidene, disubstituted vinylene, and trisubstituted vinylene in the PAO dimer of the first product effluent.

21. The process of any of paragraphs 1-19, wherein, the PAO dimer of the first product effluent comprises 94 mol % or more of vinylidene, and 2 mol % or less of disubstituted vinylene and trisubstituted vinylene, based on total moles of vinylidene, disubstituted vinylene, and trisubstituted vinylene in the PAO dimer of the first product effluent.

22. The process of any of paragraphs 1-21, wherein the first reactor effluent is transferred to a separations unit prior to introduction into the second reactor, and the separations unit preferably comprises one or more of: flash drum(s), multiple flash stages in series, atmospheric distillation column(s), vacuum distillation column(s), stripper(s), steam stripper(s), nitrogen stripper(s), membrane separation(s), chromatography column(s), crystallization(s), distillation unit(s) and filtration unit(s).

23. The process of paragraph 3 to 21, wherein one of $R^1$, $R^2$, and $R^3$ is a substituted or unsubstituted linear, branched linear, or cyclic $C_1$-$C_6$ hydrocarbyl group, and two of $R^1$, $R^2$, and $R^3$ are hydrogen.

24. The process of any of paragraphs 1-23, wherein the metallocene compound is represented by the formula:

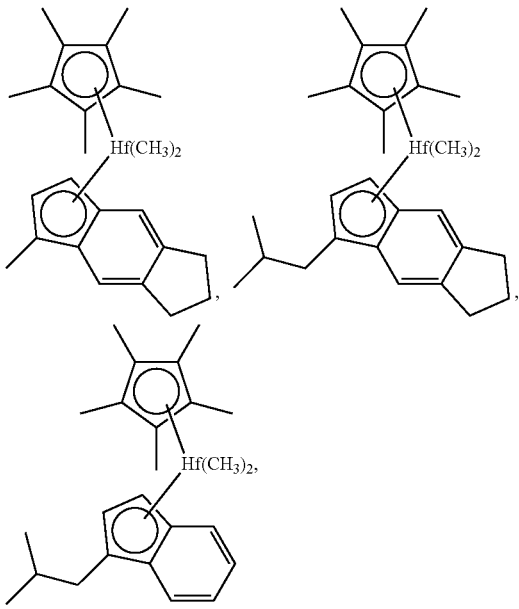

or a combination thereof.

25. The process of paragraph any of paragraphs 1 to 4, wherein the activator comprises one or more of:
N,N-di(hydrogenated tallow)methylammonium [tetrakis(perfluorophenyl)borate],
N-methyl-4-nonadecyl-N-octadecylanilinium [tetrakis(perfluorophenyl)borate],
N-methyl-4-hexadecyl-N-octadecylanilinium [tetrakis(perfluorophenyl)borate],
N-methyl-4-tetradecyl-N-octadecylanilinium [tetrakis(perfluorophenyl)borate],
N-methyl-4-dodecyl-N-octadecylanilinium [tetrakis(perfluorophenyl)borate],
N-methyl-4-decyl-N-octadecylanilinium [tetrakis(perfluorophenyl)borate],
N-methyl-4-octyl-N-octadecylanilinium [tetrakis(perfluorophenyl)borate],
N-methyl-4-hexyl-N-octadecylanilinium [tetrakis(perfluorophenyl)borate],
N-methyl-4-butyl-N-octadecylanilinium [tetrakis(perfluorophenyl)borate],
N-methyl-4-octadecyl-N-decylanilinium [tetrakis(perfluorophenyl)borate],
N-methyl-4-nonadecyl-N-dodecylanilinium [tetrakis(perfluorophenyl)borate],
N-methyl-4-nonadecyl-N-tetradecylanilinium [tetrakis(perfluorophenyl)borate],
N-methyl-4-nonadecyl-N-hexadecylanilinium [tetrakis(perfluorophenyl)borate],
N-ethyl-4-nonadecyl-N-octadecylanilinium [tetrakis(perfluorophenyl)borate],
N-methyl-N,N-dioctadecylammonium [tetrakis(perfluorophenyl)borate],
N-methyl-N,N-dihexadecylammonium [tetrakis(perfluorophenyl)borate],
N-methyl-N,N-ditetradecylammonium [tetrakis(perfluorophenyl)borate],
N-methyl-N,N-didodecylammonium [tetrakis(perfluorophenyl)borate],
N-methyl-N,N-didecylammonium [tetrakis(perfluorophenyl)borate],
N-methyl-N,N-dioctylammonium [tetrakis(perfluorophenyl)borate],
N-ethyl-N,N-dioctadecylammonium [tetrakis(perfluorophenyl)borate],
N,N-di(octadecyl)tolylammonium [tetrakis(perfluorophenyl)borate],
N,N-di(hexadecyl)tolylammonium [tetrakis(perfluorophenyl)borate],
N,N-di(tetradecyl)tolylammonium [tetrakis(perfluorophenyl)borate],
N,N-di(dodecyl)tolylammonium [tetrakis(perfluorophenyl)borate],
N-octadecyl-N-hexadecyl-tolylammonium [tetrakis(perfluorophenyl)borate],
N-octadecyl-N-hexadecyl-tolylammonium [tetrakis(perfluorophenyl)borate],
N-octadecyl-N-tetradecyl-tolylammonium [tetrakis(perfluorophenyl)borate],
N-octadecyl-N-dodecyl-tolylammonium [tetrakis(perfluorophenyl)borate],
N-octadecyl-N-decyl-tolylammonium [tetrakis(perfluorophenyl)borate],
N-hexadecyl-N-tetradecyl-tolylammonium [tetrakis(perfluorophenyl)borate],
N-hexadecyl-N-dodecyl-tolylammonium [tetrakis(perfluorophenyl)borate],
N-hexadecyl-N-decyl-tolylammonium [tetrakis(perfluorophenyl)borate],
N-tetradecyl-N-dodecyl-tolylammonium [tetrakis(perfluorophenyl)borate],
N-tetradecyl-N-decyl-tolylammonium [tetrakis(perfluorophenyl)borate],
N-dodecyl-N-decyl-tolylammonium [tetrakis(perfluorophenyl)borate],
N-methyl-N-octadecylanilinium [tetrakis(perfluorophenyl)borate],
N-methyl-N-hexadecylanilinium [tetrakis(perfluorophenyl)borate],
N-methyl-N-tetradecylanilinium [tetrakis(perfluorophenyl)borate],
N-methyl-N-dodecylanilinium [tetrakis(perfluorophenyl)borate],
N-methyl-N-decylanilinium [tetrakis(perfluorophenyl)borate], and
N-methyl-N-octylanilinium [tetrakis(perfluorophenyl)borate].

26. The process of any of paragraphs 1-25, wherein the first alpha-olefin is selected from the group consisting of 1-hexene, 1-heptene, 1-octene, 1-nonene, 1-decene, 1-undecene, 1-dodecene, 1-tridecene, 1-tetradecene, 1-pentadecene, 1-hexadecene, and combinations thereof.

27. The process of any of paragraphs 1-26, wherein the reaction conditions in the first reactor comprise a reactor temperature of from 110° C. to 180° C., a reactor pressure of from 15 psia to 750 psia, and a catalyst loading of from 25,000 g alpha-olefin (gAO) per 1 g catalyst (gCat) to 90,000 gAO/gCat.

28. The process of any of paragraphs 1-27, wherein the reactor conditions in the first reactor comprise a reactor temperature of from 110° C. to 148° C., a reactor pressure of from 30 psia to 100 psia, and a catalyst loading of from 25,000 g alpha-olefin (gAO) per 1 g catalyst (gCat) to 80,000 gAO/gCat.

29. A process to produce a poly alpha-olefin (PAO), comprising:
a) introducing a first alpha-olefin or mixture of alpha-olefins to a first catalyst system comprising non-aromatic hydrocarbon soluble activator and a metallocene compound into a reactor under first reactor conditions, to form a first reactor product comprising at least 60 wt % of PAO dimer, 40 wt % or less of higher oligomers where the higher oligomers are oligomers that have a degree of polymerization of 3 or more, and 20 wt % or less unreacted alpha-olefin; and
b) introducing the first reactor product and additional alpha-olefin or mixture of alpha-olefins to a second catalyst composition comprising an acid catalyst in a second reactor to form a second reactor product comprising PAO trimer, wherein the higher oligomers and unreacted alpha-olefin in the first reactor product are not separated prior to introduction into the second reactor.

30. A process to produce a poly alpha-olefin (PAO), comprising:
a) introducing a first alpha-olefin or mixture of alpha-olefins to a first catalyst system comprising non-aromatic hydrocarbon soluble activator and a metallocene compound into a continuous stirred tank reactor or a continuous tubular reactor under first reactor conditions, wherein the first alpha-olefin or mixture of alpha-olefins is introduced to the reactor at a flow rate of about 100 g/hr or more, to form a first reactor effluent comprising at least 60 wt % of PAO dimer, 40 wt % or less of higher oligomers, where the higher oligomers are oligomers that have a degree of polymerization of 3 or more, and 20 wt % or less unreacted alpha-olefin; and
b) introducing the first reactor effluent and a second alpha-olefin or mixture of alpha-olefins to a second catalyst composition comprising an acid catalyst in a second reactor to form a second reactor effluent comprising PAO trimer, wherein the higher oligomers and unreacted alpha-olefin in the first reactor effluent are not separated from the first effluent stream prior to introduction into the second reactor.

31. The process of any of paragraphs 1-30 where in the step to make PAO dimer, the solvent is selected from $C_4$ to $C_{10}$ linear, branched or cyclic alkanes.

32. The process of any of paragraphs 1-31 where in the step to make PAO dimer, the solvent is essentially free of all aromatic solvents.

33. The process of any of paragraphs 1-32 where in the step to make PAO dimer, the solvent is selected from one or more $C_6$ to $C_{32}$ alpha olefins.

34. The process of any of paragraphs 1-33 where in the step to make PAO dimer, the solvent is selected from one or more $C_8$ to $C_{16}$ alpha olefins.

35. The process of any of paragraphs 1-34 which is wherein the step to make PAO dimer, the solvent is essentially free of all non-alpha-olefin solvents.

36. The process of any of paragraphs 1-35, wherein the first alpha-olefin is a $C_6$-$C_{32}$ alpha-olefin and the PAO dimer comprises 85 mol % or more of vinylidene, based on total moles of vinylidene, di-substituted vinylene, and tri-substituted vinylene in the product.

EXPERIMENTAL

Gas chromatography (GC) is used to determine the composition of the synthesized oligomers by molecular weight. The gas chromatograph used in the examples was an Agilent Technologies 7890A model equipped with a 30 meter column with an internal diameter of 0.28 mm and a flame ionization detector. A ~0.2000-0.3000 g sample is diluted in methylene chloride solvent, ~0.0600-0.1000 g nonane internal standard was added, and the mixture was injected into the column. The starting temperature was about 40° C., held for about 1 minute, program-heated at about 15° C. per minute to about 250° C. and held for about 2 minutes. The sample is then heated at a rate of about 25° C. per minute to about 360° C. and held for about 17.3 minutes. The oligomer distribution IS determined by the GC method.

EXAMPLES—METALLOCENE DIMER SELECTIVE PROCESS

All catalyst syntheses were carried out in an $N_2$ purged dry box using standard air sensitive procedures. Celite (Sigma-Aldrich) and 3 Å molecular sieves (Sigma-Aldrich or Acros) were dried in a vacuum oven at 250° C. for 3 days. Solvents were purged with $N^2$ and dried and stored over 3 Å molecular sieves. NMR solvents were dried and stored over 3 Å molecular sieves. MeMgI (3 M in $Et_2O$, Sigma-Aldrich), $CH_3I$ (Sigma-Aldrich), isoButyl bromide (Sigma-Aldrich), nhexyl bromide (Sigma-Aldrich), nbutyl bromide (Sigma-Aldrich), 1,2,3,5-tetrahydro-s-indacene (GLSyntech) were used as received. Pentamethylcyclopentadienyl-hafnium trichloride ($Me_5CpHfCl_3$) was either purchased from Strem Chemicals or synthesized in a manner analogous to that described in *Journal of Organometallic Chemistry*, (1988) v. 340, pp. 37-40.

Pre-Catalyst

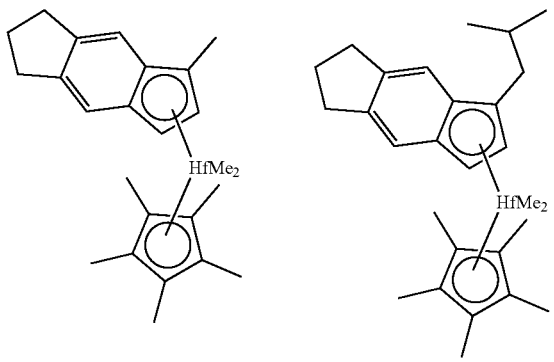

| Cat ID | A | B |
|---|---|---|
| Activator | C₁₈H₃₇\N⁺(Me)(H)/C₁₈H₃₇  ⁻B(C₆F₅)₄ | Me\N⁺(C₁₈H₃₇)(H)–C₆H₄–C₁₉H₃₉  ⁻B(C₆F₅)₄ |
| Act ID | A-1 | A-2 |

Activator A-1, N-di-octadecyl-N-methylanilinium tetrakis(perfluorophenyl)borate, was obtained from Boulder Scientific Company as a 10 wt % solution in methylcyclohexane. Activator A-2, N-methyl-4-nonadecyl-N-octadecylanilinium tetrakis(perfluorophenyl) borate, was prepared as described in U.S. Ser. No. 16/394,166, filed Apr. 25, 2019.

Synthesis of pentamethylcyclopentadienyl(1-methyl-1,5,6,7-tetrahydro-s-indacenyl)hafnium(IV) dimethyl (Catalyst A)

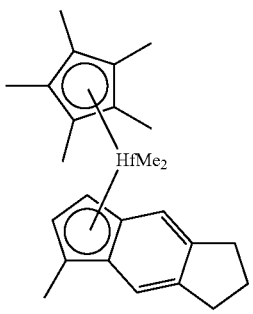

1-Methyl-1,5,6,7-tetrahydro-s-indacenyl Lithium 1,5,6,7-tetrahydro-s-indacenyl lithium was synthesized in a manner analogous to that described in U.S. Ser. No. 16/192,493, filed Nov. 15, 2018 (published as US2019/0161560).

MeI (6.74 g, 47.5 mmol) was slowly added to 1,5,6,7-tetrahydro-s-indacenyl Lithium (7.0 g, 43.2 mmol) in Et₂O (100 ml) and THF (20 ml) and stirred for 4 hours. All solvents were then removed by a stream of nitrogen and the crude product was reslurried into pentane for 15 minutes. The solid was removed by filtration on Celite, and was washed with pentane. All solvents were then removed from the filtrate under vacuo and 1-methyl-1,5,6,7-tetrahydro-s-indacene was isolated as a clear oil (6.95 g, 41.0 mmol), which was then dissolved into Et₂O (100 ml). nBuLi (3.7 ml, 11M) was then slowly added and stirred for 1 hour. Then all Et₂O was removed under vacuo and pentane added and allowed to stir for additional 10 minutes, followed by filtration to collect the product as a white solid (6.97 g, 97%), which was analyzed by ¹H NMR (500 MHz, DMSO-d6) δ 6.80 (d, J=1.0 Hz, 2H), 6.04 (d, J=3.2 Hz, 1H), 5.37 (d, J=3.9 Hz, 1H), 2.74 (dt, J=10.5, 7.0 Hz, 4H), 2.27 (s, 3H), 1.86 (p, J=7.1 Hz, 2H).

Pentamethylcyclopentadienyl(1-methyl-1,5,6,7-tetrahydro-s-indacenyl)hafnium(IV) dimethyl Mix 1-methyl (1,5,6,7-tetrahydro-s-indacenyl) Lithium (6.97 g, 40 mmol) with CpMe₅HfCl₃ (16.1 g, 40 mmol) in Et₂O (150 ml) and stir it for 3 hours. LiCl was removed by filtration. And all Et₂O was then removed by a stream of nitrogen and the crude product was reslurried into pentane for 15 minutes and was cooled under −35° C. The product was isolated by filtration as an off-white solid (15.47 g, 26 mmol), which was slurried into toluene (50 ml) and MeMgI (17.3 ml, 3 M in Et2O) was then added and the reaction was stirred at 70° C. for 16 hours. The reaction was cooled to room temperature and 1, 4 dioxane was added. The mixture was stirred for 15 minutes and solids were removed by filtration on Celite and was washed by Et₂O. All volatiles were then removed under vacuo. Final product (C₂₅H₃₄Hf) was isolated as a solid (12.3 g, 60%), which was analyzed by ¹H NMR (CD₂Cl₂, 400 MHz): δ 7.45-7.33 (m, 1H), 7.02-6.92 (m, 1H), 5.32 (dd, J=2.9, 0.9 Hz, 1H), 5.27 (dd, J=2.8, 0.6 Hz, 1H), 2.99-2.86 (m, 4H), 2.19 (s, 3H), 2.11-1.99 (m, 2H), 1.88 (s, 15H), −1.08 (s, 3H), −2.12 (s, 3H).

Synthesis of pentamethylcyclopentadienyl (1-isobutyl-1,5,6,7-tetrahydro-s-indacenyl) hafnium (IV) dimethyl (Catalyst B)

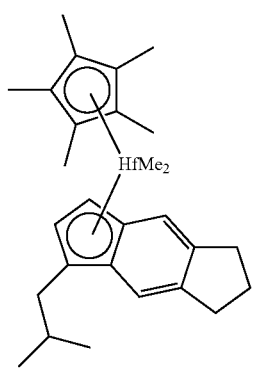

1-isoButyl-1,5,6,7-tetrahydro-s-indacenyl Lithium isoButyl bromide (1.69 g, 12 mmol) was added to 1,5,6,7-tetrahydro-s-indacenyl Lithium(2.0 g, 12 mmol) in THF (100 ml) and stirred for 16 hours. THF then removed by a stream of nitrogen and the crude product was reslurried into pentane for 15 minutes. The solid was removed by filtration on celite. And it is washed by pentane. All solvents were then removed from the filtrate under vacuo and 1-isobutyl-1,5,6,7-tetrahydro-s-indacene was isolated as a clear oil (2.54 g, 12 mmol), which is dissolved into $Et_2O$ (50 ml). nBuLi (1.1 ml, 11M) was then slowly added and stirred for 1 hour. Then all $Et_2O$ was removed under vacuo and pentane was added and stirred for an additional 10 minutes then filtered to collect the product as a white solid (2.5 g, 96%), which was analyzed by $^1H$ NMR (500 MHz, DMSO-d6) δ 6.82 (d, J=9.7 Hz, 2H), 6.06 (s, 1H), 5.39 (d, J=3.2 Hz, 1H), 2.73 (q, J=6.9 Hz, 4H), 2.50 (d, J=6.7 Hz, 2H), 1.86 (p, J=7.0 Hz, 2H), 1.70 (dt, J=13.2, 6.6 Hz, 1H), 0.83 (d, J=6.6 Hz, 6H).

Pentamethylcyclopentadienyl
(1-isobutyl-1,5,6,7-tetrahydro-s-indacenyl)
hafnium(IV) dimethyl 1-isoButyl-1,5,6,7-tetrahydro-s-indacenyl lithium (0.27 g, 1.2 mmol) was mixed with $CpMe_5HfCl_3$ (0.52 g, 1.2 mmol) in $Et_2O$ (20 ml) and stirred overnight. $Et_2O$ was then removed by a stream of nitrogen and the crude product was reslurried into pentane for 15 minutes. The mixture was cooled at −35° C. for 1 hour. The product was isolated by filtration as a mixture of LiCl and was used for the next step with no further purification. The crude hafnium dichloride (0.68 g, 1.1 mmol) was slurried into toluene (20 ml) and MeMgI (0.71 ml, 3 M in $Et_2O$) was then added and the reaction was stirred at 70° C. for 16 hours. The reaction was cooled to room temperature and 1,4-dioxane (0.38 ml) was added. The mixture was stirred for 15 minutes and solids were removed by filtration on Celite and washed by $Et_2O$. Volatiles were then removed from the filtrate under vacuo. The product slowly became a solid, to which was added 0.5 ml of pentane. This was swirled and cooled at −35° C. for 3 hours, and pentane was pipetted away. Final product ($C_{28}H_{40}Hf$) was isolated as a solid (0.4 g, 60%), which was analyzed by $^1H$ NMR ($CD_2C_{12}$, 400 MHz): δ 7.38 (s, 1H), 6.97 (d, J=1.4 Hz, 1H), 5.34 (dd, J=2.9, 0.8 Hz, 1H), 5.27 (d, J=2.9 Hz, 1H), 2.99-2.88 (m, 4H), 2.80 (dd, J=13.5, 5.8 Hz, 1H), 2.04 (p, J=7.3 Hz, 2H), 1.93-1.79 (m, 17H), 0.93 (d, J=6.5 Hz, 3H), 0.85 (d, J=6.4 Hz, 3H), −1.08 (s, 3H), −2.14 (s, 3H).

Oligomerization Example 1. Batch oligomerization reactions were conducted in a 1 L autoclave reactor equipped with paddle stirrer, an external water jacket for temperature control, a regulated supply of dry nitrogen, ethylene, propylene, and isohexane and an inlet for the introduction of other solvents, comonomers, pre-catalysts and activators. The reactor was dried by heating the reactor at 110-120° C. under a flow of dry nitrogen for about 1 hour prior to use. 560 ml of dried 1-decene and 100 uL of tri-n-octyl aluminum under nitrogen was cannulated into the reactor. Stirring was started (400 rpm) and the reactor was then heated to 110° C. Activator A-1 (145 mg) was dissolved in 10 ml of 1-decene in an activator addition tube which was attached to the reactor. A second addition tube containing 10 ml of 1-decene was attached to the activator addition tube (chaser), and high pressure nitrogen was attached to the end. High pressure nitrogen was then used to push the activator and chaser into the reactor. Catalyst B (60 mg) was dissolved in 10 ml of 1-decene in a catalyst addition tube which was attached to the reactor. A second addition tube containing 10 ml of 1-decene was attached to the catalyst addition tube (chaser), and high pressure nitrogen was attached to the end. High pressure nitrogen was then used to push the catalyst and chaser into the reactor. Timing started at the addition of Catalyst B to the reactor and was allowed to proceed for 1 hour. After this time period, heating and stirring were ceased, pressure was vented from the reactor and the reactor was opened and lowered exposing the contents to air. The liquid product was allowed to cool to room temperature and was then filtered through Celite to remove catalyst residual. A total of 420 g of clear and colorless oligomer was isolated after filtration. Additional information can be found in Tables A and 1.

Oligomerization example 2. Using the procedure described in Example 1, the run was repeated and 421 g of clear and colorless oligomer was isolated after filtration. Additional information can be found in Tables A and 1.

Oligomerization example 3. Using the procedure described in Example 1, the run was repeated, and 424 g of clear and colorless oligomer was isolated after filtration. Additional information can be found in Tables A and 1.

The product mixture from the oligomerization examples was analyzed via GC to determine the oligomer distribution (Table A).

TABLE A

| | | | Product Mixture from Oligomerization—Batch Reactor (GC) | | |
|---|---|---|---|---|---|
| EX # | Cat ID | Act ID | T (C) | Dimer, wt % | Trimer, wt % | Tetramer+, wt % |
| 1 | B | A-1 | 110 | 76 | 15 | 5 |
| 2 | B | A-1 | 110 | 74 | 15 | 7 |
| 3 | B | A-1 | 110 | 68 | 20 | 9 |

High dimer selectivities are obtained with the use of the aforementioned catalyst system.

TABLE 1

| (Catalyst B combined with Activator A-1), polymerization Temp = 110° C. | | | | | | | |
|---|---|---|---|---|---|---|---|
| EX# | yield (g) | % conversion | Activity (g P/ mmol cat · hr) | mol % vinyl-ene | mol % trisub | mol % vinyl | mol % vinyl-idene | Mn (g/mol) |
| 1 | 420 | 94 | 3,886 | 2.2 | 3.5 | 0.3 | 94.1 | 299 |
| 2 | 421 | 95 | 3,895 | 2.4 | 3.6 | 0.5 | 93.5 | 335 |
| 3 | 424 | 95 | 3,923 | 1.9 | 3.7 | 0.2 | 94.1 | 312 |

Characterization of Isolated PAO

The unsaturated PAO product was analyzed (as follows) to determine the distributions of vinylidenes ("Vd"), di-substituted vinylenes ("Di"), tri-substituted vinylenes ("Tri-sub"), and vinyls ("Vi"), the catalyst activity level, and physical properties such as number average molecular weight. Conversion percentages of the reactions were calculated from the isolated yield of products and the amount of alpha-olefin used in the reaction. Specifically, conversion=grams isolated PAO/grams alpha-olefin used (when reported in %, conversion=(grams isolated PAO/grams alpha-olefin used)×100).

Proton NMR ($^1H$-NMR) was used to determine the number average molecular weight of the unsaturated PAO and the quantitative breakdown of the olefinic structure types (e.g., vinyl, vinylene, di-substituted vinylene, tri-substituted vinylene, and vinylidene).

Specifically, an NMR instrument of 400 or 500 MHz is run under the following conditions: a ~30° flip angle RF pulse, 128 scans, with a relaxation delay of ~5 seconds between pulses; sample (60-100 mg) dissolved in $CDCl_3$ (deuterated chloroform) in a 5 mm NMR tube; and signal collection temperature at ~25° C. The following approach is taken in determining the concentrations of the various olefins among all of the olefins from an NMR spectrum. First, peaks corresponding to different types of hydrogen atoms in vinyls (T1), vinylidenes (T2), di-substituted vinylenes (T3), and tri-substituted vinylenes (T4) are identified at the peak regions in TABLE 2 below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations ($C_1$, $C_2$, $C_3$, and $C_4$, respectively, in mol %) of each type of olefin, on the basis of the total molar quantity of all of the olefins, is then calculated (in each case, Ci=100*Qi/Qt).

TABLE 2

| Type No. | Hydrogen Atoms Olefin Structure | Peak Region (ppm) | Peak Area | Number of Hydrogen Atoms | Quantity of Olefin (mol) | Concentration of Olefin (mol %) |
|---|---|---|---|---|---|---|
| T1 | $CH_2=CH-R^1$ | 4.95-5.10 | A1 | 2 | Q1 = A1/2 | C1 |
| T2 | $CH_2=CR^1R^2$ | 4.65-4.84 | A2 | 2 | Q2 = A2/2 | C2 |
| T3 | $CHR^1=CHR^2$ | 5.31-5.55 | A3 | 2 | Q3 = A3/2 | C3 |
| T4 | $CR^1R^2=CH R^3$ | 5.11-5.30 | A4 | 1 | Q4 = A4 | C4 |

The number average molecular weight was determined by: Mn = {[Saturated + (vinylene + vinylidene + vinyl + trisubstituted × 2)]/ (vinylene + vinylidenevinyl + trisubstituted × 2)} × 14 ("Saturated", "vinylene", "vinyl", "trisubstituted" in this equation refer to peak area integration)

Oligomerization Step 2. The oligomer effluent from oligomerization Example 1 was used as feed for this process. The reactor effluent produced from the above procedure was mixed with 1-decene in a composition of about 68 wt % metallocene PAO effluent and about 32 wt % 1-decene and degassed by pulling a light vacuum in a stirred Parr reactor that acts as a feed mix vessel. The catalyst system used was butanol/butyl acetate in a molar ratio of about 1:1, saturated with $BF_3$ at atmospheric temperature and pressure. This catalyst was made by charging the butanol and butyl acetate into a 5 L roundbottom flask and then bubbling $BF_3$ into the mixture through a dip tube. About 613 grams of the degassed olefin mixture was charged into a second 2 L stirred Parr reactor from the feed mix vessel. The catalyst component (fed at a ratio of about 15 mmol/100 g olefin) was fed into a 2 L stainless steel Parr reactor over the span of about 1 hour using pressure and a flow controller. The reactor temperature was held 21° C. using chilled propylene glycol cooling. A $BF_3$ atmosphere of about 140 kPa (about 20 psia) was maintained in the reactor. After the first hour, the catalyst flow was stopped and the reactor was held at the above temperature and pressure for about 4 hours before the reactor effluent was discharged by pump into a vessel filled with 10% caustic. The resultant sample was water

TABLE 3

| PAO Collection | Cut Number 1 wt % |
|---|---|
| 1-Decene | 4.97 |
| Dimer (C16-C24) | 6.53 |
| Trimer (C24-32) | 67.58 |
| Tetramer+ | 20.92 |

Oligomerization Example 4: A 2 gallon pressurized Parr reactor was used to conduct a continuously stirred oligomerization reaction. The reactor has an inlet line for various types of linear-alpha-olefins as well as a dip tube for the catalyst batch injection. The reactor is equipped with an external heater, as well as an internal cooling loop to control the temperature of the reaction. 77 grams of Activator A-1 was received in methylcyclohexane at 11 wt % concentration. The methylcylcohexane was left to evaporate off in the glove box, after 24 hours, 15 grams of the solution remained (8.5 grams of Activator A-1 and 6.5 grams of methylcylcohexane). 19 g of 1-decene was added into the solution to lower the concentration of the activator from 57% to 25%. Commercially available adsorbent was used to dry 1.25 gallons of 1-decene. The adsorbent was loaded into two adsorbent beds in series, and its outlet was lined to a glove box to ensure that the 1-decene did not pick up any polar contaminants like moisture or oxygen from open container handling. 400 grams of the aforementioned dried 1-decene was then added into a clean empty jar with a magnetic stirrer on a stirring plate, 0.15 grams of tri-n-octyl aluminum was then added into the 1-decene to scavenge any contaminants that were not captured in the adsorbent beds. After 5 minutes of mixing, 9.2 grams of the 25% Activator A-1 solution was dissolved into the mixture, and mixed for 10 minutes. 400 grams of 1-decene was added into a second empty jar with magnetic stirrer on a stirring plate. 0.77 g of tri-n-octyl aluminum was added into the 1-decene to scavenge any contaminants that were not captured in the adsorbent beds and scavenge any polar species in the reactor as well. After 5 minutes of mixing, 1 gram of Catalyst B was added, and mixed for 10 minutes. 1-decene was feed at 2000 g/hr into a Parr reactor operated under vacuum where it was initially degassed. The 1-decene was then fed through two adsorbent beds in series and finally entered the reactor through the LAO line. The catalyst batch was connected to a piston pump, where it was fed at 10.4 g/hr (equivalent to 13 ppm of catalyst 1 in the reactor) and entered the reactor through the catalyst dip tube. The activator batch was also connected to a piston pump, where it was fed at 10.4 g/hr; the activator solution mixed with the 1-decene in the LAO line. The reactor was operated liquid full (3 hour residence time), with back pressure of 25 psig and at 140° C. The reactor effluent was sent to the quench vessel, where the catalyst was quenched with water at 90° C. at the same pressure as the reactor. The quench effluent then passed through 1 micron filter, and filled the product collection pails. The product results were analyzed via GC to determine conversion and selectivity. Results are presented in Table 4.

TABLE 4

| PAO Collection | Cut Number 3 wt % |
|---|---|
| Decene | 13.37 |
| Other LAOs | 0.3 |
| Dimer (C16-C24) | 80.82 |
| Trimer (C24-32) | 5.16 |
| Tetramer+ | 0.35 |

Figure 3:
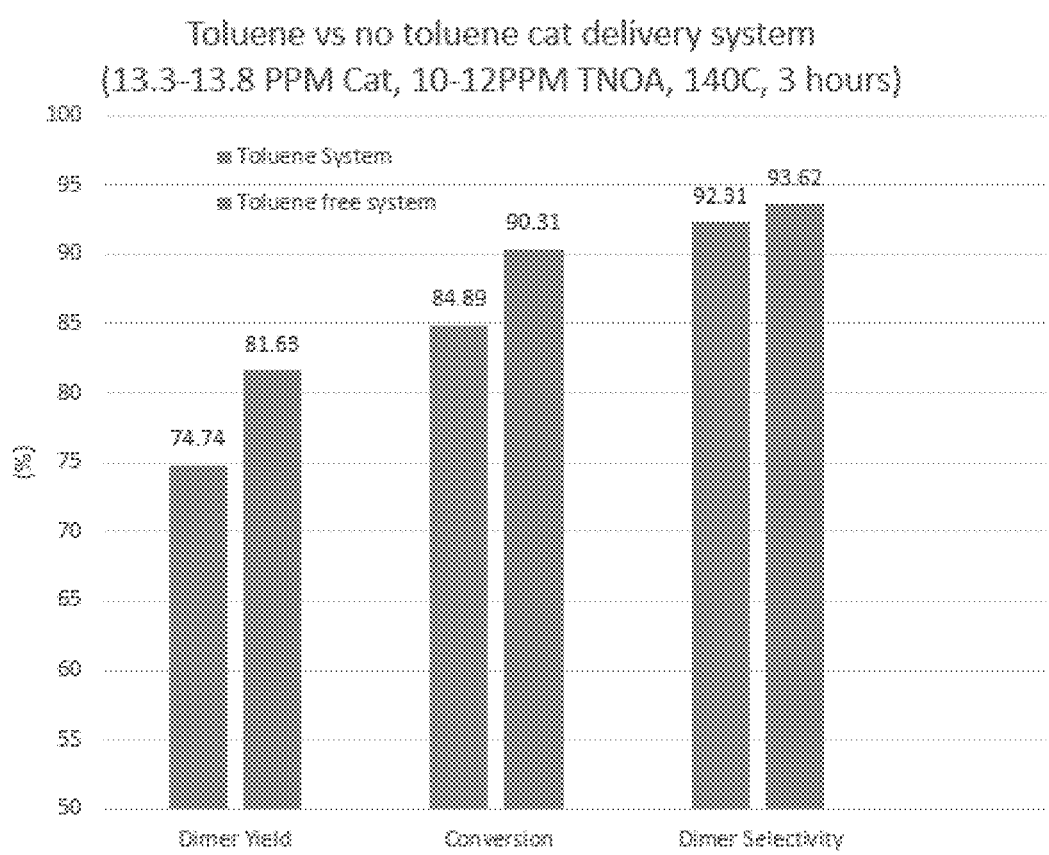
FIG. 3 is a graph comparing toluene and non-toluene containing catalysts systems.

The above results are an improvement from typical toluene metallocene systems in which the catalyst and the activator are both mixed together in 1 jar of toluene and fed through a dip tube. In the chart below (FIG. 3), an increase in dimer selectivity and conversion is noticeable, leading to an increase in dimer yield.

Oligomerization Step 2 for Oligomerization Example 4: Two 2 liter pressurized Parr reactors was used to conduct step 2 of the oligmerization. Reactor 1 has an inlet for various types of linear-alpha-olefins as well as a dip tube for the catalyst system. The second reactor is connected to reactor 1 to drive the conversion further. The reactor effluent from oliomerization example 4 was distilled to obtain unreacted monomers and dimers. Additional 1-decene was added to the aforementioned mixture, to generate 1:1 mol ratio of monomer to dimer mixture. The catalyst system used was butanol/butyl acetate in a molar ratio of about 1:1, saturated with $BF_3$ at atmospheric temperature and pressure. This catalyst was made by charging the butanol and butyl acetate into a 5 L roundbottom flask and then bubbling $BF_3$ into the mixture through a dip tube. About 613 grams of the degassed olefin mixture was charged into a second 2 L stirred Parr reactor from the feed mix vessel. The feed mixture is fed at 500 g/hr into a Parr reactor operated under vacuum where it is initially degassed. The feed then enters the reactor where it meets the catalyst mixture which is fed at a ratio of about 7 mmol/100 g olefin which equals to 6.1 g/hr. Reactor 1 is held at 1000 ml level, and reactor 2 is held at 500 ml level (1.5 hours residence time in reactor 1 and 0.75 hours in reactor 2). The reactor is also held at 5 psig of $BF_3$ pressure. 1:1 mole ratio of butanol/butyl acetate mixture is then added to the reactor effluent to capture any free $BF_3$. The effluent is then sent to the quench reactor where the acidic catalyst was quenched with 10% caustic. The resultant sample was water washed multiple times and the oil phase analyzed by GC. Results in table 5.

TABLE 5

| PAO Collection | Cut Number 2 wt % |
|---|---|
| Decene | 0.54 |
| Dimer (C16-C24) | 6.63 |
| Trimer (C24-32) | 67.78 |
| Tetramer+ | 25.08 |

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

What is claimed is:

1. A process to produce a poly alpha-olefin (PAO), comprising:
   a) introducing a first alpha-olefin to a first catalyst system comprising non-aromatic hydrocarbon soluble activator and a metallocene compound into a first reactor under first reactor conditions to form a first reactor effluent comprising PAO dimer; and
   b) introducing the first reactor effluent and an optional second alpha-olefin to a second catalyst composition comprising an acid catalyst in a second reactor under second reactor conditions to form a second reactor effluent comprising PAO trimer, wherein the metallocene compound is represented by the formula (III):

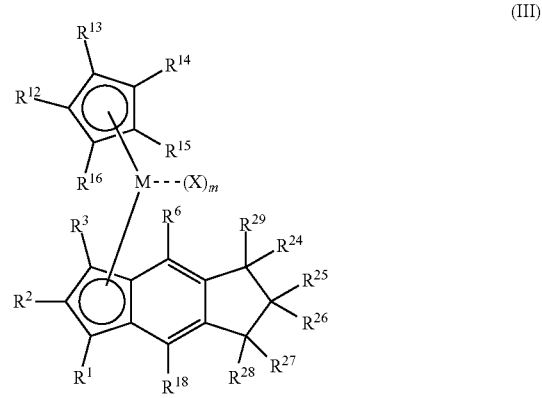

(III)

wherein one of $R^1$ and $R^3$ is a substituted or unsubstituted linear, branched, or cyclic $C_1$-$C_{20}$ hydrocarbyl group; two of $R^1$, $R^2$, and $R^3$ are each hydrogen;
$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annelated to the cyclopentan-indenyl ring;

$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a group 3, 4, or 5 transition metal having an integer coordination number of v;

and m is an integer equal to v-2.

2. The process of claim 1 wherein the activator is represented by the formula (V):

where E is nitrogen or phosphorous; d is 1, 2 or 3; k is 1, 2, or 3; n is 1, 2, 3, 4, 5, or 6; n−k=d; $R^{1'}$, $R^{2'}$, and $R^{3'}$ are independently $C_1$ to $C_{50}$ hydrocarbyl group optionally substituted with one or more alkoxy groups, silyl groups, a halogen atoms, or halogen containing groups, wherein $R^{1'}$, $R^{2'}$, and $R^{3'}$ together comprise 15 or more carbon atoms; Mt is an element selected from group 13 of the Periodic Table of the Elements; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

3. The process of claim 1, wherein the first alpha-olefin is introduced to the reactor at a flow rate of about 100 g/hr or more.

4. The process of claim 1, where the first reactor effluent comprises at least 60 wt % of PAO dimer and 40 wt % or less of higher oligomers, where the higher oligomers are oligomers that have a degree of polymerization of three or more.

5. The process of claim 1, wherein the first alpha-olefin is a $C_6$-$C_{32}$ alpha-olefin and the PAO dimer comprises 85 mol % or more of vinylidene, based on total moles of vinylidene, di-substituted vinylene, and tri-substituted vinylene in the product.

6. The process of claim 1, wherein the first reactor effluent is transferred to a separations unit prior to introduction into the second reactor.

7. The process of claim 6, wherein the separations unit comprises one or more of: flash drum(s), multiple flash stages in series, atmospheric distillation column(s), vacuum distillation column(s), stripper(s), steam stripper(s), nitrogen stripper(s), membrane separation(s), chromatography column(s), crystallization(s), distillation unit(s) and filtration unit(s).

8. The process of claim 1, further comprising: introducing the second reactor effluent to a first distillation unit to form a first distillation effluent; and introducing the first distillation effluent to a hydrogenation unit and hydrogenating the first distillation effluent to form a hydrogenated effluent.

9. The process of claim 8, further comprising: introducing the hydrogenated effluent to a second distillation unit to form a second distillation effluent; and introducing the second distillation effluent to a third distillation unit to form PAO effluents having a viscosity of from 3 cSt to about 10 cSt.

10. The process of claim 1, wherein the reaction conditions in the first reactor conditions comprise a reactor temperature of about 110° C. or greater and a reactor pressure of from 15 psia to 750 psia.

11. The process of claim 1, wherein the first reactor conditions comprise a catalyst loading of at least 5,000 g alpha-olefin (gAO) per gram of catalyst (gCat) and a flow rate of the catalyst system of at least 6 gCat/hr.

12. The process of claim 1, wherein the reaction conditions in the first reactor comprise a reactor residence time of less than 5 hours.

13. The process of claim 1, wherein the acid catalyst is a Lewis acid.

14. The process of claim 1, wherein the acid catalyst is present in the second reactor at an acid catalyst loading of from about 5 mmolCat/100 gLAO to about 15 mmolCat/100 gLAO.

15. The process of claim 1, wherein the second reactor conditions comprise a temperature of from about 10° C. to about 40° C.

16. The process of claim 1, wherein the acid catalyst is $BF_3$.

17. The process of claim 1, wherein the first reactor effluent includes 50 wt % or less of higher oligomers, based on a total weight percent of the first reactor effluent, where the higher oligomers are oligomers that have a degree of polymerization of three or more.

18. The process of claim 1, wherein the first alpha-olefin and the second alpha-olefin are different.

19. The process of claim 1, wherein the second reactor effluent comprises 50 wt % or more of the PAO trimer based on a total weight percent of the second reactor effluent.

20. The process of claim 1, wherein the second reactor effluent comprises 75 wt % or more of the PAO trimer, based on a total weight percent of the second reactor effluent.

21. The process of claim 1, wherein the second reactor conditions include a second reactor temperature of less than 60° C.

22. The process of claim 1, wherein the second catalyst composition further comprises an alcohol and an alkyl acetate.

23. The process of claim 1, wherein, the PAO dimer of the first product effluent comprises 93 mol % or more of vinylidene, and 4 mol % or less of disubstituted vinylene and trisubstituted vinylene, based on total moles of vinylidene, disubstituted vinylene, and trisubstituted vinylene in the PAO dimer of the first product effluent.

24. The process of claim 1, wherein, the PAO dimer of the first product effluent comprises 94 mol % or more of vinylidene, and 2 mol % or less of disubstituted vinylene and trisubstituted vinylene, based on total moles of vinylidene, disubstituted vinylene, and trisubstituted vinylene in the PAO dimer of the first product effluent.

25. The process of claim 3, wherein one of $R^1$, $R^2$, and $R^3$ is a substituted or unsubstituted linear, branched linear, or cyclic $C_1$-$C_6$ hydrocarbyl group, and two of $R^1$, $R^2$, and $R^3$ are hydrogen.

26. The process of claim 1, wherein M is hafnium (Hf).

27. The process of claim 1, wherein the metallocene compound comprises one or more of:

pentamethylcyclopentadienyl(1-methyl-1,5,6,7-tetrahydro-s-indacenyl)hafnium dimethyl, pentamethylcyclopentadienyl(1-ethyl-1,5,6,7-tetrahydro-s-indacenyl)hafnium dimethyl, pentamethylcyclopentadienyl(1-n-propyl-1,5,6,7-tetrahydro-s-indacenyl)hafnium dimethyl, pentamethylcyclopentadienyl(1-isopropyl-1,5,6,7-tetrahydro-s-indacenyl)hafnium dimethyl, pentamethylcyclopentadienyl(1-n-butyl-1,5,6,7-tetrahydro-s-indacenyl)hafnium dimethyl, pentamethylcyclopentadienyl(1-isobutyl-1,5,6,7-tetrahydro-s-indacenyl)hafnium dimethyl,
pentamethylcyclopentadienyl(1-sec-butyl-1,5,6,7-tetrahydro-s-indacenyl)hafnium dimethyl,
pentamethylcyclopentadienyl(1-tert-butyl-1,5,6,7-tetrahydro-s-indacenyl)hafnium dimethyl,
pentamethylcyclopentadienyl(1-pentyl-1,5,6,7-tetrahydro-s-indacenyl)hafnium dimethyl,
pentamethylcyclopentadienyl(1-neopentyl-1,5,6,7-tetrahydro-s-indacenyl)hafnium dimethyl,
pentamethylcyclopentadienyl(1-n-hexyl-1,5,6,7-tetrahydro-s-indacenyl)hafnium dimethyl,
pentamethylcyclopentadienyl(1-n-heptyl-1,5,6,7-tetrahydro-s-indacenyl)hafnium dimethyl,
pentamethylcyclopentadienyl(1-n-octyl-1,5,6,7-tetrahydro-s-indacenyl)hafnium dimethyl,
pentamethylcyclopentadienyl(1-benzyl-1,5,6,7-tetrahydro-s-indacenyl)hafnium dimethyl,
pentamethylcyclopentadienyl(1-phenethyl-1,5,6,7-tetrahydro-s-indacenyl)hafnium dimethyl,
pentamethylcyclopentadienyl(1-(2-phenylpropyl)-1,5,6,7-tetrahydro-s-indacenyl)hafnium dimethyl,
pentamethylcyclopentadienyl(1,6,6-trimethyl-1,5,6,7-tetrahydro-s-indacenyl)hafnium dimethyl,
pentamethylcyclopentadienyl(1-ethyl-6,6-dimethyl-1,5,6,7-tetrahydro-s-indacenyl)hafnium dimethyl,
pentamethylcyclopentadienyl(1-n-propyl-6,6-dimethyl-1,5,6,7-tetrahydro-s-indacenyl)hafnium dimethyl,
pentamethylcyclopentadienyl(1-isopropyl-6,6-dimethyl-1,5,6,7-tetrahydro-s-indacenyl)hafnium dimethyl,
pentamethylcyclopentadienyl(1-n-butyl-6,6-dimethyl-1,5,6,7-tetrahydro-s-indacenyl)hafnium dimethyl,
pentamethylcyclopentadienyl(1-isobutyl-6,6-dimethyl-1,5,6,7-tetrahydro-s-indacenyl)hafnium dimethyl,
pentamethylcyclopentadienyl(1-sec-butyl-6,6-dimethyl-1,5,6,7-tetrahydro-s-indacenyl)hafnium dimethyl,
pentamethylcyclopentadienyl(1-tert-butyl-6,6-dimethyl-1,5,6,7-tetrahydro-s-indacenyl)hafnium dimethyl,
pentamethylcyclopentadienyl(1-pentyl-6,6-dimethyl-1,5,6,7-tetrahydro-s-indacenyl)hafnium dimethyl,
pentamethylcyclopentadienyl(1-neopentyl-6,6-dimethyl-1,5,6,7-tetrahydro-s-indacenyl)hafnium dimethyl,
pentamethylcyclopentadienyl(1-n-hexyl-6,6-dimethyl-1,5,6,7-tetrahydro-s-indacenyl)hafnium dimethyl,
pentamethylcyclopentadienyl(1-n-heptyl-6,6-dimethyl-1,5,6,7-tetrahydro-s-indacenyl)hafnium dimethyl,
pentamethylcyclopentadienyl(1-n-octyl-6,6-dimethyl-1,5,6,7-tetrahydro-s-indacenyl)hafnium dimethyl,
pentamethylcyclopentadienyl(1-benzyl-6,6-dimethyl-1,5,6,7-tetrahydro-s-indacenyl)hafnium dimethyl,
pentamethylcyclopentadienyl(1-phenethyl-6,6-dimethyl-1,5,6,7-tetrahydro-s-indacenyl)hafnium dimethyl,
pentamethylcyclopentadienyl(1-(2-phenylpropyl)-6,6-dimethyl-1,5,6,7-tetrahydro-s-indacenyl)hafnium dimethyl,
pentamethylcyclopentadienyl(1-methyl-6,6-diethyl-1,5,6,7-tetrahydro-s-indacenyl)hafnium dimethyl,
pentamethylcyclopentadienyl(1,6,6-triethyl-1,5,6,7-tetrahydro-s-indacenyl)hafnium dimethyl,
pentamethylcyclopentadienyl(1-n-propyl-6,6-diethyl-1,5,6,7-tetrahydro-s-indacenyl)hafnium dimethyl,
pentamethylcyclopentadienyl(1-isopropyl-6,6-diethyl-1,5,6,7-tetrahydro-s-indacenyl)hafnium dimethyl,
pentamethylcyclopentadienyl(1-n-butyl-6,6-diethyl-1,5,6,7-tetrahydro-s-indacenyl)hafnium dimethyl,
pentamethylcyclopentadienyl(1-isobutyl-6,6-diethyl-1,5,6,7-tetrahydro-s-indacenyl)hafnium dimethyl,
pentamethylcyclopentadienyl(1-sec-butyl-6,6-diethyl-1,5,6,7-tetrahydro-s-indacenyl)hafnium dimethyl,
pentamethylcyclopentadienyl(1-tert-butyl-6,6-diethyl-1,5,6,7-tetrahydro-s-indacenyl)hafnium dimethyl,
pentamethylcyclopentadienyl(1-pentyl-6,6-diethyl-1,5,6,7-tetrahydro-s-indacenyl)hafnium dimethyl,
pentamethylcyclopentadienyl(1-neopentyl-6,6-diethyl-1,5,6,7-tetrahydro-s-indacenyl)hafnium dimethyl,
pentamethylcyclopentadienyl(1-benzyl-6,6-diethyl-1,5,6,7-tetrahydro-s-indacenyl)hafnium dimethyl,
pentamethylcyclopentadienyl(1-phenethyl-6,6-diethyl-1,5,6,7-tetrahydro-s-indacenyl)hafnium dimethyl,
pentamethylcyclopentadienyl(1-(2-phenylpropyl)-6,6-diethyl-1,5,6,7-tetrahydro-s-indacenyl)hafnium dimethyl,
pentamethylcyclopentadienyl(1-methyl-1,5,6,7-tetrahydro-s-indacenyl)zirconium dimethyl,
pentamethylcyclopentadienyl(1-isobutyl-1,5,6,7-tetrahydro-s-indacenyl)zirconium dimethyl,
pentamethylcyclopentadienyl(1,6,6-trimethyl-1,5,6,7-tetrahydro-s-indacenyl)zirconium dimethyl,
ethyltetramethylcyclopentadienyl(1-methyl-1,5,6,7-tetrahydro-s-indacenyl)hafnium dimethyl,
ethyltetramethylcyclopentadienyl(1-isobutyl-1,5,6,7-tetrahydro-s-indacenyl)hafnium dimethyl,
ethyltetramethylcyclopentadienyl(1,6,6-trimethyl-1,5,6,7-tetrahydro-s-indacenyl)hafnium dimethyl,
pentamethylcyclopentadienyl(1-methyl-1,5,6,7-tetrahydro-s-indacenyl)hafnium dibenzyl,
pentamethylcyclopentadienyl(1-isobutyl-1,5,6,7-tetrahydro-s-indacenyl)hafnium dibenzyl, and
pentamethylcyclopentadienyl(1,6,6-trimethyl-1,5,6,7-tetrahydro-s-indacenyl)hafnium dibenzyl.

28. The process of claim 1, wherein the metallocene compound comprises one or more of:
pentamethylcyclopentadienyl(1-methyl-1,5,6,7-tetrahydro-s-indacenyl)hafnium dimethyl,
pentamethylcyclopentadienyl(1-ethyl-1,5,6,7-tetrahydro-s-indacenyl)hafnium dimethyl,
pentamethylcyclopentadienyl(1-n-propyl-1,5,6,7-tetrahydro-s-indacenyl)hafnium dimethyl,
pentamethylcyclopentadienyl(1-isopropyl-1,5,6,7-tetrahydro-s-indacenyl)hafnium dimethyl,
pentamethylcyclopentadienyl(1-n-butyl-1,5,6,7-tetrahydro-s-indacenyl)hafnium dimethyl,
pentamethylcyclopentadienyl(1-isobutyl-1,5,6,7-tetrahydro-s-indacenyl)hafnium dimethyl,
pentamethylcyclopentadienyl(1,6,6-trimethyl-1,5,6,7-tetrahydro-s-indacenyl)hafnium dimethyl,
pentamethylcyclopentadienyl(1-isobutyl-6,6-dimethyl-1,5,6,7-tetrahydro-s-indacenyl)hafnium dimethyl,
pentamethylcyclopentadienyl(1-methyl-6,6-diethyl-1,5,6,7-tetrahydro-s-indacenyl)hafnium dimethyl,
pentamethylcyclopentadienyl(1,6,6-triethyl-1,5,6,7-tetrahydro-s-indacenyl)hafnium dimethyl, and
pentamethylcyclopentadienyl(1-isobutyl-6,6-diethyl-1,5,6,7-tetrahydro-s-indacenyl)hafnium dimethyl.

29. The process of claim 1, wherein the activator comprises one or more of:
N,N-di(hydrogenated tallow)methylammonium [tetrakis(perfluorophenyl)borate],
N-methyl-4-nonadecyl-N-octadecylanilinium [tetrakis(perfluorophenyl)borate],
N-methyl-4-hexadecyl-N-octadecylanilinium [tetrakis(perfluorophenyl)borate],
N-methyl-4-tetradecyl-N-octadecylanilinium [tetrakis(perfluorophenyl)borate], N-methyl-4-dodecyl-N-octadecylanilinium [tetrakis(perfluorophenyl)borate],
N-methyl-4-decyl-N-octadecylanilinium [tetrakis(perfluorophenyl)borate],
N-methyl-4-octyl-N-octadecylanilinium [tetrakis(perfluorophenyl)borate],
N-methyl-4-hexyl-N-octadecylanilinium [tetrakis(perfluorophenyl)borate],
N-methyl-4-butyl-N-octadecylanilinium [tetrakis(perfluorophenyl)borate],
N-methyl-4-octadecyl-N-decylanilinium [tetrakis(perfluorophenyl)borate],
N-methyl-4-nonadecyl-N-dodecylanilinium [tetrakis(perfluorophenyl)borate],
N-methyl-4-nonadecyl-N-tetradecylanilinium [tetrakis(perfluorophenyl)borate],
N-methyl-4-nonadecyl-N-hexadecylanilinium [tetrakis(perfluorophenyl)borate],
N-ethyl-4-nonadecyl-N-octadecylanilinium [tetrakis(perfluorophenyl)borate],
N-methyl-N,N-dioctadecylaammonium [tetrakis(perfluorophenyl)borate],
N-methyl-N,N-dihexadecylaammonium [tetrakis(perfluorophenyl)borate],
N-methyl-N,N-ditetradecylammonium [tetrakis(perfluorophenyl)borate],
N-methyl-N,N-didodecylammonium [tetrakis(perfluorophenyl)borate],
N-methyl-N,N-didecylammonium [tetrakis(perfluorophenyl)borate],
N-methyl-N,N-dioctylammonium [tetrakis(perfluorophenyl)borate],
N-ethyl-N,N-dioctadecylammonium [tetrakis(perfluorophenyl)borate],
N,N-di(octadecyl)tolylammonium [tetrakis(perfluorophenyl)borate],
N,N-di(hexadecyl)tolylammonium [tetrakis(perfluorophenyl)borate],
N,N-di(tetradecyl)tolylammonium [tetrakis(perfluorophenyl)borate],
N,N-di(dodecyl)tolylammonium [tetrakis(perfluorophenyl)borate],
N-octadecyl-N-hexadecyl-tolylammonium [tetrakis(perfluorophenyl)borate],
N-octadecyl-N-hexadecyl-tolylammonium [tetrakis(perfluorophenyl)borate],
N-octadecyl-N-tetradecyl-tolylammonium [tetrakis(perfluorophenyl)borate],
N-octadecyl-N-dodecyl-tolylammonium [tetrakis(perfluorophenyl)borate],
N-octadecyl-N-decyl-tolylammonium [tetrakis(perfluorophenyl)borate],
N-hexadecyl-N-tetradecyl-tolylammonium [tetrakis(perfluorophenyl)borate],
N-hexadecyl-N-dodecyl-tolylammonium [tetrakis(perfluorophenyl)borate],
N-hexadecyl-N-decyl-tolylammonium [tetrakis(perfluorophenyl)borate],
N-tetradecyl-N-dodecyl-tolylammonium [tetrakis(perfluorophenyl)borate],
N-tetradecyl-N-decyl-tolylammonium [tetrakis(perfluorophenyl)borate],
N-dodecyl-N-decyl-tolylammonium [tetrakis(perfluorophenyl)borate],
N-methyl-N-octadecylanilinium [tetrakis(perfluorophenyl)borate],
N-methyl-N-hexadecylanilinium [tetrakis(perfluorophenyl)borate],
N-methyl-N-tetradecylanilinium [tetrakis(perfluorophenyl)borate],
N-methyl-N-dodecylanilinium [tetrakis(perfluorophenyl)borate],
N-methyl-N-decylanilinium [tetrakis(perfluorophenyl)borate], and
N-methyl-N-octylanilinium [tetrakis(perfluorophenyl)borate].

30. The process of claim 1, wherein the first alpha-olefin is selected from the group consisting of 1-hexene, 1-heptene, 1-octene, 1-nonene, 1-decene, 1-undecene, 1-dodecene, 1-tridecene, 1-tetradecene, 1-pentadecene, 1-hexadecene, and combinations thereof.

31. The process of claim 1, wherein the reaction conditions in the first reactor comprise a reactor temperature of from 110° C. to 180° C., a reactor pressure of from 15 psia to 750 psia, and a catalyst loading of from 25,000 g alpha-olefin (gAO) per 1 g catalyst (gCat) to 90,000 gAO/gCat.

32. The process of claim 1, where in the step to make PAO dimer, a solvent is used that is selected from $C_4$ to $C_{10}$ linear, branched or cyclic alkanes and/or $C_6$ to $C_{32}$ alpha olefins.

33. The process of claim 1, where in the step to make PAO dimer, a solvent is used that is essentially free of all aromatic solvents.

34. A process to produce a poly alpha-olefin (PAO), comprising:
   a) introducing a first alpha-olefin to a first catalyst system comprising non-aromatic hydrocarbon soluble activator and a metallocene compound into a first reactor under first reactor conditions to form a first reactor effluent comprising PAO dimer; and
   b) introducing the first reactor effluent and an optional second alpha-olefin to a second catalyst composition comprising an acid catalyst in a second reactor under second reactor conditions to form a second reactor effluent comprising PAO trimer, wherein the metallocene compound comprises one or more of:
pentamethylcyclopentadienyl(1-methyl-1,5,6,7-tetrahydro-s-indacenyl)hafnium dimethyl,
pentamethylcyclopentadienyl(1-ethyl-1,5,6,7-tetrahydro-s-indacenyl)hafnium dimethyl,
pentamethylcyclopentadienyl(1-n-propyl-1,5,6,7-tetrahydro-s-indacenyl)hafnium dimethyl,
pentamethylcyclopentadienyl(1-isopropyl-1,5,6,7-tetrahydro-s-indacenyl)hafnium dimethyl,
pentamethylcyclopentadienyl(1-n-butyl-1,5,6,7-tetrahydro-s-indacenyl)hafnium dimethyl,
pentamethylcyclopentadienyl(1-isobutyl-1,5,6,7-tetrahydro-s-indacenyl)hafnium dimethyl,
pentamethylcyclopentadienyl(1-sec-butyl-1,5,6,7-tetrahydro-s-indacenyl)hafnium dimethyl,
pentamethylcyclopentadienyl(1-tert-butyl-1,5,6,7-tetrahydro-s-indacenyl)hafnium dimethyl,
pentamethylcyclopentadienyl(1-pentyl-1,5,6,7-tetrahydro-s-indacenyl)hafnium dimethyl,
pentamethylcyclopentadienyl(1-neopentyl-1,5,6,7-tetrahydro-s-indacenyl)hafnium dimethyl,
pentamethylcyclopentadienyl(1-n-hexyl-1,5,6,7-tetrahydro-s-indacenyl)hafnium dimethyl,
pentamethylcyclopentadienyl(1-n-heptyl-1,5,6,7-tetrahydro-s-indacenyl)hafnium dimethyl,
pentamethylcyclopentadienyl(1-n-octyl-1,5,6,7-tetrahydro-s-indacenyl)hafnium dimethyl, pentamethylcyclopentadienyl(1-benzyl-1,5,6,7-tetrahydro-s-indacenyl)hafnium dimethyl,
pentamethylcyclopentadienyl(1-phenethyl-1,5,6,7-tetrahydro-s-indacenyl)hafnium dimethyl,
pentamethylcyclopentadienyl(1-(2-phenylpropyl)-1,5,6,7-tetrahydro-s-indacenyl)hafnium dimethyl,
pentamethylcyclopentadienyl(1,6,6-trimethyl-1,5,6,7-tetrahydro-s-indacenyl)hafnium dimethyl,
pentamethylcyclopentadienyl(1-ethyl-6,6-dimethyl-1,5,6,7-tetrahydro-s-indacenyl)hafnium dimethyl,
pentamethylcyclopentadienyl(1-n-propyl-6,6-dimethyl-1,5,6,7-tetrahydro-s-indacenyl)hafnium dimethyl,
pentamethylcyclopentadienyl(1-isopropyl-6,6-dimethyl-1,5,6,7-tetrahydro-s-indacenyl)hafnium dimethyl,
pentamethylcyclopentadienyl(1-n-butyl-6,6-dimethyl-1,5,6,7-tetrahydro-s-indacenyl)hafnium dimethyl,
pentamethylcyclopentadienyl(1-isobutyl-6,6-dimethyl-1,5,6,7-tetrahydro-s-indacenyl)hafnium dimethyl,
pentamethylcyclopentadienyl(1-sec-butyl-6,6-dimethyl-1,5,6,7-tetrahydro-s-indacenyl)hafnium dimethyl,
pentamethylcyclopentadienyl(1-tert-butyl-6,6-dimethyl-1,5,6,7-tetrahydro-s-indacenyl)hafnium dimethyl,
pentamethylcyclopentadienyl(1-pentyl-6,6-dimethyl-1,5,6,7-tetrahydro-s-indacenyl)hafnium dimethyl,
pentamethylcyclopentadienyl(1-neopentyl-6,6-dimethyl-1,5,6,7-tetrahydro-s-indacenyl)hafnium dimethyl,
pentamethylcyclopentadienyl(1-n-hexyl-6,6-dimethyl-1,5,6,7-tetrahydro-s-indacenyl)hafnium dimethyl,
pentamethylcyclopentadienyl(1-n-heptyl-6,6-dimethyl-1,5,6,7-tetrahydro-s-indacenyl)hafnium dimethyl,
pentamethylcyclopentadienyl(1-n-octyl-6,6-dimethyl-1,5,6,7-tetrahydro-s-indacenyl)hafnium dimethyl,
pentamethylcyclopentadienyl(1-benzyl-6,6-dimethyl-1,5,6,7-tetrahydro-s-indacenyl)hafnium dimethyl,
pentamethylcyclopentadienyl(1-phenethyl-6,6-dimethyl-1,5,6,7-tetrahydro-s-indacenyl)hafnium dimethyl,
pentamethylcyclopentadienyl(1-(2-phenylpropyl)-6,6-dimethyl-1,5,6,7-tetrahydro-s-indacenyl)hafnium dimethyl,
pentamethylcyclopentadienyl(1-methyl-6,6-diethyl-1,5,6,7-tetrahydro-s-indacenyl)hafnium dimethyl,
pentamethylcyclopentadienyl(1,6,6-triethyl-1,5,6,7-tetrahydro-s-indacenyl)hafnium dimethyl,
pentamethylcyclopentadienyl(1-n-propyl-6,6-diethyl-1,5,6,7-tetrahydro-s-indacenyl)hafnium dimethyl,
pentamethylcyclopentadienyl(1-isopropyl-6,6-diethyl-1,5,6,7-tetrahydro-s-indacenyl)hafnium dimethyl,
pentamethylcyclopentadienyl(1-n-butyl-6,6-diethyl-1,5,6,7-tetrahydro-s-indacenyl)hafnium dimethyl,
pentamethylcyclopentadienyl(1-isobutyl-6,6-diethyl-1,5,6,7-tetrahydro-s-indacenyl)hafnium dimethyl,
pentamethylcyclopentadienyl(1-sec-butyl-6,6-diethyl-1,5,6,7-tetrahydro-s-indacenyl)hafnium dimethyl,
pentamethylcyclopentadienyl(1-tert-butyl-6,6-diethyl-1,5,6,7-tetrahydro-s-indacenyl)hafnium dimethyl,
pentamethylcyclopentadienyl(1-pentyl-6,6-diethyl-1,5,6,7-tetrahydro-s-indacenyl)hafnium dimethyl,
pentamethylcyclopentadienyl(1-neopentyl-6,6-diethyl-1,5,6,7-tetrahydro-s-indacenyl)hafnium dimethyl,
pentamethylcyclopentadienyl(1-benzyl-6,6-diethyl-1,5,6,7-tetrahydro-s-indacenyl)hafnium dimethyl,
pentamethylcyclopentadienyl(1-phenethyl-6,6-diethyl-1,5,6,7-tetrahydro-s-indacenyl)hafnium dimethyl,
pentamethylcyclopentadienyl(1-(2-phenylpropyl)-6,6-diethyl-1,5,6,7-tetrahydro-s-indacenyl)hafnium dimethyl,
pentamethylcyclopentadienyl(1-methyl-1,5,6,7-tetrahydro-s-indacenyl)zirconium dimethyl,
pentamethylcyclopentadienyl(1-isobutyl-1,5,6,7-tetrahydro-s-indacenyl)zirconium dimethyl,
pentamethylcyclopentadienyl(1,6,6-trimethyl-1,5,6,7-tetrahydro-s-indacenyl)zirconium dimethyl,
ethyltetramethylcyclopentadienyl(1-methyl-1,5,6,7-tetrahydro-s-indacenyl)hafnium dimethyl,
ethyltetramethylcyclopentadienyl(1-isobutyl-1,5,6,7-tetrahydro-s-indacenyl)hafnium dimethyl,
ethyltetramethylcyclopentadienyl(1,6,6-trimethyl-1,5,6,7-tetrahydro-s-indacenyl)hafnium dimethyl,
pentamethylcyclopentadienyl(1-methyl-1,5,6,7-tetrahydro-s-indacenyl)hafnium dibenzyl,
pentamethylcyclopentadienyl(1-isobutyl-1,5,6,7-tetrahydro-s-indacenyl)hafnium dibenzyl,
pentamethylcyclopentadienyl(1,6,6-trimethyl-1,5,6,7-tetrahydro-s-indacenyl)hafnium dibenzyl,
pentamethylcyclopentadienyl(1-methyl-1,5,6,7-tetrahydro-s-indacenyl)hafnium dimethyl,
pentamethylcyclopentadienyl(1-ethyl-1,5,6,7-tetrahydro-s-indacenyl)hafnium dimethyl,
pentamethylcyclopentadienyl(1-n-propyl-1,5,6,7-tetrahydro-s-indacenyl)hafnium dimethyl,
pentamethylcyclopentadienyl(1-isopropyl-1,5,6,7-tetrahydro-s-indacenyl)hafnium dimethyl,
pentamethylcyclopentadienyl(1-n-butyl-1,5,6,7-tetrahydro-s-indacenyl)hafnium dimethyl,
pentamethylcyclopentadienyl(1-isobutyl-1,5,6,7-tetrahydro-s-indacenyl)hafnium dimethyl,
pentamethylcyclopentadienyl(1,6,6-trimethyl-1,5,6,7-tetrahydro-s-indacenyl)hafnium dimethyl,
pentamethylcyclopentadienyl(1-isobutyl-6,6-dimethyl-1,5,6,7-tetrahydro-s-indacenyl)hafnium dimethyl,
pentamethylcyclopentadienyl(1-methyl-6,6-diethyl-1,5,6,7-tetrahydro-s-indacenyl)hafnium dimethyl,
pentamethylcyclopentadienyl(1,6,6-triethyl-1,5,6,7-tetrahydro-s-indacenyl)hafnium dimethyl, and pentamethylcyclopentadienyl(1-isobutyl-6,6-diethyl-1,5,6,7-tetrahydro-s-indacenyl)hafnium dimethyl.

35. A process to produce a poly alpha-olefin (PAO), comprising:
a) introducing a first alpha-olefin to a first catalyst system comprising non-aromatic hydrocarbon soluble activator and a metallocene compound into a first reactor under first reactor conditions to form a first reactor effluent comprising PAO dimer; and
b) introducing the first reactor effluent and an optional second alpha-olefin to a second catalyst composition comprising an acid catalyst in a second reactor under second reactor conditions to form a second reactor effluent comprising PAO trimer, wherein the activator is represented by the formula (VIII):

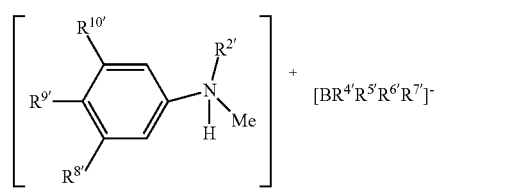

wherein N is nitrogen;
$R^{2'}$ is a $C_6$-$C_{40}$ hydrocarbyl group optionally substituted with one or more alkoxy groups, silyl groups, a halogen atoms, or halogen containing groups;

$R^{8'}$, $R^{9'}$, and $R^{10'}$ are independently a $C_4$-$C_{30}$ hydrocarbyl or substituted $C_4$-$C_{30}$ hydrocarbyl group;

B is boron; and $R^{4'}$, $R^{5'}$, $R^{6'}$, and $R^{7'}$ are each independently hydride, a bridged or unbridged dialkylamido, halide, alkoxide, aryloxide, hydrocarbyl, substituted hydrocarbyl, halocarbyl, substituted halocarbyl, or halosubstituted-hydrocarbyl radical.

36. The process of claim 35, wherein the activator comprises one or more of:

N-methyl-4-nonadecyl-N-octadecylanilinium [tetrakis(perfluorophenyl)borate],

N-methyl-4-hexadecyl-N-octadecylanilinium [tetrakis(perfluorophenyl)borate],

N-methyl-4-tetradecyl-N-octadecylanilinium [tetrakis(perfluorophenyl)borate],

N-methyl-4-dodecyl-N-octadecylanilinium [tetrakis(perfluorophenyl)borate],

N-methyl-4-decyl-N-octadecylanilinium [tetrakis(perfluorophenyl)borate],

N-methyl-4-octyl-N-octadecylanilinium [tetrakis(perfluorophenyl)borate],

N-methyl-4-hexyl-N-octadecylanilinium [tetrakis(perfluorophenyl)borate],

N-methyl-4-butyl-N-octadecylanilinium [tetrakis(perfluorophenyl)borate],

N-methyl-4-octadecyl-N-decylanilinium [tetrakis(perfluorophenyl)borate],

N-methyl-4-nonadecyl-N-dodecylanilinium [tetrakis(perfluorophenyl)borate],

N-methyl-4-nonadecyl-N-tetradecylanilinium [tetrakis(perfluorophenyl)borate],

N-methyl-4-nonadecyl-N-hexadecylanilinium [tetrakis(perfluorophenyl)borate],

N-ethyl-4-nonadecyl-N-octadecylanilinium [tetrakis(perfluorophenyl)borate],

N-methyl-N-octadecylanilinium [tetrakis(perfluorophenyl)borate],

N-methyl-N-hexadecylanilinium [tetrakis(perfluorophenyl)borate],

N-methyl-N-tetradecylanilinium [tetrakis(perfluorophenyl)borate],

N-methyl-N-dodecylanilinium [tetrakis(perfluorophenyl)borate],

N-methyl-N-decylanilinium [tetrakis(perfluorophenyl)borate], and

N-methyl-N-octylanilinium [tetrakis(perfluorophenyl)borate].

\* \* \* \* \*